(12) United States Patent
Heo et al.

(10) Patent No.: US 11,878,962 B2
(45) Date of Patent: Jan. 23, 2024

(54) COMPOUND AND ORGANIC LIGHT EMITTING DEVICE COMPRISING SAME

(71) Applicant: LG CHEM, LTD., Seoul (KR)

(72) Inventors: Dong Uk Heo, Daejeon (KR); Jin Joo Kim, Daejeon (KR); Dong Hoon Lee, Daejeon (KR); Jungoh Huh, Daejeon (KR); Yongbum Cha, Daejeon (KR); Wanpyo Hong, Daejeon (KR)

(73) Assignee: LG Chem, Ltd., Seoul (KR)

( * ) Notice: Subject to any disclaimer, the term of this patent is extended or adjusted under 35 U.S.C. 154(b) by 468 days.

(21) Appl. No.: 16/762,245

(22) PCT Filed: Mar. 8, 2019

(86) PCT No.: PCT/KR2019/002693
§ 371 (c)(1),
(2) Date: May 7, 2020

(87) PCT Pub. No.: WO2019/172699
PCT Pub. Date: Sep. 12, 2019

(65) Prior Publication Data
US 2021/0114998 A1    Apr. 22, 2021

(30) Foreign Application Priority Data
Mar. 9, 2018   (KR) .......................... 10-2018-0028012

(51) Int. Cl.
*C07D 251/24*   (2006.01)
*C07D 311/96*   (2006.01)
(Continued)

(52) U.S. Cl.
CPC .......... *C07D 251/24* (2013.01); *C07D 311/96* (2013.01); *C07D 335/10* (2013.01);
(Continued)

(58) Field of Classification Search
CPC .. C07D 251/24; C07D 311/96; C07D 335/10; C07D 405/04; H01L 51/0052;
(Continued)

(56) References Cited

U.S. PATENT DOCUMENTS

| 2016/0118599 A1 | 4/2016 | Jeong et al. |
| 2017/0222157 A1 | 8/2017 | Jatsch et al. |
| 2018/0337341 A1 | 11/2018 | Heo et al. |

FOREIGN PATENT DOCUMENTS

| JP | 2003-096072 | 4/2003 |
| JP | 2009-191232 | 8/2009 |

(Continued)

OTHER PUBLICATIONS

Cao et al., Journal of Molecular Structure, 1196, (2019), pp. 132-138 . (Year: 2019).*
(Continued)

*Primary Examiner* — Dawn L Garrett
(74) *Attorney, Agent, or Firm* — Bryan Cave Leighton Paisner LLP

(57) ABSTRACT

Provided is a compound of Chemical Formula 1:

Chemical Formula 1

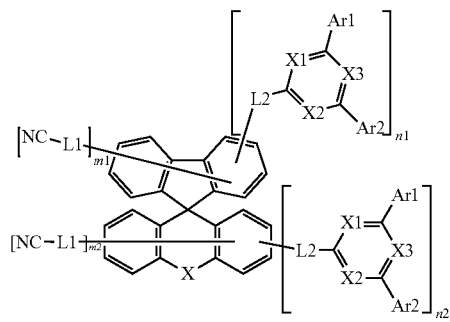

wherein X is O or S; L1 and L2 each independently is a direct bond or a substituted or unsubstituted arylene group; X1 is N or CR1, X2 is N or CR2, X3 is N or
(Continued)

CR3, and at least two of X1 to X3 are N; R1 to R3 each independently is hydrogen, deuterium, or a substituted or unsubstituted alkyl, aryl or heteroaryl group; Ar1 and Ar2 each independently is hydrogen, deuterium, or a substituted or unsubstituted alkyl, aryl or heteroaryl group;
positions at which

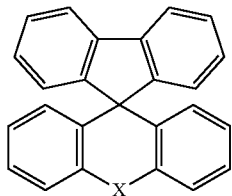

is substituted with

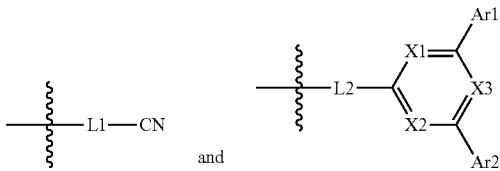

are asymmetric;
m1, m2, n1 and n2 each independently is 0 or 1; and m1+m2 is 1, and n1+n2 is 1, and an organic light emitting device comprising the same.

17 Claims, 5 Drawing Sheets

(51) Int. Cl.
*C07D 335/10* (2006.01)
*H10K 85/60* (2023.01)
*H10K 50/165* (2023.01)
*H10K 50/17* (2023.01)

(52) U.S. Cl.
CPC ......... *H10K 85/615* (2023.02); *H10K 85/654* (2023.02); *H10K 85/6574* (2023.02); *H10K 85/6576* (2023.02); *H10K 50/165* (2023.02); *H10K 50/171* (2023.02)

(58) Field of Classification Search
CPC ............. H01L 51/0067; H01L 51/0073; H01L 51/0074; H01L 51/5076; H01L 51/5092; H01L 51/5012; H01L 51/5048; C09K 11/06; C09K 2211/1088; C09K 2211/1092; H10K 85/615; H10K 85/654; H10K 85/6574; H10K 85/6576; H10K 50/165; H10K 50/171; H10K 50/11; H10K 50/14
See application file for complete search history.

(56) References Cited

FOREIGN PATENT DOCUMENTS

| | | | |
|---|---|---|---|
| KR | 10-20080096733 | 11/2008 | |
| KR | 10-20130140303 | 12/2013 | |
| KR | 10-1593368 | 2/2016 | |
| KR | 10-20160047670 | 5/2016 | |
| KR | 10-20170032414 | 3/2017 | |
| KR | 10-1755986 | 7/2017 | |
| KR | 10-20190014472 | 2/2019 | |
| WO | WO-2019027189 A1 * | 2/2019 | ............. H01L 51/00 |

OTHER PUBLICATIONS

Liang, X., Tu, Z. L., & Zheng, Y. X. (2019). Thermally activated delayed fluorescence materials: towards realization of high efficiency through strategic small molecular design. Chemistry—A European Journal, 25(22), 5623-5642. (Year: 2019).*
International Search Report and the Written Opinion of PCT/KR2019/002693, dated Jun. 14, 2019.

* cited by examiner

[FIG. 1]
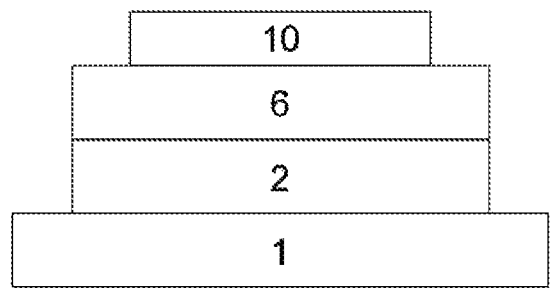
[FIG. 2]
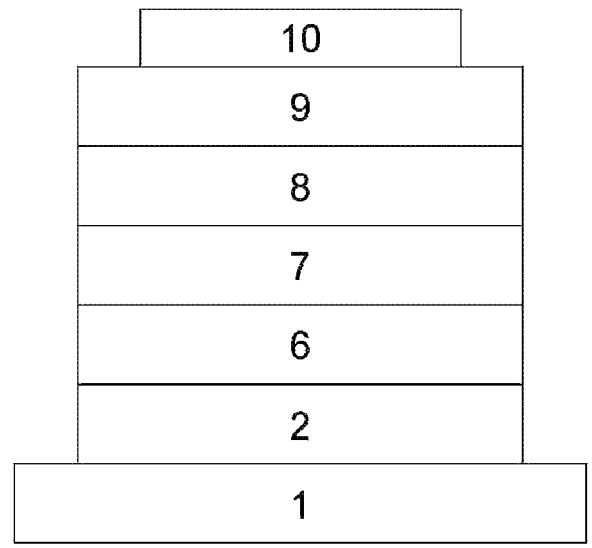

【FIG. 3】
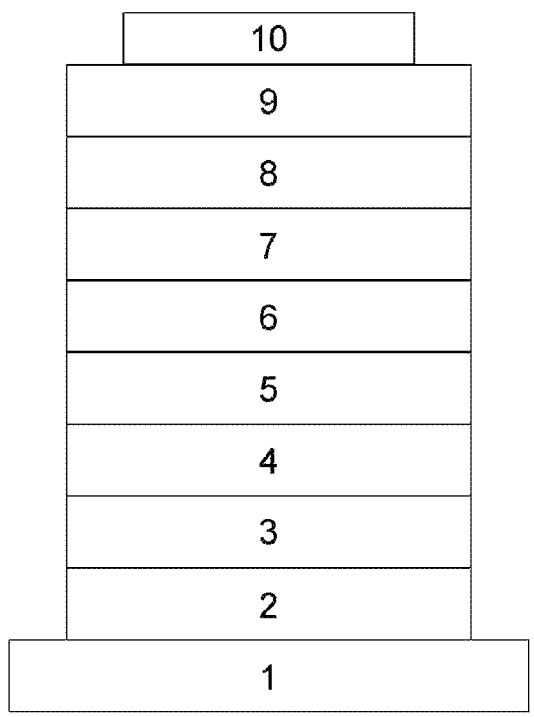
【FIG. 4】
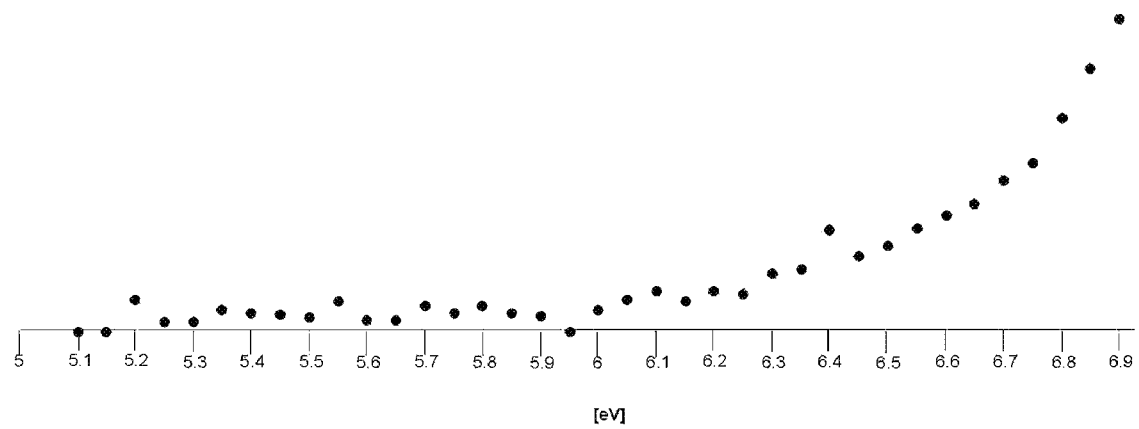

【FIG. 5】
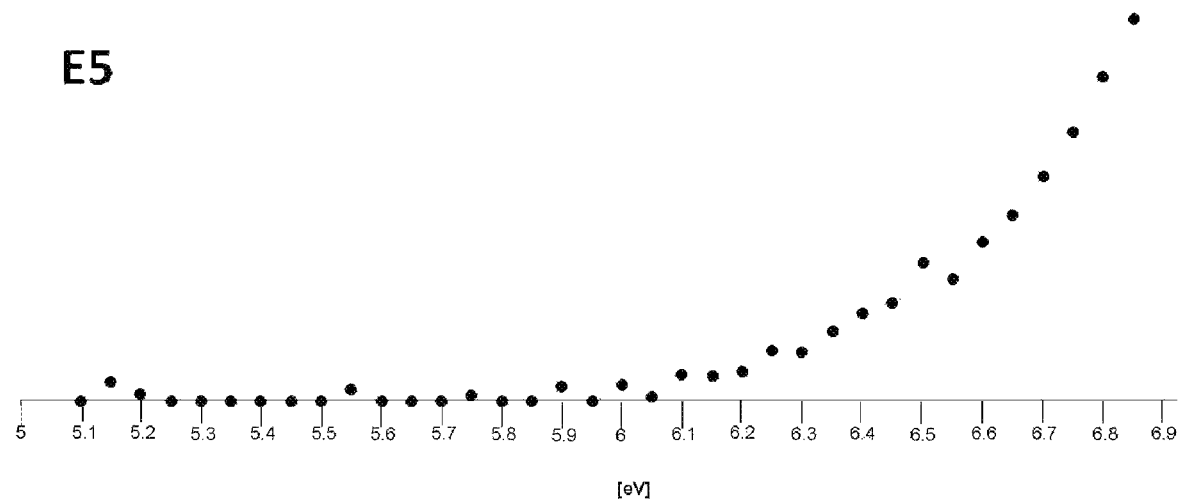
【FIG. 6】
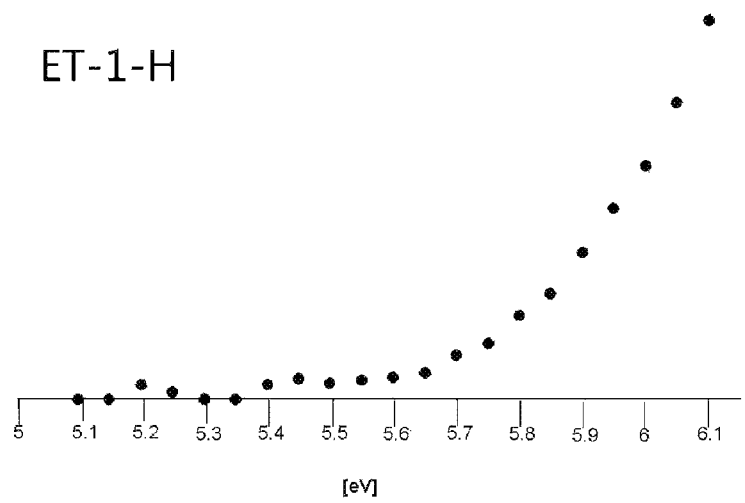

COMPOUND AND ORGANIC LIGHT EMITTING DEVICE COMPRISING SAME

CROSS-REFERENCE TO RELATED APPLICATIONS

This application is a National Stage Application of International Application No. PCT/KR2019/002693 filed on Mar. 8, 2019, which claims priority to and the benefits of Korean Patent Application No. 10-2018-0028012, filed with the Korean Intellectual Property Office on Mar. 9, 2018, the entire contents of which are incorporated herein by reference.

TECHNICAL FIELD

The present disclosure relates to a compound of Chemical Formula 1, and an organic light emitting device comprising the same.

BACKGROUND

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is formed in a multilayer structure formed with different materials in order to increase efficiency and stability of the organic light emitting device, and for example, can be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

BRIEF DESCRIPTION

Technical Problem

The present specification is directed to providing a compound capable of enhancing efficiency, driving voltage and/or lifetime properties of a device, and an organic light emitting device comprising the same.

Technical Solution

One embodiment of the present specification provides a compound of Chemical Formula 1:

Chemical Formula 1

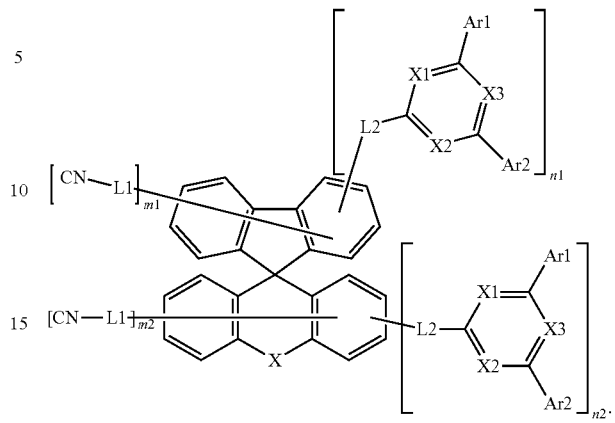

In Chemical Formula 1:

X is O or S;

L1 is a direct bond, or a substituted or unsubstituted arylene group;

L2 is a direct bond, or a substituted or unsubstituted arylene group;

X1 is N or CR1, X2 is N or CR2, X3 is N or CR3, and at least two of X1 to X3 are N;

R1 to R3 are the same as or different from each other, and each independently is hydrogen, deuterium, a substituted or unsubstituted alkyl group, a substituted or unsubstituted aryl group, or a substituted or unsubstituted heteroaryl group;

Ar1 and Ar2 are the same as or different from each other, and each independently is hydrogen, deuterium, a substituted or unsubstituted alkyl group, a substituted or unsubstituted aryl group, or a substituted or unsubstituted heteroaryl group;

positions at which

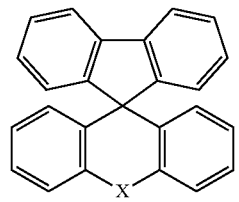

is substituted with

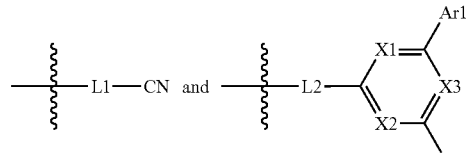

are asymmetric;

m1, m2, n1 and n2 each independently is 0 or 1, and m1+m2 is 1, and n1+n2 is 1.

Another embodiment of the present specification provides an organic light emitting device comprising a first electrode, a second electrode, and one or more organic material layers provided between the first electrode and the second electrode, wherein the compound described above is included in the organic material layer provided between the first electrode and the second electrode.

Advantageous Effects

A compound described in the present specification can be used as a material of an organic material layer of an organic light emitting device. The compound described in the present specification can be used as a hole injection, a hole transfer, a hole injection and hole transfer, a hole control, a light emitting, an electron control, an electron transfer or an electron injection material. The compound described in the present specification can be preferably used as an electron transfer and electron injection material, and more preferably used as an electron transfer material.

In some embodiments, an organic light emitting device comprising the compound of the present disclosure can have enhanced efficiency.

In some embodiments, an organic light emitting device comprising the compound of the present disclosure can have enhanced lifetime properties.

DESCRIPTION OF DRAWINGS

FIG. 1 illustrates an example of an organic light emitting device formed with a substrate (1), an anode (2), a light emitting layer (6) and a cathode (10).

FIG. 2 illustrates an example of an organic light emitting device formed with a substrate (1), an anode (2), a light emitting layer (6), an electron control layer (7), an electron transfer layer (8), an electron injection layer (9) and a cathode (10).

FIG. 3 illustrates an example of an organic light emitting device formed with a substrate (1), an anode (2), a hole injection layer (3), a hole transfer layer (4), a hole control layer (5), a light emitting layer (6), an electron control layer (7), an electron transfer layer (8), an electron injection layer (9) and a cathode (10).

FIG. 4 shows HOMO energy level measurement data of Compound E2.

FIG. 5 shows HOMO energy level measurement data of Compound E5.

FIG. 6 shows HOMO energy level measurement data of Compound ET-1-H.

DETAILED DESCRIPTION

Figure 7:
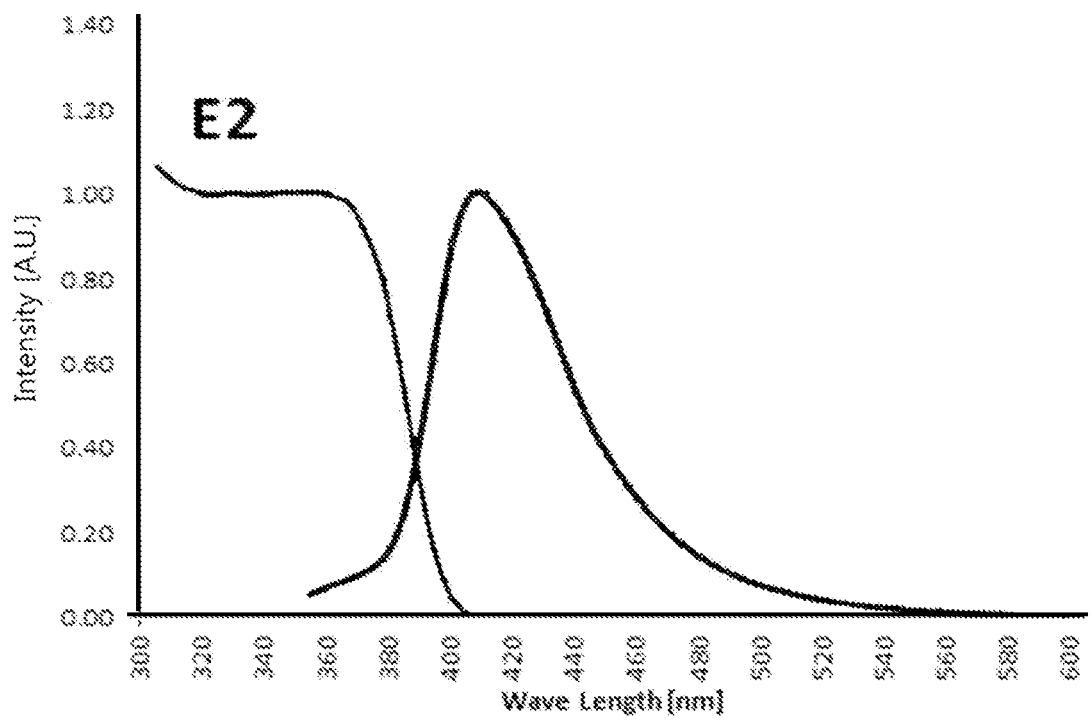
FIG. 7 shows a result of a light emission spectrum (PL) of Compound E2.
Figure 8:
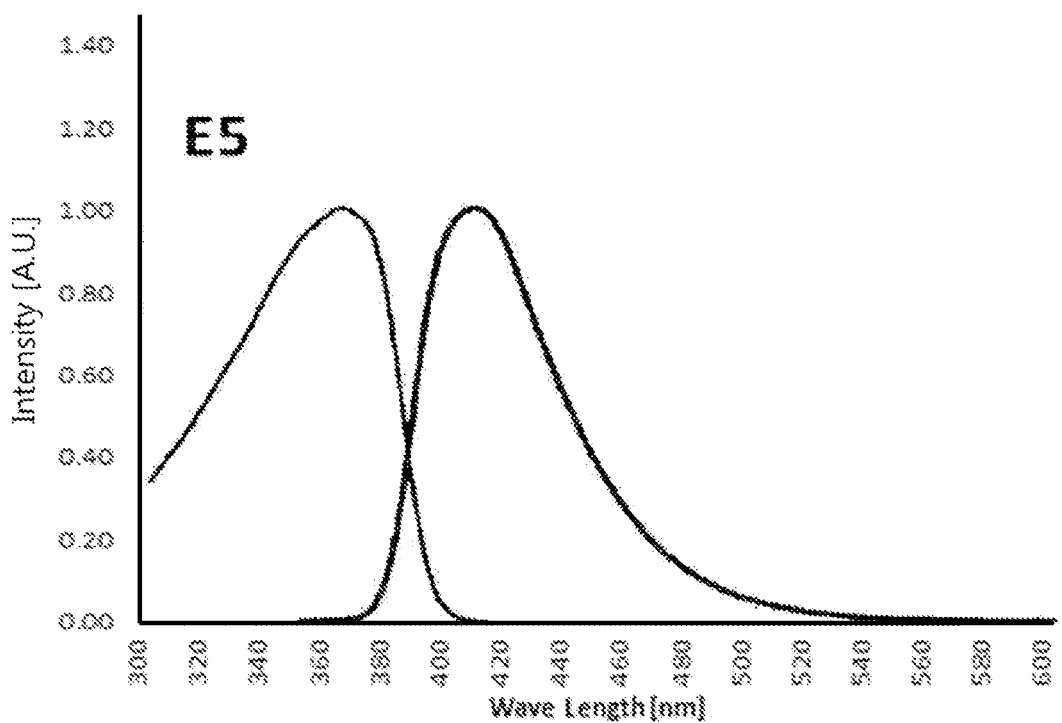
FIG. 8 shows a result of a light emission spectrum (PL) of Compound E5.
Figure 9:
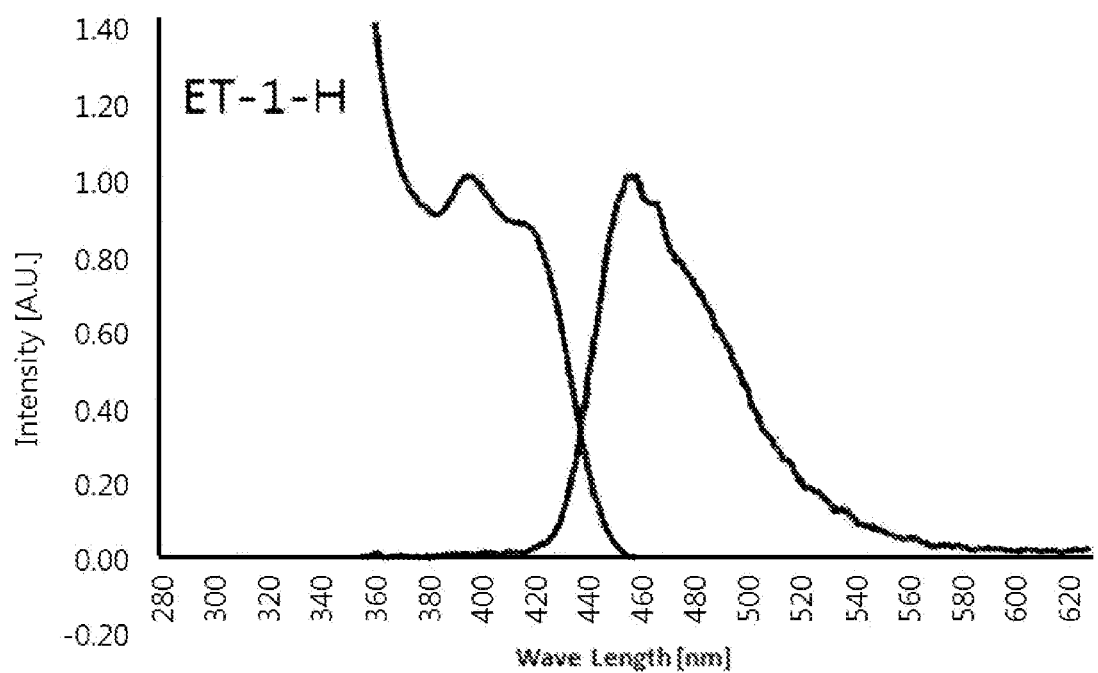
FIG. 9 shows a result of a light emission spectrum (PL) of Compound ET-1-H.

Hereinafter, the present disclosure will be described in more detail.

One embodiment of the present specification provides a compound of Chemical Formula 1.

In the present specification,

means a site bonding to other substituents or bonding sites.

Examples of the substituents are described below, however, the substituents are not limited thereto.

The term "substitution" means a hydrogen atom bonding to a carbon atom of a compound is changed to another substituent, and the position of substitution is not limited as long as it is a position at which a hydrogen atom is substituted, that is, a position at which a substituent can substitute, and when two or more substituents substitute, the two or more substituents can be the same as or different from each other.

In the present specification, the term "substituted or unsubstituted" means being substituted with one or more groups selected from the group consisting of deuterium, a halogen group, a nitrile group, a nitro group, a hydroxyl group, an alkyl group, an aralkyl group, an alkoxy group, an alkenyl group, an aryloxy group, an aryl group, and a heteroaryl group or being unsubstituted, or being substituted with a substituent linking two or more groups selected from the group or being unsubstituted.

As one example, the tam "substituted or unsubstituted" means being substituted with one or more groups selected from the group consisting of deuterium, a halogen group, a nitrile group, a nitro group, a hydroxyl group, an alkyl group, an aralkyl group, an alkoxy group, an alkenyl group, an aryloxy group, an aryl group, a heteroaryl group including an N-including hexagonal ring, and a heteroaryl group including one or more of O and S or being unsubstituted, or being substituted with a substituent linking two or more groups selected from the group or being unsubstituted. For example, the arylalkenyl group can be an alkenyl group, or can be interpreted as an alkenyl group substituted with an aryl group.

In the present specification, examples of the halogen group can include fluorine, chlorine, bromine or iodine.

In the present specification, the alkoxy group means a group in which an alkyl group bonds to an oxygen atom, and although not particularly limited thereto, the number of carbon atoms is preferably from 1 to 20. According to one embodiment, the number of carbon atoms of the alkoxy group is from 1 to 10. According to another embodiment, the number of carbon atoms of the alkoxy group is from 1 to 6. Specific examples of the alkoxy group can include a methoxy group, an ethoxy group, a propoxy group, an isobutyloxy group, a sec-butyloxy group, a pentyloxy group, an iso-amyloxy group, a hexyloxy group and the like, but are not limited thereto.

In the present specification, the aryloxy group means a group in which an aryl group bonds to an oxygen atom, and although not particularly limited thereto, the number of carbon atoms is preferably from 6 to 40. According to another embodiment, the number of carbon atoms of the aryloxy group is from 6 to 30. Specific examples of the aryloxy group can include a phenoxy group, a p-tolyloxy group, an m-tolyloxy group, a 3,5-dimethylphenoxy group, a 2,4,6-trimethylphenoxy group, a 3-biphenyloxy group, a 1-naphthyloxy group, a 2-naphthyloxy group, a 1-anthryloxy group, a 2-anthryloxy group, a 9-anthryloxy group, a 1-phenanthryloxy group, a 3-phenanthryloxy group, a 9-phenanthryloxy group and the like.

In the present specification, the alkyl group is a linear or branched hydrocarbon group. According to one embodiment, the number of carbon atoms of the alkyl group is from 1 to 20. According to another embodiment, the number of carbon atoms of the alkyl group is from 1 to 10. According to another embodiment, the number of carbon atoms of the alkyl group is from 1 to 6. Specific examples of the alkyl group can include methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methylpentyl, 2-methylpentyl, 3,3-dimethylbutyl, 2-ethylbutyl, heptyl, n-heptyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 4-methylhexyl, 5-methylhexyl and the like, but are not limited thereto.

In the present specification, a cyclic hydrocarbon group among the alkyl group is referred to as a cycloalkyl group. According to one embodiment, the number of carbon atoms of the cycloalkyl group is from 3 to 30. According to another embodiment, the number of carbon atoms of the cycloalkyl group is from 3 to 20. According to another embodiment, the number of carbon atoms of the cycloalkyl group is from 3 to 6. Specific examples thereof can include cyclopropyl, cyclobutyl, cyclopentyl, 3-methyl-cyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkenyl group represents a linear or branched unsaturated hydrocarbon group including a carbon-carbon double bond, and although not particularly limited thereto, the number of carbon atoms is preferably from 2 to 30. According to one embodiment, the number of carbon atoms of the alkenyl group is from 2 to 20. According to one embodiment, the number of carbon atoms of the alkenyl group is from 2 to 10. Specific examples thereof can include ethenyl, vinyl, propenyl, allyl, isopropenyl, butenyl, isobutenyl, n-pentenyl and n-hexenyl, but are not limited thereto.

In the present specification, the aralkenyl group means an alkenyl group substituted with an aryl group.

In the present specification, the aryl group means totally or partially unsaturated substituted or unsubstituted monocyclic or polycyclic. Although not particularly limited thereto, the number of carbon atoms is preferably from 6 to 60, and the aryl group can be a monocyclic aryl group or a polycyclic aryl group. According to one embodiment, the number of carbon atoms of the aryl group is from 6 to 40. According to one embodiment, the number of carbon atoms of the aryl group is from 6 to 30. The aryl group can be a monocyclic aryl group or a polycyclic aryl group. Examples of the monocyclic aryl group can include a phenyl group, a biphenyl group, a terphenyl group and the like, but are not limited thereto. Examples of the polycyclic aryl group can include a naphthyl group, an anthracenyl group, a phenanthrenyl group, a perylenyl group, a fluoranthenyl group, a triphenylenyl group, a phenalenyl group, a pyrenyl group, a tetracenyl group, a chrysenyl group, a pentacenyl group, a fluorenyl group, an indenyl group, an acenaphthylenyl group, a benzofluorenyl group, a spirofluorenyl group and the like, but are not limited thereto.

In the present specification, the fluorenyl group can be substituted, and two substituents bond to each other to form a spiro structure.

Examples of the substituted fluorenyl group include

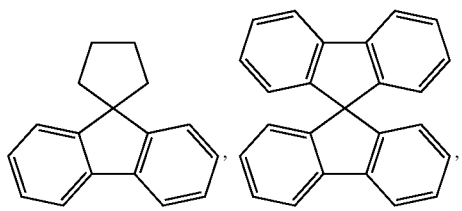

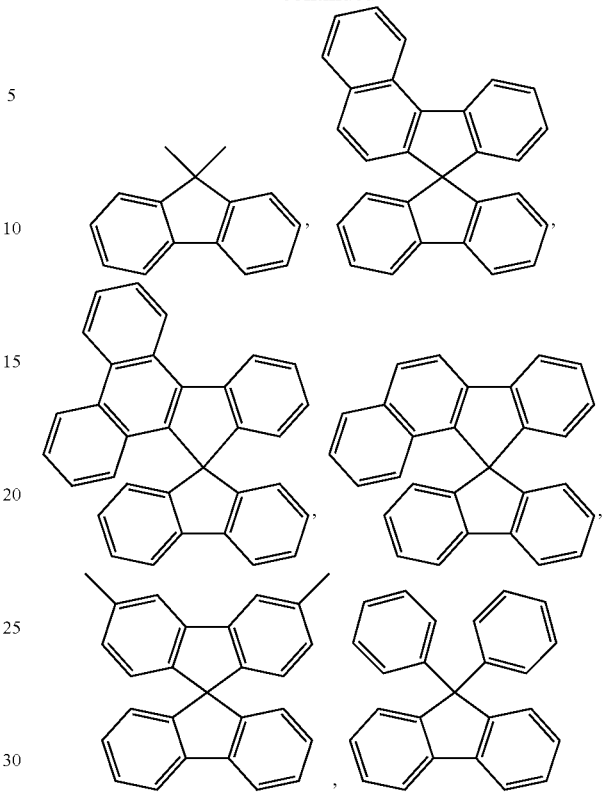

and the like, but are not limited thereto.

In the present specification, the heteroaryl group is an aromatic cyclic group including one or more of N, O and S as a heteroatom, and although not particularly limited thereto, the number of carbon atoms is preferably from 2 to 40. According to one embodiment, the number of carbon atoms of the heteroaryl group is from 2 to 30. According to another embodiment, the number of carbon atoms of the heteroaryl group is from 2 to 20. Examples of the heteroaryl group can include a thiophenyl group, a furanyl group, a pyrrolyl group, an imidazolyl group, a triazolyl group, an oxazolyl group, an oxadiazolyl group, a triazolyl group, a pyridinyl group, a bipyridyl group, a pyrimidyl group, a triazinyl group, a triazolyl group, an acridinyl group, a carbolinyl group, an acenaphthoquinoxalinyl group, an indenoquinazolinyl group, an indenoisoquinolinyl group, an indenoquinolinyl group, a pyridoindolyl group, a pyridazinyl group, a pyrazinyl group, a quinolinyl group, a quinazolinyl group, a quinoxalinyl group, a phthalazinyl group, a pyridopyrimidinyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophenyl group, a dibenzothiophenyl group, a benzofuranyl group, a dibenzofuranyl group, a phenanthrolinyl group, a thiazolyl group, an isoxazolyl group, an oxadiazolyl group, a thiadiazolyl group, a benzothiazolyl group, a phenoxazinyl group, a phenothiazinyl group and the like, but are not limited thereto.

In the present specification, the number of carbon atoms of the heteroaryl group including an N-including hexagonal ring is not particularly limited, but is from 2 to 30. According to another embodiment, the number of carbon atoms of the heteroaryl group including an N-including hexagonal ring is from 2 to 20. Examples of the heteroaryl group including an N-including hexagonal ring can include a pyridinyl group, a bipyridinyl group, a pyrimidinyl group, a triazinyl group, an acridinyl group, an acenaphthoquinoxalinyl group, an indenoquinazolinyl group, an indenoisoquinolinyl group, an indenoquinolinyl group, a pyridoindolyl group, a pyridazinyl group, a pyrazinyl group, a quinolinyl group, a quinazolinyl group, a quinoxalinyl group, a phthalazinyl group, a pyridopyrimidinyl group, a pyridopyrazinyl group, a pyrazinopyrazinyl group, an isoquinolinyl group, a phenanthrolinyl group and the like, but are not limited thereto.

In the present specification, the heteroaryl group including one or more of O and S is a cyclic group including one or more of O and S as a heteroatom, and although not particularly limited thereto, the number of carbon atoms is from 2 to 30. According to another embodiment, the number of carbon atoms of the heteroaryl group is from 2 to 20. Examples of the heteroaryl group including one or more of O and S can include a thiophenyl group, a furanyl group, a thiazolyl group, an oxazolyl group, an oxadiazolyl group, a benzoxazolyl group, a benzothiazolyl group, a benzothiophenyl group, a dibenzothiophenyl group, a benzofuranyl group, a dibenzofuranyl group, a thiazolyl group, isoxazolyl group, an oxadiazolyl group, a thiadiazolyl group, a benzothiazolyl group, a phenoxazinyl group, a phenothiazinyl group and the like, but are not limited thereto.

Descriptions on the aryl group provided above can be applied to the aryl group in the aralkyl group and the aryloxy group.

In the present specification, the arylene group means a divalent aryl group, and descriptions on the aryl group provided above can be applied to the arylene group.

One embodiment of the present disclosure provides a compound of Chemical Formula 1.

The compound of Chemical Formula 1 includes a heterocyclic group having an excellent electron transfer ability such as triazine or pyrimidine and a cyano group controlling electron transfer as substituents, and therefore, when using the compound of Chemical Formula 1 in an organic material layer, particularly an electron transfer and electron injection layer, of an organic light emitting device, properties of long lifetime and high efficiency of a device can be obtained.

Particularly, -L1-CN contributes to enhancing device lifetime by controlling electron injection and transfer effects, and

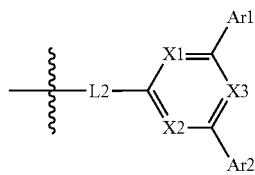

contributes to enhancing device efficiency by having excellent electron transfer properties.

In one embodiment of the present specification, the compound of Chemical Formula 1 has a HOMO energy level of 6 eV or greater. In one embodiment of the present specification, the compound of Chemical Formula 1 has a HOMO energy level of greater than or equal to 6 eV and less than or equal to 7 eV. In one embodiment of the present specification, when the compound of Chemical Formula 1 has a deep HOMO energy level, holes can be effectively blocked from a light emitting layer, which can provide high light emission efficiency, and can provide a device with long lifetime by enhancing device stability.

In one embodiment of the present specification, the compound of Chemical Formula 1 has a LUMO energy level of 2.5 eV or greater. In one embodiment of the present specification, the compound of Chemical Formula 1 has a LUMO energy level of greater than or equal to 2.5 eV and less than or equal to 3.5 eV.

When the compound of Chemical Formula 1 has the above-mentioned HOMO and LUMO energy levels, the compound of Chemical Formula 1 can be used in an organic material layer in an organic light emitting device. Particularly, when the compound of Chemical Formula 1 is used in an electron transfer layer, holes can be effectively blocked from a light emitting layer, and electrons can be effectively transferred to the light emitting layer.

In the present specification, the energy level means energy magnitude. Therefore, even when an energy level is expressed in a negative (−) direction from a vacuum level, the energy level is interpreted to mean an absolute value of the corresponding energy value. In the present specification, the highest occupied molecular orbital (HOMO) energy level means a distance from a vacuum level to the highest occupied molecular orbital. In the present specification, the lowest unoccupied molecular orbital (LUMO) energy level means a distance from a vacuum level to the lowest unoccupied molecular orbital.

In the present specification, the expression of the energy level being "~or greater", "~larger than", "~higher than" and the like means an absolute value of the energy level being larger. For example, the meaning of the HOMO energy level being 6 eV or greater means an energy level value having an absolute value of 6 or greater, and can include a level value such as 6.1 eV and 6.2 eV.

In one embodiment of the present specification, the HOMO level can be measured using a photoelectron spectrophotometer in air (AC3, manufactured by RIKEN KEIKI Co., Ltd.). Specifically, the HOMO level can be measured by irradiating light on a material, and measuring the amount of electrons produced by charge separation at the time.

In one embodiment of the present specification, the LUMO energy level can be calculated as a value obtained by, after measuring an absorption spectrum (abs.) and a light emission spectrum (PL) of the prepared sample, calculating an edge energy of each of the spectra, employing the difference as a band gap, and subtracting the band gap difference from the HOMO energy level measured using the AC3 apparatus.

In one embodiment of the present specification, L1 is a direct bond, or a substituted or unsubstituted arylene group having 6 to 40 carbon atoms.

In one embodiment of the present specification, L1 is a direct bond, or a substituted or unsubstituted arylene group having 6 to 30 carbon atoms.

In one embodiment of the present specification, L1 is a direct bond, a substituted or unsubstituted phenylene group, a substituted or unsubstituted biphenylene group, a substituted or unsubstituted terphenylene group, a substituted or unsubstituted quaterphenylene group, a substituted or unsubstituted naphthylene group, a substituted or unsubstituted anthracenylene group, a substituted or unsubstituted phenanthrenylene group, a substituted or unsubstituted triphenylenylene group, a substituted or unsubstituted pyrenylene group, a substituted or unsubstituted 9,9-dimethylfluorenylene group, a substituted or unsubstituted 9,9-diphenylfluorenylene group, a substituted or unsubstituted 9,9-methylphenylfluorenylene group, or a substituted or unsubstituted spiro[cyclopentane-1,9'-fluorenylene] group.

In one embodiment of the present specification, L1 is a direct bond, or an arylene group unsubstituted or substituted with one or more of deuterium, a cyano group, an aryl group and a heteroaryl group.

In one embodiment of the present specification, L1 is a direct bond, or an arylene group unsubstituted or substituted with one or more of deuterium, a cyano group, an aryl group, a heteroaryl group comprising an N-comprising hexagonal ring, and a heteroaryl group comprising one or more of O and S.

In one embodiment of the present specification, L1 is a direct bond; a group selected from the group consisting of a phenylene group unsubstituted or substituted with a phenyl group, a cyano group, a pyridinyl group or a quinolinyl group; a biphenylene group unsubstituted or substituted with a cyano group or a phenyl group; and a naphthylene group unsubstituted or substituted with a cyano group, or a group linking two or more groups selected from the above-described group.

In one embodiment of the present specification, two of X1 to X3 are N, and the other one is CH.

In one embodiment of the present specification, X1 to X3 are each N.

In one embodiment of the present specification, R1 to R3 are the same as or different from each other, and each independently is hydrogen, deuterium, or a substituted or unsubstituted alkyl group having 1 to 10 carbon atoms.

In one embodiment of the present specification, R1 to R3 are the same as or different from each other, and each independently is hydrogen or deuterium.

In one embodiment of the present specification, L2 is a direct bond, or a substituted or unsubstituted arylene group having 6 to 40 carbon atoms.

In one embodiment of the present specification, L2 is a direct bond, or a substituted or unsubstituted arylene group having 6 to 30 carbon atoms.

In one embodiment of the present specification, L2 is a direct bond, a substituted or unsubstituted phenylene group, a substituted or unsubstituted biphenylene group, a substituted or unsubstituted terphenylene group, a substituted or unsubstituted quaterphenylene group, a substituted or unsubstituted naphthylene group, a substituted or unsubstituted anthracenylene group, a substituted or unsubstituted phenanthrenylene group, a substituted or unsubstituted triphenylenylene group, a substituted or unsubstituted pyrenylene group, a substituted or unsubstituted 9,9-dimethylfluorenylene group, a substituted or unsubstituted 9,9-diphenylfluorenylene group, a substituted or unsubstituted 9,9-methylphenylfluorenylene group, or a substituted or unsubstituted spiro[cyclopentane-1,9'-fluorenylene] group.

In one embodiment of the present specification, L2 is a direct bond, a phenylene group, a biphenylene group, a terphenylene group, a quaterphenylene group, a naphthylene group, an anthracenylene group, a phenanthrenylene group, a triphenylenylene group, a pyrenylene group, a 9,9-dimethylfluorenylene group, a pyrenylene group, a 9,9-dimethylfluorenylene group, a 9,9-diphenylfluorenylene group, a 9,9-methylphenylfluorenylene group, or a spiro[cyclopentane-1,9'-fluorenylene] group.

In one embodiment of the present specification, L2 is a direct bond, or a substituted or unsubstituted phenylene group.

In one embodiment of the present specification, L2 is a direct bond, or a phenylene group.

In one embodiment of the present specification, Ar1 and Ar2 are the same as or different from each other, and each independently is hydrogen, deuterium, a substituted or unsubstituted alkyl group having 1 to 20 carbon atoms, a substituted or unsubstituted aryl group having 6 to 24 carbon atoms, or a substituted or unsubstituted heteroaryl group having 2 to 20 carbon atoms.

In one embodiment of the present specification, Ar1 and Ar2 are the same as or different from each other, and each independently is hydrogen, deuterium, an alkyl group having 1 to 20 carbon atoms unsubstituted or substituted with deuterium, an aryl group having 6 to 24 carbon atoms unsubstituted or substituted with deuterium, or a heteroaryl group having 2 to 20 carbon atoms unsubstituted or substituted with deuterium.

In one embodiment of the present specification, Ar1 and Ar2 are the same as or different from each other, and each independently is hydrogen, deuterium, a substituted or unsubstituted alkyl group having 1 to 20 carbon atoms, a substituted or unsubstituted aryl group having 6 to 24 carbon atoms, a substituted or unsubstituted heteroaryl group having 2 to 20 carbon atoms comprising one or more atoms of O and S, or a substituted or unsubstituted heteroaryl group having 2 to 20 carbon atoms comprising an N-comprising 6-membered ring.

In one embodiment of the present specification, Ar1 and Ar2 are the same as or different from each other, and each independently is hydrogen, deuterium, a substituted or unsubstituted phenyl group, a substituted or unsubstituted biphenyl group, a substituted or unsubstituted naphthyl group, a substituted or unsubstituted dibenzofuranyl group, or a substituted or unsubstituted dibenzothiophenyl group.

In one embodiment of the present specification, Ar1 and Ar2 are the same as or different from each other, and each independently is hydrogen, deuterium, a phenyl group unsubstituted or substituted with deuterium, a biphenyl group unsubstituted or substituted with deuterium, or a naphthyl group unsubstituted or substituted with deuterium, a dibenzofuranyl group unsubstituted or substituted with deuterium, or a dibenzothiophenyl group unsubstituted or substituted with deuterium.

In one embodiment of the present specification, Ar1 and Ar2 are the same as or different from each other, and each independently is a phenyl group, a $D_5$-phenyl group, a biphenyl group, a naphthyl group, a dibenzofuranyl group, or a dibenzothiophenyl group.

In one embodiment of the present specification, m1 is 0, and m2 is 1.

In one embodiment of the present specification, m1 is 1, and m2 is 0.

In one embodiment of the present specification, n1 is 0, and n2 is 1.

In one embodiment of the present specification, n1 is 1, and n2 is 0.

In one embodiment of the present specification, positions at which

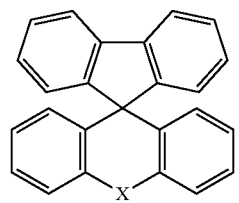

is substituted with

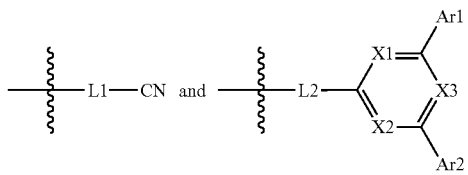

being asymmetric means that substituents do not substitute symmetric positions based on the center line in the following Chemical Formula A. This means that, when AZ (Z is an integer of 1 to 8) is substituted with

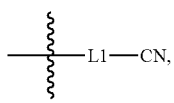

AZ' is not substituted with

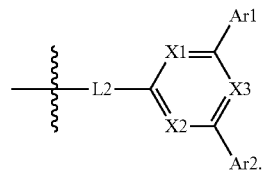

Chemical Formula A

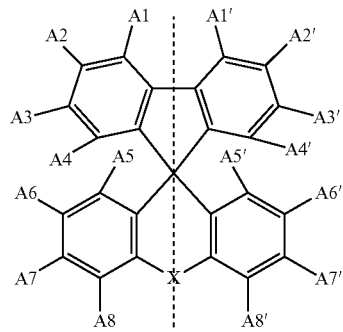

In one embodiment of the present specification, the compound of Chemical Formula 1 is any one of the following Chemical Formulae 2 to 7:

Chemical Formula 2

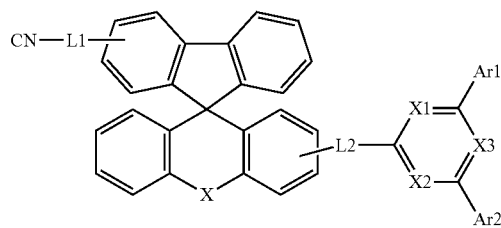

Chemical Formula 3

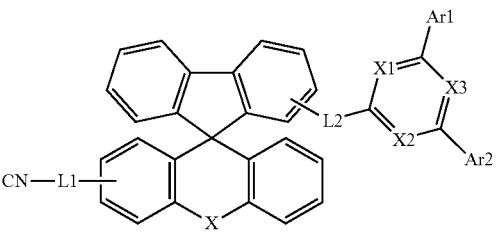

Chemical Formula 4

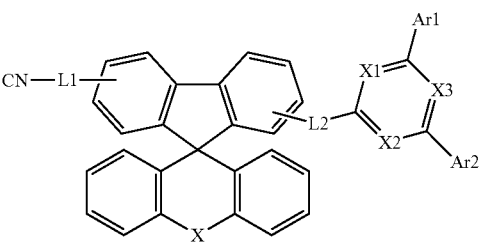

Chemical Formula 5

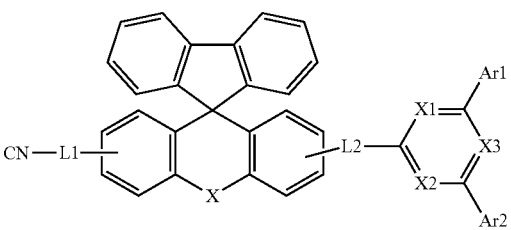

Chemical Formula 6

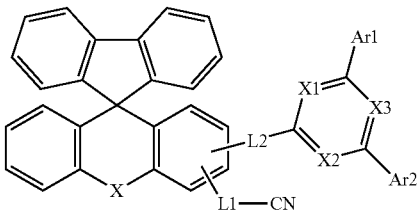

Chemical Formula 7

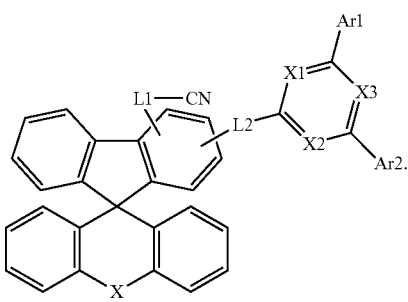

In Chemical Formulae 2 to 7,

X, L1, L2, X1 to X3, Ar1 and Ar2 have the same definitions as in Chemical Formula 1, and positions at which

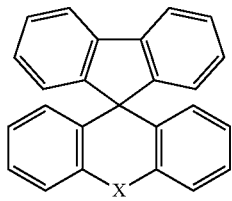

is substituted with

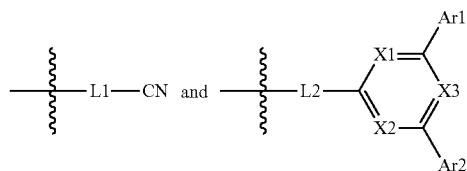

are asymmetrical.

In the compound of Chemical Formula 1, CN is a substituent controlling electron transfer.

In one embodiment of the present specification, Chemical Formula 2 is any one of the following Chemical Formula 2-A or Chemical Formula 2-B:

Chemical Formula 2-A

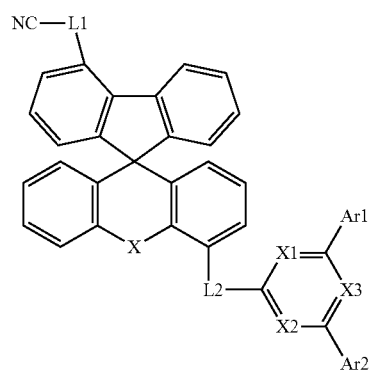

Chemical Formula 2-B

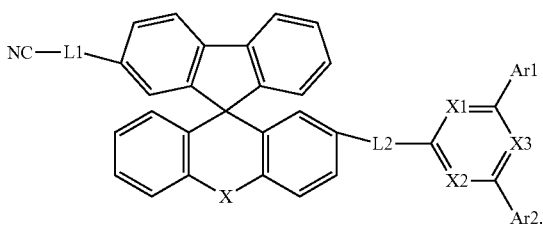

In Chemical Formulae 2-A and 2-B:

X, L1, L2, X1 to X3, Ar1 and Ar2 have the same definitions as in Chemical Formula 2.

In one embodiment of the present specification, Chemical Formula 3 is any one of the following Chemical Formula 3-A or Chemical Formula 3-B:

Chemical Formula 3-A

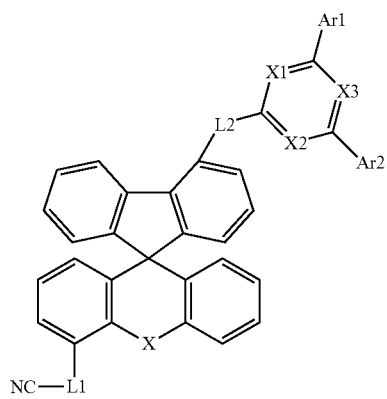

Chemical Formula 3-B

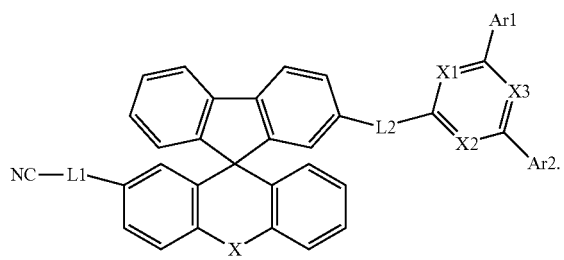

In Chemical Formulae 3-A and 3-B:

X, L1, L2, X1 to X3, Ar1 and Ar2 have the same definitions as in Chemical Formula 3.

In one embodiment of the present specification, Chemical Formula 4 is any one of the following Chemical Formulae 4-A to 4-C:

Chemical Formula 4-A

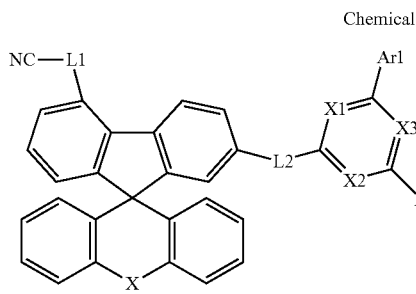

Chemical Formula 4-B

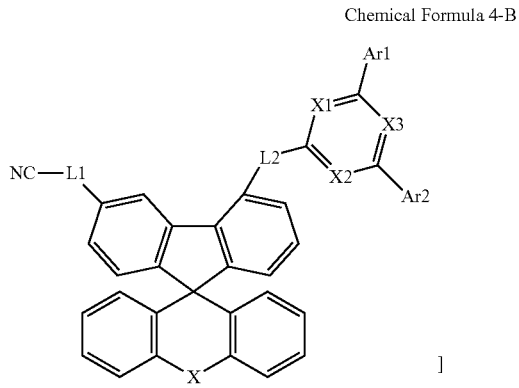

-continued

Chemical Formula 4-C

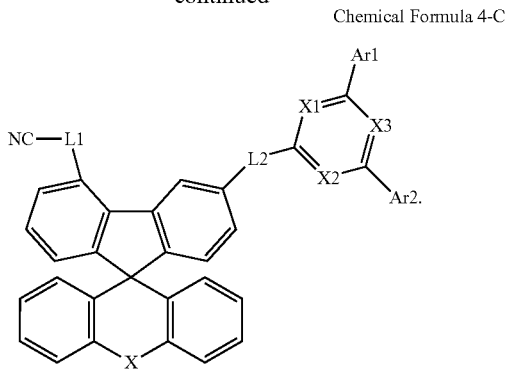

In Chemical Formulae 4-A to 4-C:
X, L1, L2, X1 to X3, Ar1 and Ar2 have the same definitions as in Chemical Formula 4.

In one embodiment of the present specification, Chemical Formula 5 can be Chemical Formula 5-A:

Chemical Formula 5-A

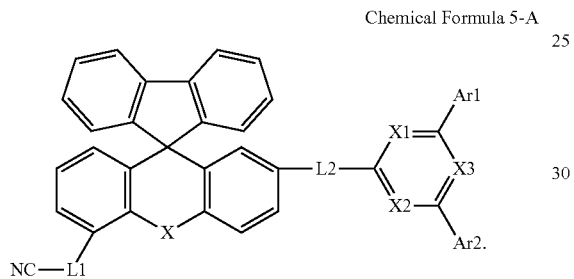

In Chemical Formula 5-A:
X, L1, L2, X1 to X3, Ar1 and Ar2 have the same definitions as in Chemical Formula 5.

In one embodiment of the present specification, Chemical Formula 6 is any one of the following Chemical Formula 6-A or Chemical Formula 6-B:

Chemical Formula 6-A

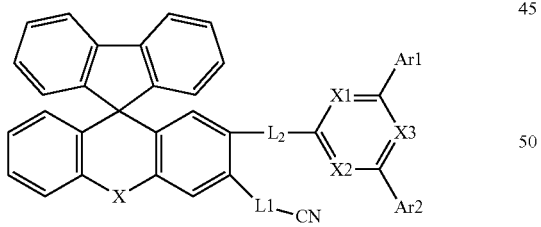

Chemical Formula 6-B

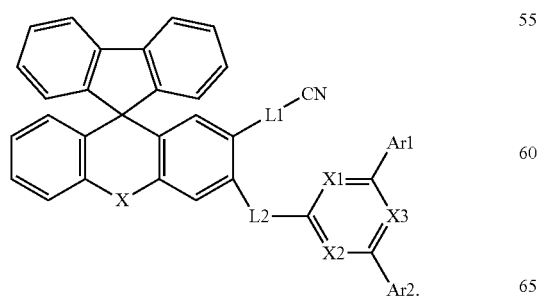

In Chemical Formulae 6-A and 6-B:
X, L1, L2, X1 to X3, Ar1 and Ar2 have the same definitions as in Chemical Formula 6.

In one embodiment of the present specification, the compound of Chemical Formula 7 is any one of the following Chemical Formula 7-A or Chemical Formula 7-B:

Chemical Formula 7-A

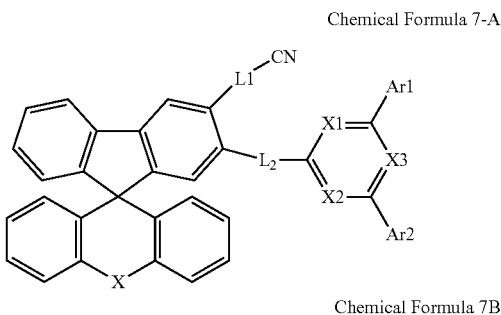

Chemical Formula 7B

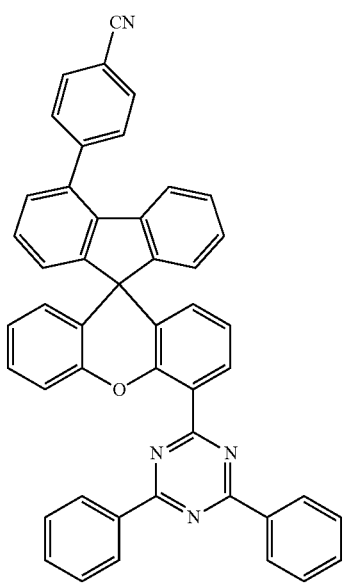

In Chemical Formulae 7-A and 7-B:
X, L1, L2, X1 to X3, Ar1 and Ar2 have the same definitions as in Chemical Formula 7.

In one embodiment of the present specification, the compound of Chemical Formula 2 is any one compound selected from among the following compounds:

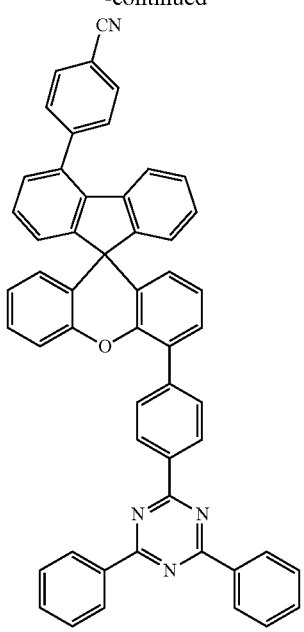
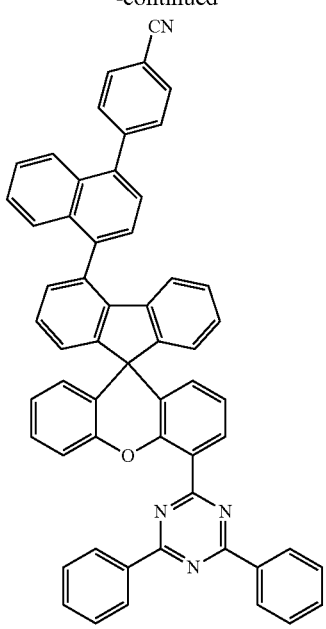
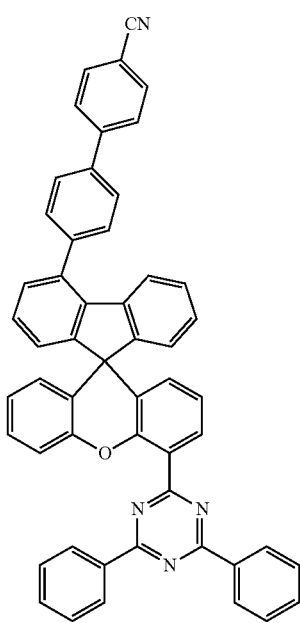
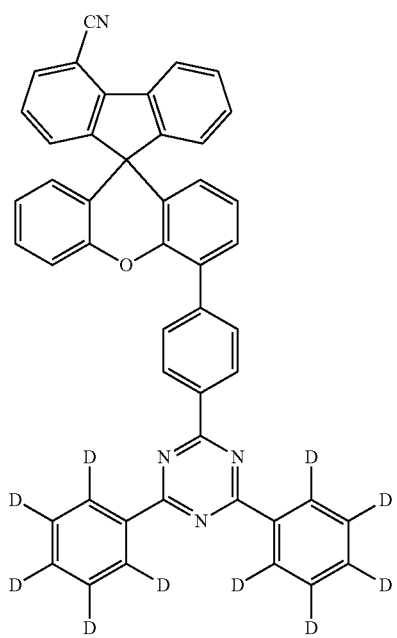

-continued
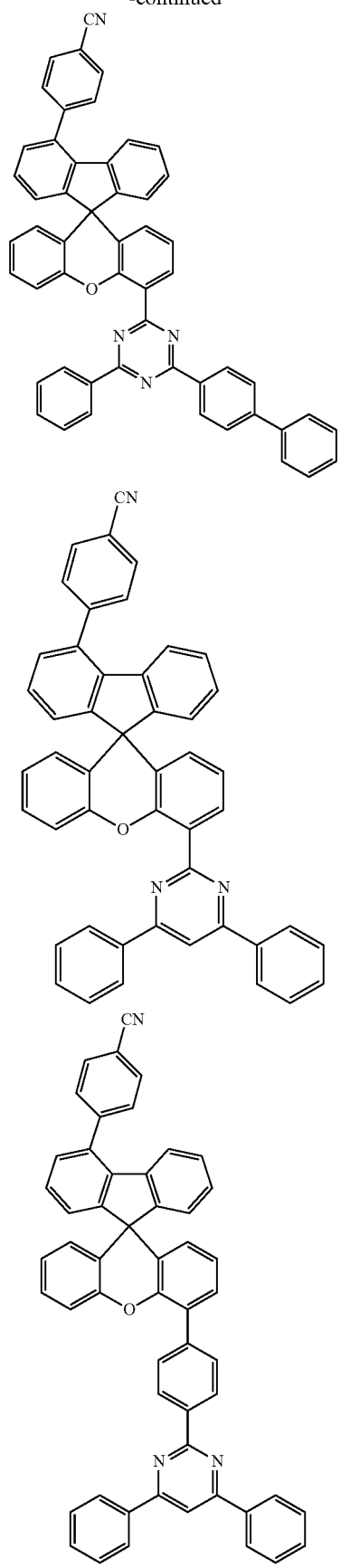

21
-continued
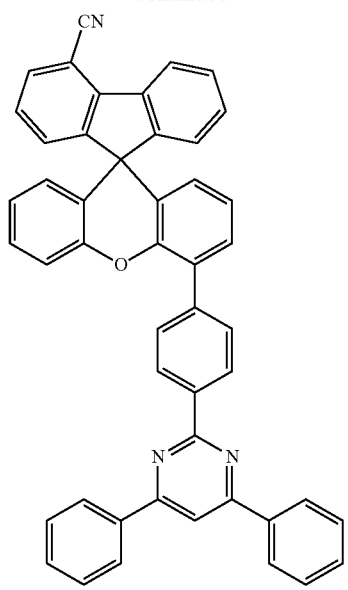
22
-continued
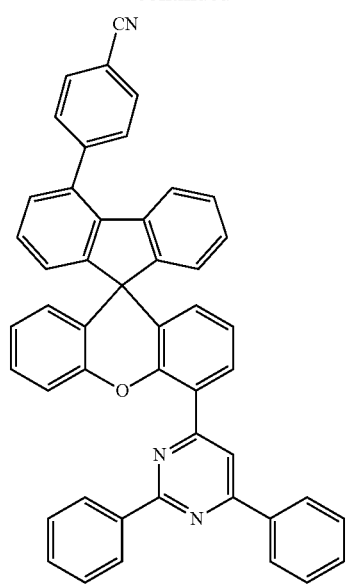
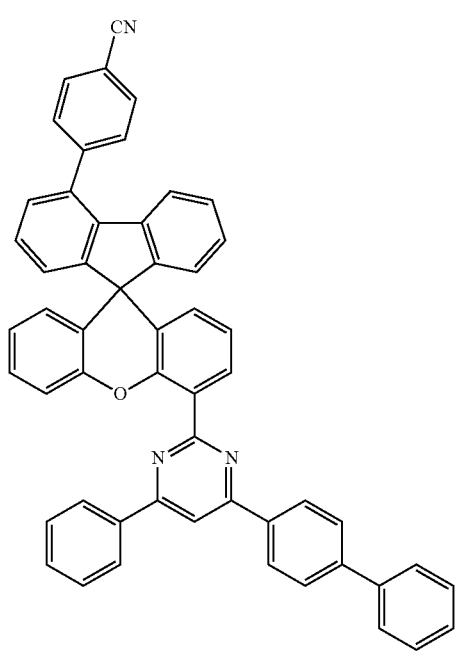
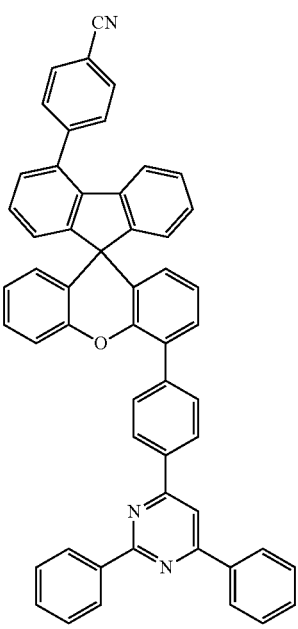

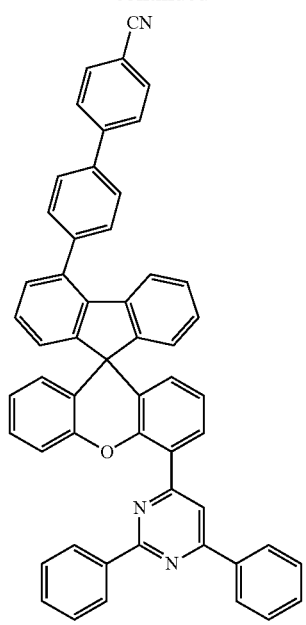
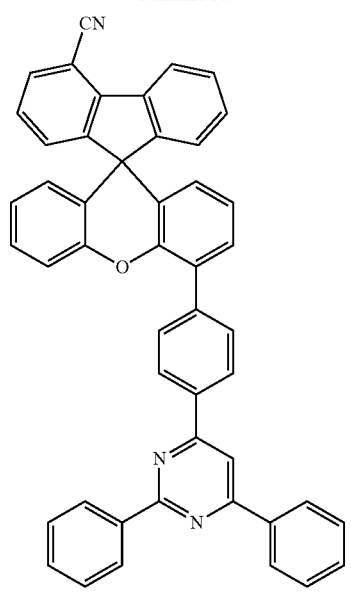
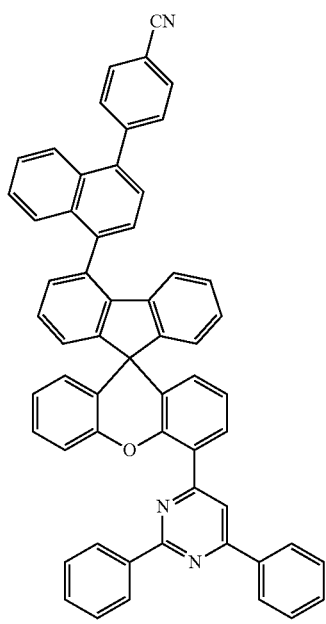
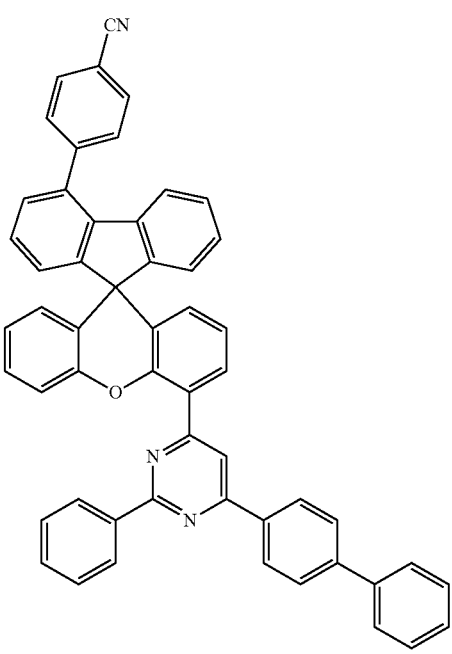

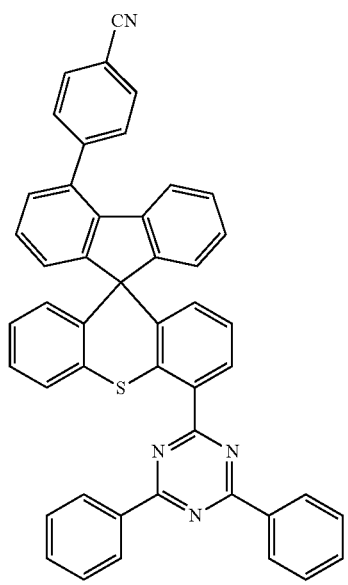
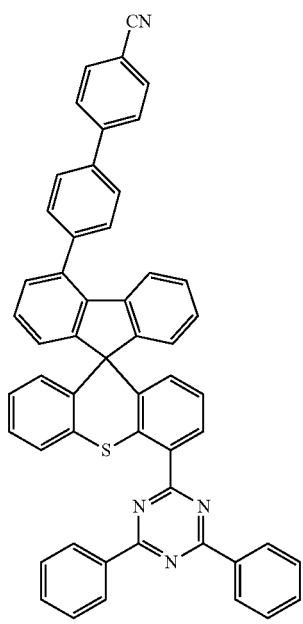
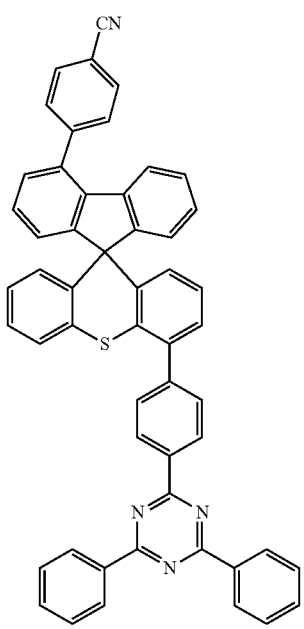
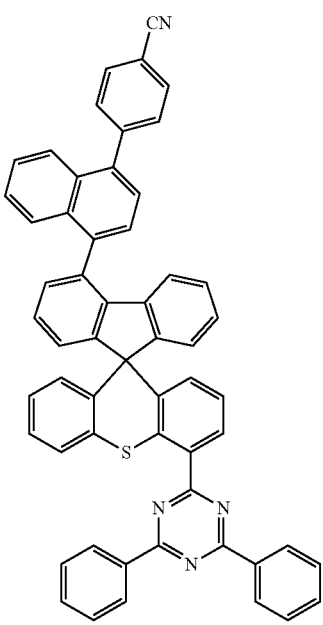

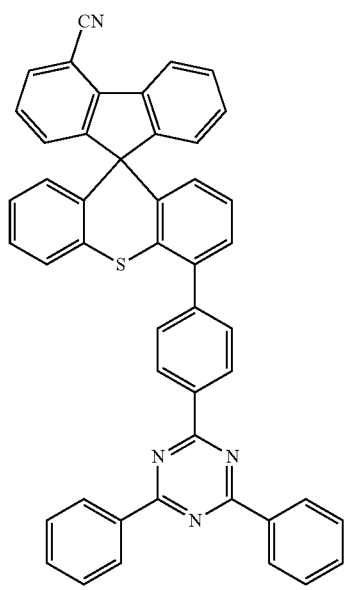
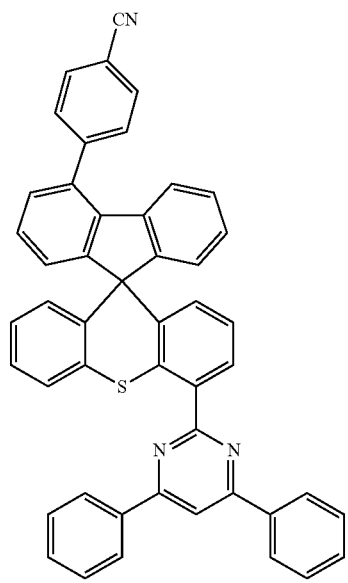

29
-continued
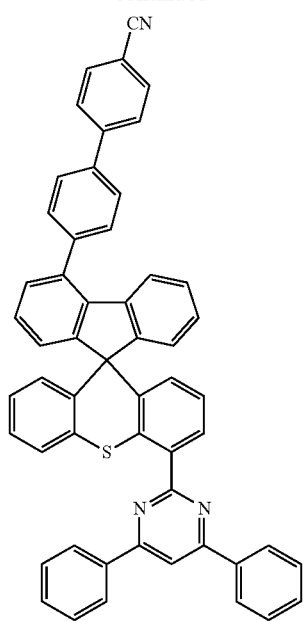
30
-continued
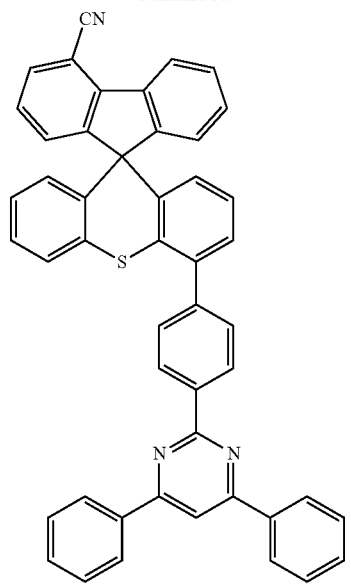
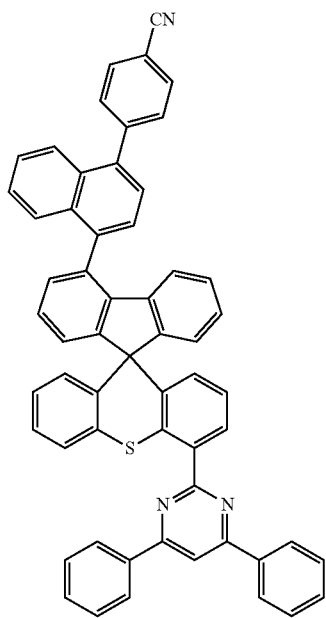
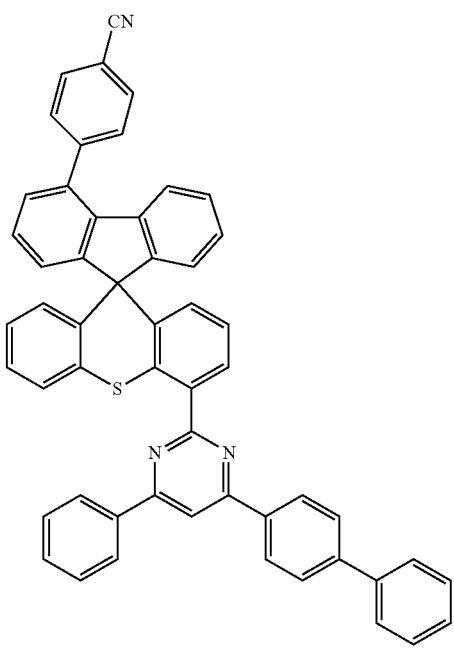

31
-continued
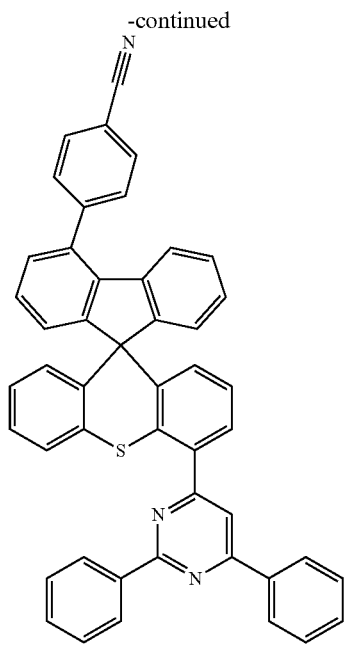
32
-continued
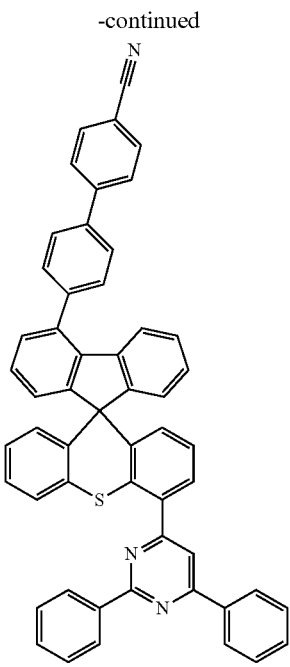
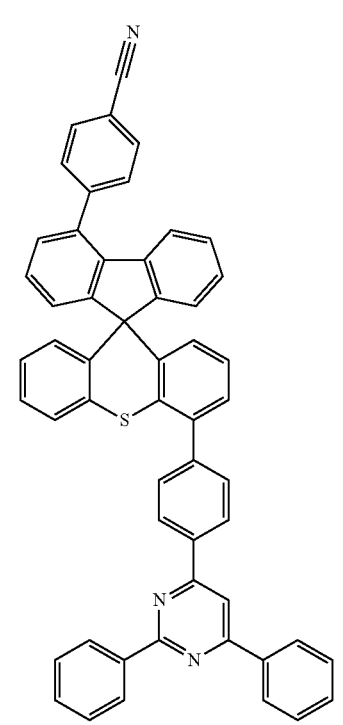
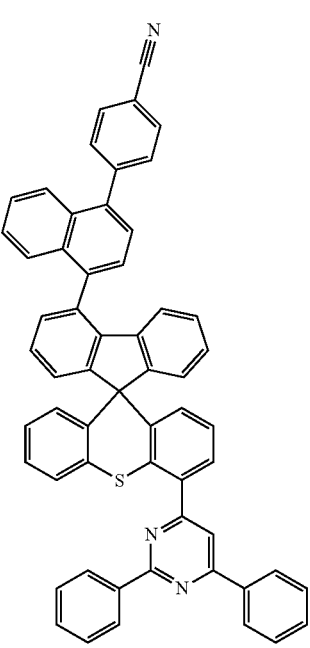

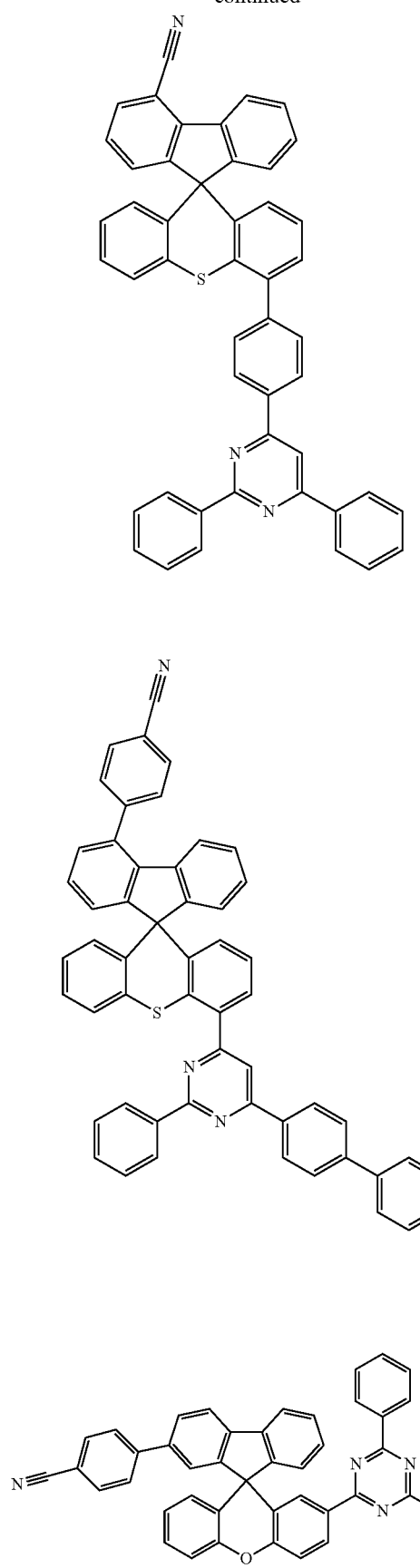
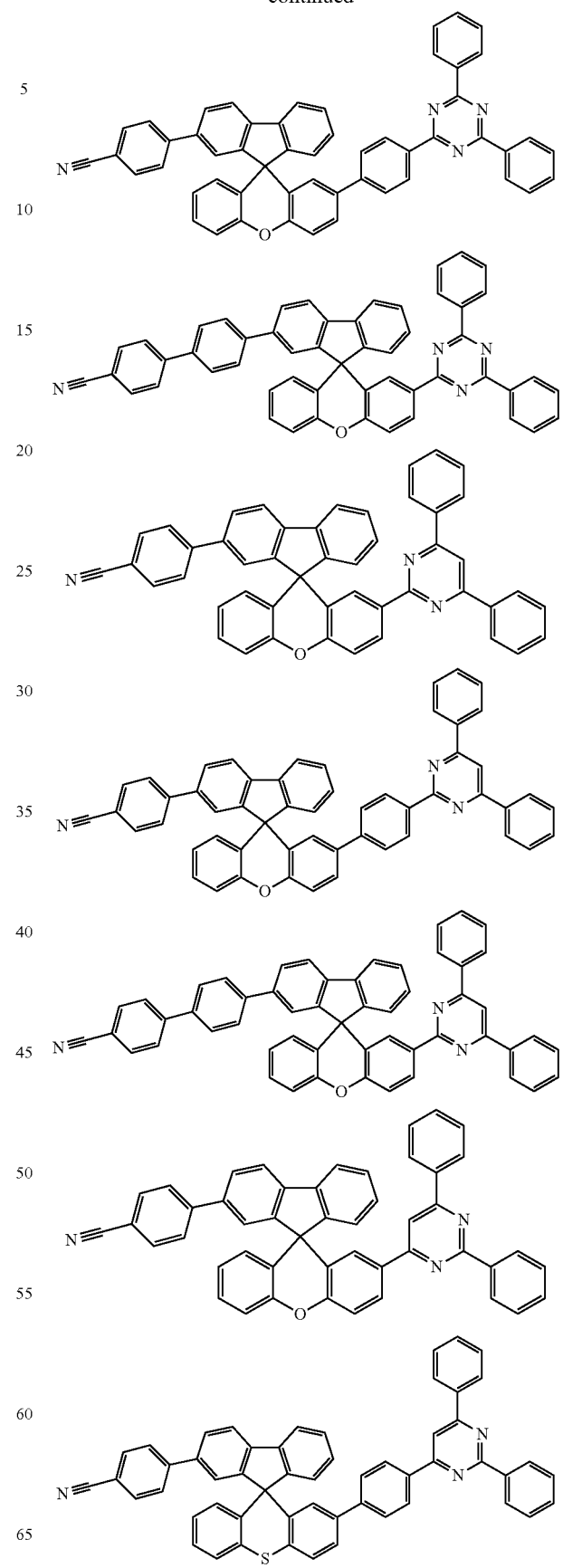

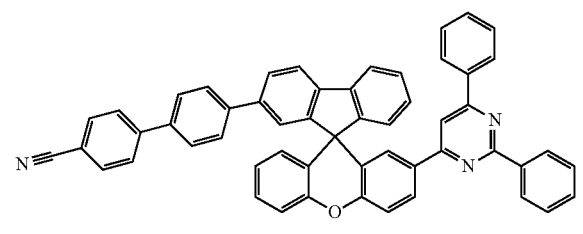
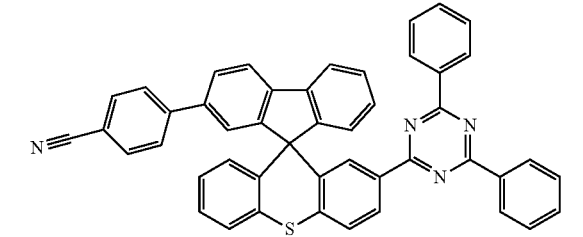
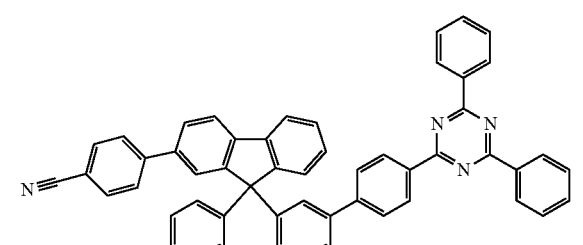
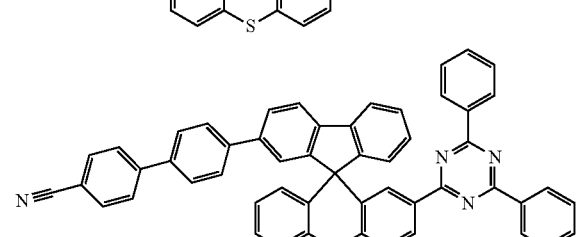
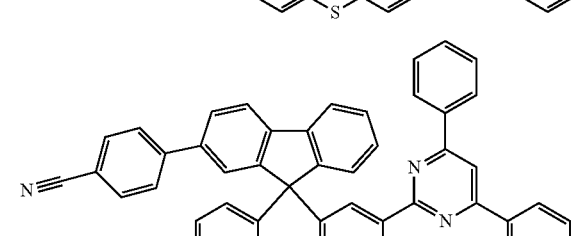
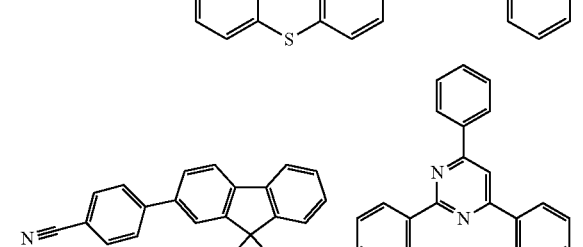
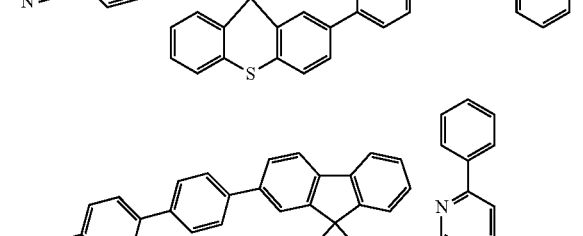
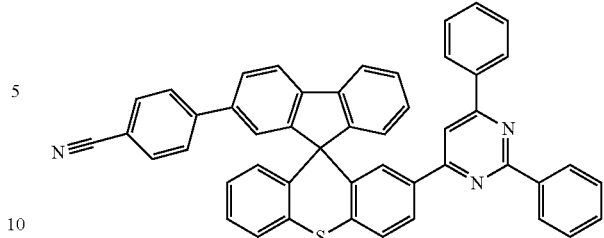
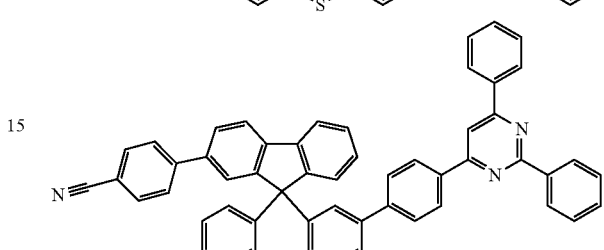
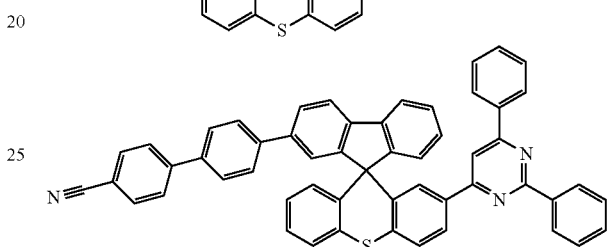
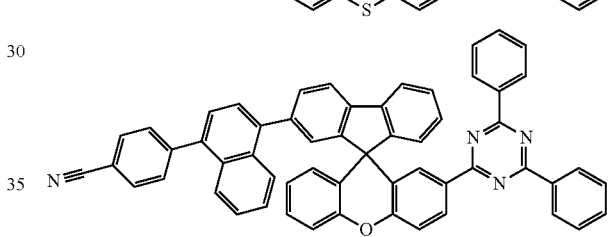
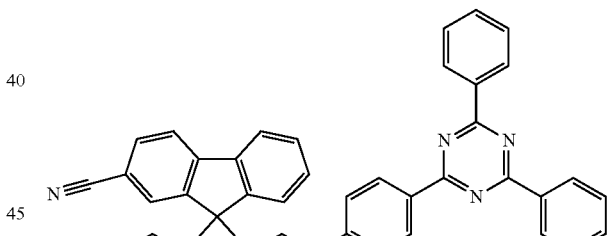
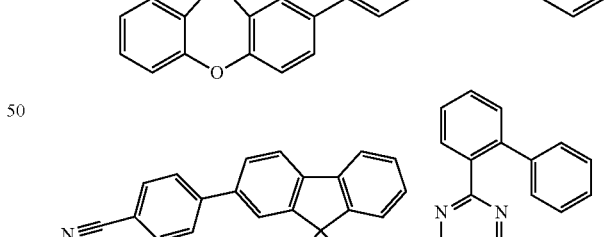
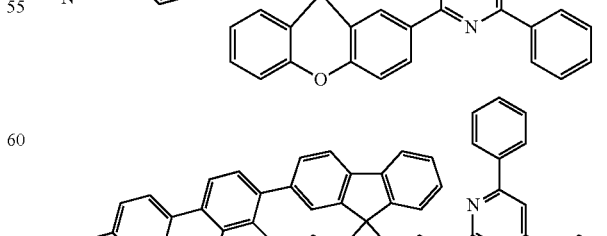

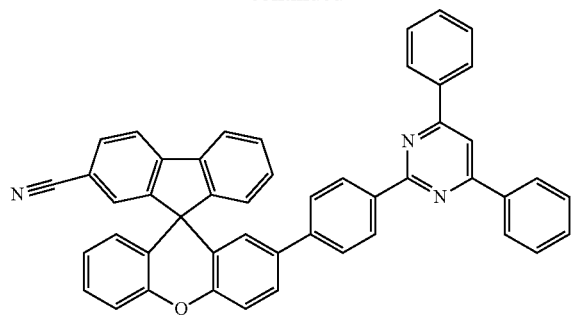
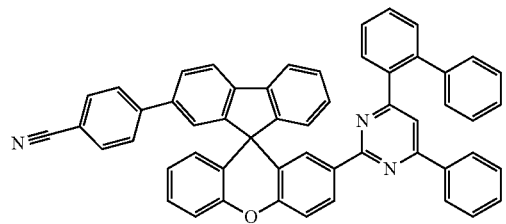
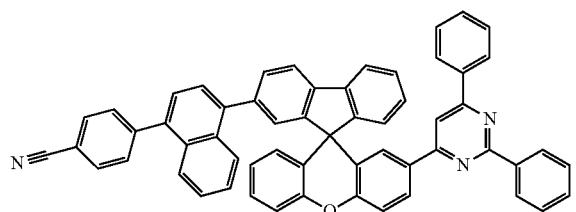
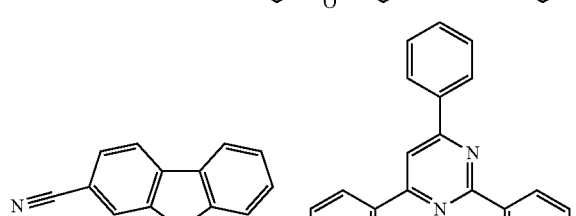
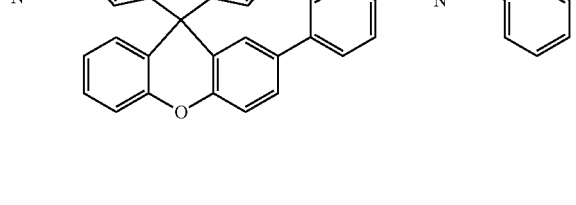
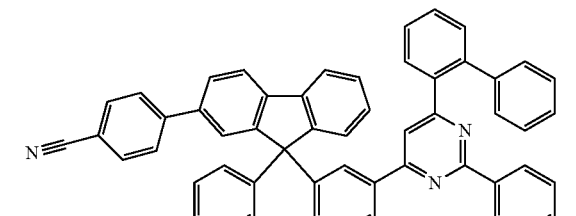
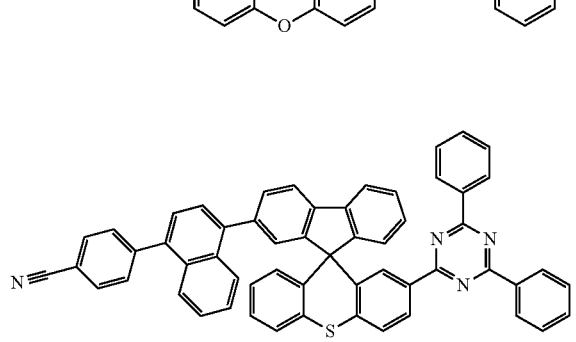
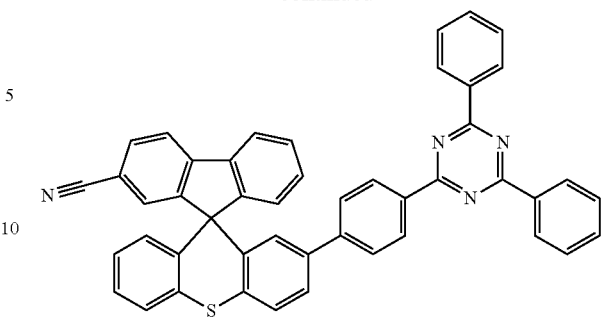
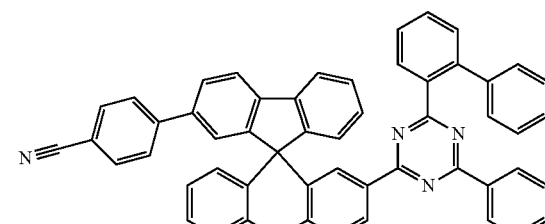
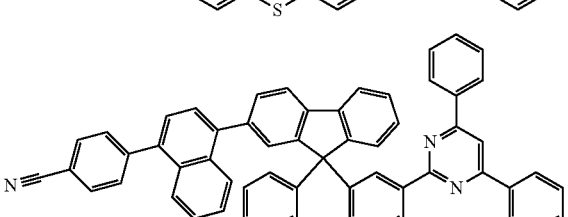
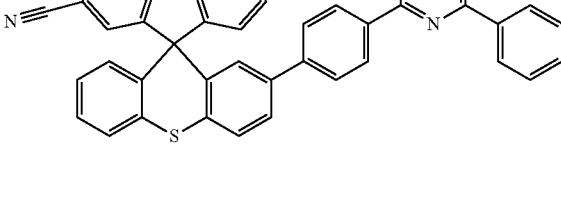
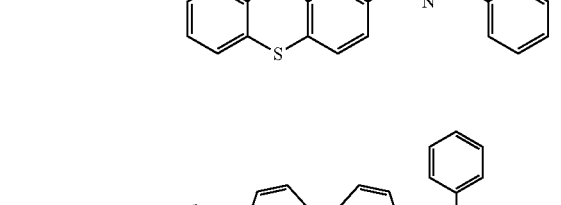
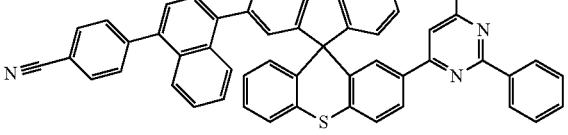

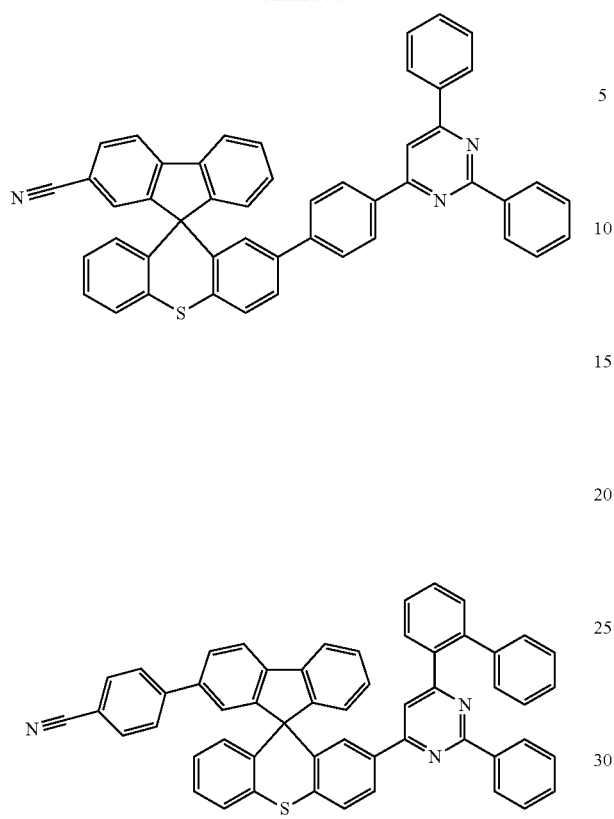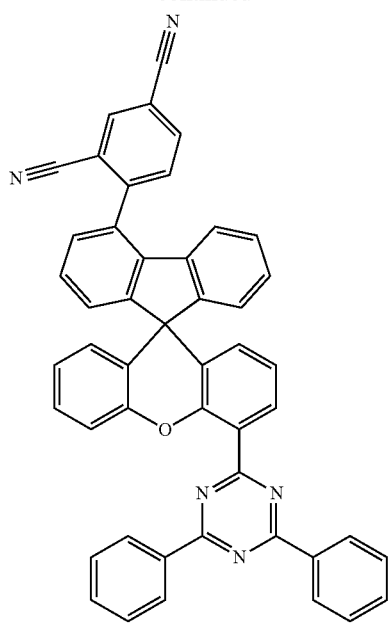

41
-continued
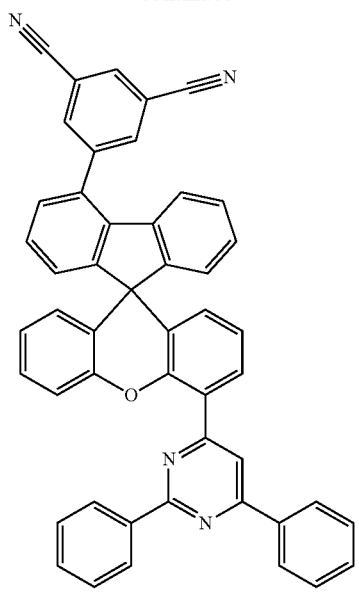
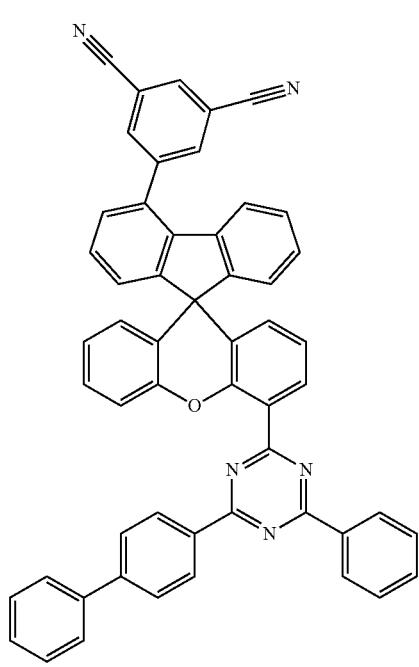
42
-continued
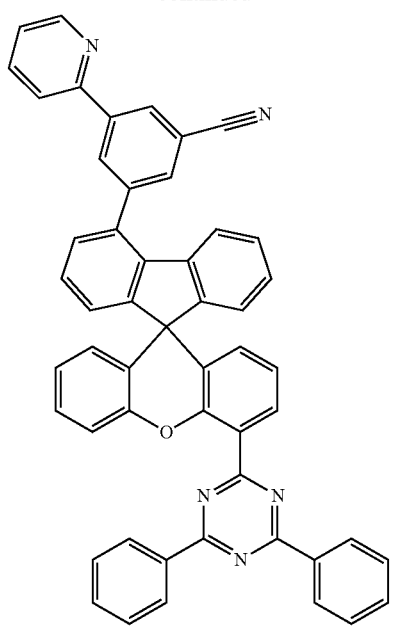
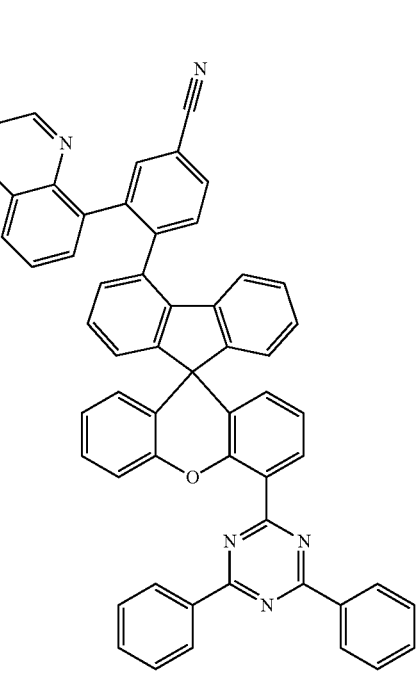

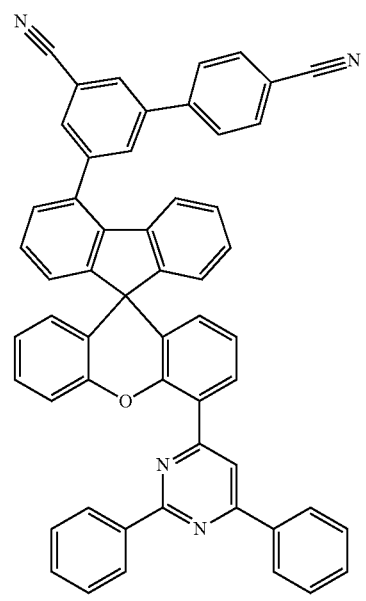

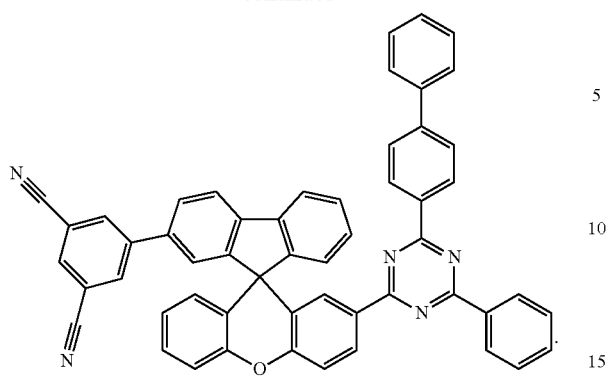
In one embodiment of the present specification, the compound of Chemical Formula 3 is any one compound selected from among the following compounds:
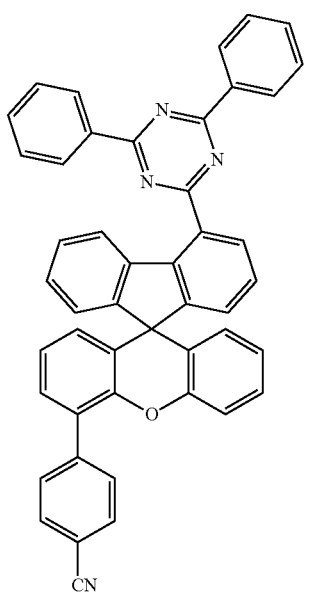
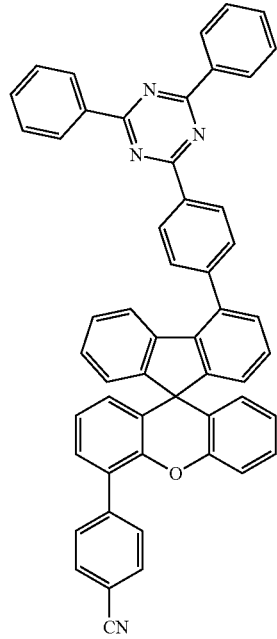
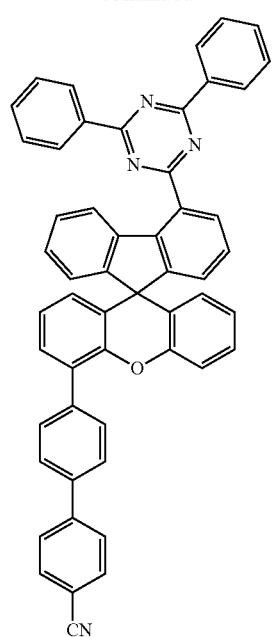
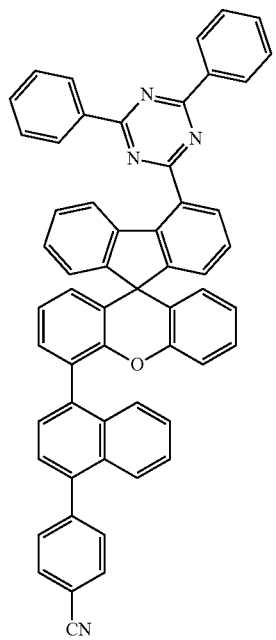

47
-continued
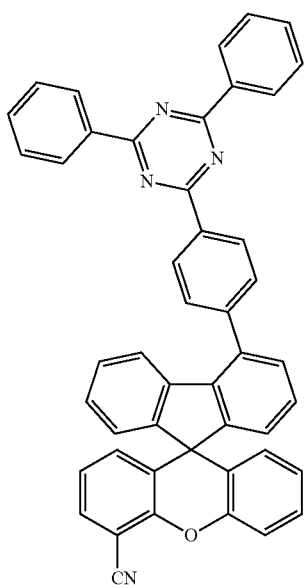
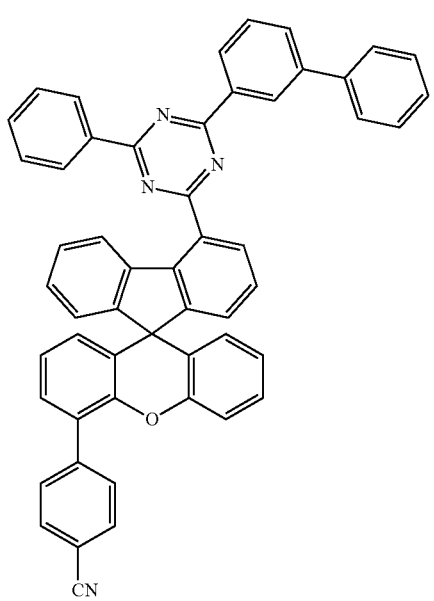
48
-continued
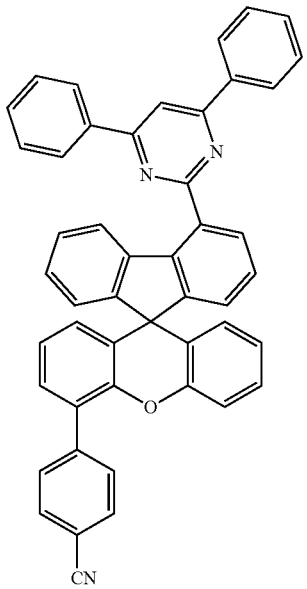
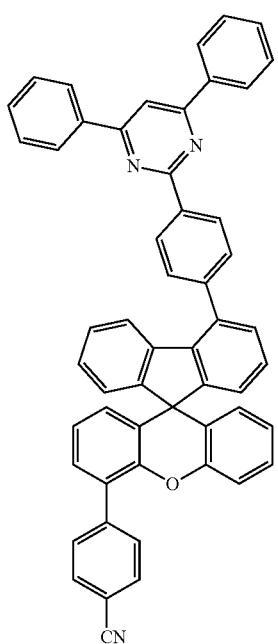

49
-continued
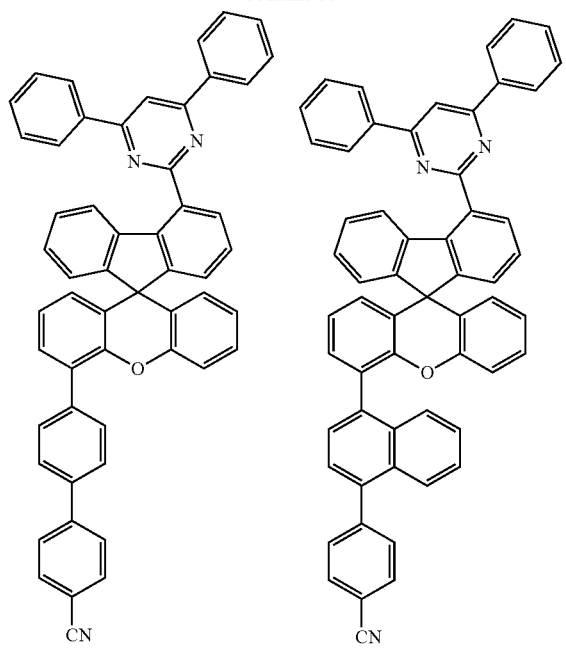
50
-continued
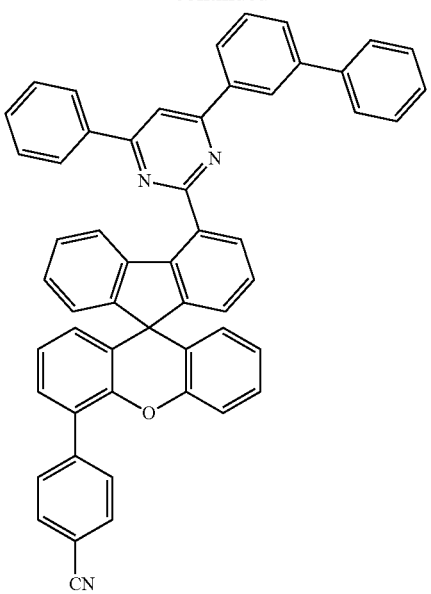
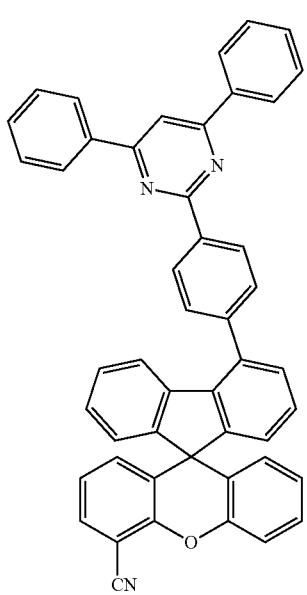
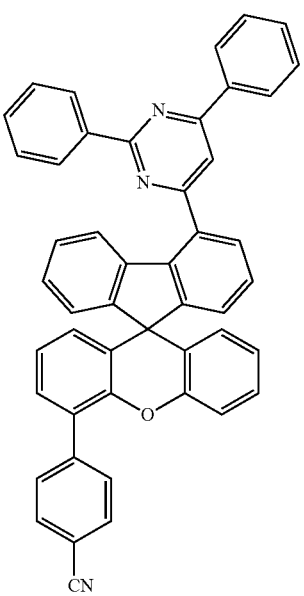

51
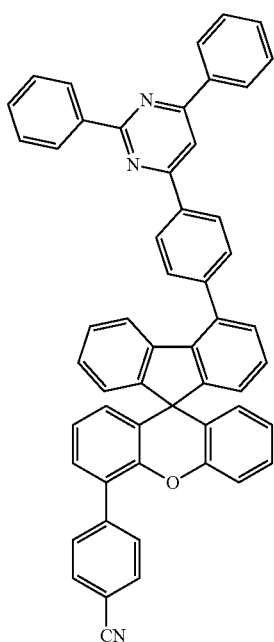
52
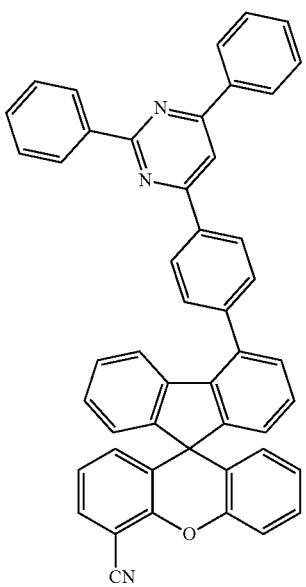
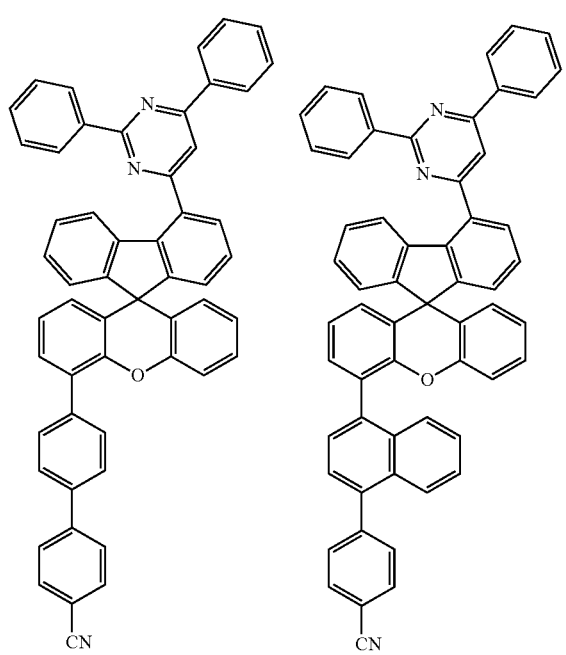
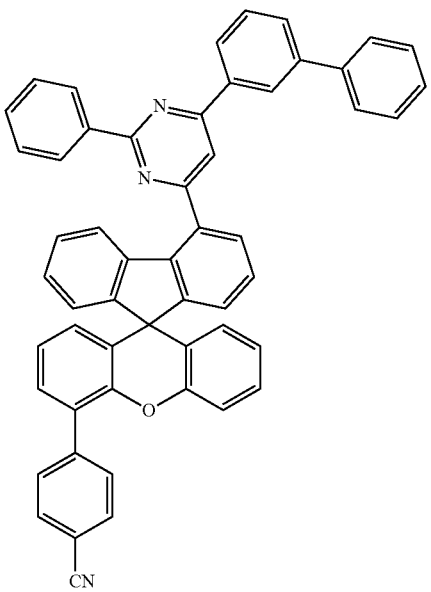

53
-continued
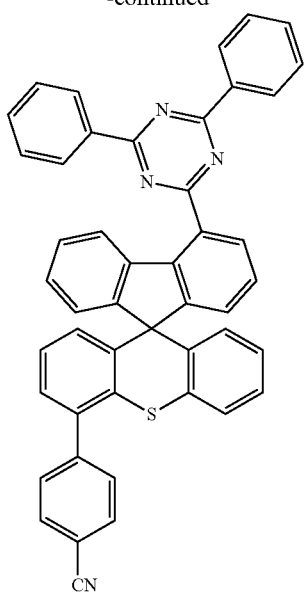
54
-continued
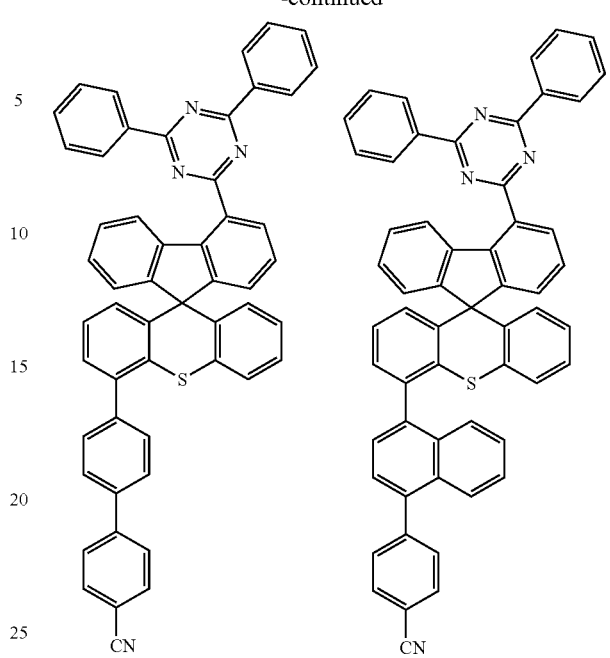
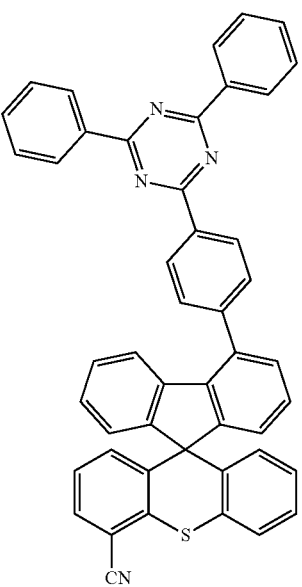

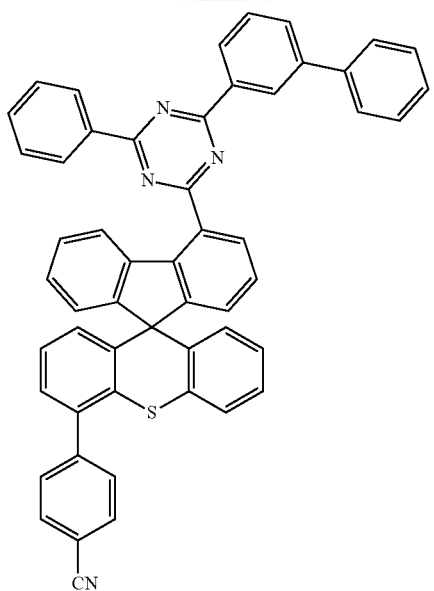
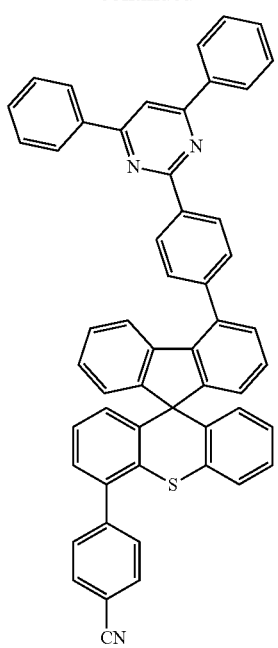
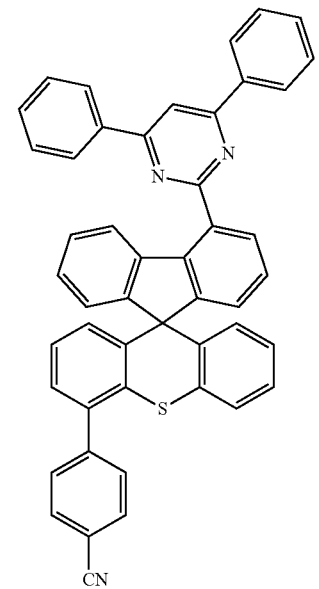
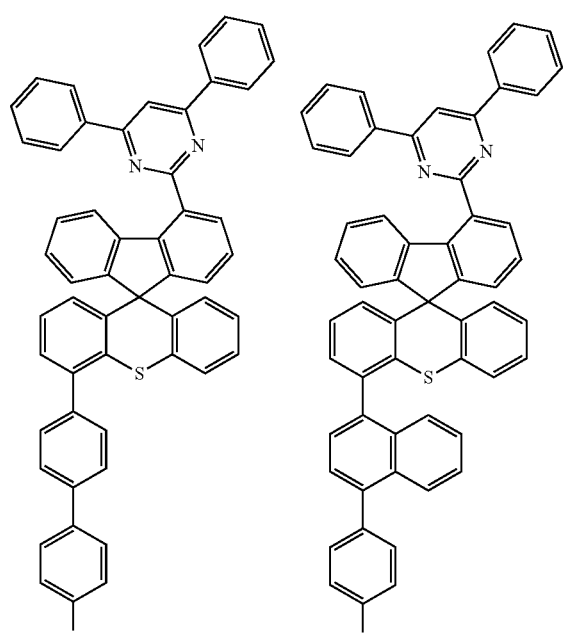

57
-continued
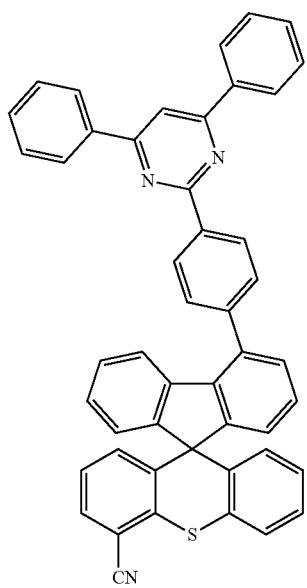
58
-continued
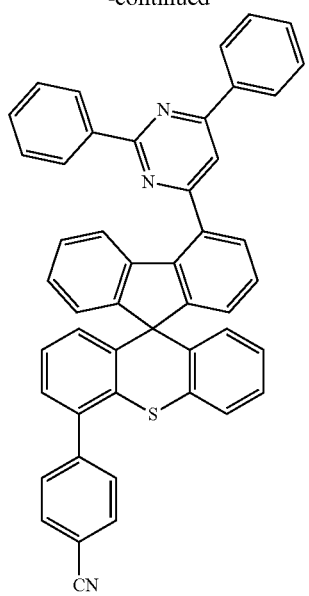
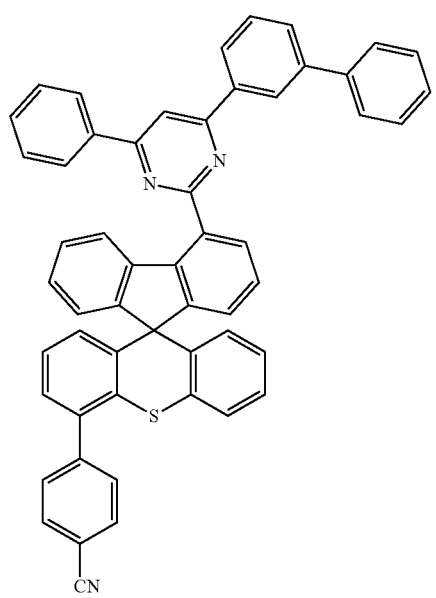
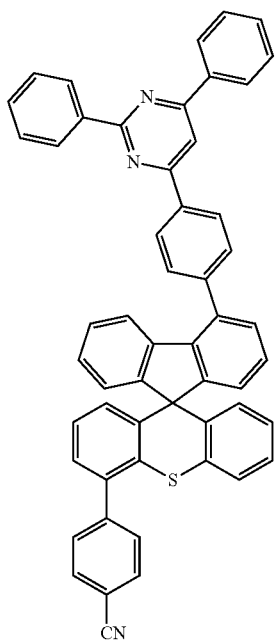

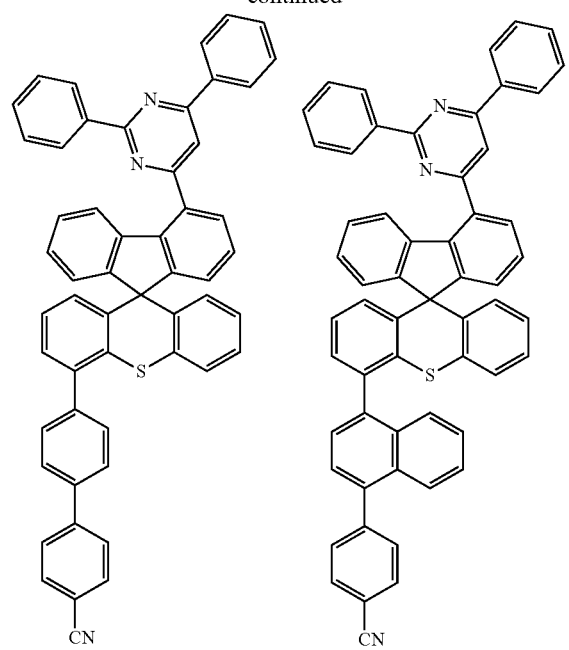
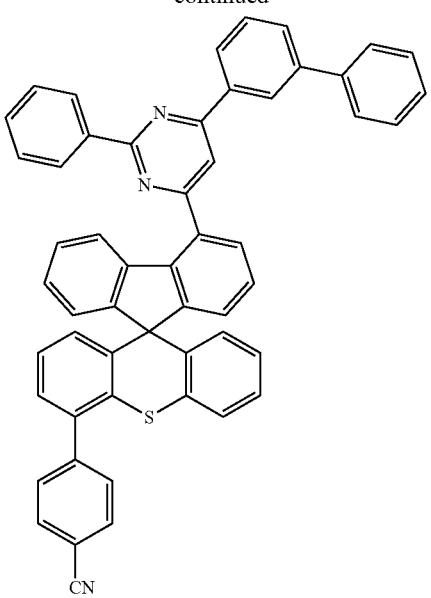
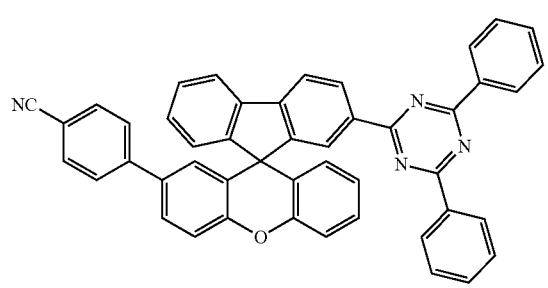
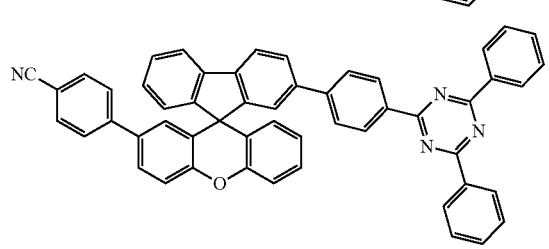
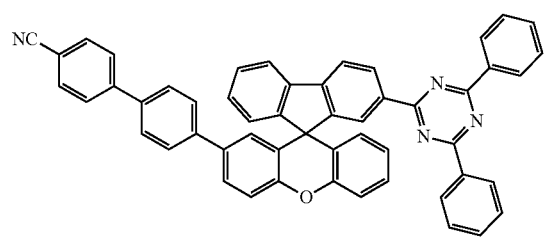
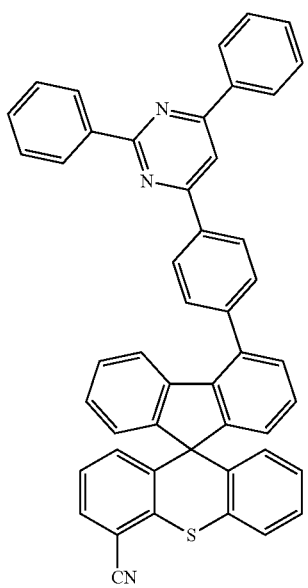
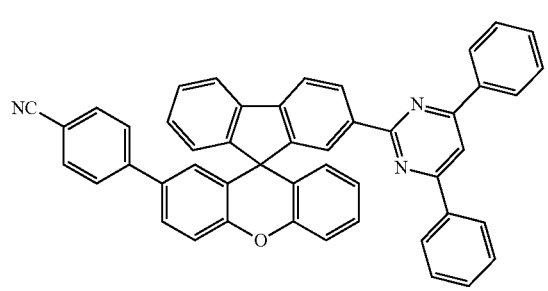

-continued
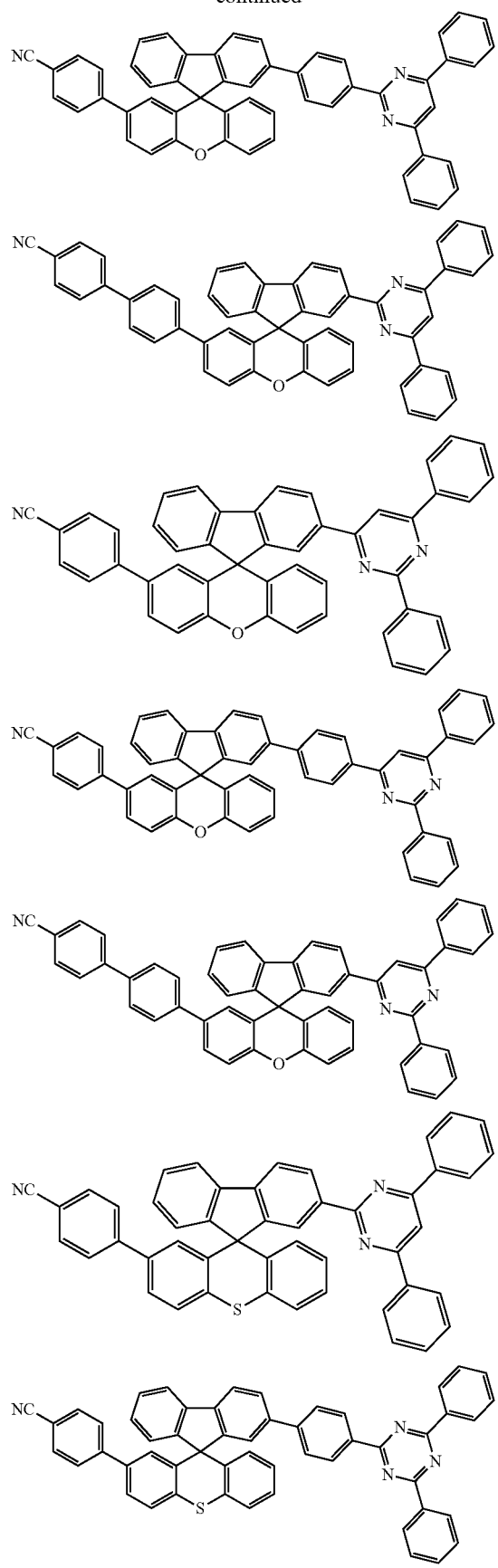
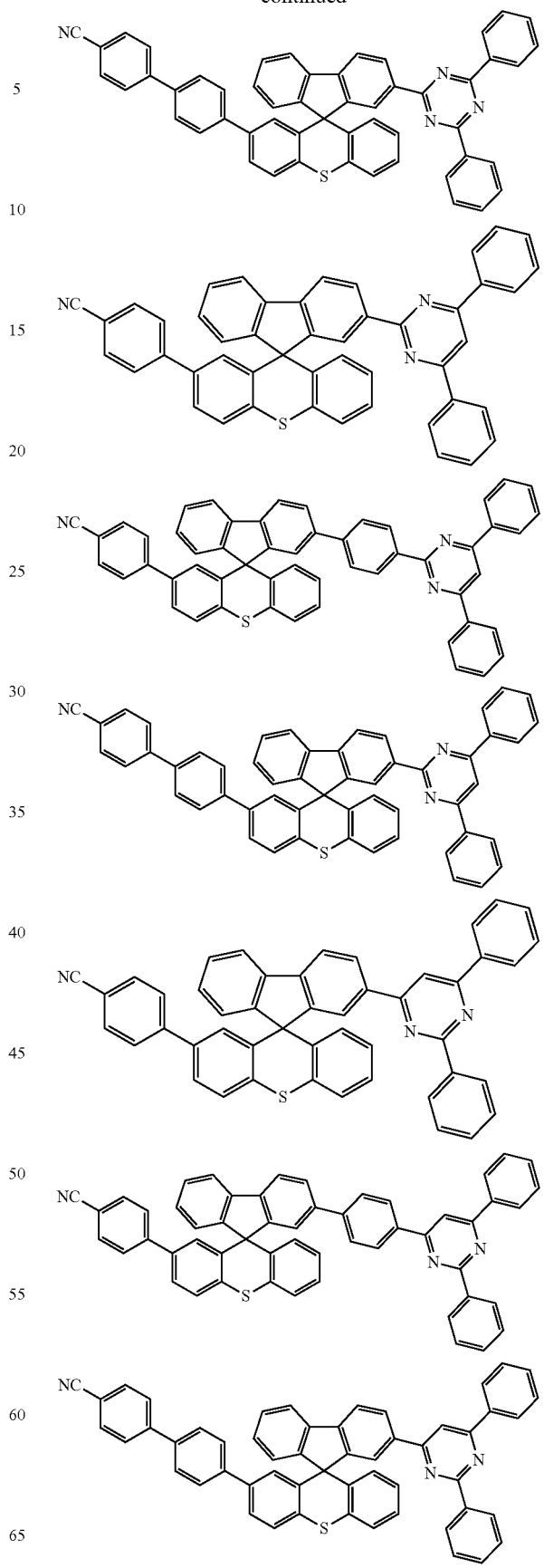

-continued
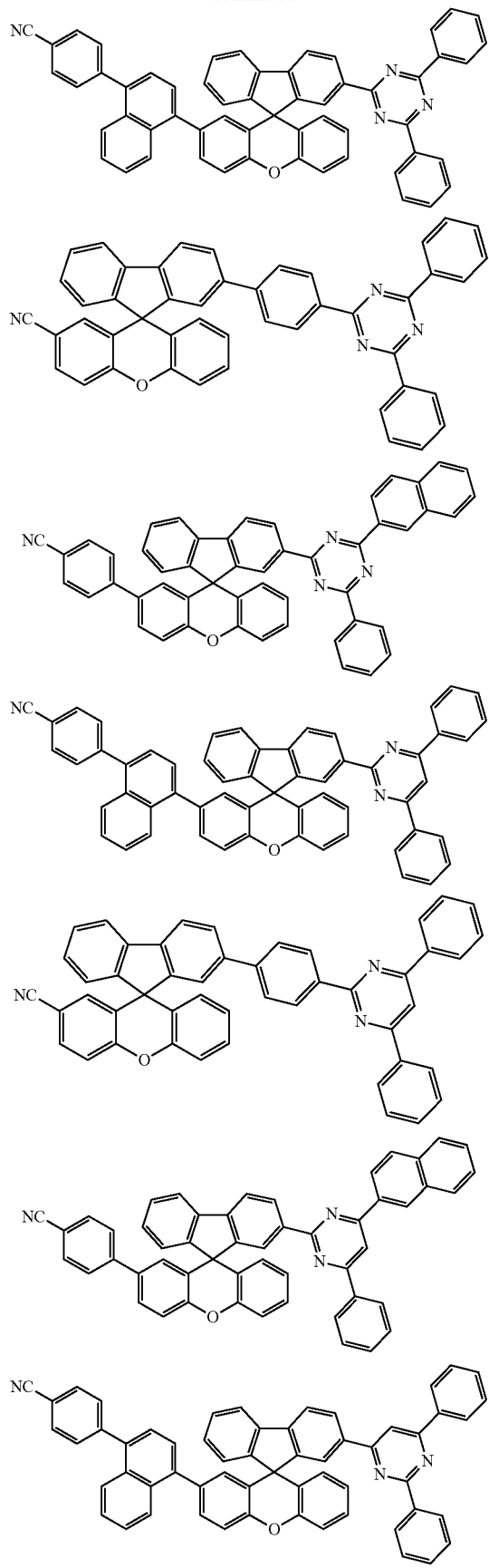
-continued
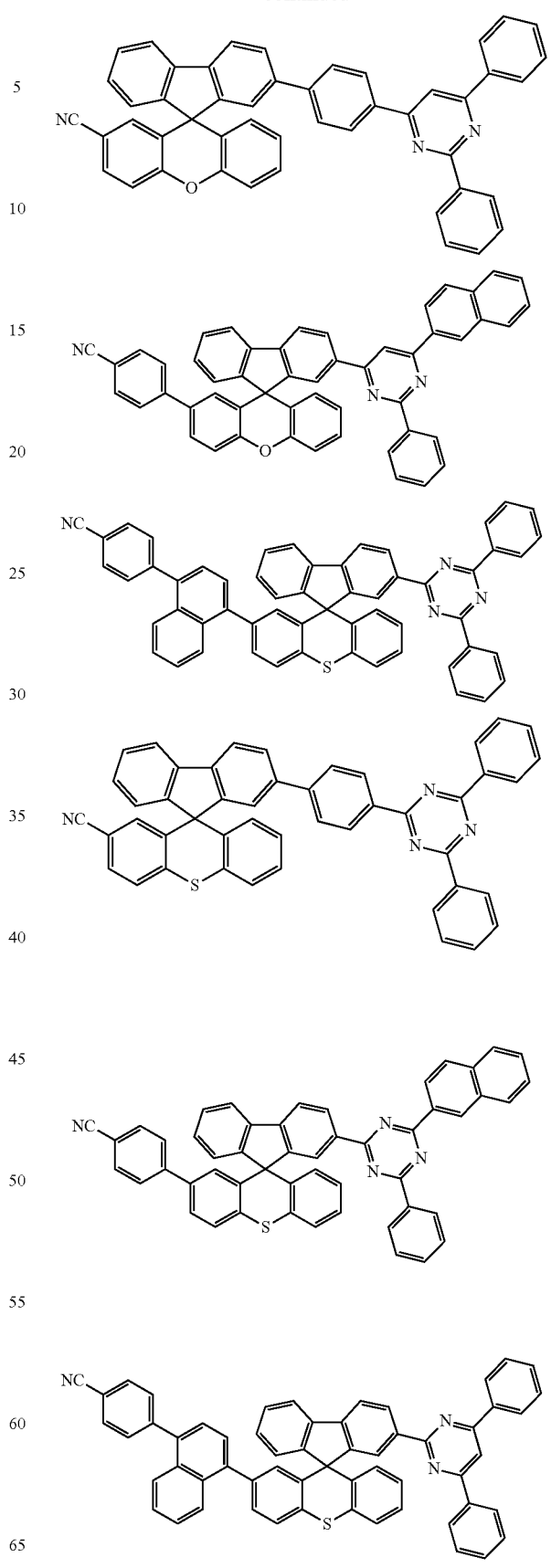

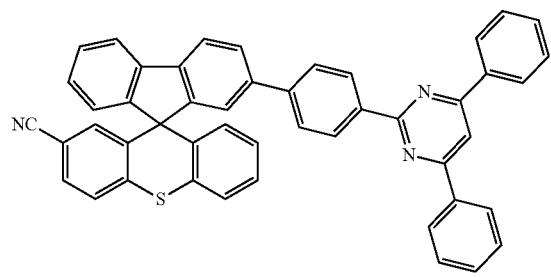
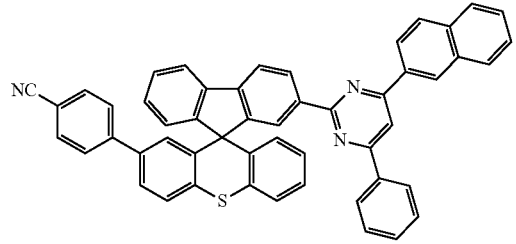
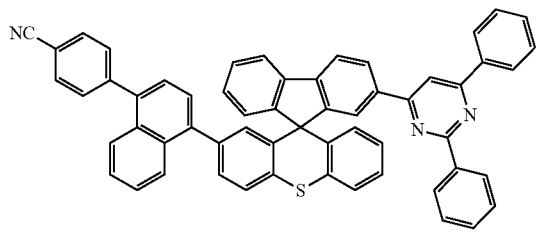
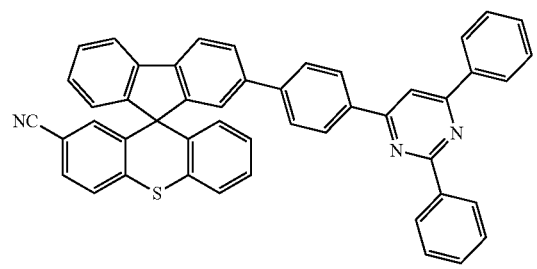
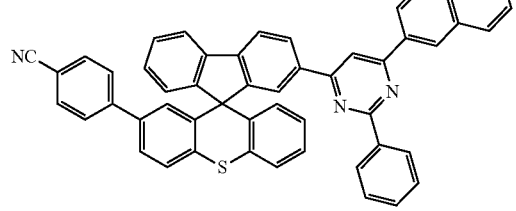
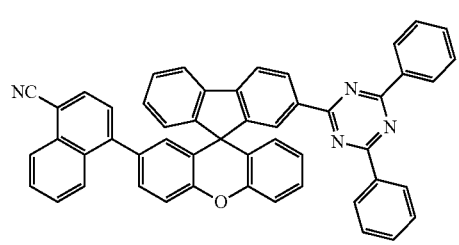
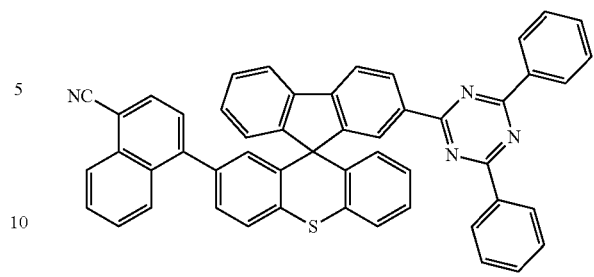
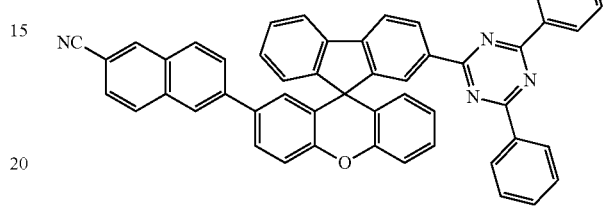
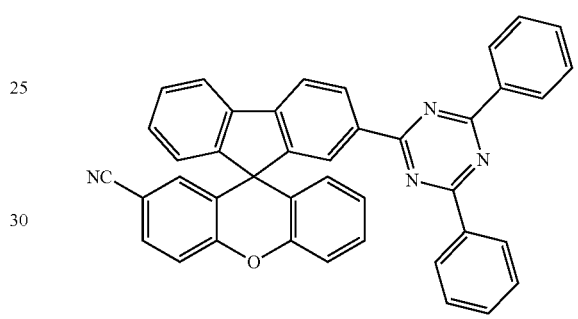
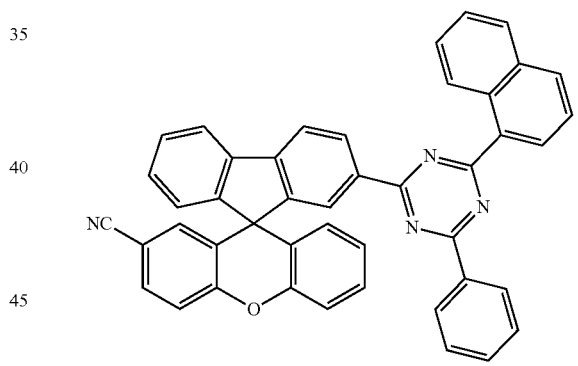
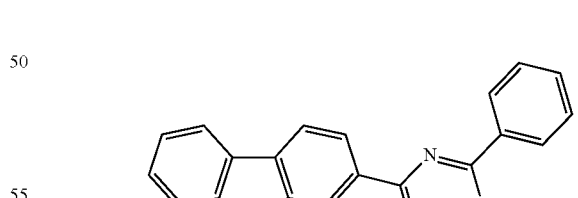
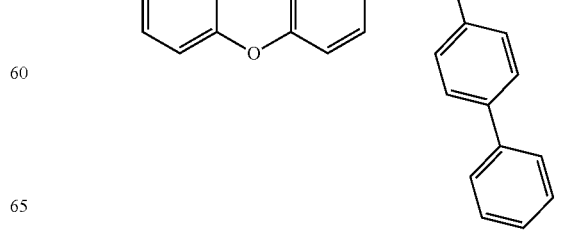

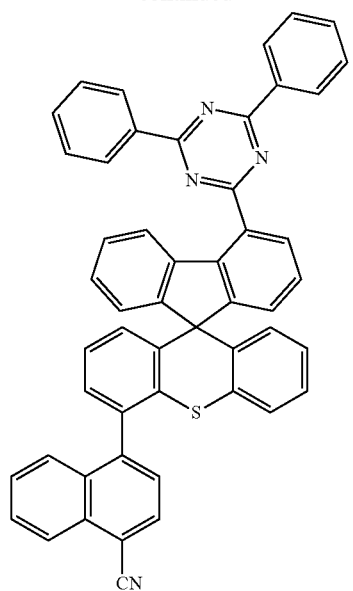
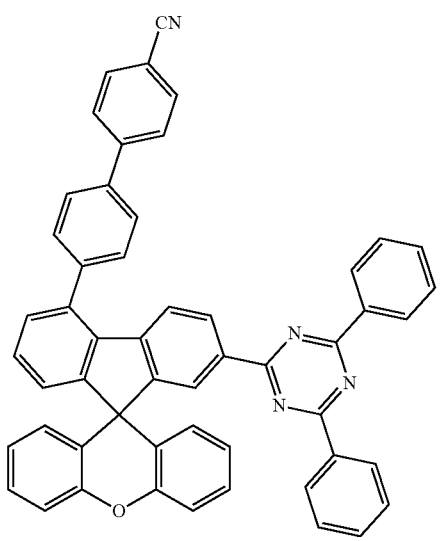
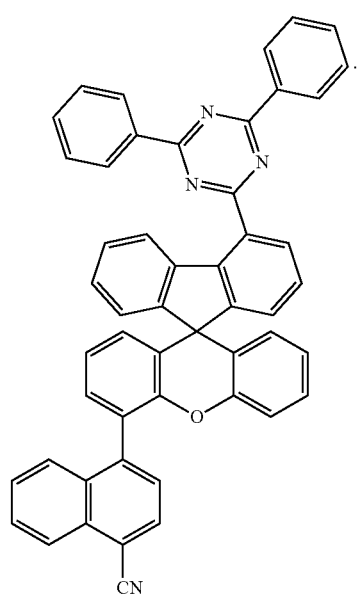
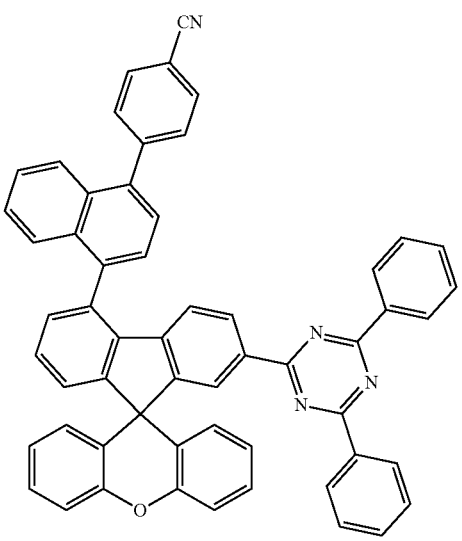
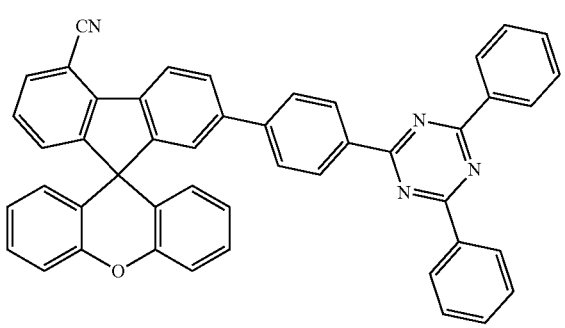
In one embodiment of the present specification, the compound of Chemical Formula 4 is any one compound selected from among the following compounds:

-continued
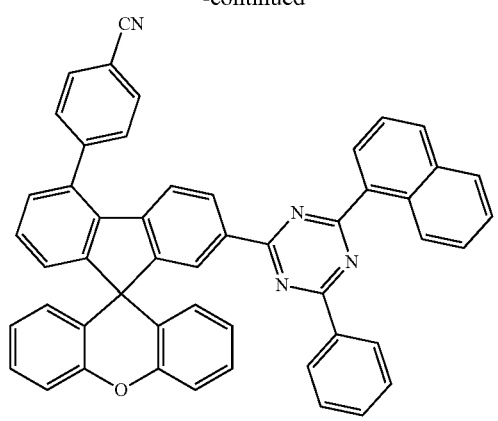
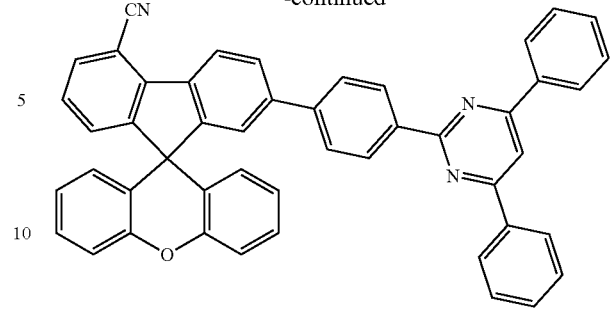
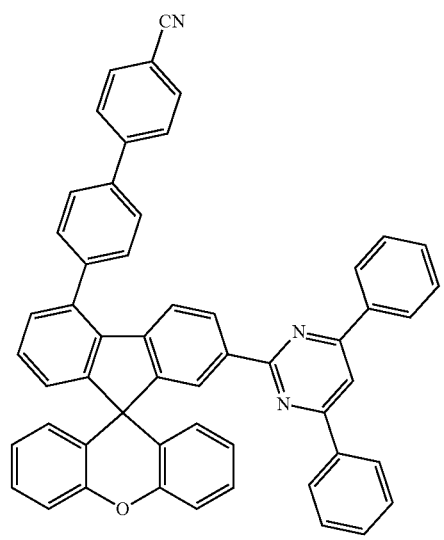
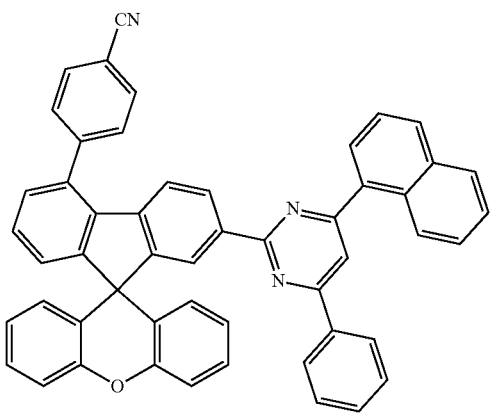
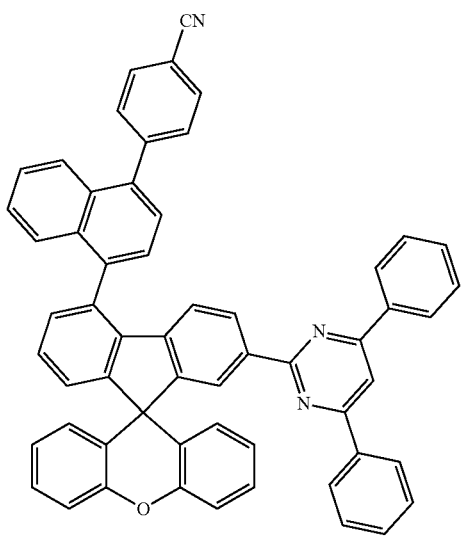
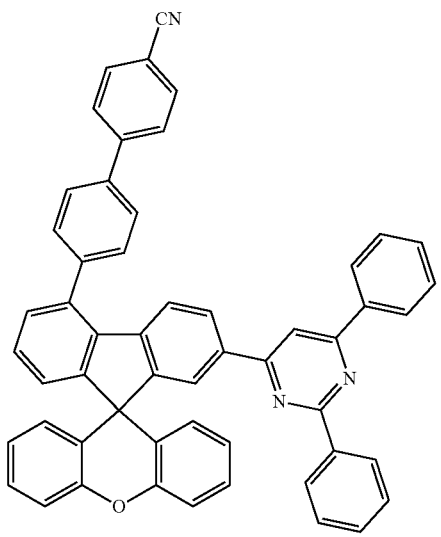

-continued
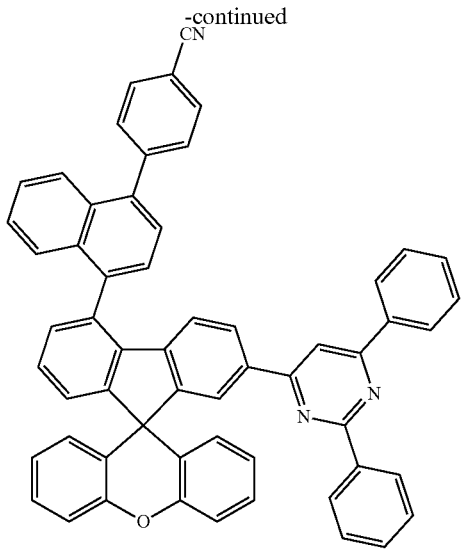
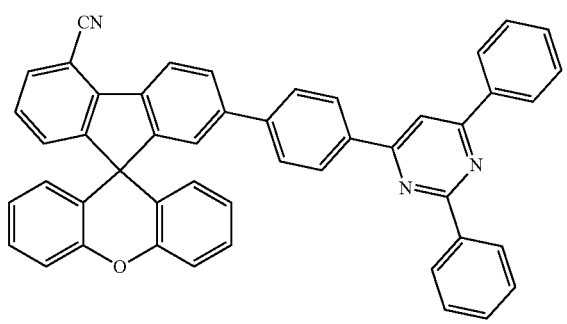
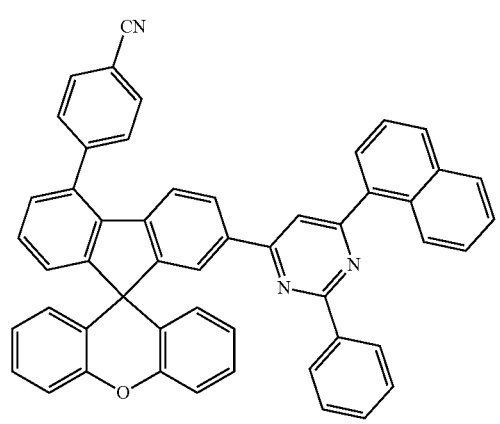
-continued
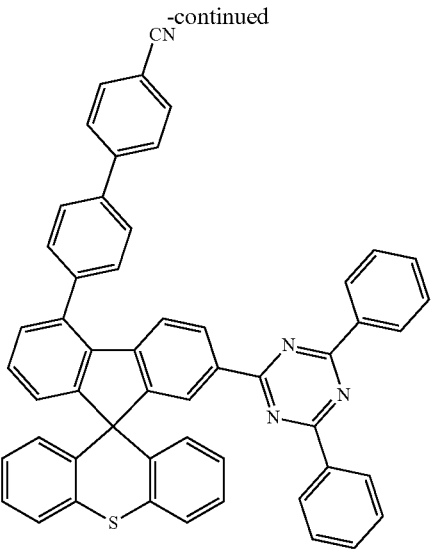
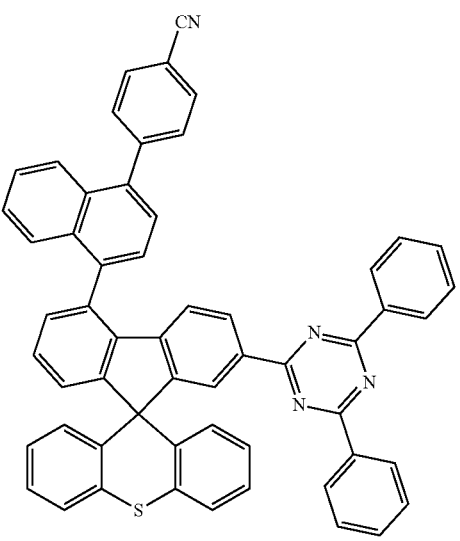
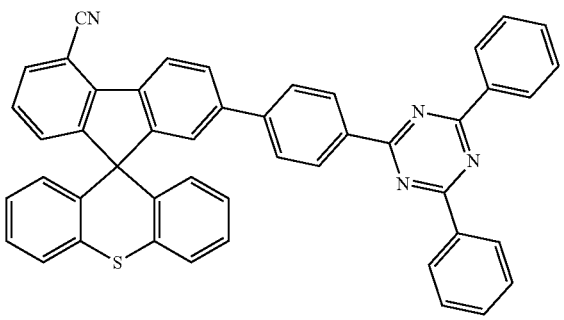

73
-continued
74
-continued
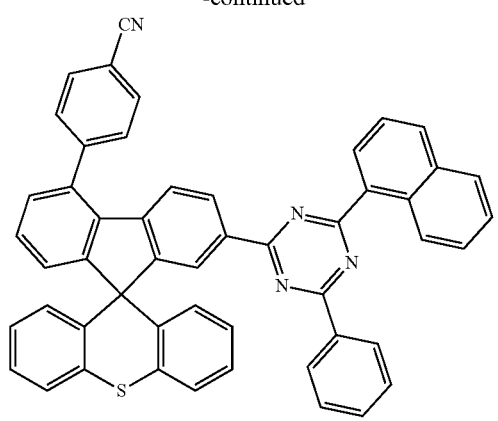
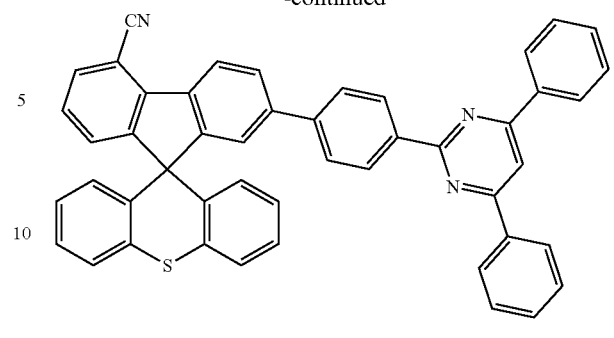
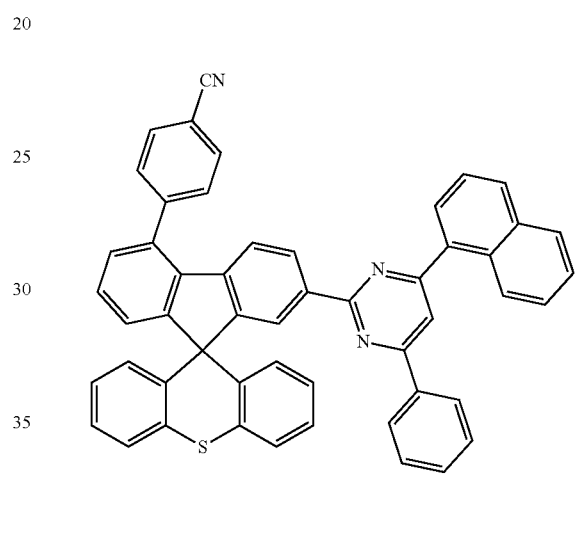
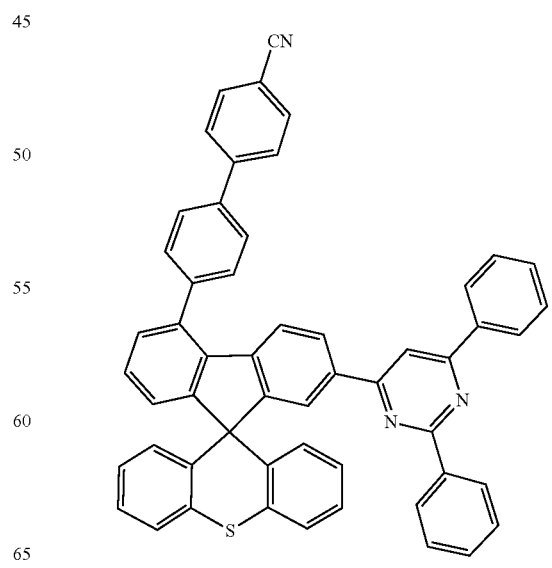

-continued
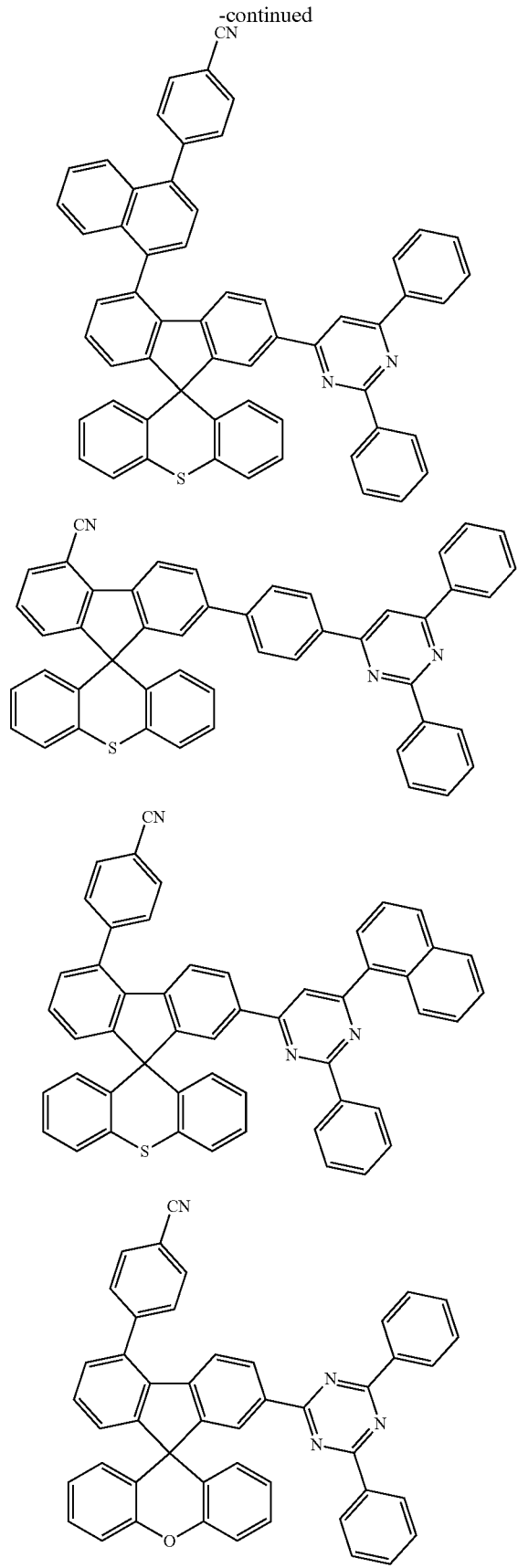
-continued
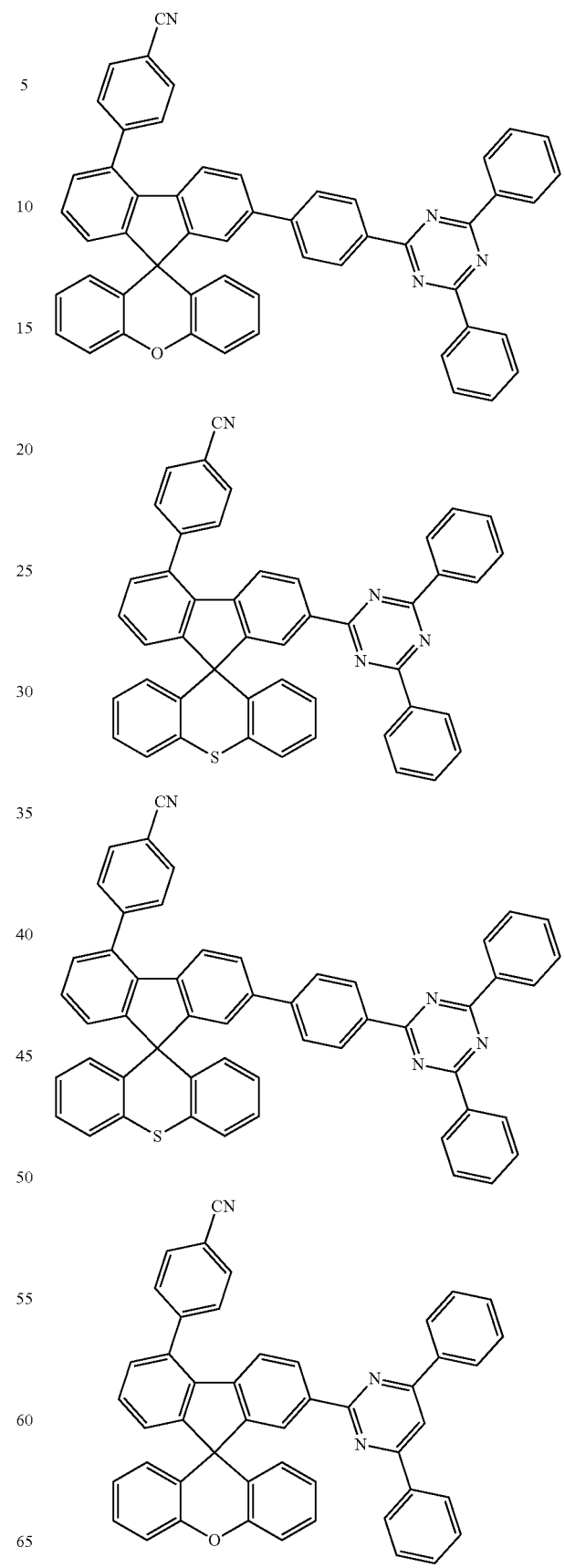

77
-continued
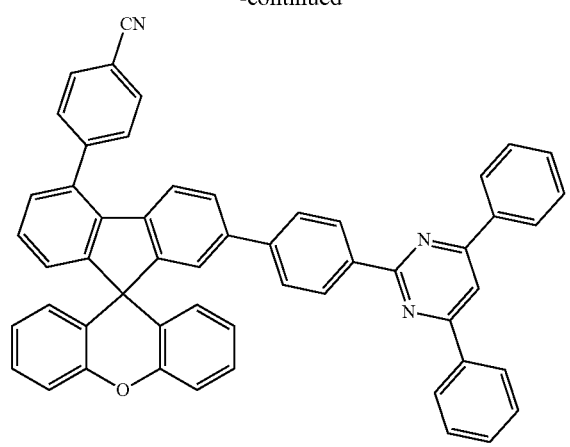
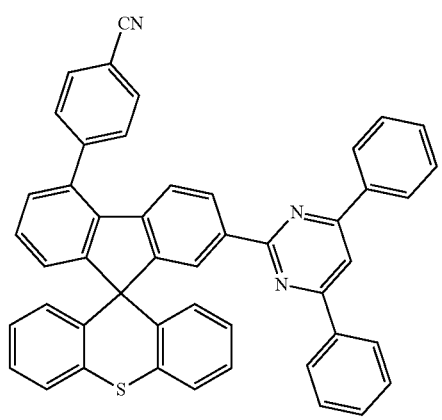
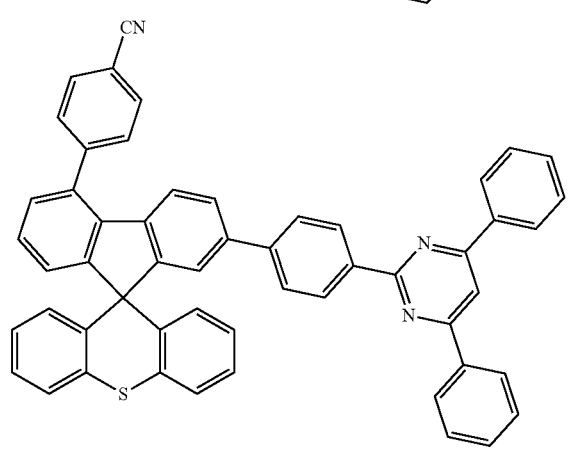
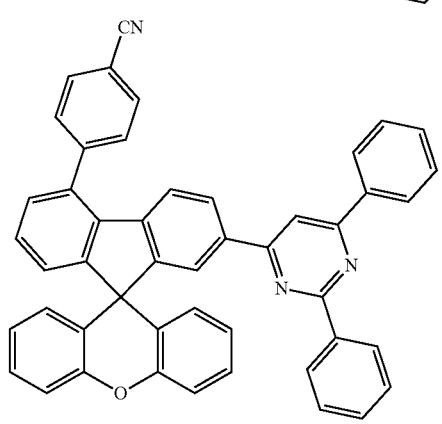
78
-continued
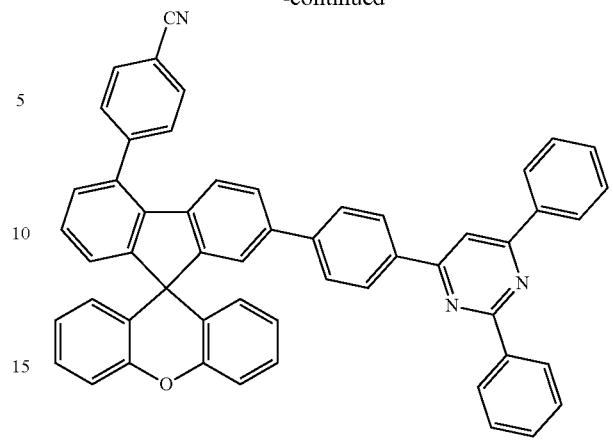
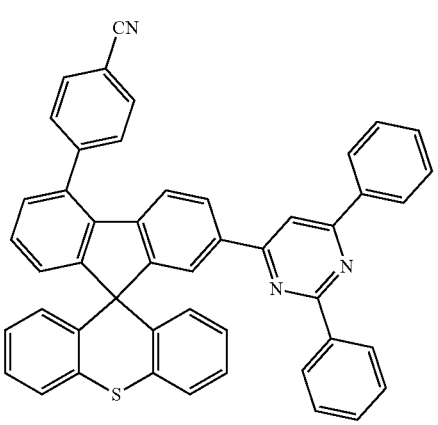
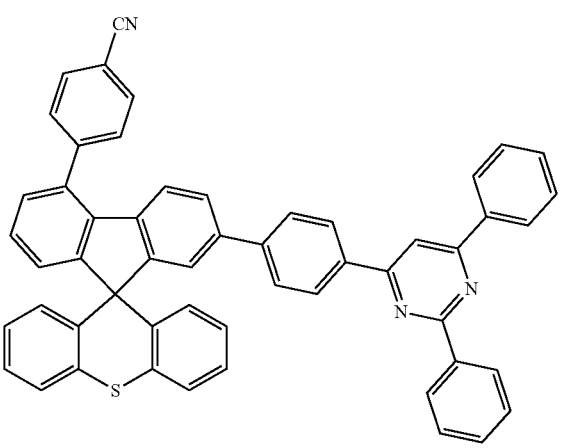

-continued
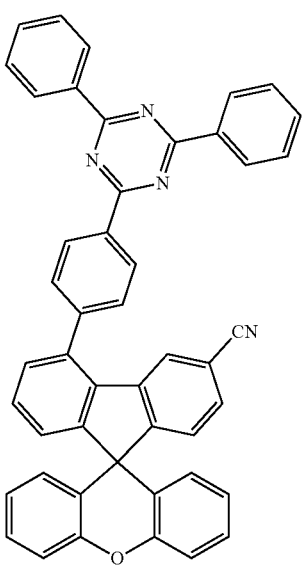
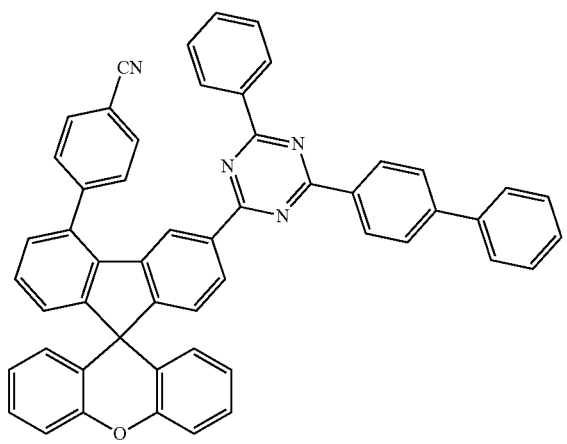
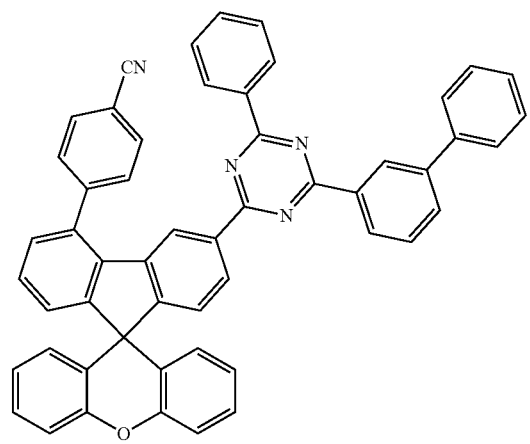
-continued
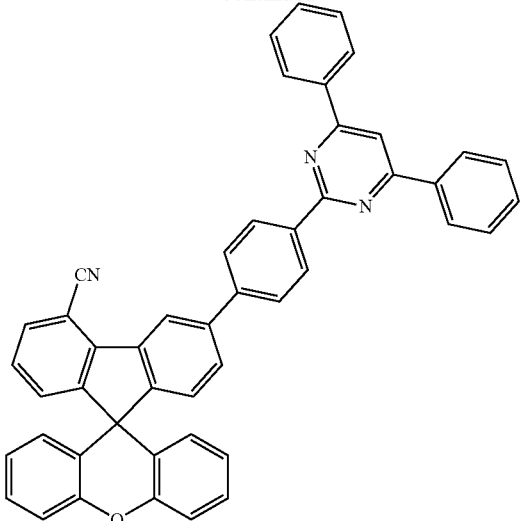
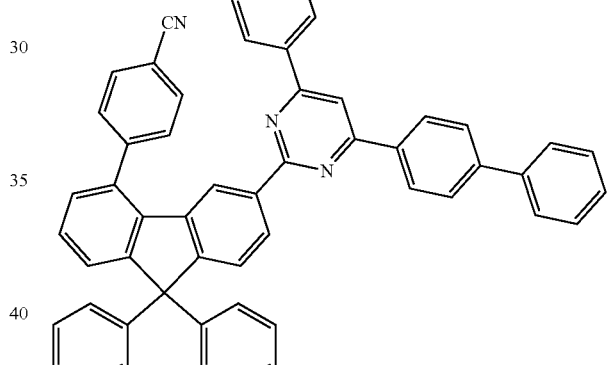
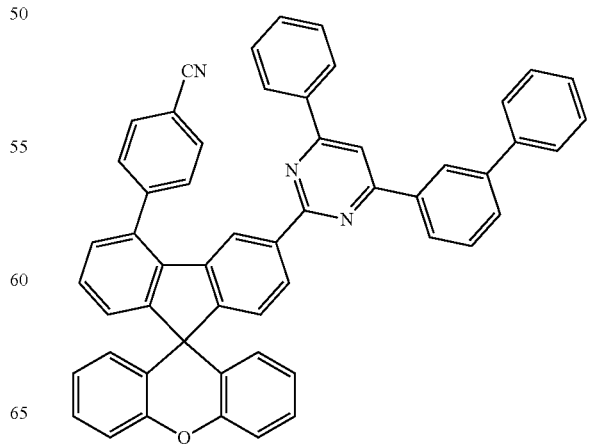

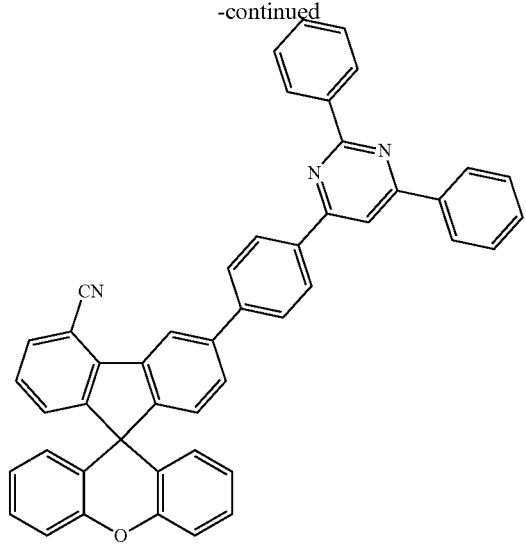
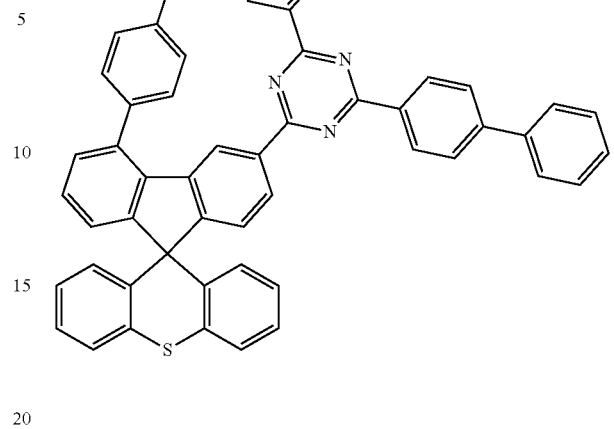
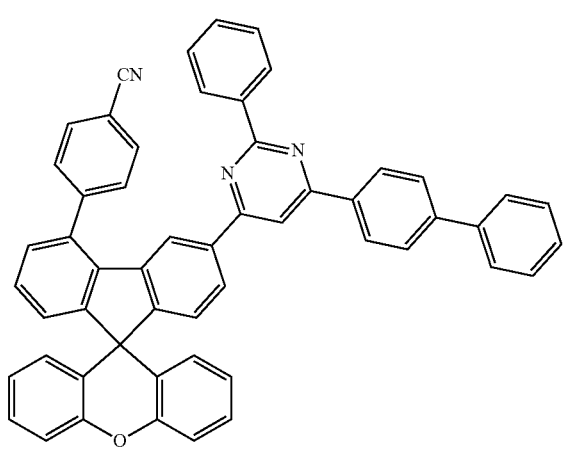
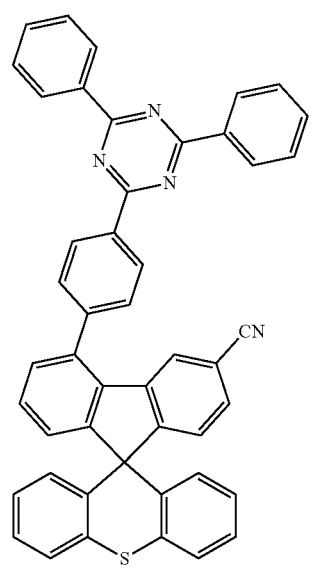
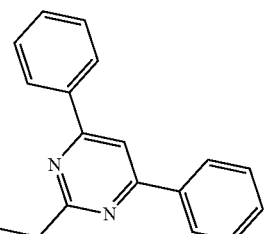

83
-continued
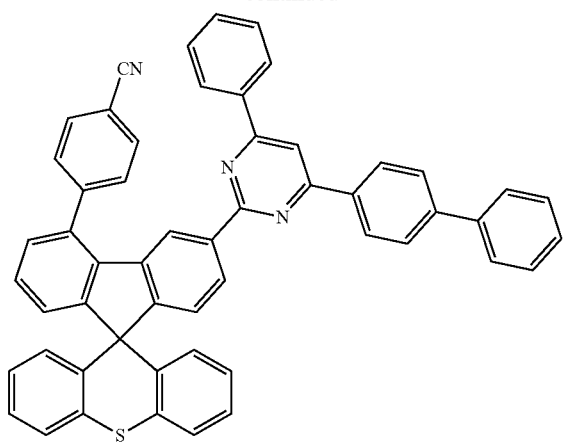
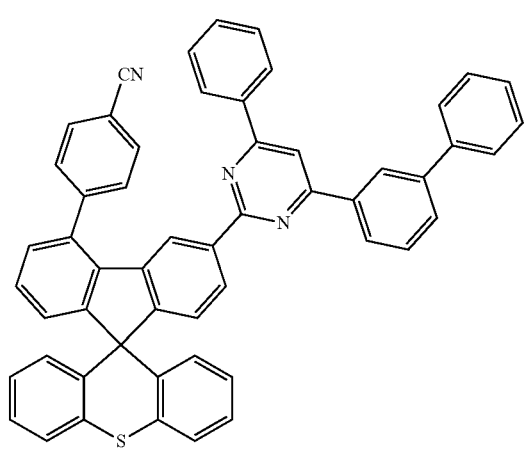
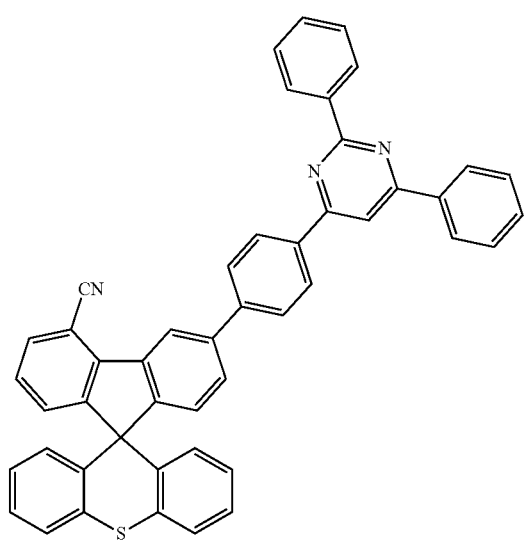
84
-continued
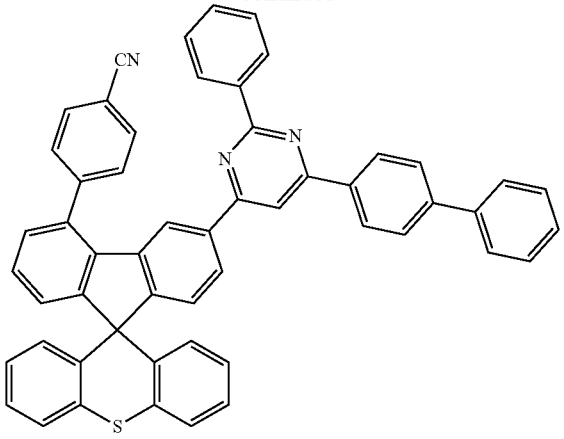
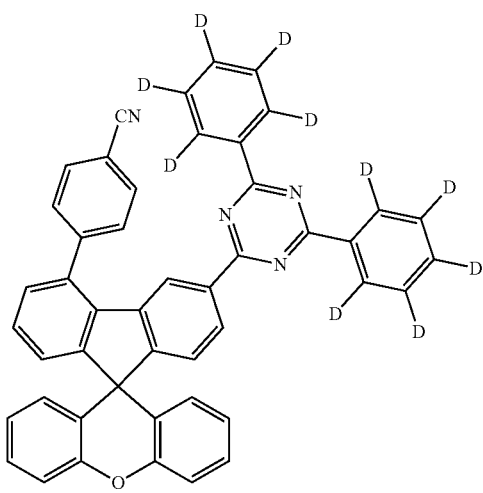
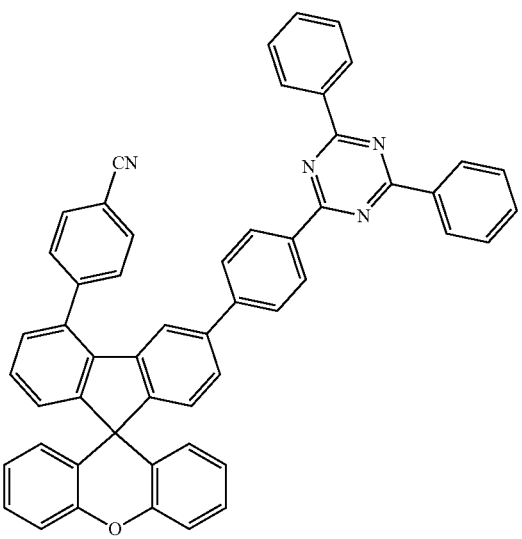

-continued
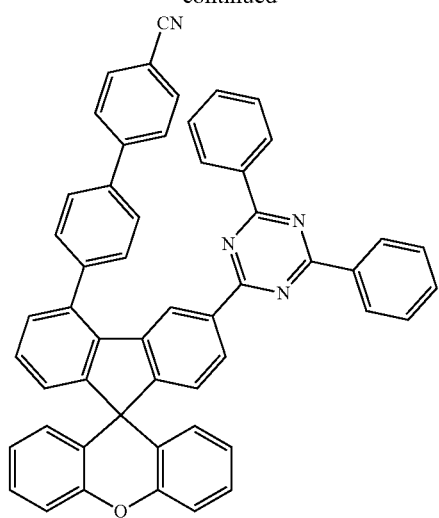
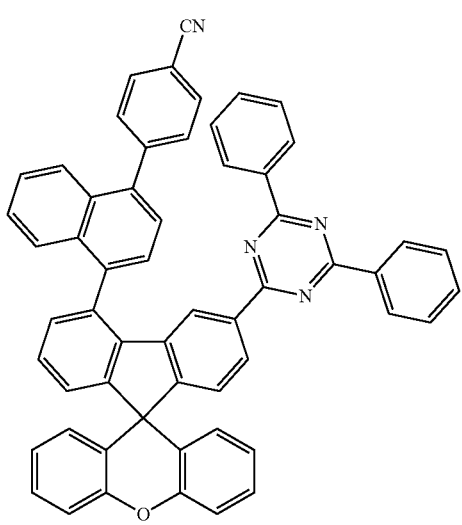
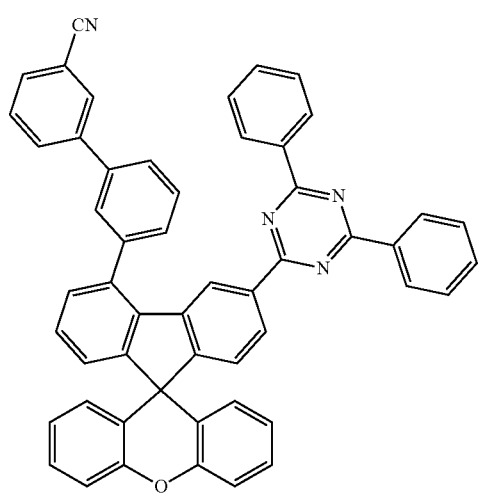
-continued
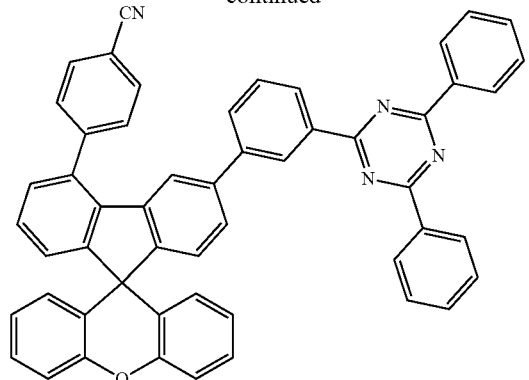
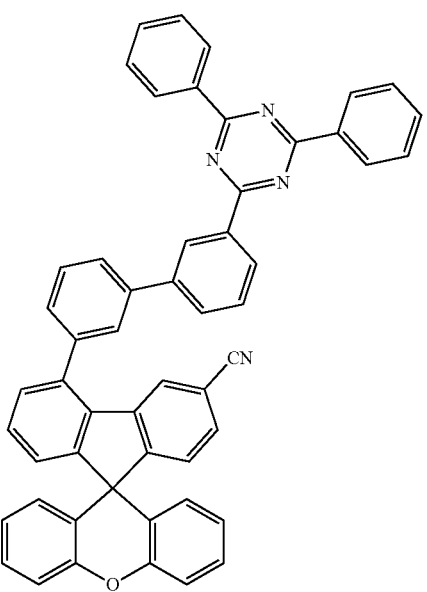
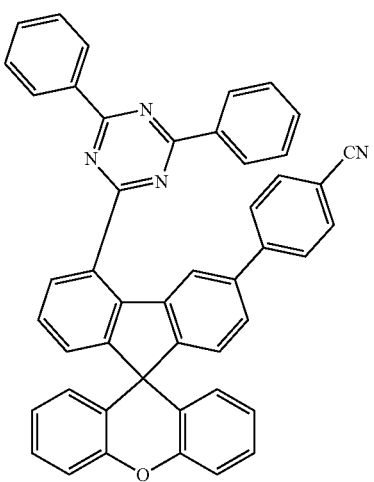

87
-continued
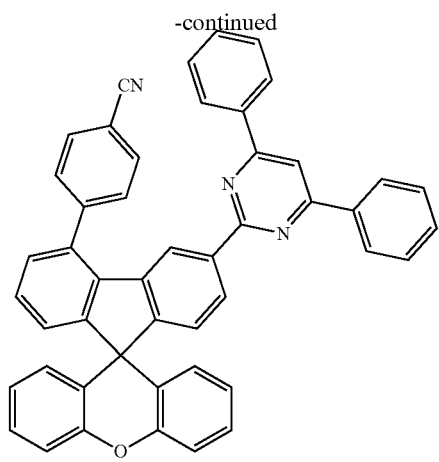
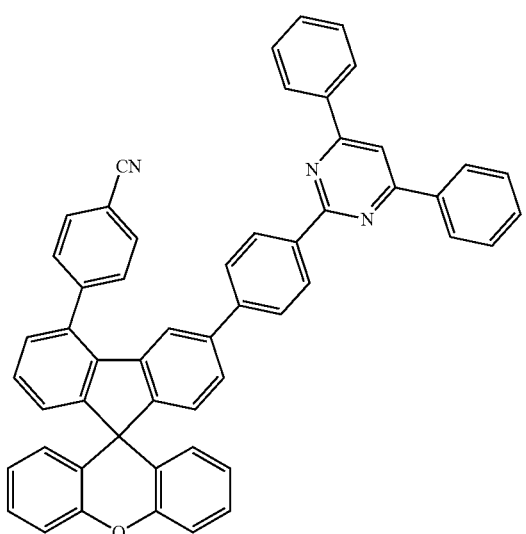
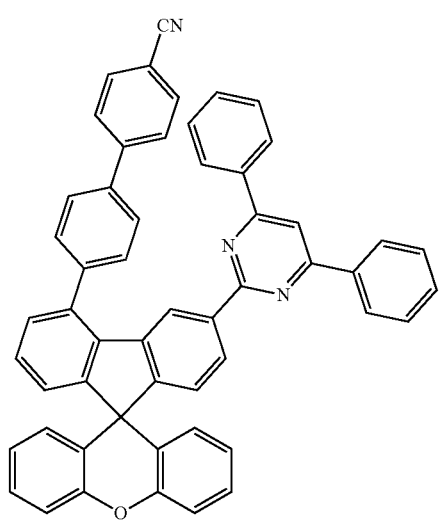
88
-continued
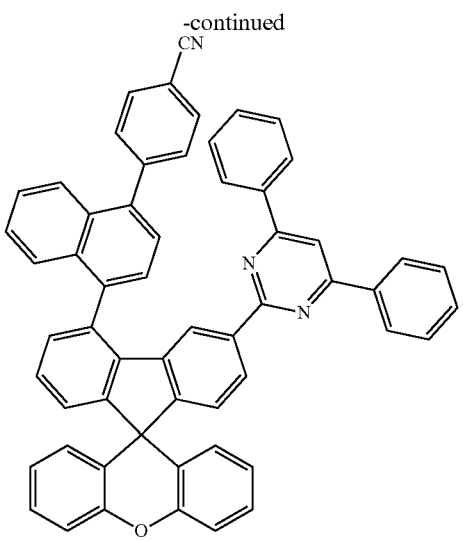
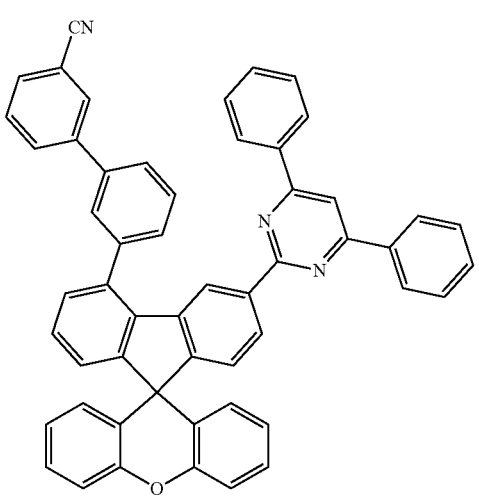
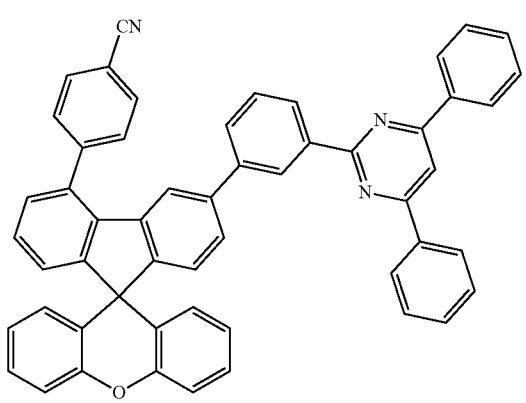

-continued
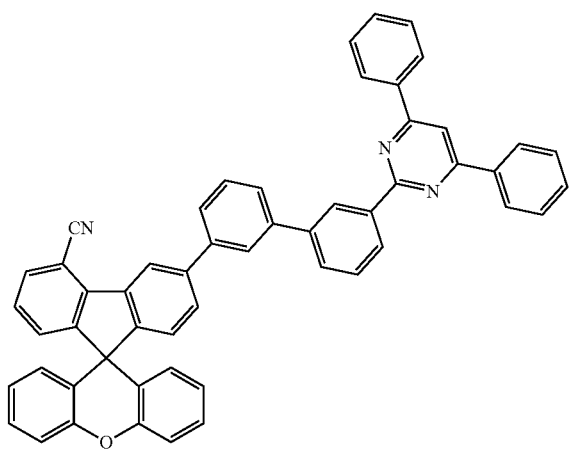
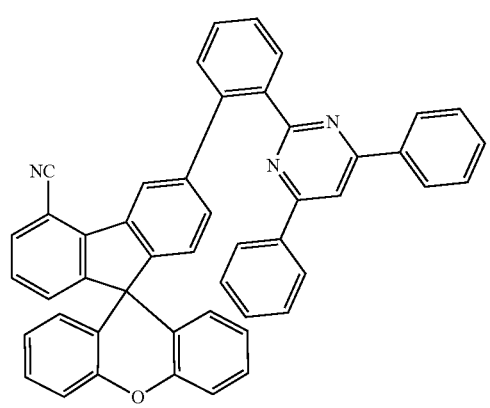
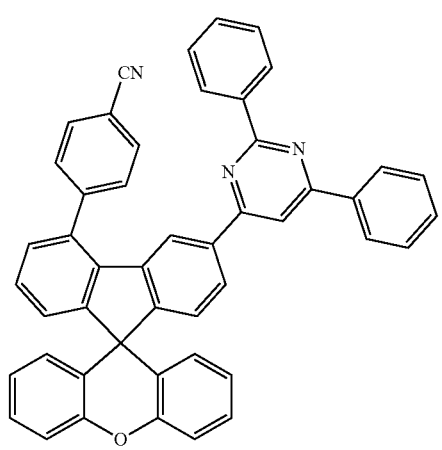
-continued
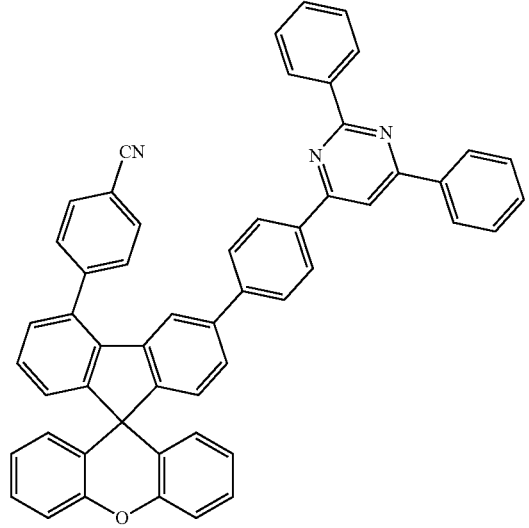
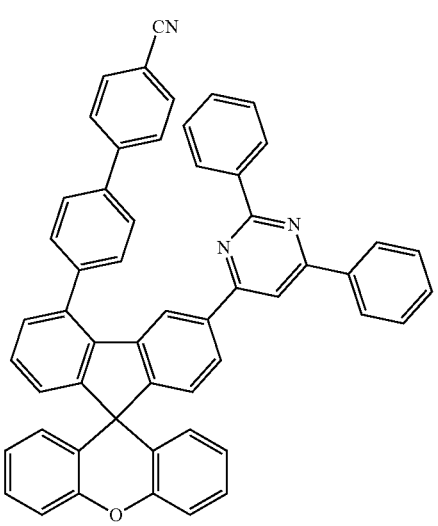
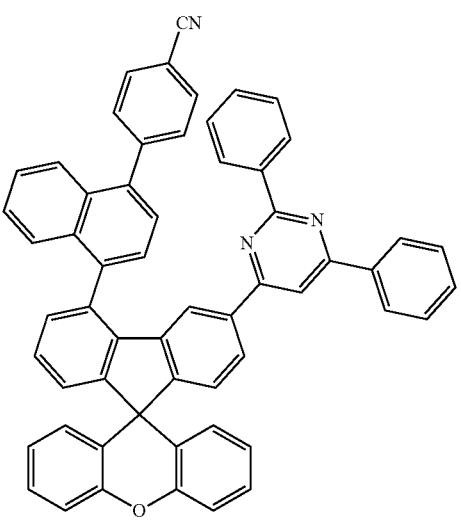

91
-continued
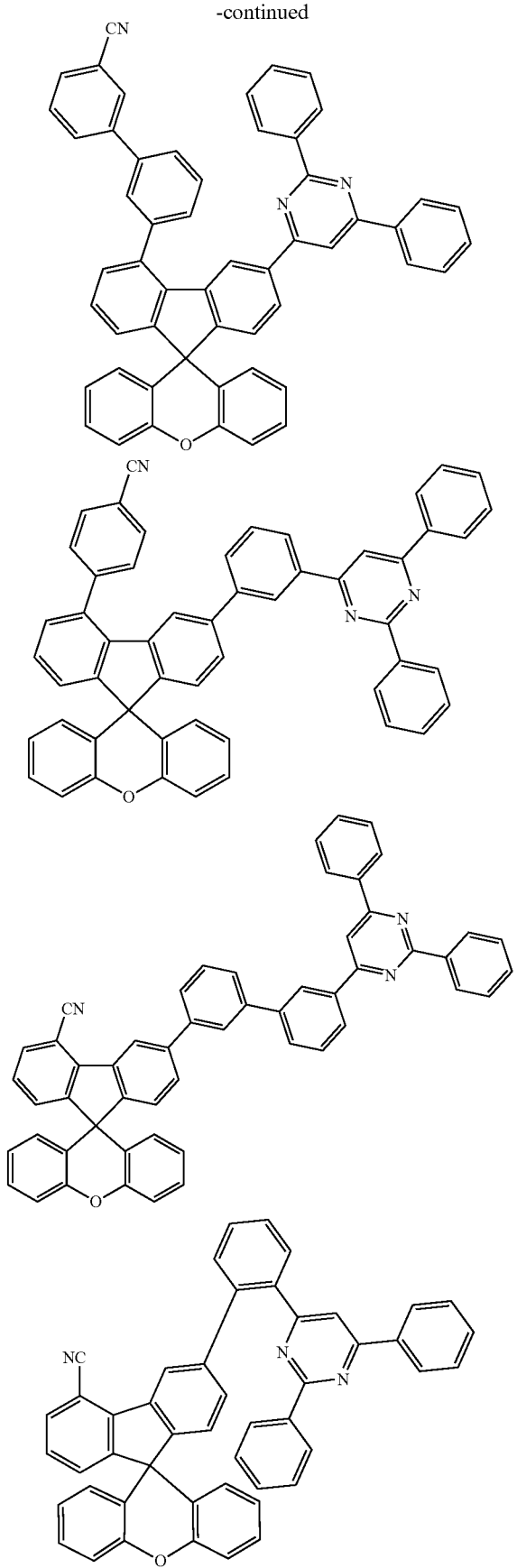
92
-continued
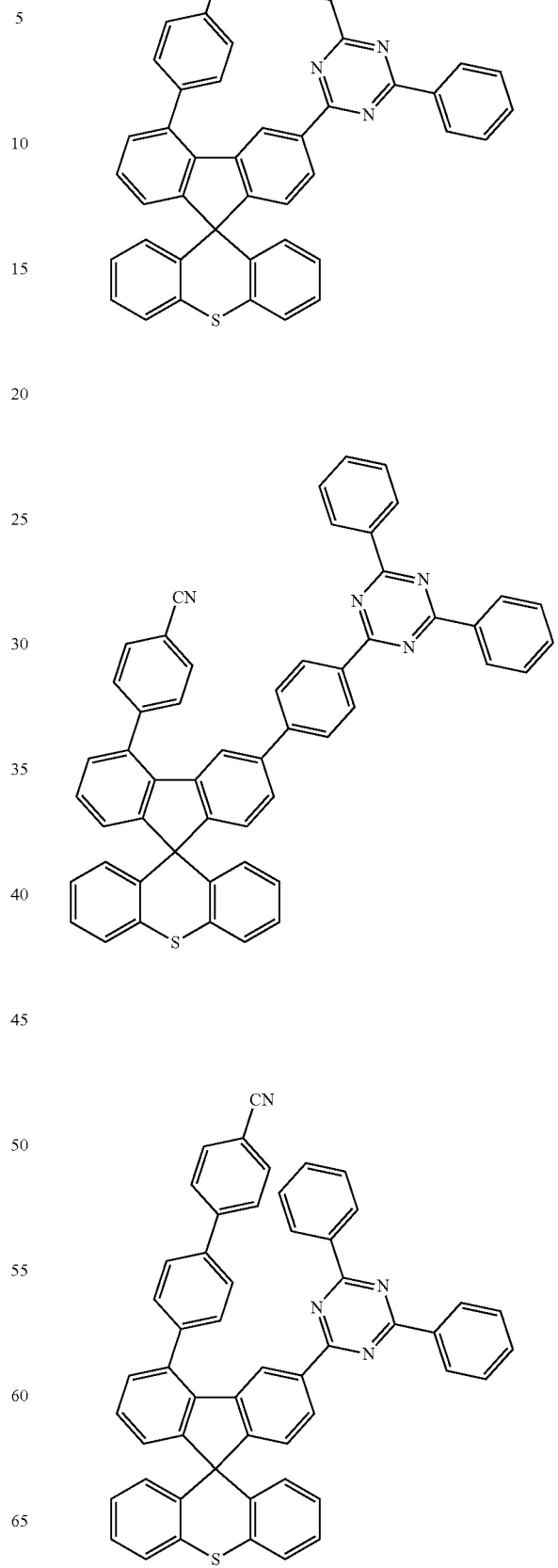

93
-continued
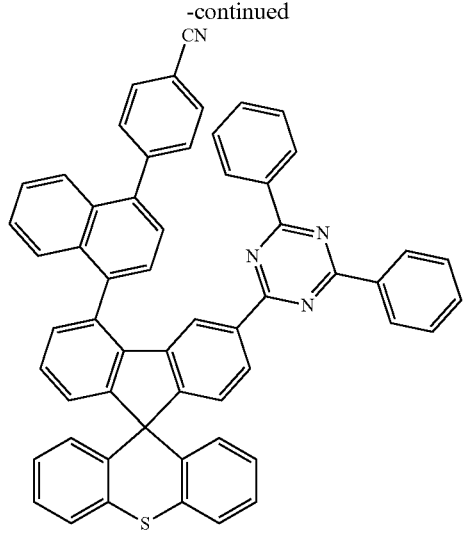
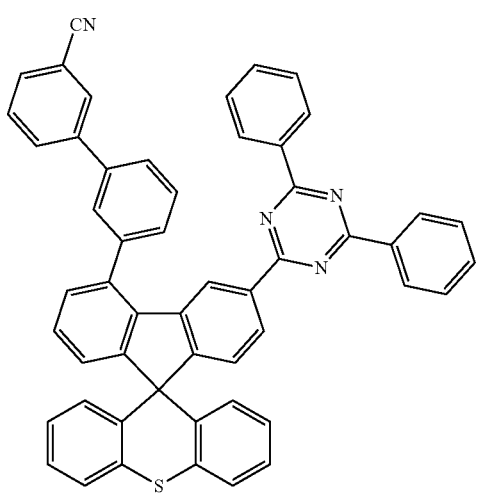
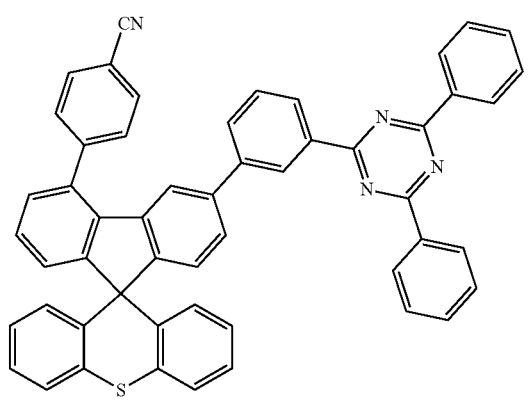
94
-continued
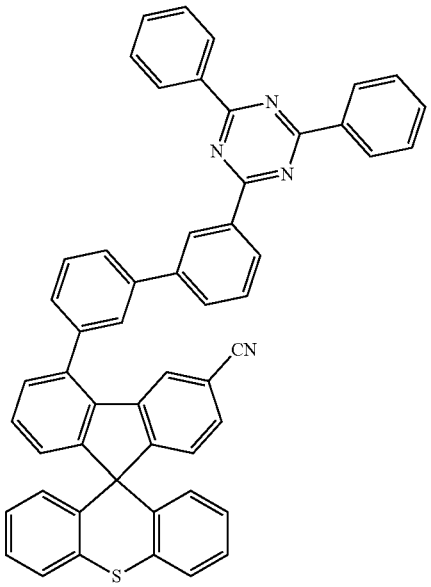
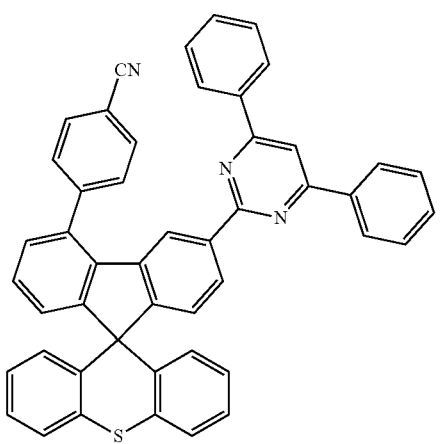

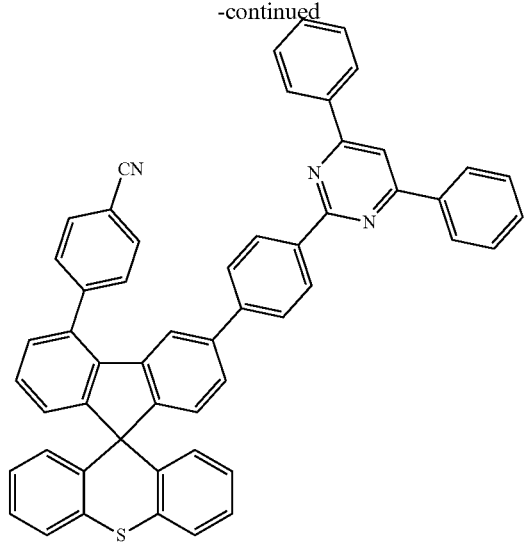
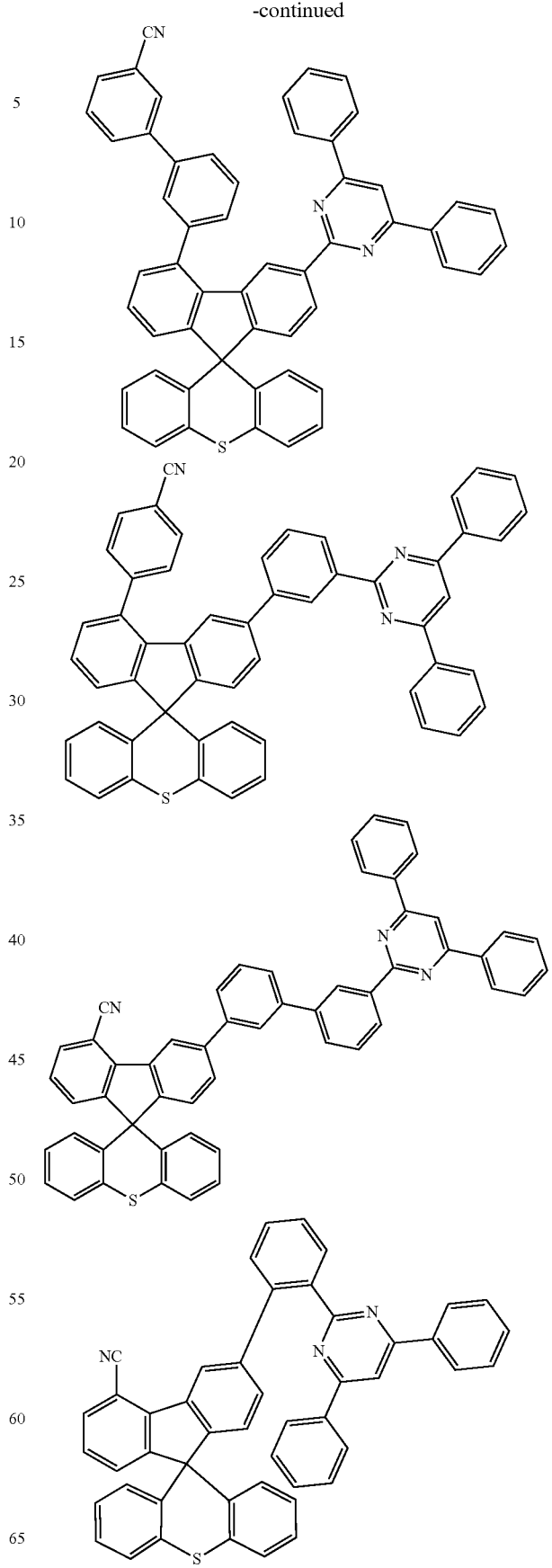

97
-continued
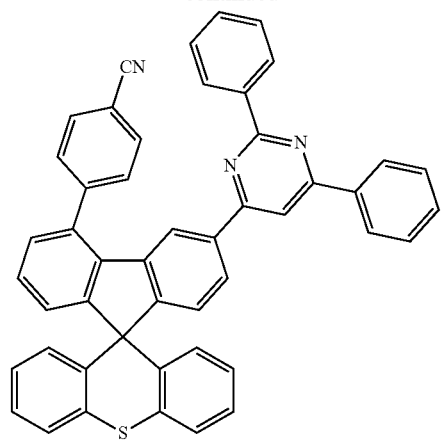
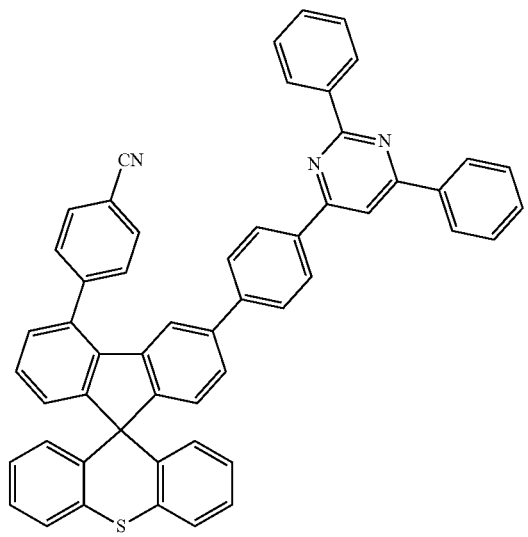
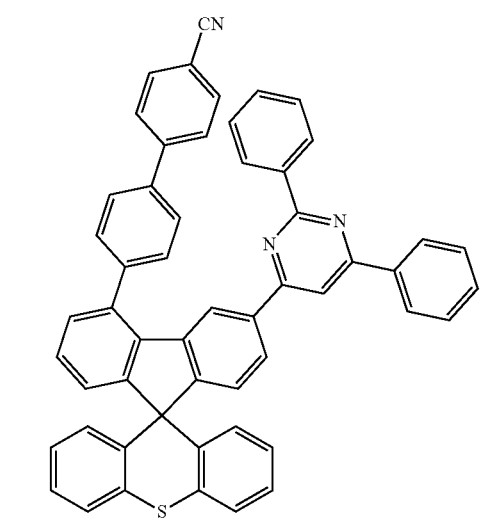
98
-continued
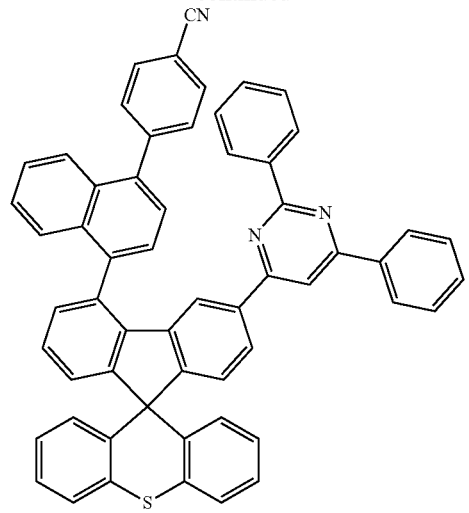
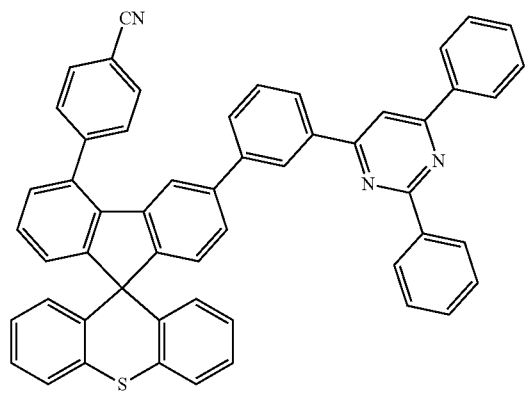

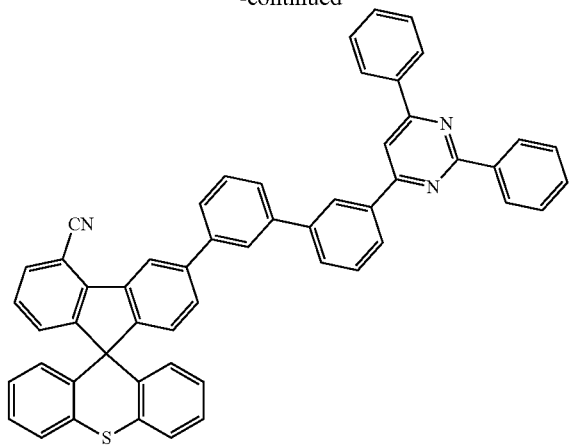
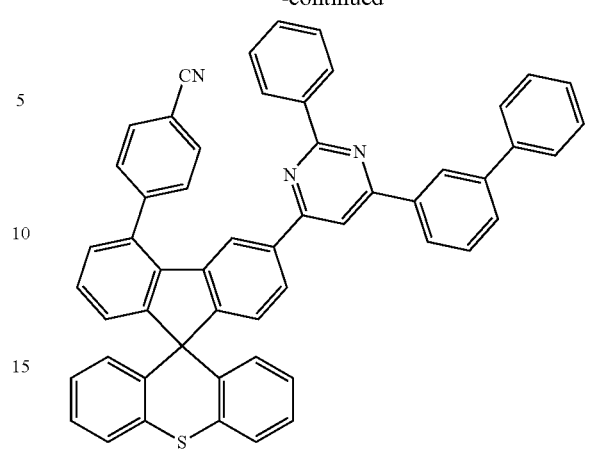
In one embodiment of the present specification, the compound of Chemical Formula 5 is any one compound selected from among the following compounds:
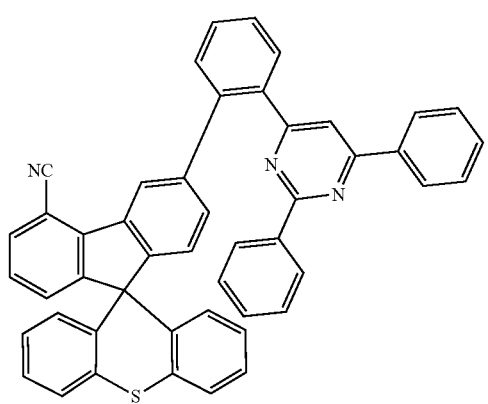
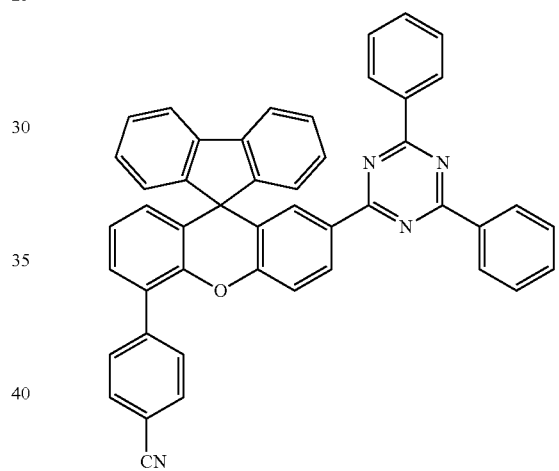
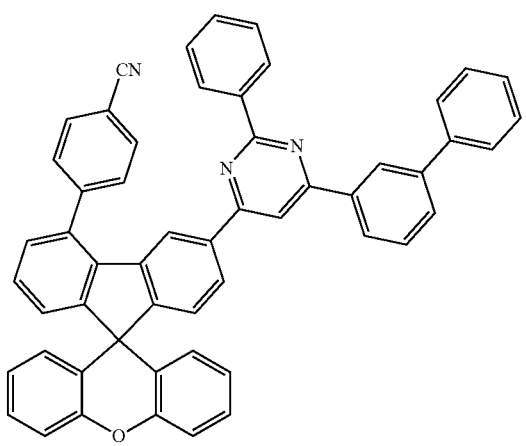
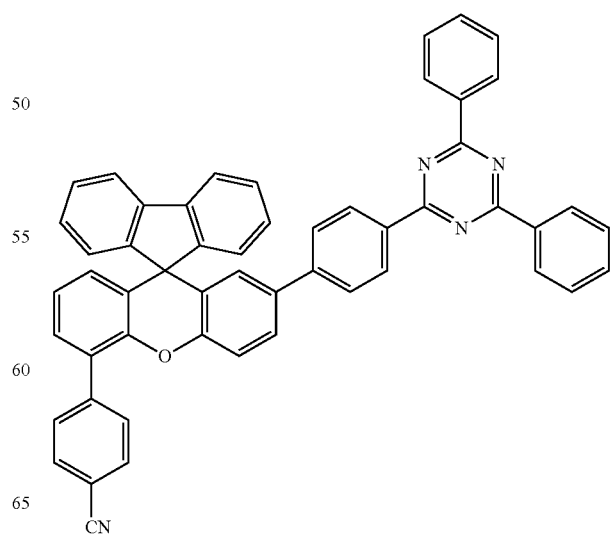

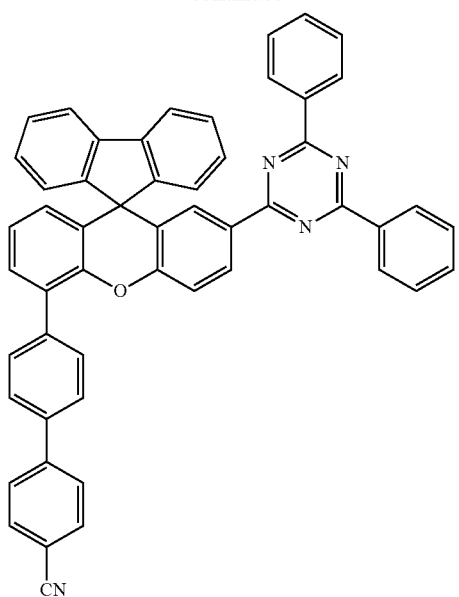
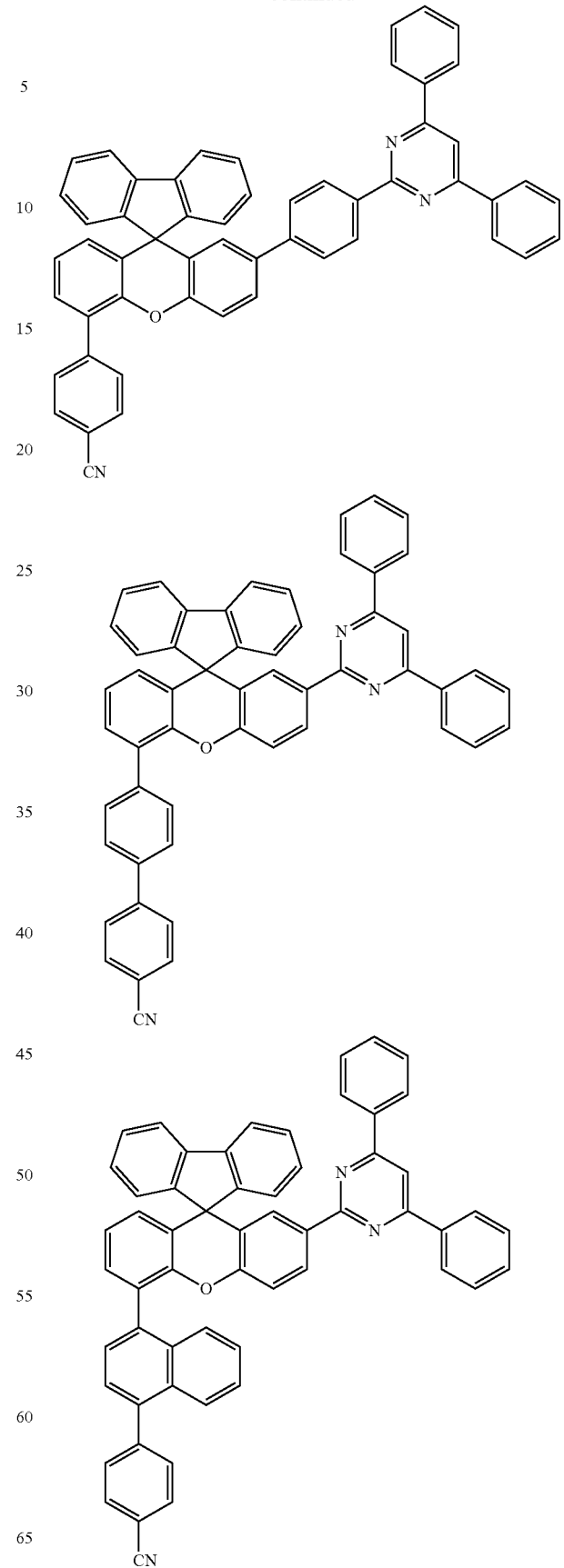

103
-continued
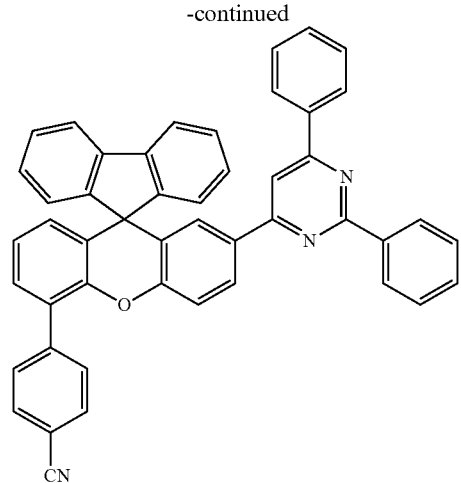
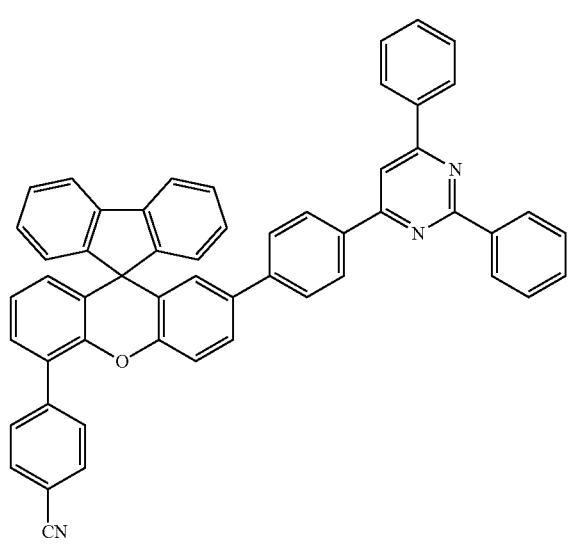
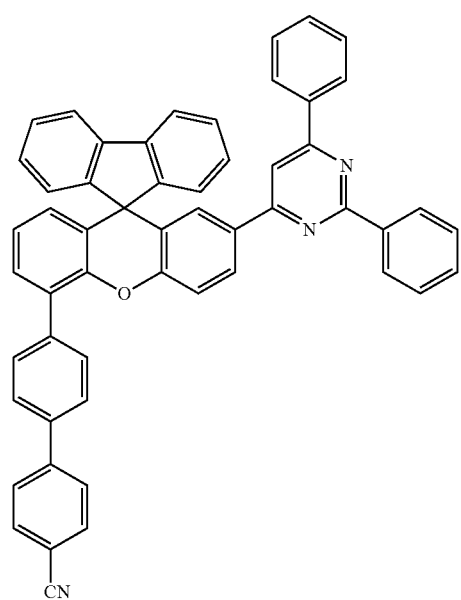
104
-continued
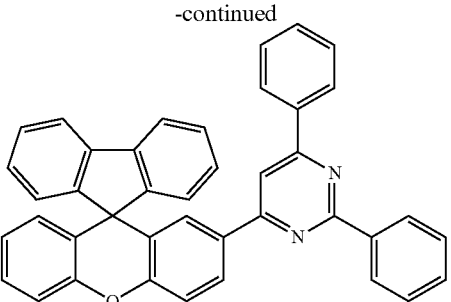
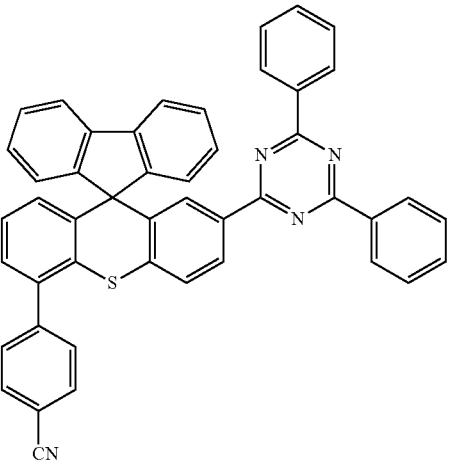

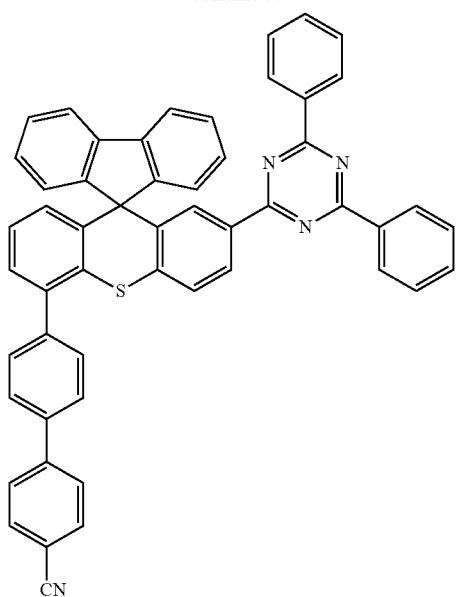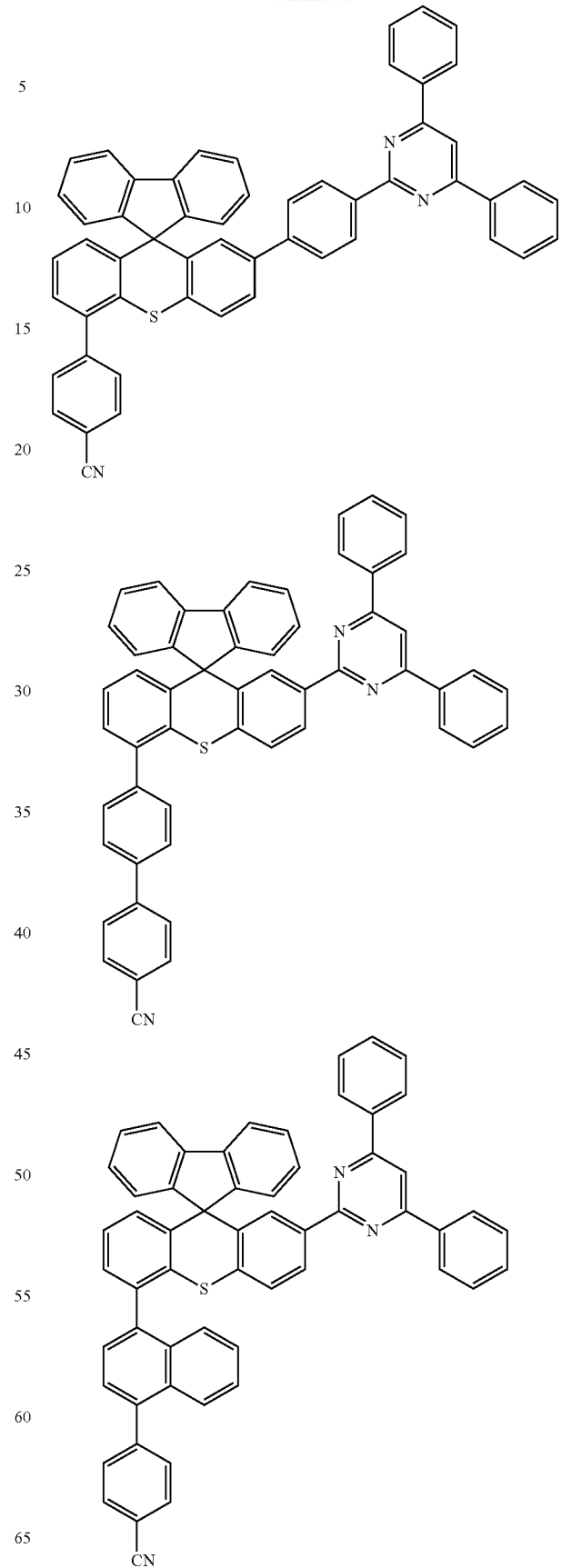

-continued
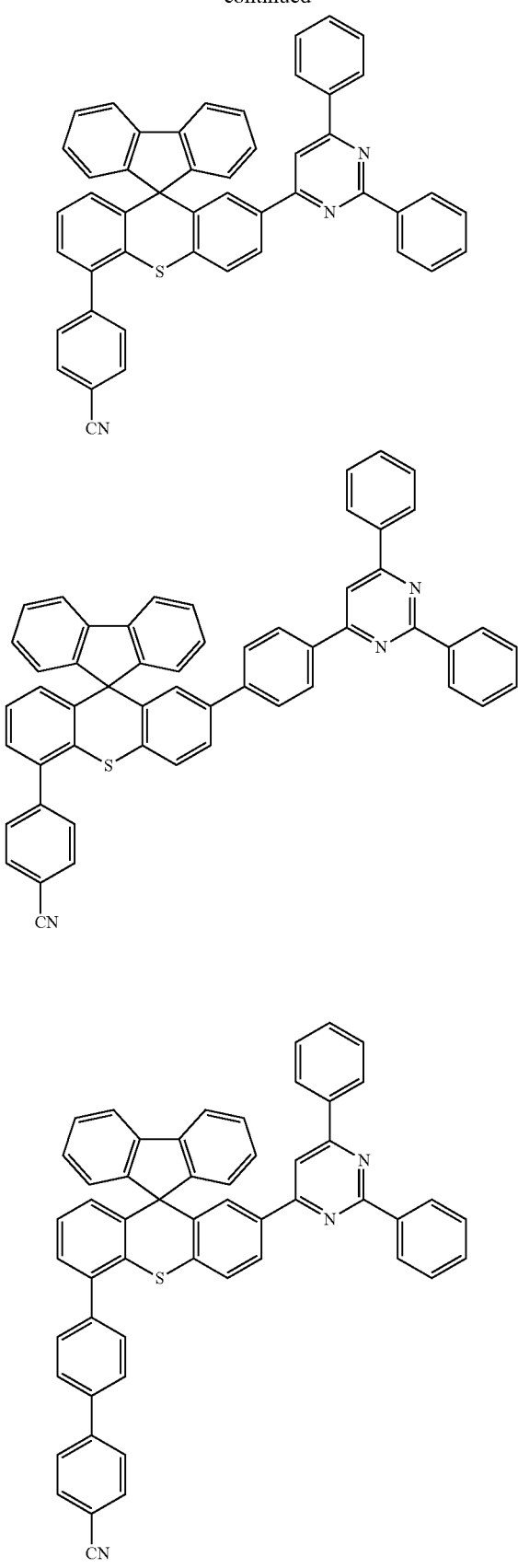
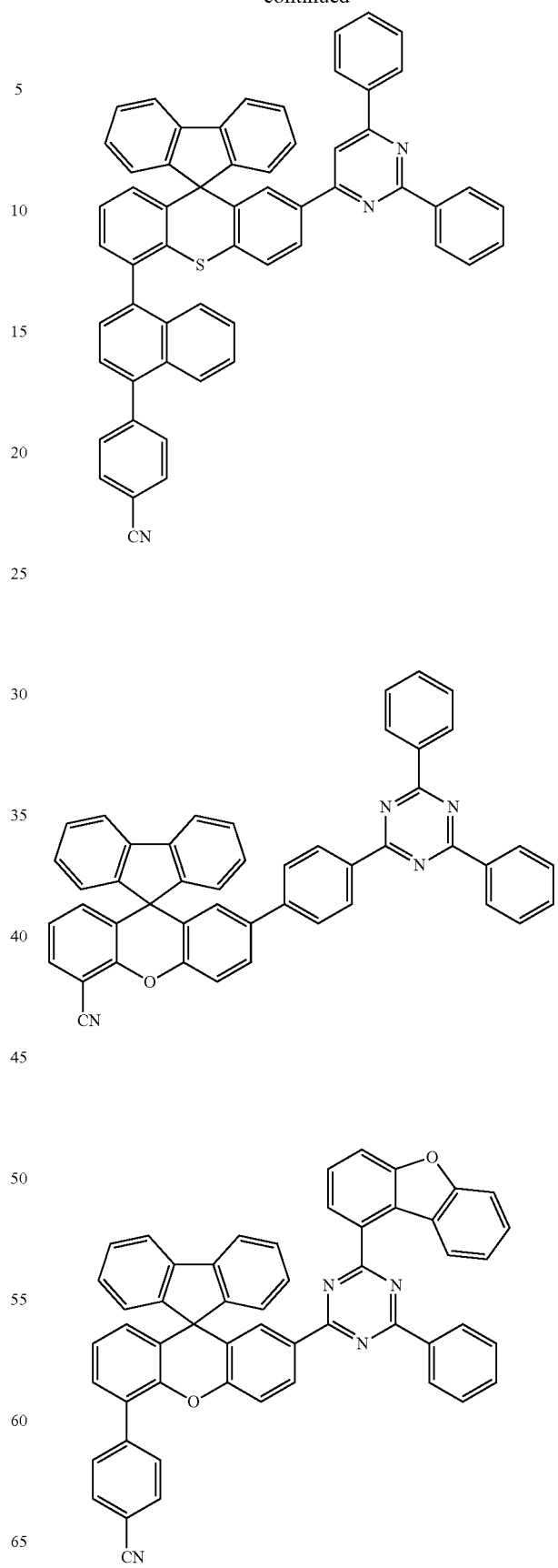

109
-continued
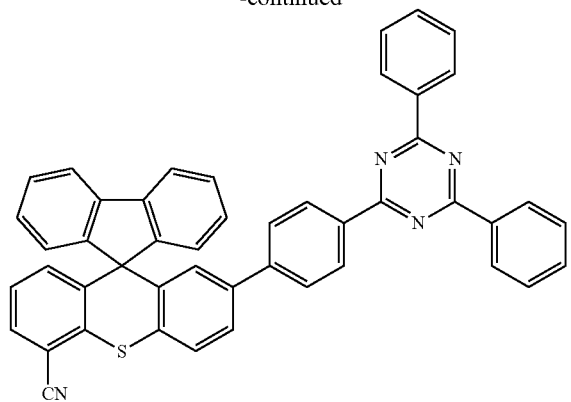
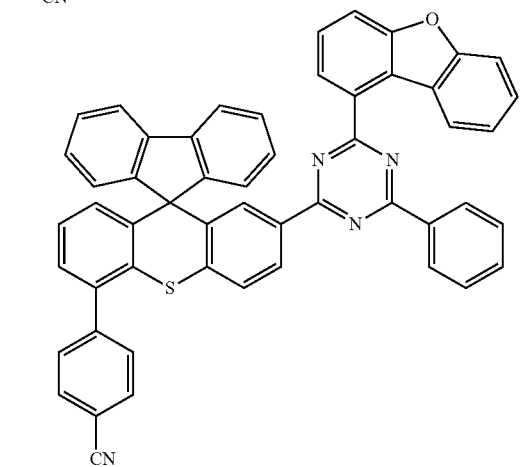
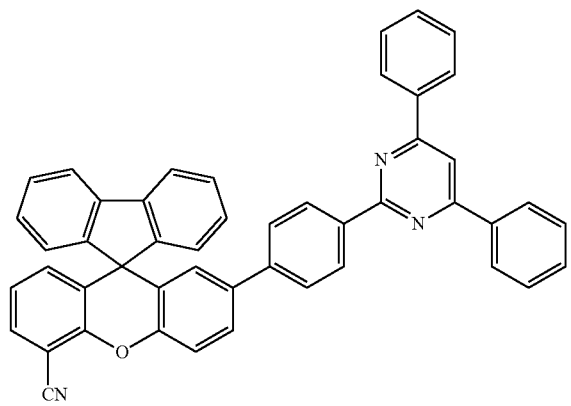
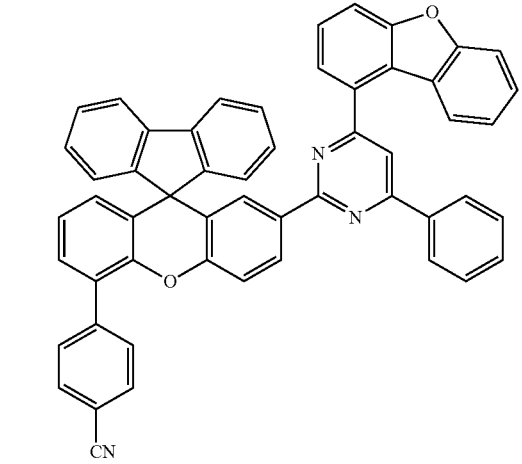
110
-continued
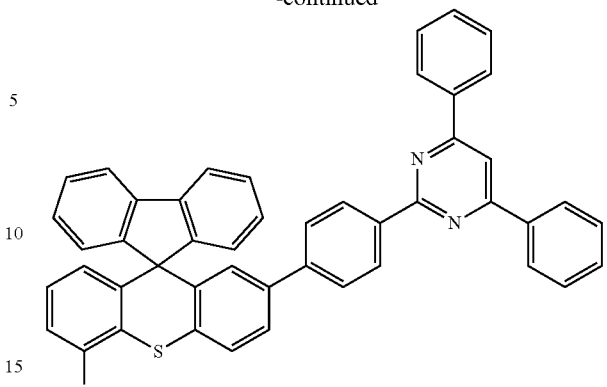
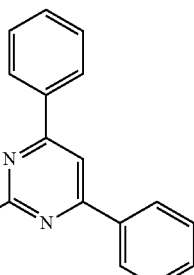
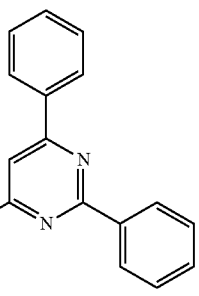
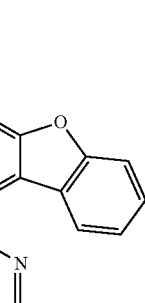

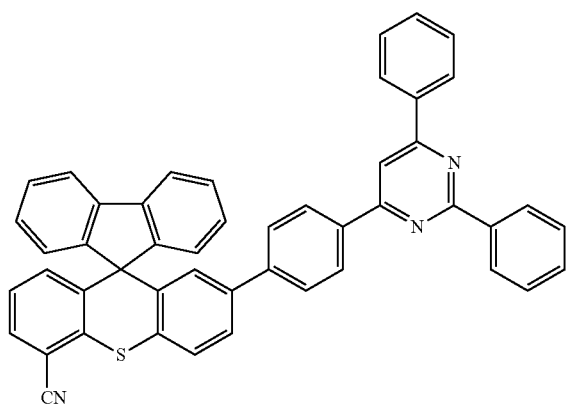
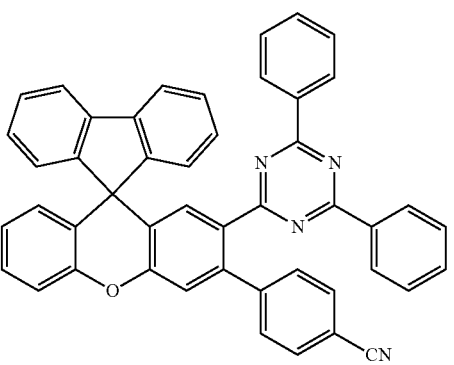
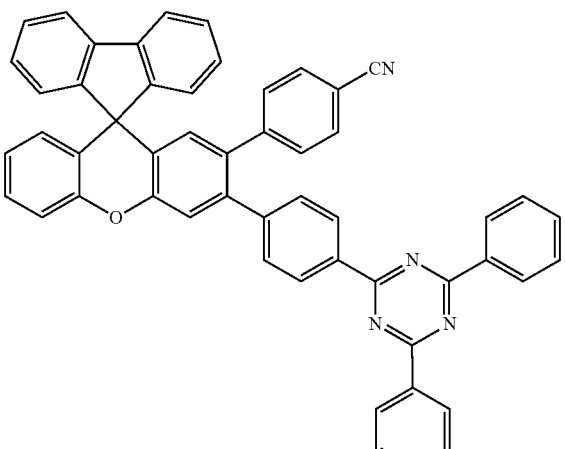
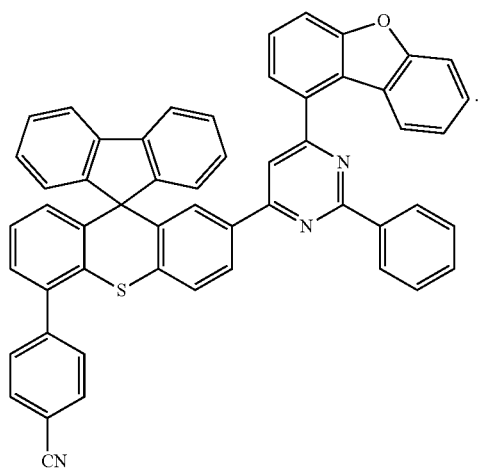
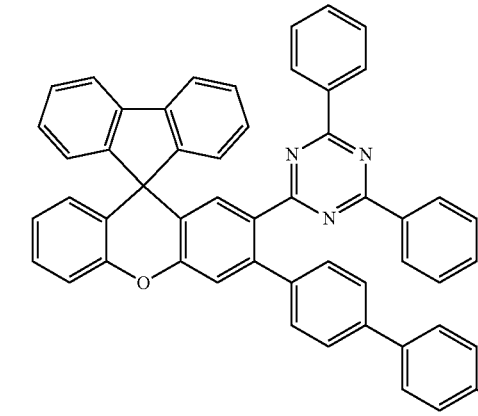
According to one embodiment of the present specification, the compound of Chemical Formula 6 is any one compound selected from among the following compounds:
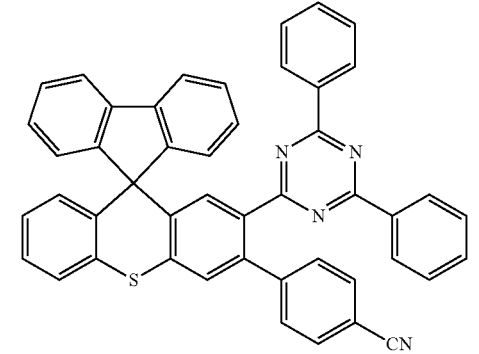
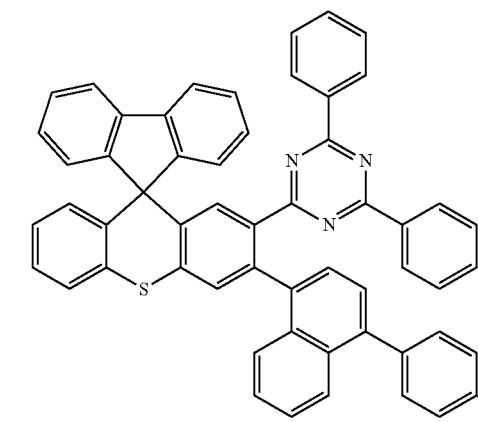

-continued
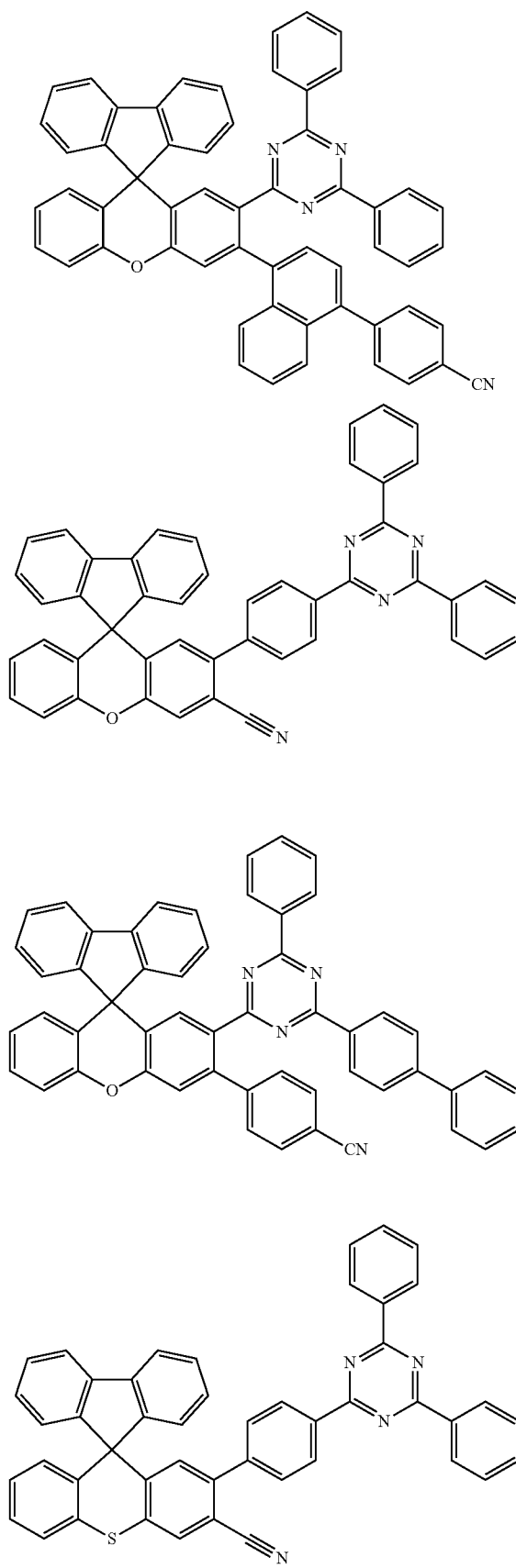
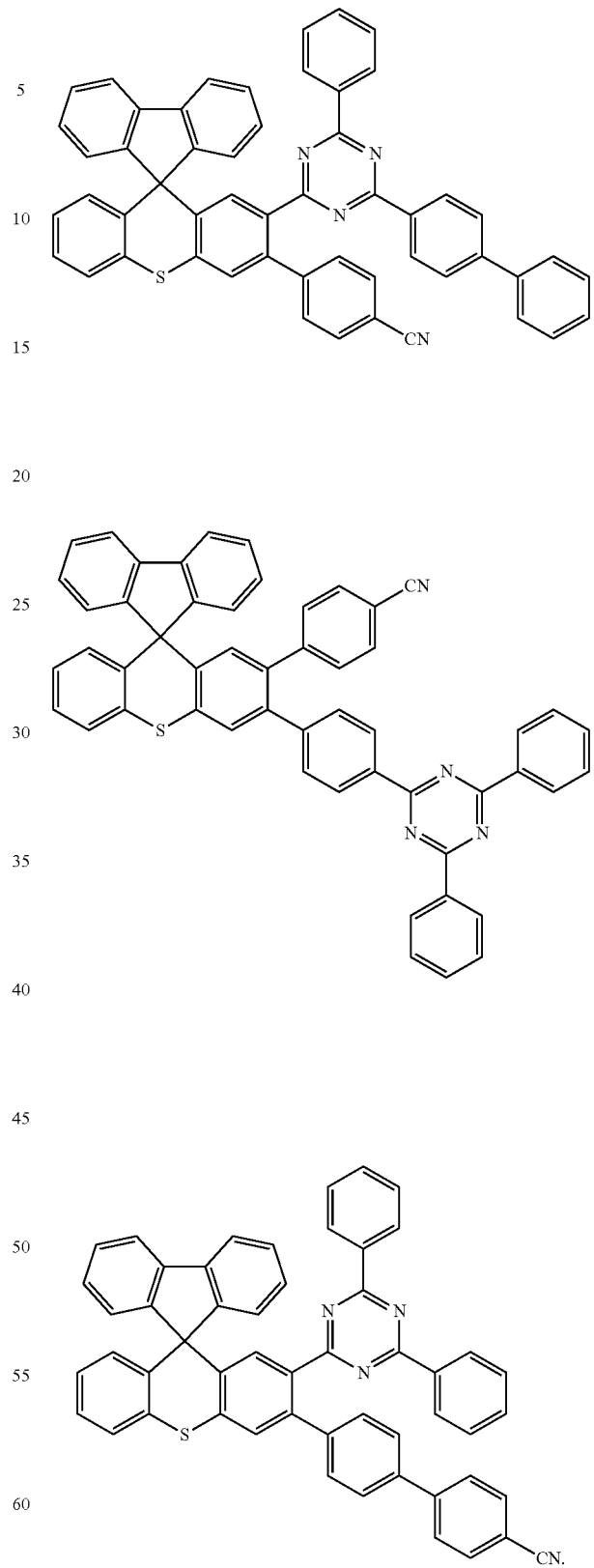
According to one embodiment of the present specification, the compound of Chemical Formula 7 is any one compound selected from among the following compounds:

115
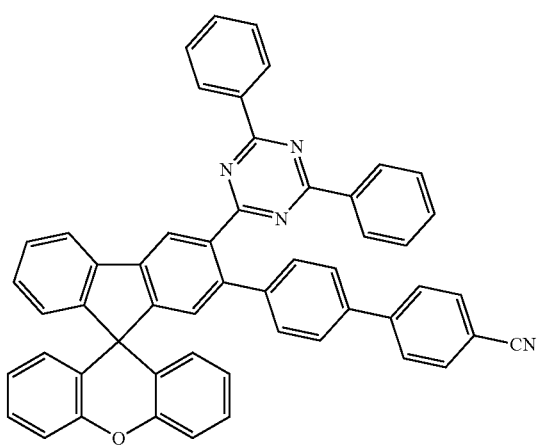
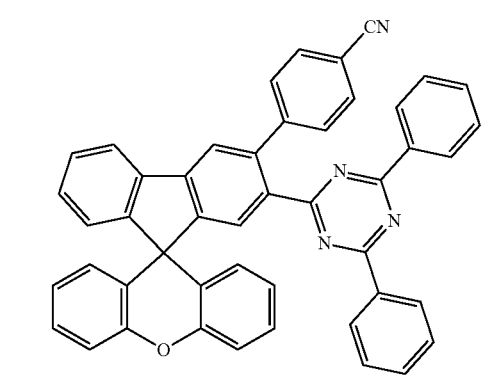
116
-continued
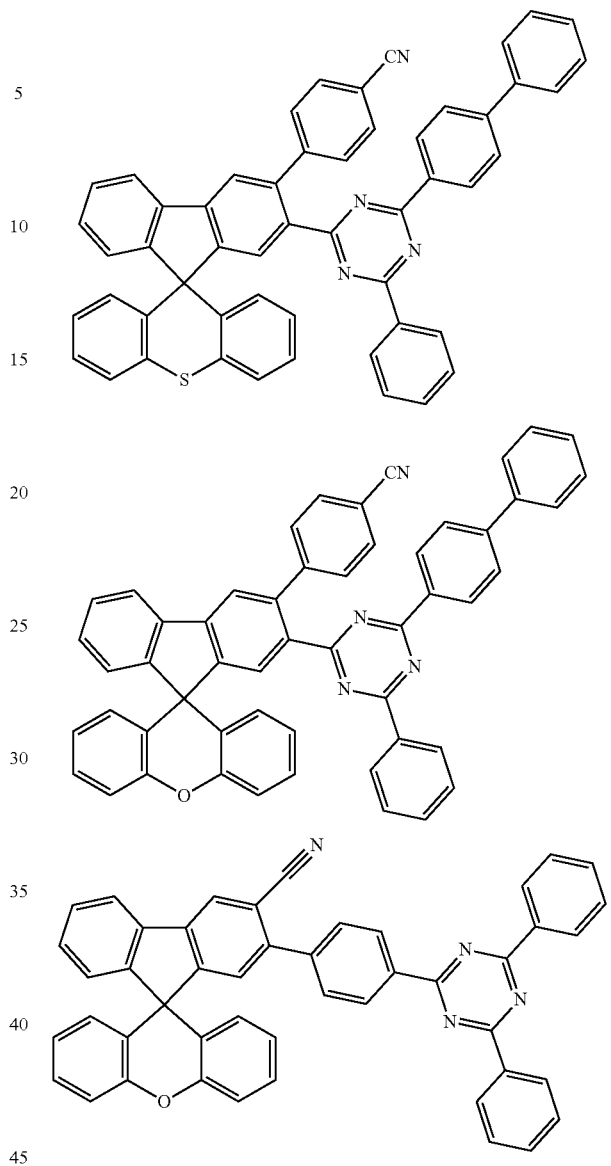

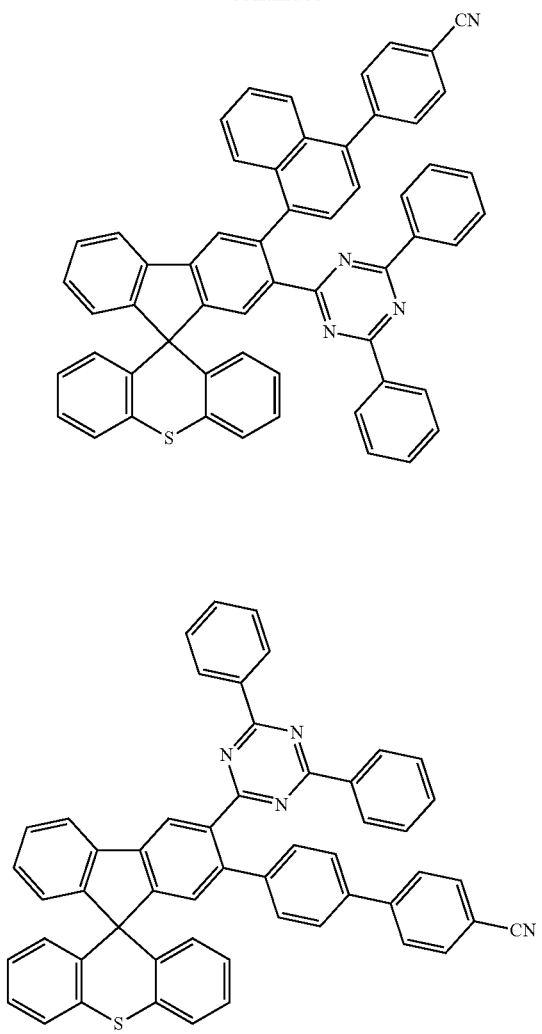

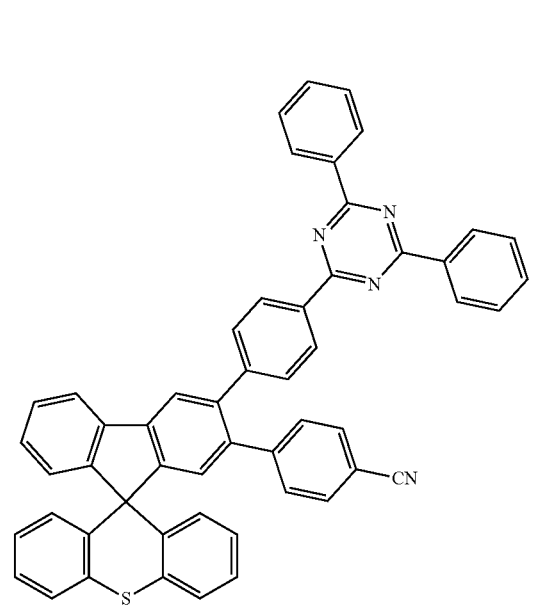

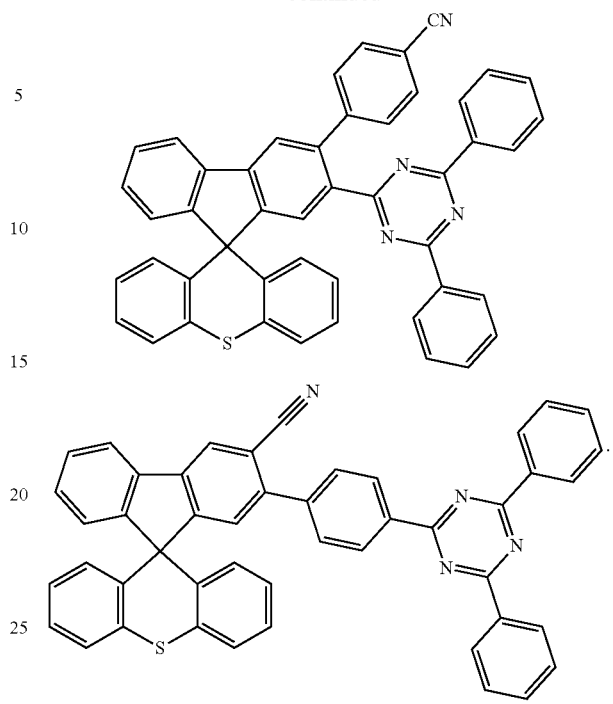

According to one embodiment of the present specification, the compound of Chemical Formula 1 can be prepared using a method of consecutively going through the following Reaction Formula 1, Reaction Formula 2 and Reaction Formula 3. The method for preparing the compound by the following Reaction Formulae 1 to 3 illustrates a preparation method according to one embodiment of the compound of Chemical Formula 1, and positions of substitution of the substituents can vary depending on the compound structure. A more specified preparation method will be described in the following examples.

[Reaction Formula 1]

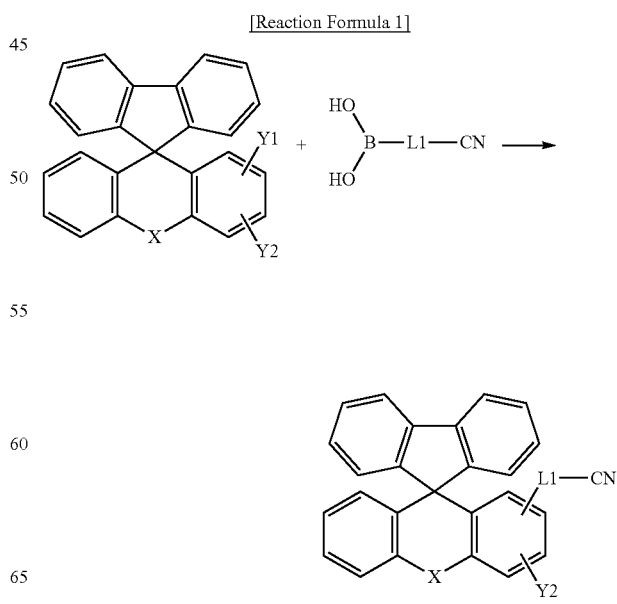

-continued
[Reaction Formula 2]

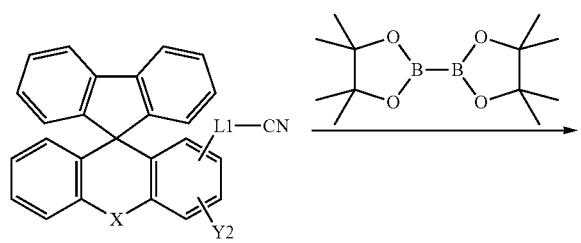

[Reaction Formula 3]

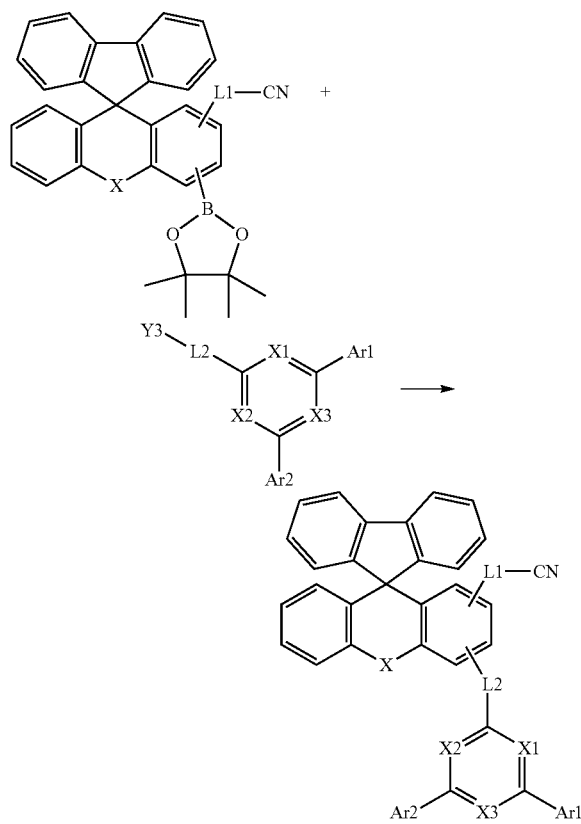

In Reaction Formulae 1 to 3:

X1, X2, X3, L1, L2, Ar1, Ar2 and X have the same definitions as in Chemical Formula 1; and Y1 to Y3 are the same as or different from each other, and each independently is a halogen group.

In addition, the present specification provides an organic light emitting device comprising the compound of Chemical Formula 1.

One embodiment of the present specification provides an organic light emitting device comprising a first electrode, a second electrode, and one or more organic material layers provided between the first electrode and the second electrode, wherein the organic material layer comprises the compound of Chemical Formula 1 described above.

One embodiment of the present specification provides an organic light emitting device comprising a first electrode, a second electrode, and one or more organic material layers provided between the first electrode and the second electrode, wherein the compound described above is included in the organic material layer provided between the first electrode and the second electrode.

One embodiment of the present specification provides an organic light emitting device comprising a first electrode, a second electrode, a light emitting layer provided between the first electrode and the second electrode, and one or more organic material layers provided between the first electrode and the light emitting layer, wherein the compound described above is included in the organic material layer provided between the first electrode and the light emitting layer.

One embodiment of the present specification provides an organic light emitting device comprising an anode, a cathode, a light emitting layer provided between the anode and the cathode, and an organic material layer provided between the anode and the light emitting layer, wherein the compound described above is included in the organic material layer provided between the anode and the light emitting layer.

The organic material layer of the organic light emitting device of the present specification can be formed in a single layer structure, but can also be formed in a multilayer structure in which two or more organic material layers are laminated. For example, the organic light emitting device of the present disclosure can have a structure comprising a hole injection layer, a hole transfer layer, a light emitting layer, an electron transfer layer, an electron injection layer and the like as the organic material layer. However, the structure of the organic light emitting device is not limited thereto, and can include a larger number of organic layers.

In one embodiment of the present specification, the one or more organic material layers comprise at least one of an electron injection layer, an electron transfer layer, a layer carrying out electron injection and transfer at the same time, and an electron control layer, and the compound of Chemical Formula 1 is included in at least one of the electron injection layer, the electron transfer layer, the layer carrying out electron injection and transfer at the same time, and the electron control layer.

In one embodiment of the present specification, the organic material layer comprises a light emitting layer, and the compound is included in the light emitting layer.

In one embodiment of the present specification, the organic material layer comprises a light emitting layer, and the compound is included in the light emitting layer as a host.

In one embodiment of the present specification, the light emitting layer further comprises a dopant.

In one embodiment of the present specification, the compound of Chemical Formula 1 is included in 5 parts by weight to 90 parts by weight based on the total weight 100 parts by weight of the light emitting layer.

In one embodiment of the present specification, the organic material layer includes at least one of a hole injection layer, a hole transfer layer, a hole control layer and a layer carrying out hole transfer and injection at the same time, and the compound of Chemical Formula 1 is included in at least one of the hole injection layer, the hole transfer layer, the hole control layer, and the layer carrying out hole transfer and injection at the same time.

In one embodiment of the present specification, the organic material layer includes two or more electron transfer layers, and at least one of the two or more electron transfer layers includes the compound of Chemical Formula 1. In one embodiment of the present specification, the compound of Chemical Formula 1 can be included in one of the two or more electron transfer layers, or can be included in each of the two or more electron transfer layers.

In addition, when the compound of Chemical Formula 1 is included in each of the two or more electron transfer layers in one embodiment of the present specification, materials other than the compound of Chemical Formula 1 can be the same as or different from each other.

In another embodiment, the organic light emitting device can be an organic light emitting device having a structure in which an anode, one or more organic material layers and a cathode are consecutively laminated on a substrate (normal type).

In another embodiment, the organic light emitting device can be an organic light emitting device having a structure in a reverse direction in which a cathode, one or more organic material layers and an anode are consecutively laminated on a substrate (inverted type).

In one embodiment of the present specification, the first electrode is an anode, and the second electrode is a cathode.

In another embodiment, the first electrode is a cathode, and the second electrode is an anode.

The organic light emitting device according to one embodiment of the present specification can have structures as illustrated in FIGS. 1 to 3.

FIG. 1 illustrates an example of the organic light emitting device formed with a substrate (1), an anode (2), a light emitting layer (6) and a cathode (10). In one embodiment, the compound of Chemical Formula 1 is included in the light emitting layer.

FIG. 2 illustrates an example of the organic light emitting device formed with a substrate (1), an anode (2), a light emitting layer (6), an electron control layer (7), an electron transfer layer (8), an electron injection layer (9) and a cathode (10).

FIG. 3 illustrates an example of the organic light emitting device formed with a substrate (1), an anode (2), a hole injection layer (3), a hole transfer layer (4), a hole control layer (5), a light emitting layer (6), an electron control layer (7), an electron transfer layer (8), an electron injection layer (9) and a cathode (10).

In FIG. 2 and FIG. 3, the compound of Chemical Formula 1 is included in one or more layers of the light emitting layer (6), the electron control layer (7), the electron transfer layer (8) and the electron injection layer (9). In one embodiment, the compound of Chemical Formula 1 is preferably included in one or more layers of the light emitting layer (6) and the electron transfer layer (8).

In one embodiment of the present specification, the organic material layer can comprise two or more hole transfer layers. In this case, materials of the two or more hole transfer layers are the same as or different from each other.

The organic light emitting device of the present specification can be manufactured using materials and methods known in the art, except that the organic material layer comprises the compound of Chemical Formula 1.

When the organic light emitting device comprises a plurality of organic material layers, the organic material layers can be formed with materials the same as or different from each other.

For example, the organic light emitting device of the present specification can be manufactured by consecutively laminating a first electrode, an organic material layer and a second electrode on a substrate. Herein, the organic light emitting device can be manufactured by forming an anode on a substrate by depositing a metal, a metal oxide having conductivity, or an alloy thereof using a physical vapor deposition (PVD) method such as sputtering or e-beam evaporation, forming an organic material layer including a hole injection layer, a hole transfer layer, a light emitting layer and an electron transfer layer thereon, and then depositing a material capable of being used as a cathode thereon. In addition to such a method, the organic light emitting device can also be manufactured by consecutively depositing a cathode material, an organic material layer and an anode material on a substrate.

In addition, the compound of Chemical Formula 1 can be formed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

In addition to such a method, the organic light emitting device can also be manufactured by consecutively laminating a cathode material, an organic material layer and an anode material on a substrate. However, the manufacturing method is not limited thereto.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2/Al$, and the like, but are not limited thereto.

The hole injection layer is a layer that injects holes transferred from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suited. Specific examples thereof include arylamine-based organic materials, conductive polymers, block copolymers having conjugated parts and non-conjugated parts together, and the like, but are not limited thereto.

The hole control layer is a layer controlling performance of the whole device by preventing electrons from flowing into an anode from a light emitting layer and controlling a flow of holes flowing into a light emitting layer. The hole control material is preferably a compound having abilities of preventing electrons from flowing into an anode from a light emitting layer, and controlling a flow of holes injected to a light emitting layer or a light emitting material.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxy-quinoline aluminum complexes ($Alq_3$); carbazole-based compounds; dimerized styryl compounds; BAlq; 10-hydroxybenzoquinoline-metal compounds; benzoxazole-, benzothiazole- and benzimidazole-based compounds; poly(p-phenylenevinylene) (PPV)-based polymers; spiro compounds; polyfluorene, rubrene, and the like, but are not limited thereto.

The light emitting layer can include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, however, the material is not limited thereto.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamine group and includes arylamine group-including pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamine group are substituted or unsubstituted. Specifically, styrylamine, styryldiamine, styryltriamine, styryltetramine or the like is included, however, the styrylamine compound is not limited thereto. In addition, the metal complex includes iridium complexes, platinum complexes or the like, but is not limited thereto.

The electron control layer is a layer controlling performance of the whole device by preventing holes from flowing into a cathode from a light emitting layer and controlling a flow of electrons flowing into a light emitting layer. The electron control material is preferably a compound having abilities of preventing holes from flowing into a cathode from a light emitting layer, and controlling a flow of electrons injected to a light emitting layer or a light emitting material. As the electron control material, proper materials can be used depending on the constitution of organic material layers used in the device. The electron control layer is located between a light emitting layer and a cathode, and is preferably provided directly in contact with a light emitting layer.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suited. Specific examples thereof include Al complexes of 8-hydroxyquinoline, complexes including $Alq_3$, organic radical compounds, hydroxyflavon-metal complexes, and the like, but are not limited thereto. The electron transfer layer can be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition thereto, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited there.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)berylium, bis(10-hydroxybenzo[h]quinolinato)zinc, bis(2-methyl-8-quinolinato)-chlorogallium, bis(2-methyl-8-quinolinato)(o-cresolato)-gallium, bis(2-methyl-8-quinolinato) (1-naphtholato)aluminum, bis(2-methyl-8-quinolinato) (2-naphtholato)gallium and the like, but is not limited thereto.

The organic light emitting device according to the present specification can be a top-emission type, a bottom-emission type or a dual-emission type depending on the materials used.

Hereinafter, preparation methods and characteristics of the compound of the present disclosure and the organic light emitting device including the same will be described in order to illuminate the present disclosure in detail.

Example 1 (E1)

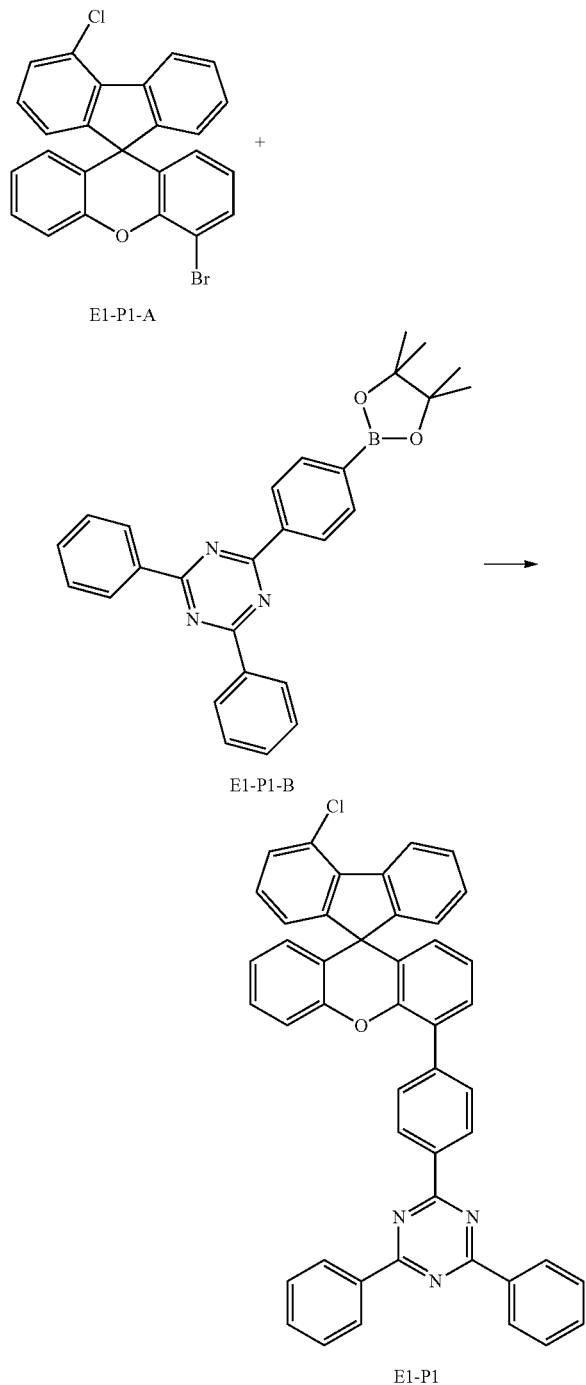

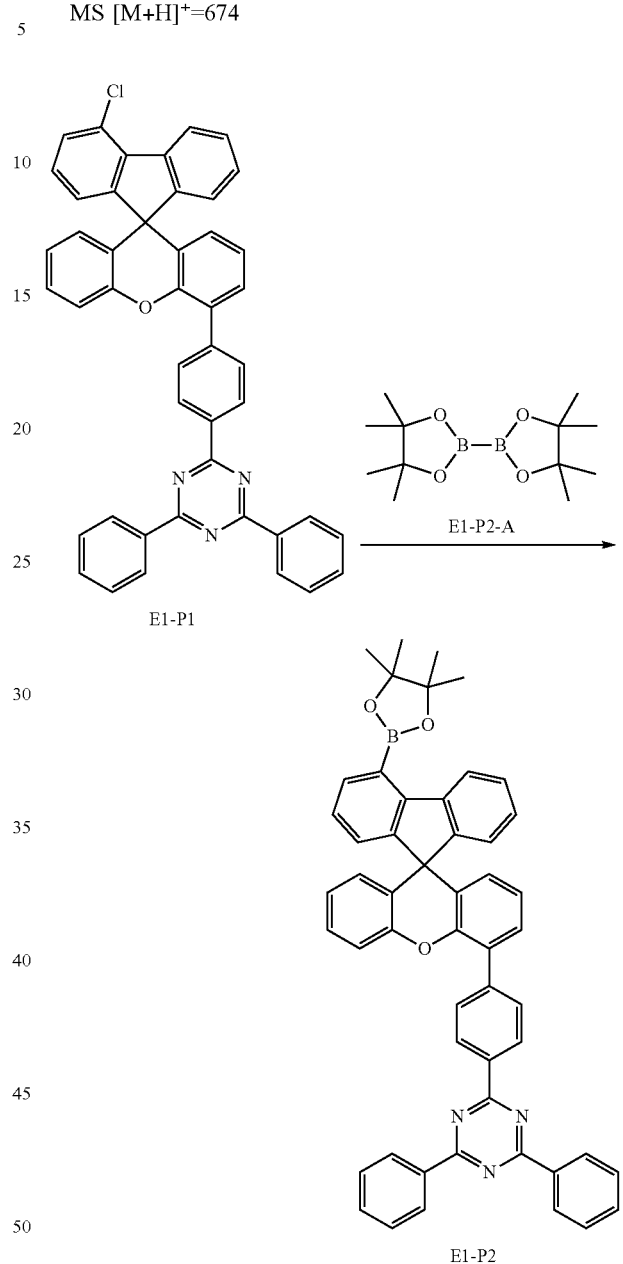

After completely dissolving a compound of Chemical Formula E1-P1-A (10 g, 22.4 mmol) and a compound of Chemical Formula E1-P1-B (9.8 g, 22.4 mmol) in THF (100 mL), potassium carbonate (9.3 g, 67.3 mmol) dissolved in water (40 mL) was added thereto. After introducing tetrakistriphenyl-phosphino palladium (0.8 g, 0.67 mmol) thereto, the result was stirred for 8 hours while heating. After lowering the temperature to room temperature and terminating the reaction, the potassium carbonate solution was removed to filter white solids. The filtered white solids were washed twice each with THF and ethyl acetate to prepare a compound of Chemical Formula E1-P1 (13.5 g, yield 89%).

MS [M+H]$^+$=674

After completely dissolving the compound of Chemical Formula E1-P1 (10 g, 14.8 mmol) and a compound of Chemical Formula E1-P2-A (4.1 g, 16.3 mmol) in dioxane (100 mL), potassium acetate (8.6 g, 87.8 mmol) was added thereto, and the result was stirred while heating. After lowering the temperature to room temperature and terminating the reaction, the potassium carbonate solution was removed and filtered to remove the potassium acetate. The filtered solution was solidified with ethanol and filtered. White solids were washed twice each with ethanol to prepare a compound of Chemical Formula E1-P2 (10.2 g, yield 90%).

MS [M+H]$^+$=766

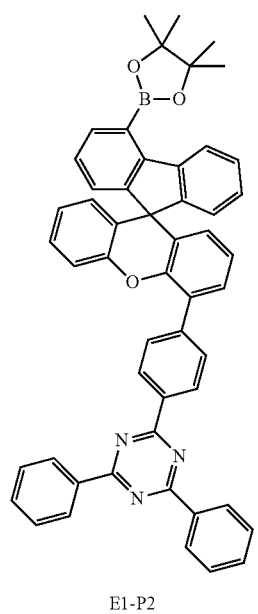

E1-P2

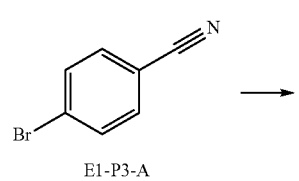

E1-P3-A

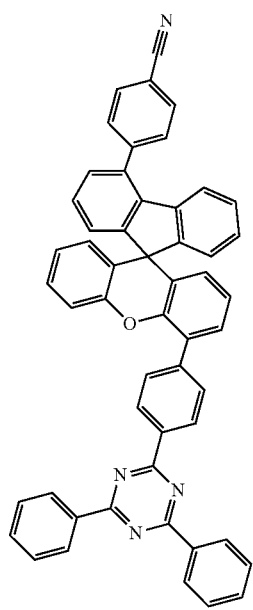

E1 istriphenyl-phosphino palladium (0.5 g, 0.392 mmol) thereto, the result was stirred for 8 hours while heating. After lowering the temperature to room temperature and terminating the reaction, the potassium carbonate solution was removed to filter white solids. The filtered white solids were washed twice each with THF and ethyl acetate to prepare a compound of Chemical Formula E1 (6.8 g, yield 70%).

MS [M+H]$^+$=741

Example 2 (E2)

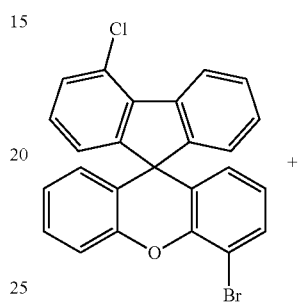

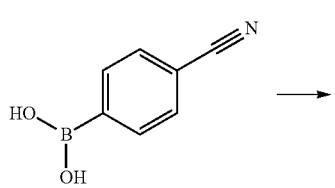

E2-P1

After completely dissolving the compound of Chemical Formula E1-P2 (10 g, 13.1 mmol) and a compound of Chemical Formula E1-P3-A (2.4 g, 13.1 mmol) in THF (100 mL), potassium carbonate (5.4 g, 39.2 mmol) dissolved in water (40 mL) was added thereto. After introducing tetrak- A compound of Chemical Formula E2-P1 was prepared in the same manner as in the preparation method of E1-P1 of Example 1 except that each starting material was employed as in the reaction formula shown above.

MS [M+H]$^+$=468

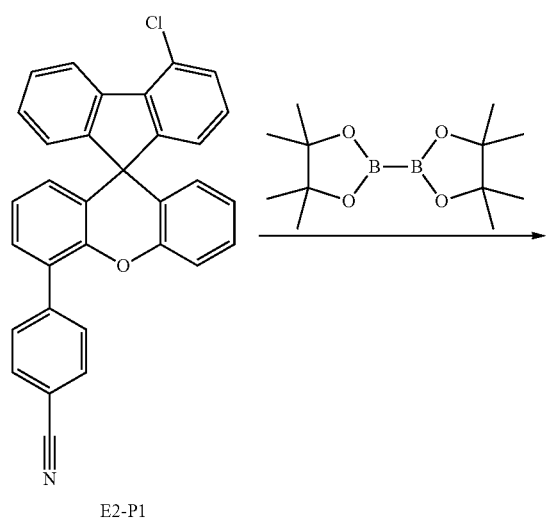

E2-P1

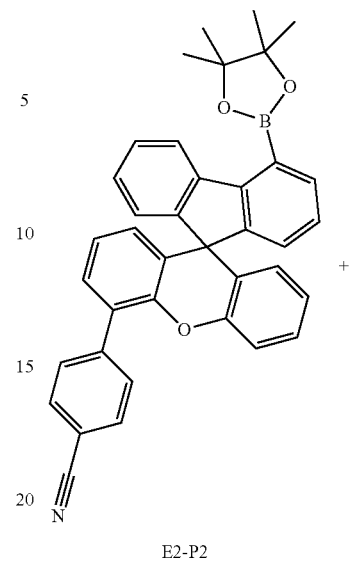

E2-P2

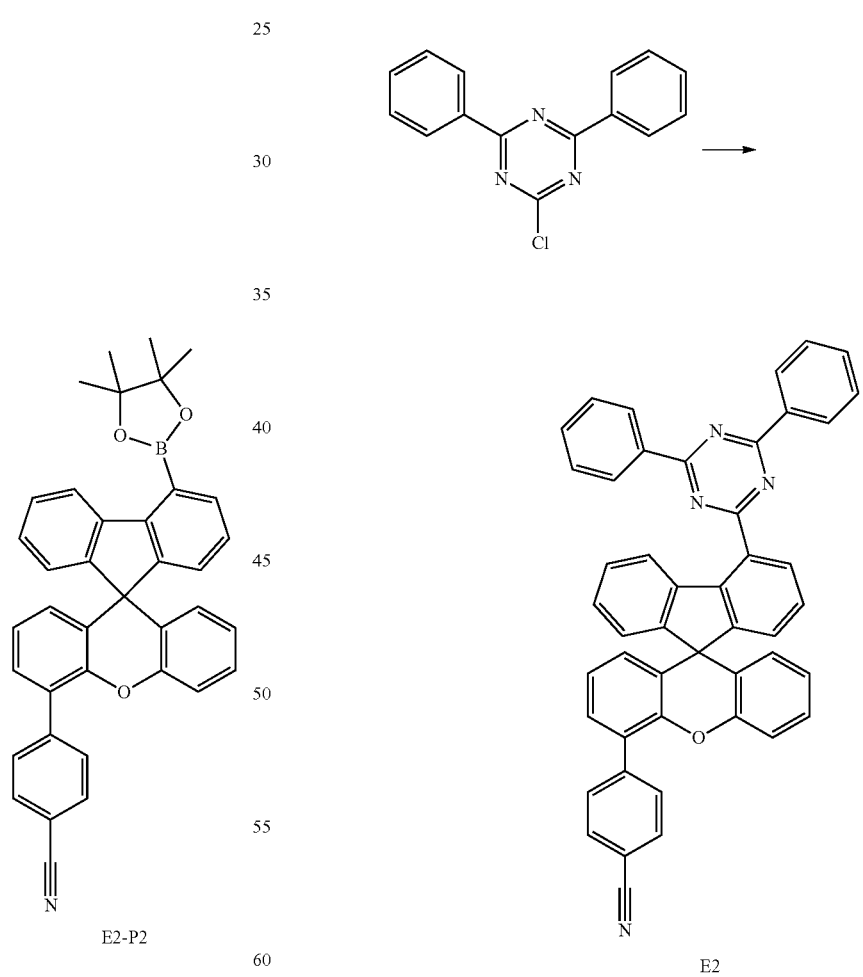

E2-P2

E2

A compound of Chemical Formula E2-P2 was prepared in the same manner as in the preparation method of E1-P2 of Example 1 except that each starting material was employed as in the reaction formula shown above.

MS [M+H]$^+$=560

A compound of Chemical Formula E2 was prepared in the same manner as in the preparation method of E1 of Example 1 except that each starting material was employed as in the reaction formula shown above.

MS [M+H]$^+$=665

Example 3 (E3)

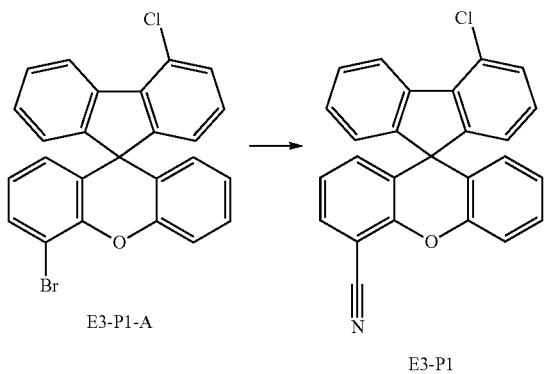 [SMILES: Clc1cccc2c1-c1ccccc1C21c2ccccc2Oc2c(Br)cccc21 ; N#Cc1cccc2c1Oc1ccccc1C21c2ccccc2-c2c(Cl)cccc21]

E3-P1-A → E3-P1

After completely dissolving a compound of Chemical Formula E3-P1-A (20 g, 44.9 mmol) and a zinc cyanide compound (2.6 g, 22.4 mmol) in dimethylacetamide (200 mL), tetrakistriphenyl-phosphino palladium (1.6 g, 1.34 mmol) was introduced thereto, and the result was stirred for 2 hours while heating. After lowering the temperature to room temperature and terminating the reaction, water (200 ml) was introduced thereto, and white solids were filtered. The filtered white solids were washed twice each with ethanol and water to prepare a compound of Chemical Formula E3-P1 (14.1 g, yield 80%).

MS $[M+H]^+$=392

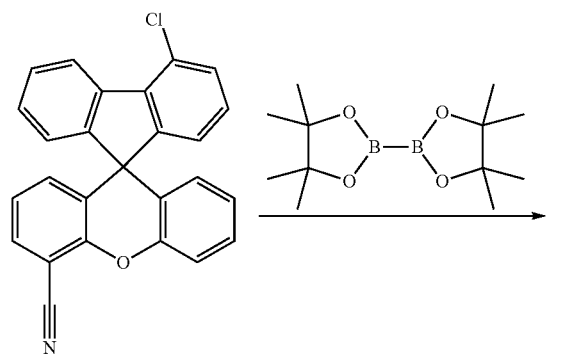

E3-P1 → E3-P2

A compound of Chemical Formula E3-P2 was prepared in the same manner as in the preparation method of E1-P2 of Example 1 except that each starting material was employed as in the reaction formula shown above.

MS $[M+H]^+$=484

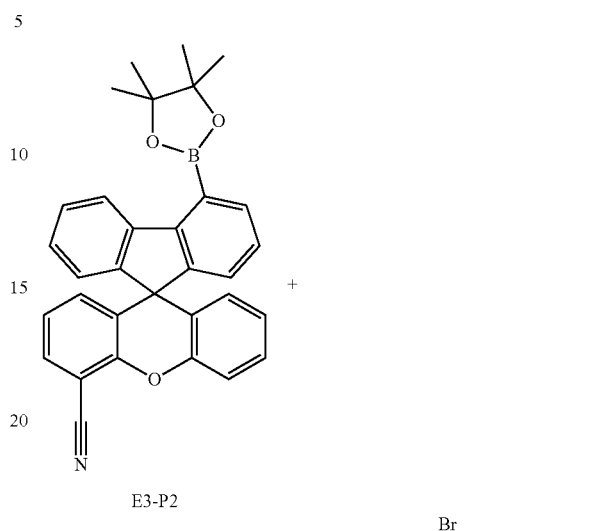

E3-P2

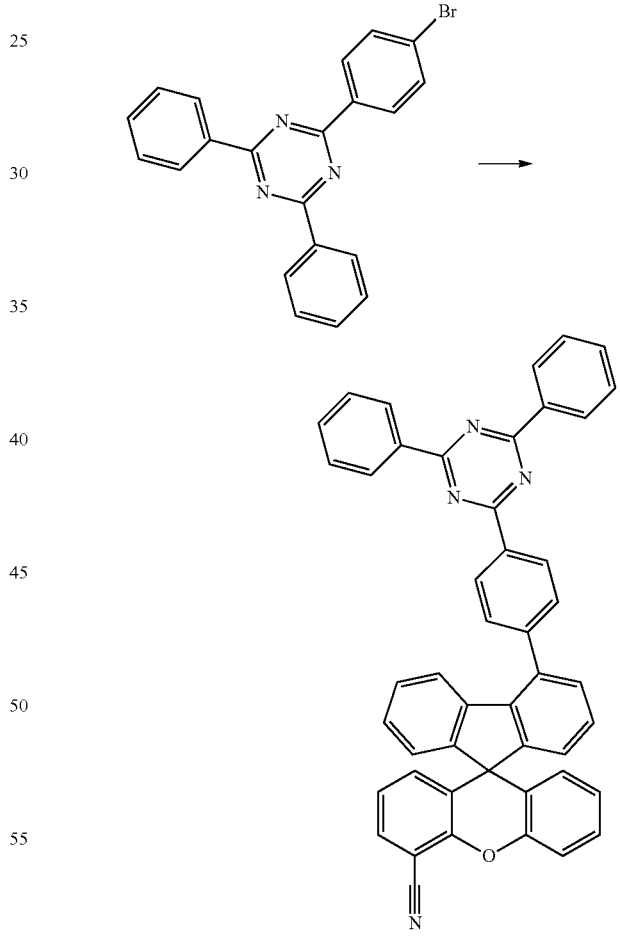

E3

A compound of Chemical Formula E3 was prepared in the same manner as in the preparation method of E1 of Example 1 except that each starting material was employed as in the reaction formula shown above.

MS $[M+H]^+$=665

Example 4 (E4)
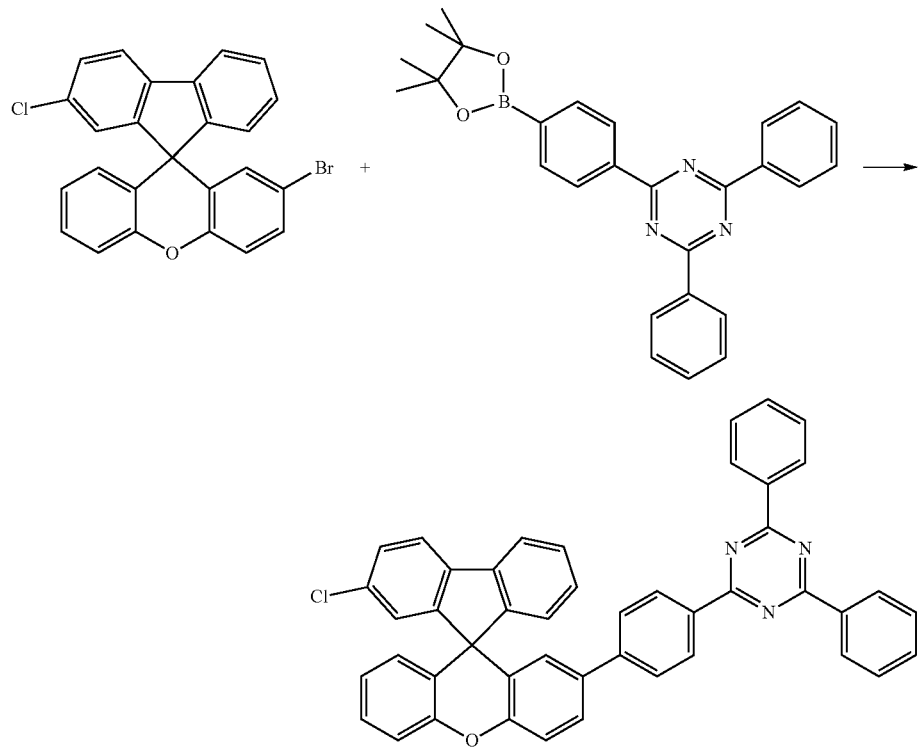
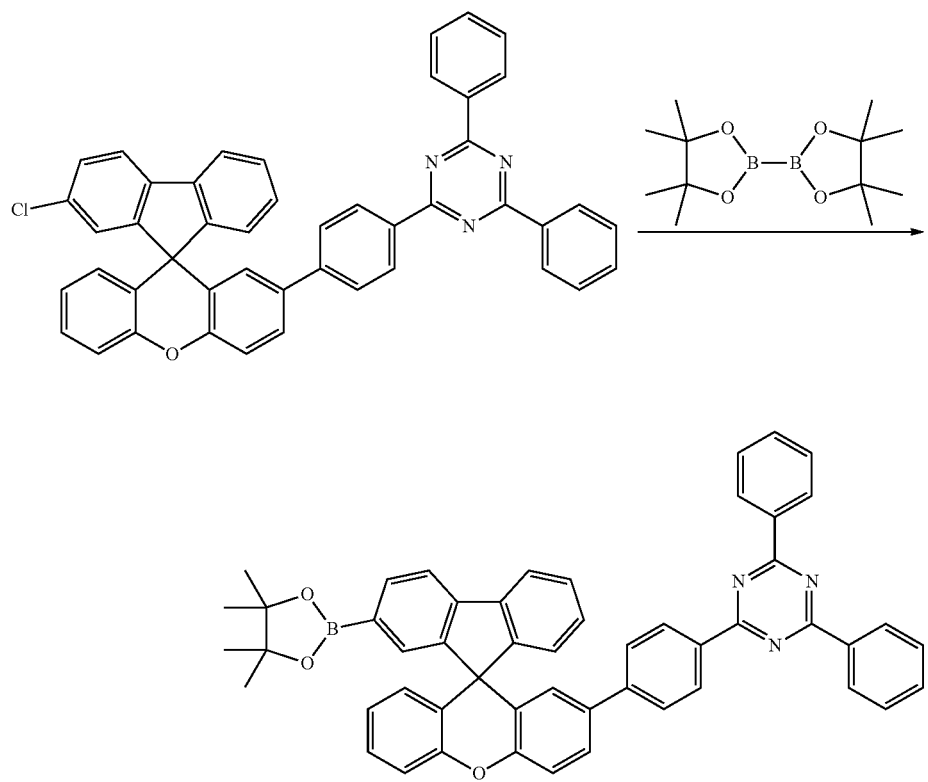

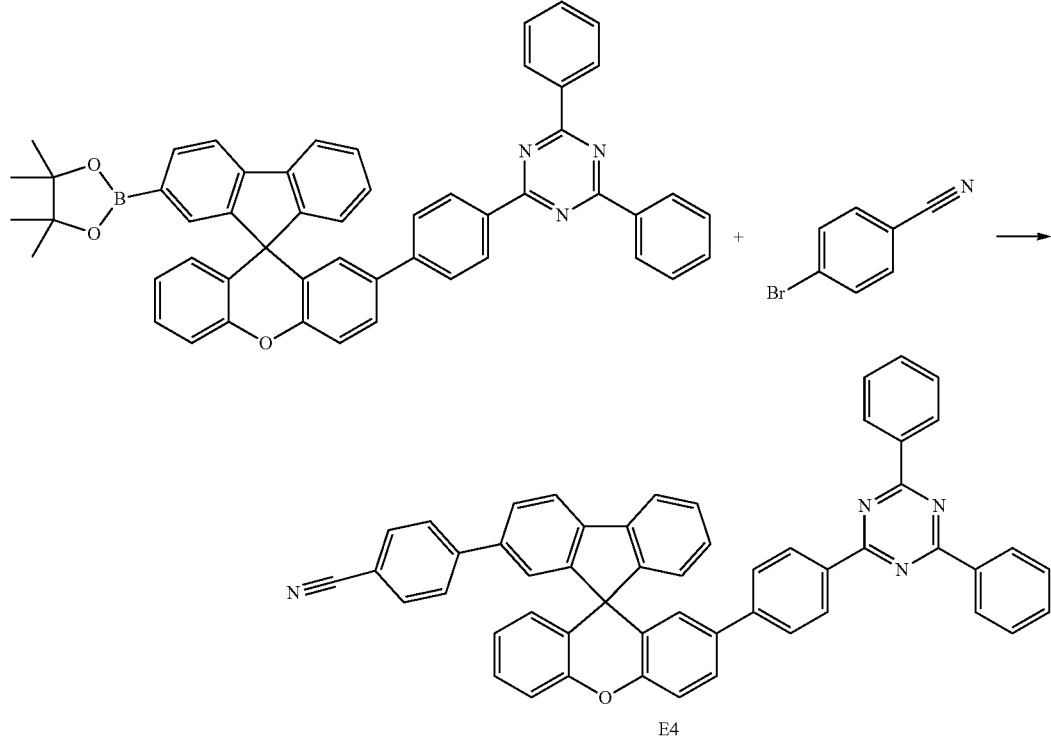
E4
A compound of Chemical Formula E4 was prepared in the same manner as in the preparation method of E1 of Example 1 except that each starting material was employed as in the reaction formula shown above.
MS [M+H]$^+$=741
Example 5 (E5)
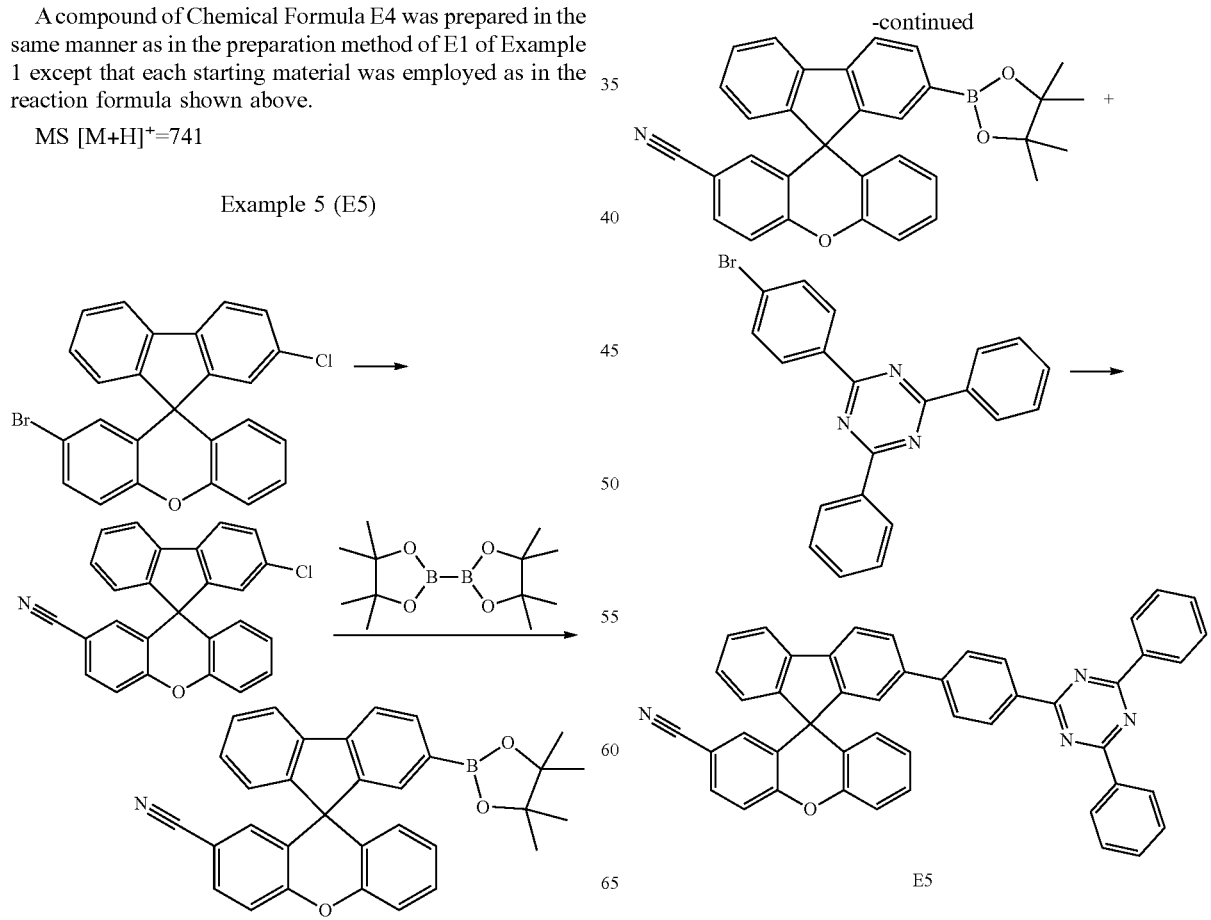
E5

A compound of Chemical Formula E5 was prepared in the same manner as in the preparation method of E3 of Example 3 except that each starting material was employed as in the reaction formula shown above.

MS [M+H]$^+$=665

Example 6 (E6)

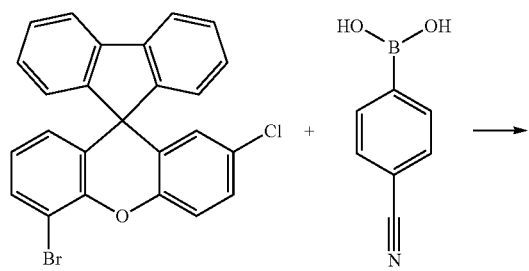

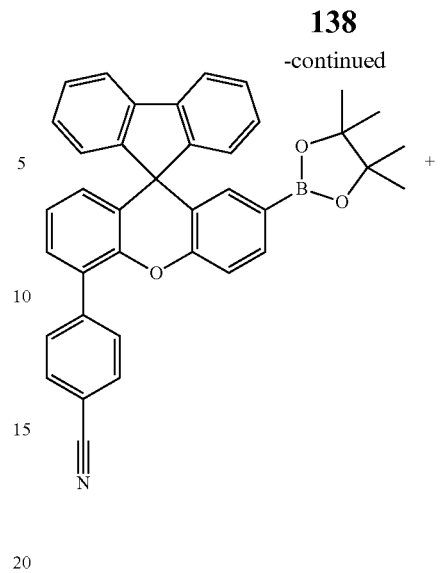

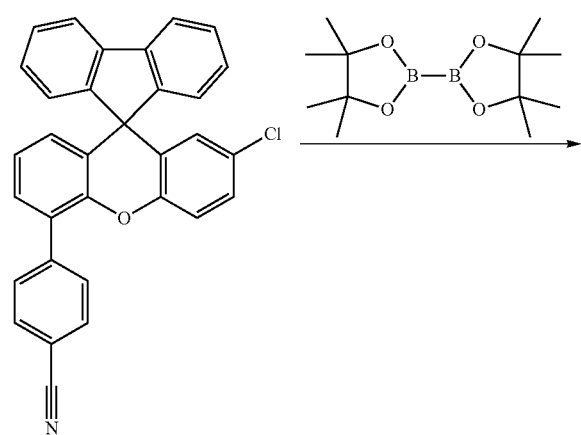

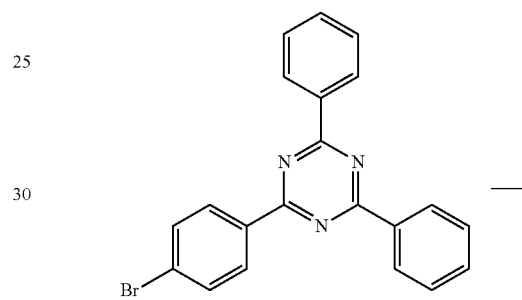

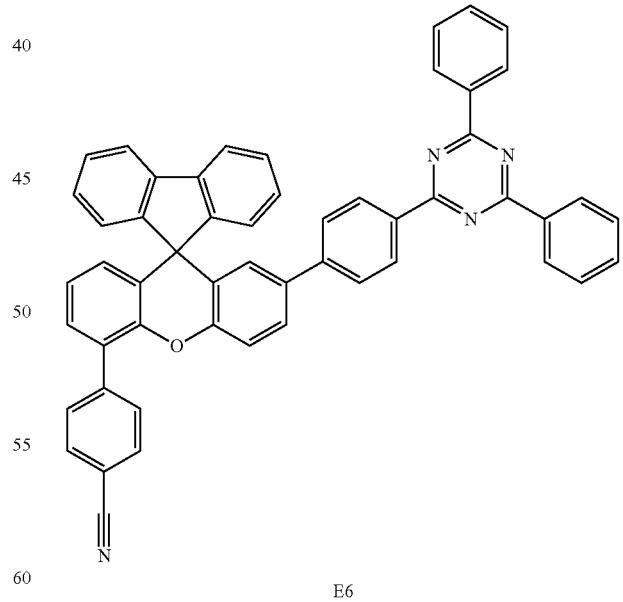

E6

A compound of Chemical Formula E6 was prepared in the same manner as in the preparation method of E1 of Example 1 except that each starting material was employed as in the reaction formula shown above.

MS [M+H]$^+$=741

Example 7 (E7)
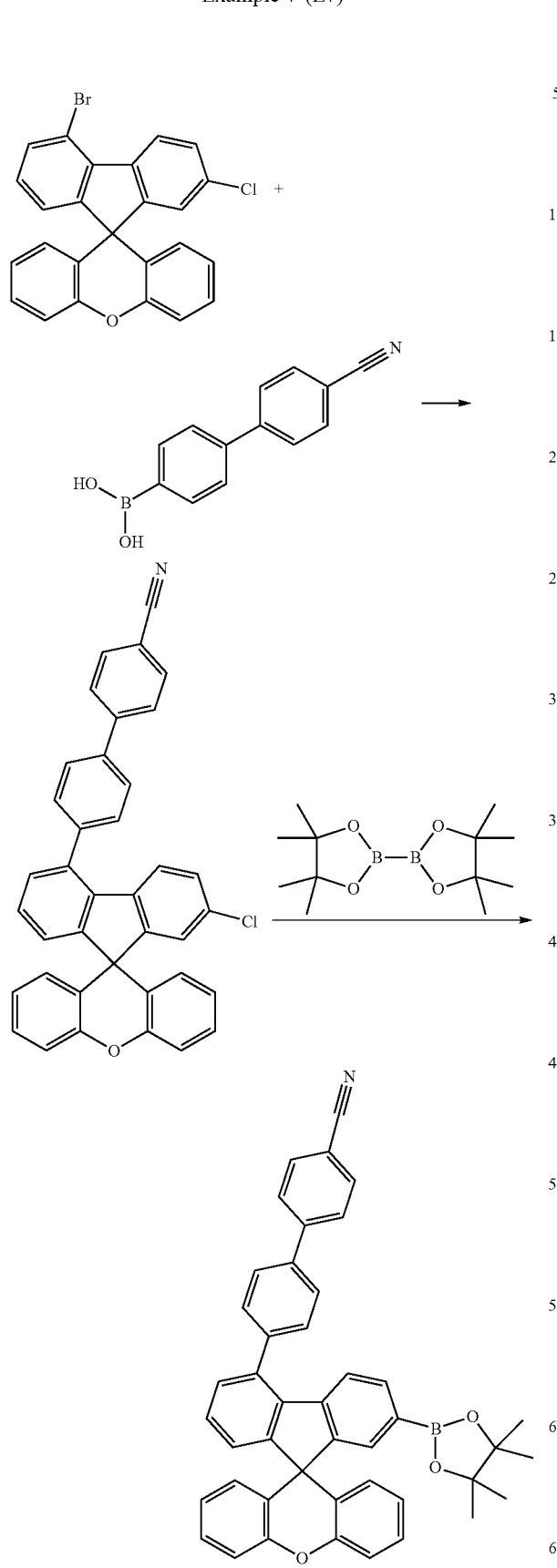
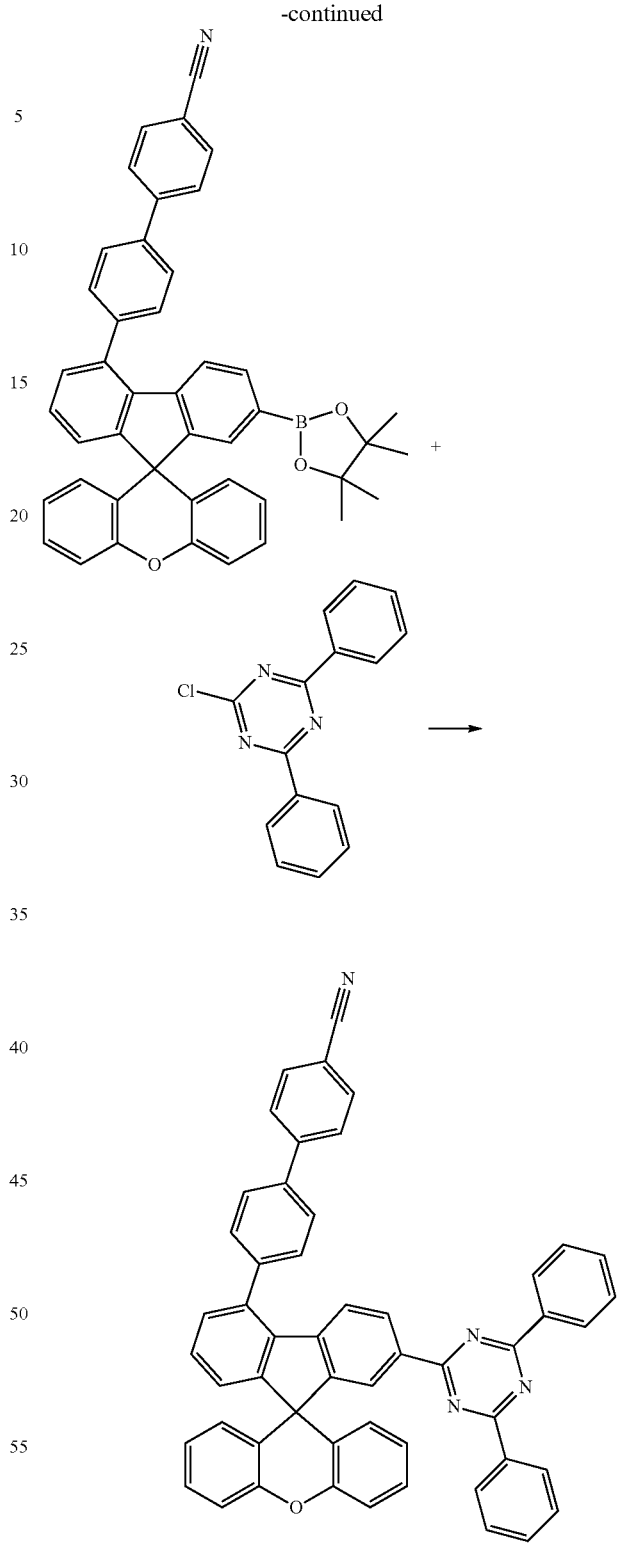
A compound of Chemical Formula E7 was prepared in the same manner as in the preparation method of E1 of Example 1 except that each starting material was employed as in the reaction formula shown above.
MS [M+H]$^+$=741

Example 8 (E8)
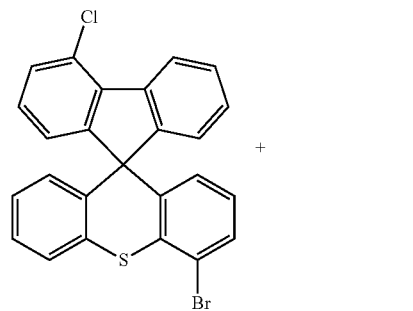
+
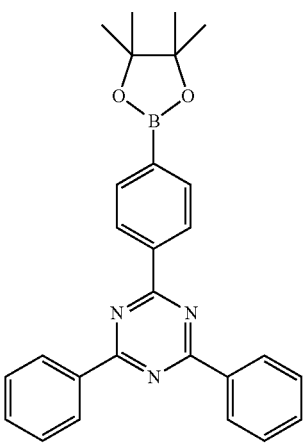
→
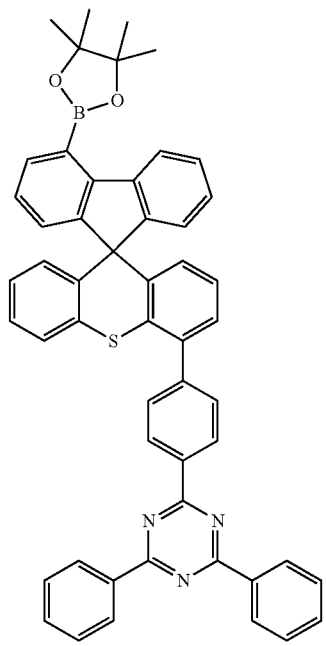 [SMILES: CC1(C)OB(c2cccc3c2-c2ccccc2C32c3ccccc3Sc3c(-c4ccc(-c5nc(-c6ccccc6)nc(-c6ccccc6)n5)cc4)cccc32)OC1(C)C]
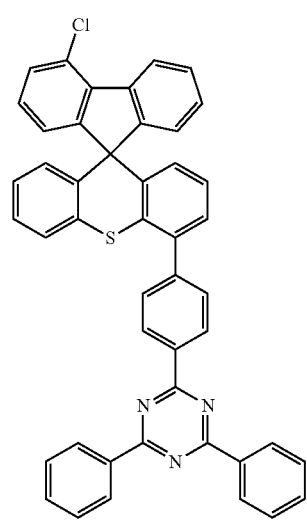 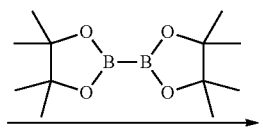 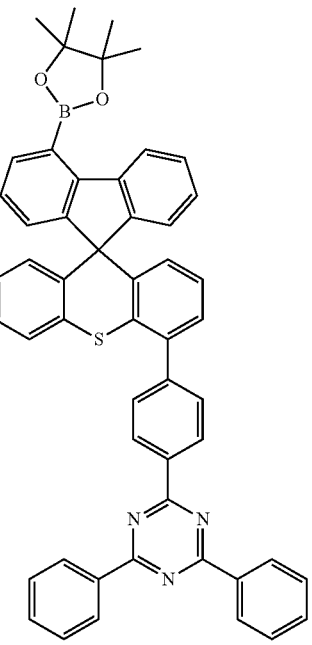
+

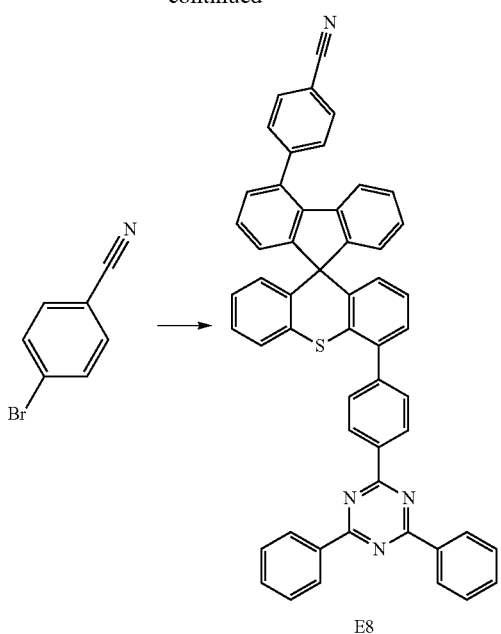
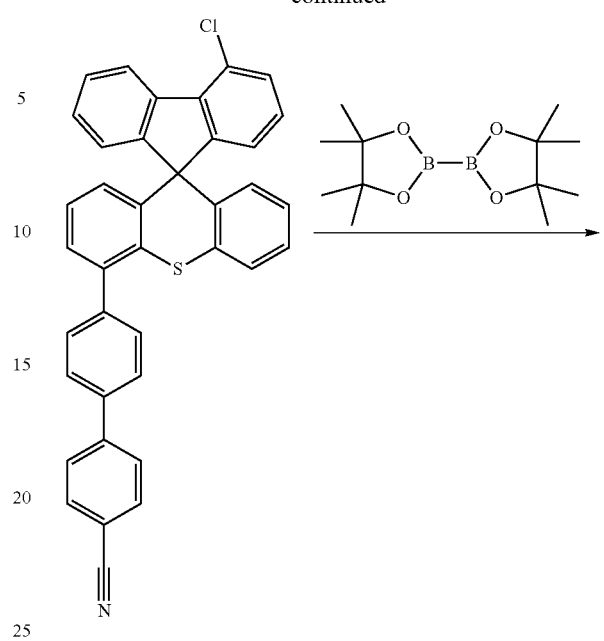
A compound of Chemical Formula E8 was prepared in the same manner as in the preparation method of E1 of Example 1 except that each starting material was employed as in the reaction formula shown above.
MS [M+H]$^+$=757
Example 9 (E9)
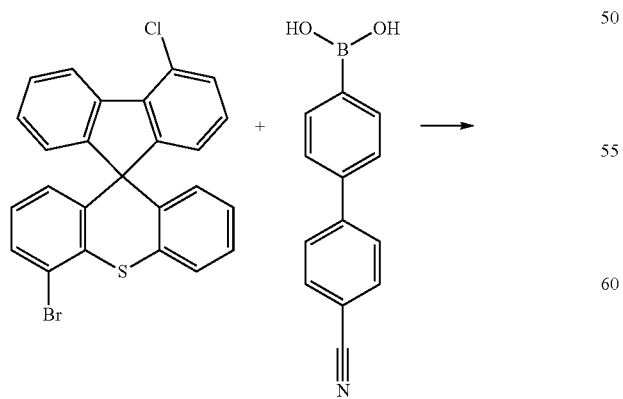
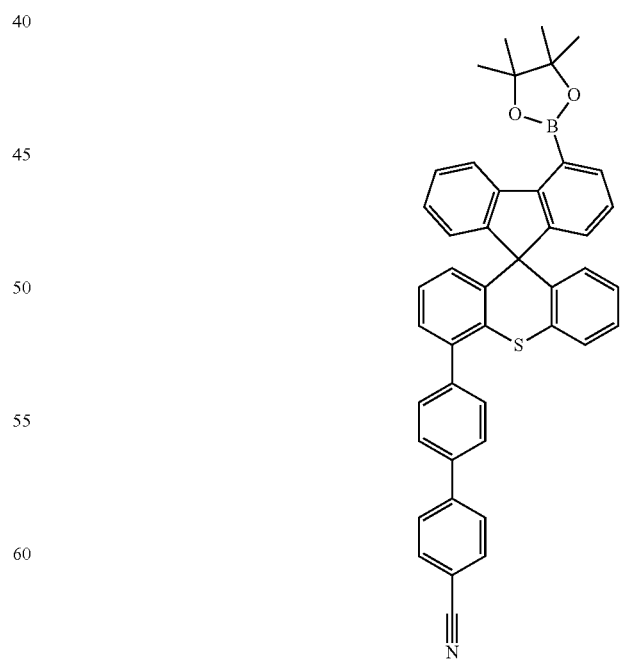

Example 10 (E10)

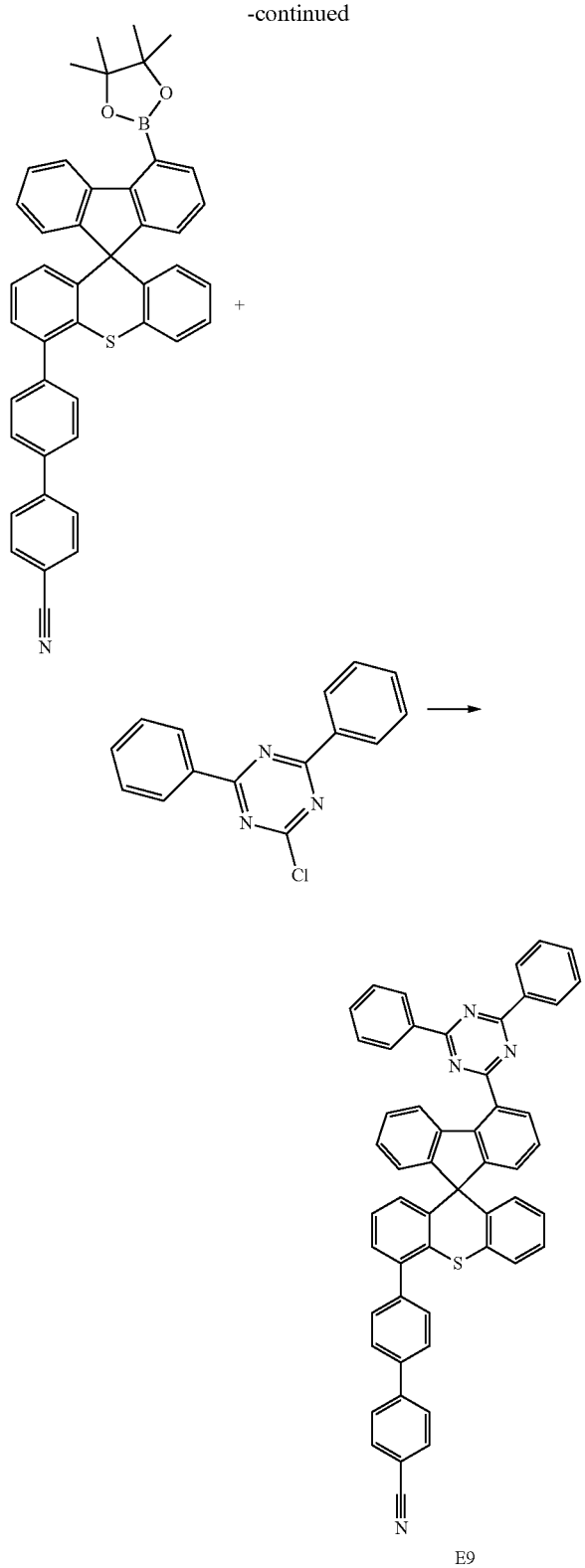

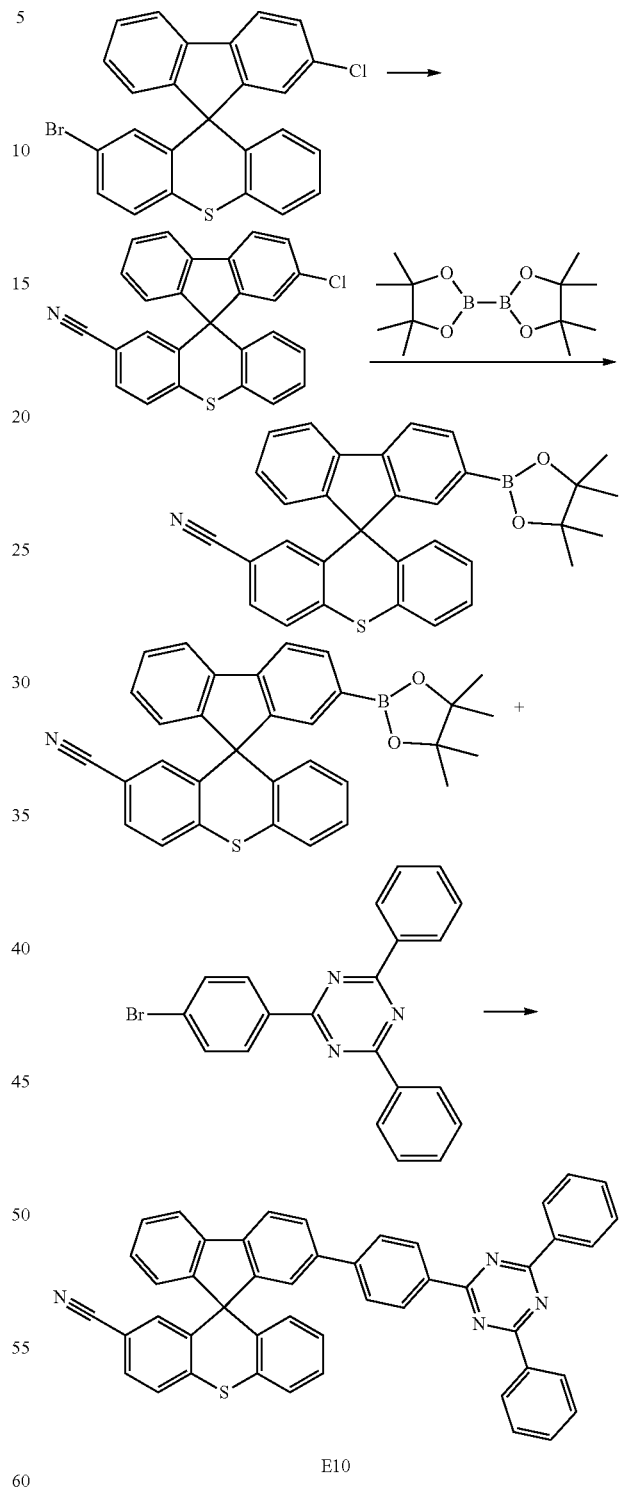

A compound of Chemical Formula E9 was prepared in the same manner as in the preparation method of E1 of Example 1 except that each starting material was employed as in the reaction formula shown above.

MS [M+H]$^+$=757

A compound of Chemical Formula E10 was prepared in the same manner as in the preparation method of E3 of Example 3 except that each starting material was employed as in the reaction formula shown above.

MS [M+H]$^+$=681

Example 11 (E11)
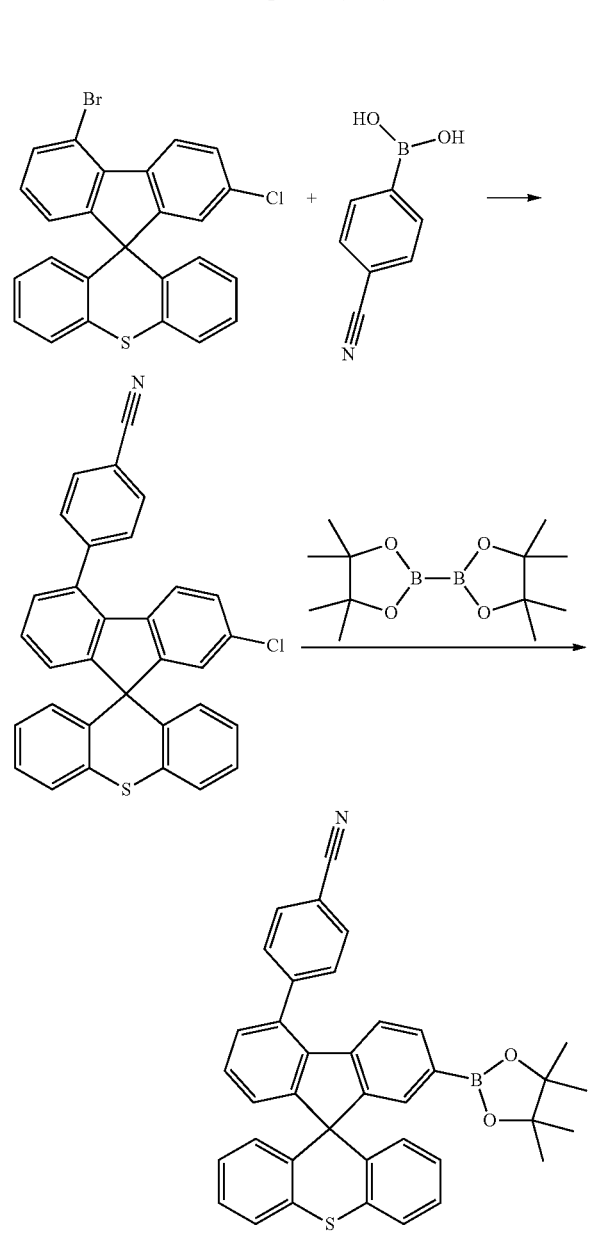
A compound of Chemical Formula E11 was prepared in the same manner as in the preparation method of E1 of Example 1 except that each starting material was employed as in the reaction formula shown above.
MS [M+H]$^+$=681
Example 12 (E12)

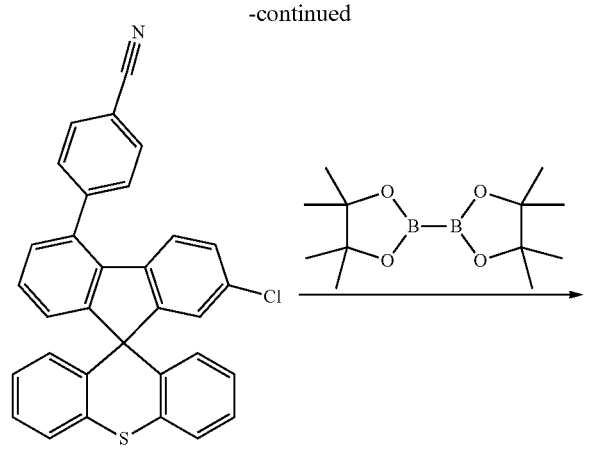
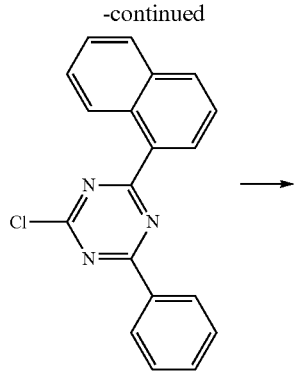
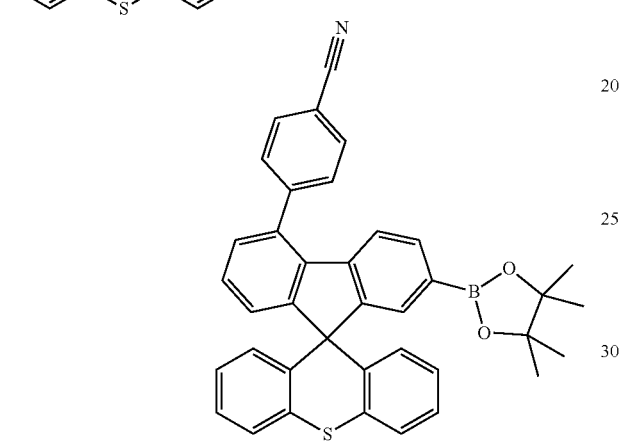
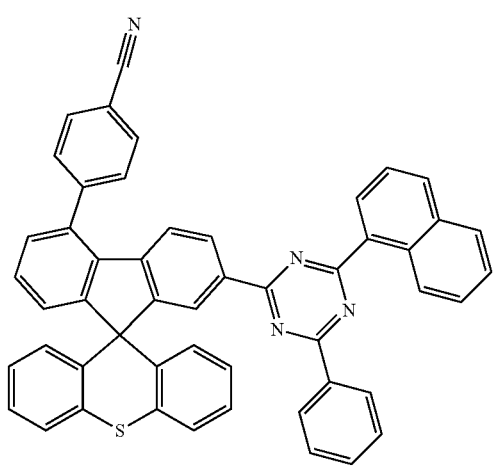
E12
A compound of Chemical Formula E12 was prepared in the same manner as in the preparation method of E1 of Example 1 except that each starting material was employed as in the reaction formula shown above.
MS [M+H]$^+$=731
Example 13 (E13)
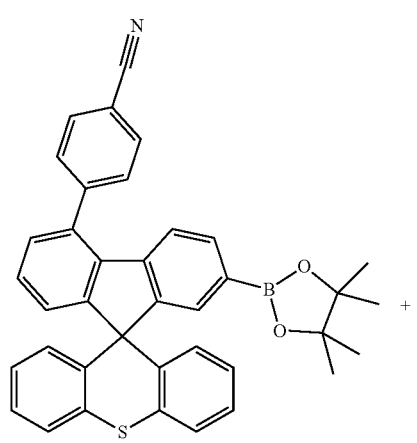
+
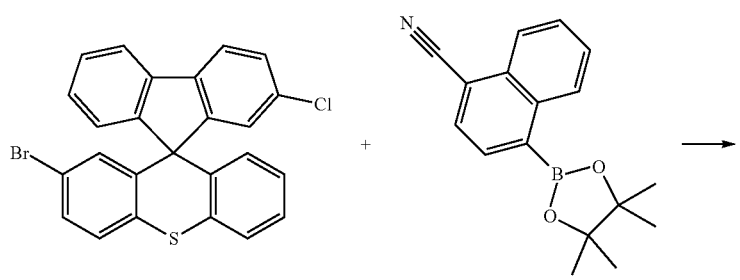

-continued
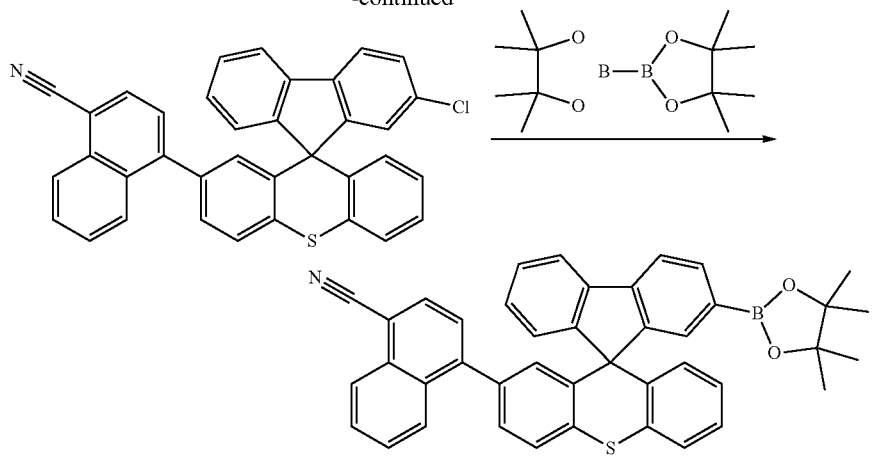
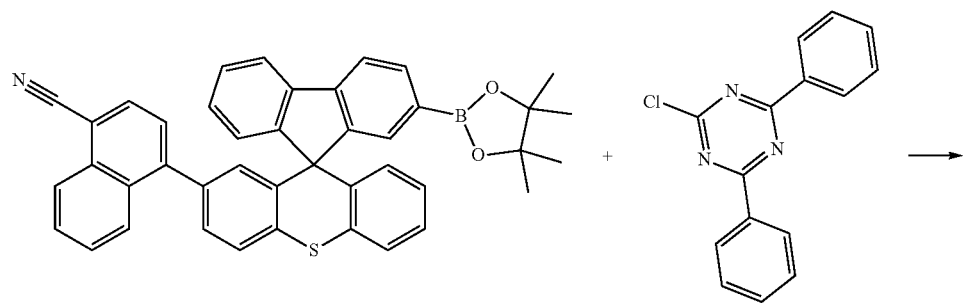
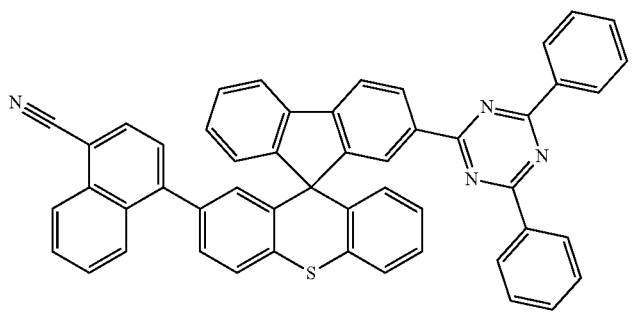
E13
A compound of Chemical Formula E13 was prepared in the same manner as in the preparation method of E1 of Example 1 except that each starting material was employed as in the reaction formula shown above.
MS [M+H]$^+$=731

Example 14 (E14)
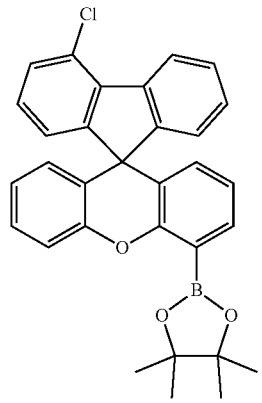
+
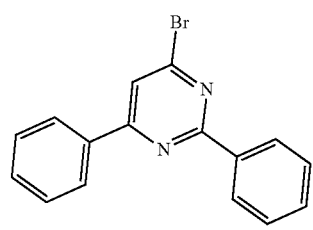
→
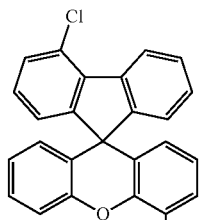
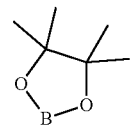
→
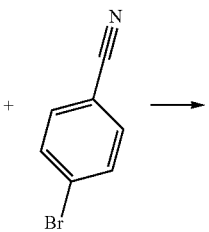
+
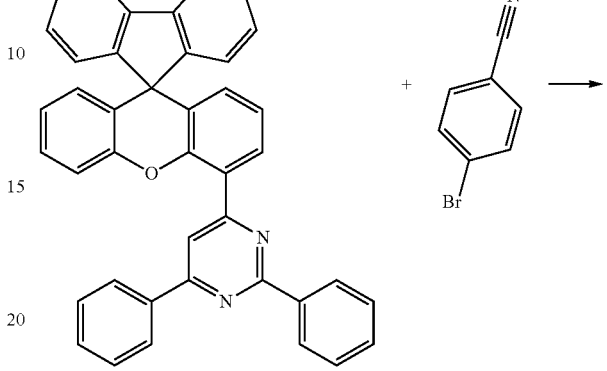
→
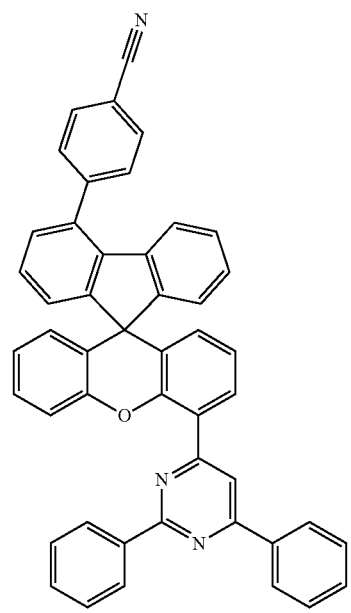
E14
A compound of Chemical Formula E14 was prepared in the same manner as in the preparation method of E1 of Example 1 except that each starting material was employed as in the reaction formula shown above.
MS [M+H]$^+$=664

Example 15 (E15)
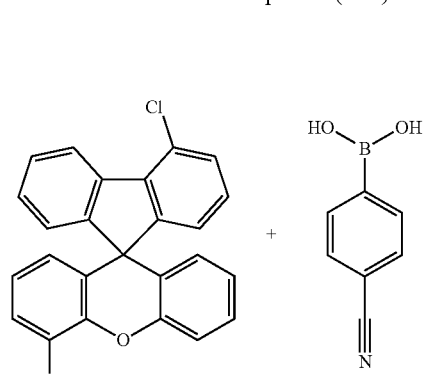
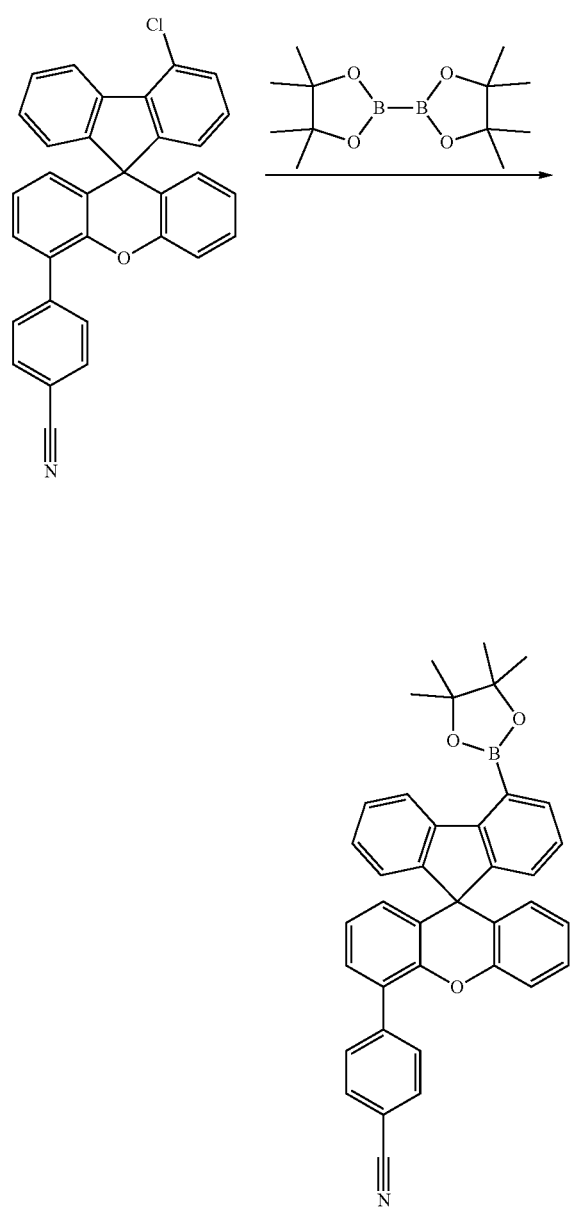
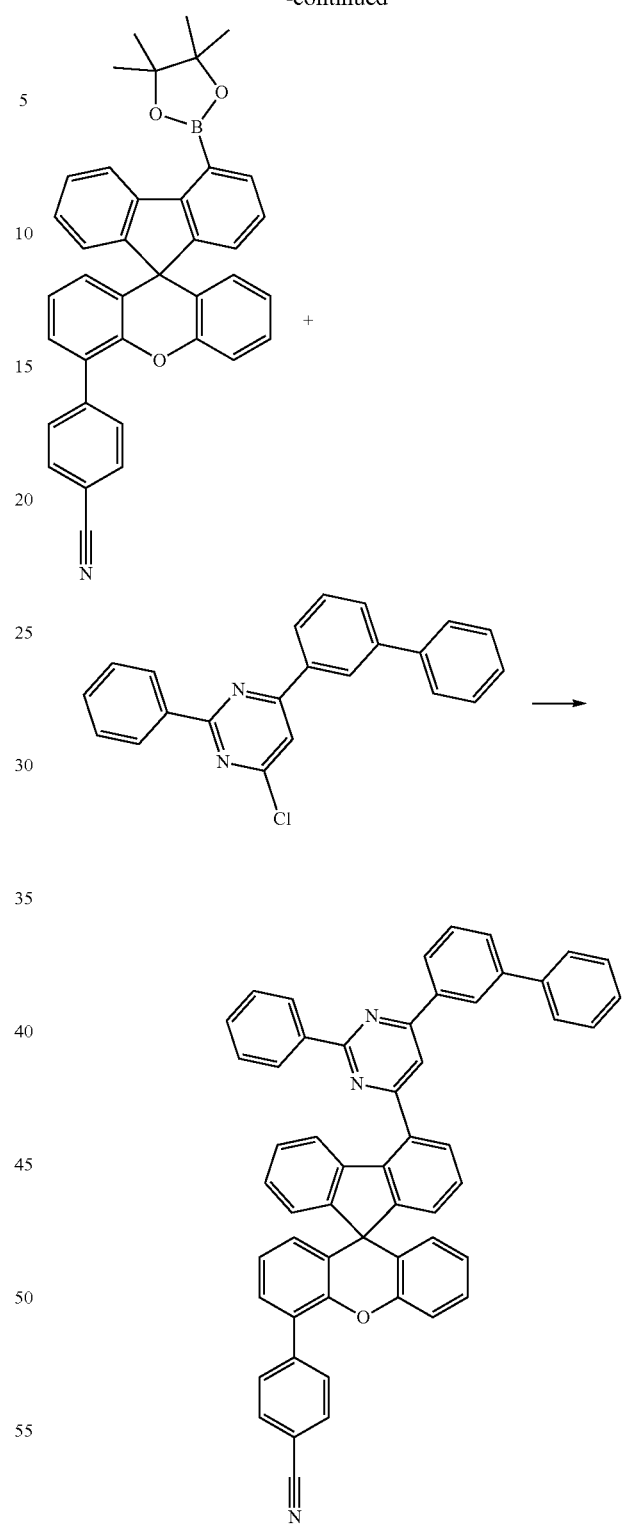
A compound of Chemical Formula E15 was prepared in the same manner as in the preparation method of E1 of Example 1 except that each starting material was employed as in the reaction formula shown above.
MS $[M+H]^+=740$

Example 16 (E16)
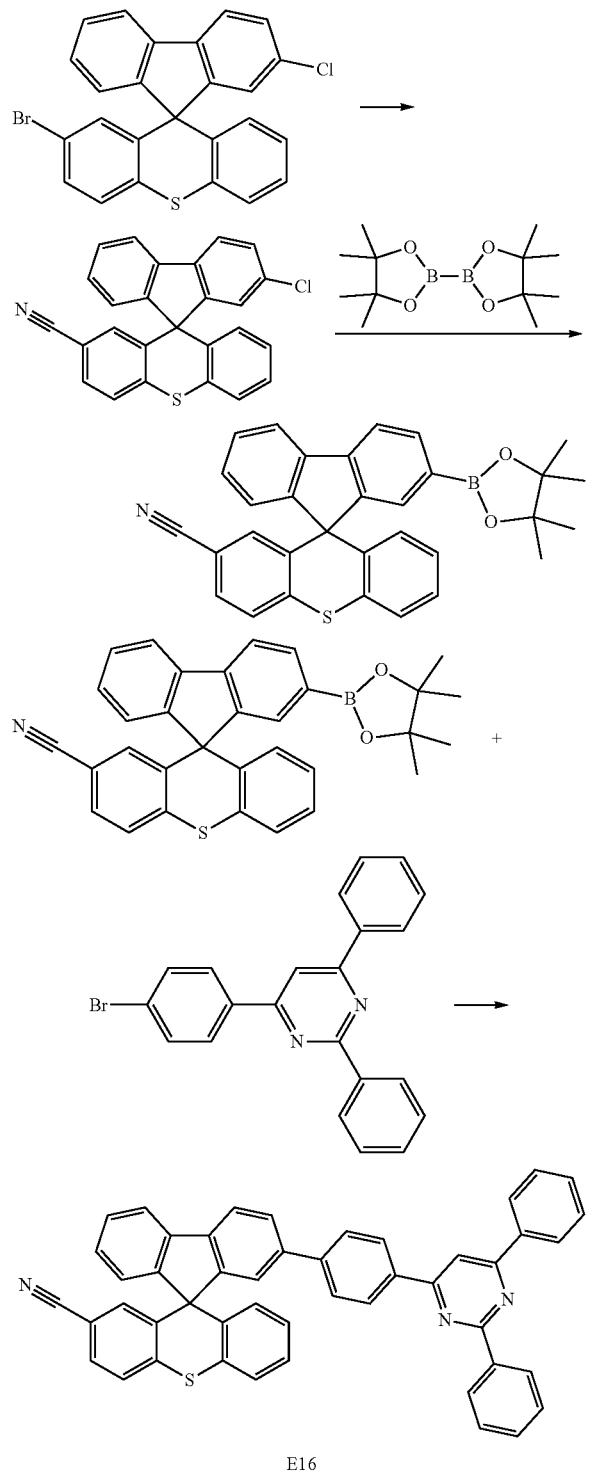
E16
A compound of Chemical Formula E16 was prepared in the same manner as in the preparation method of E3 of Example 3 except that each starting material was employed as in the reaction formula shown above.
MS [M+H]$^+$=680
Example 17 (E17)
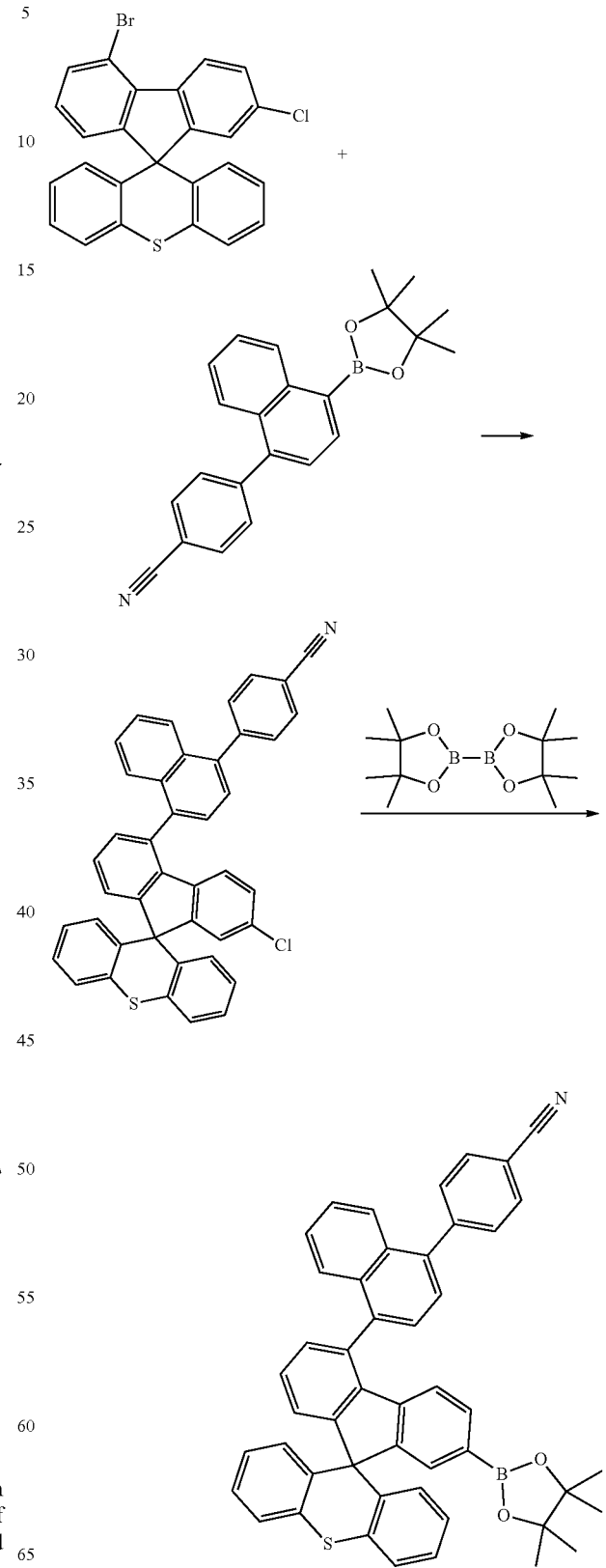

159
-continued
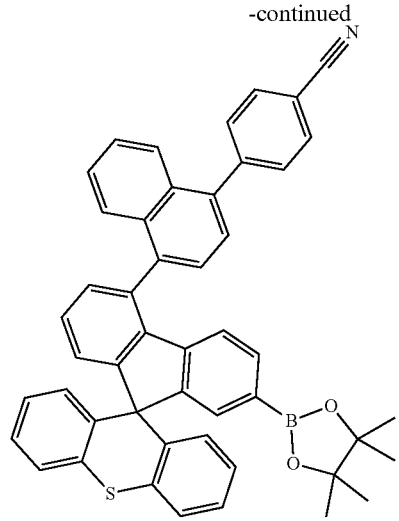
+
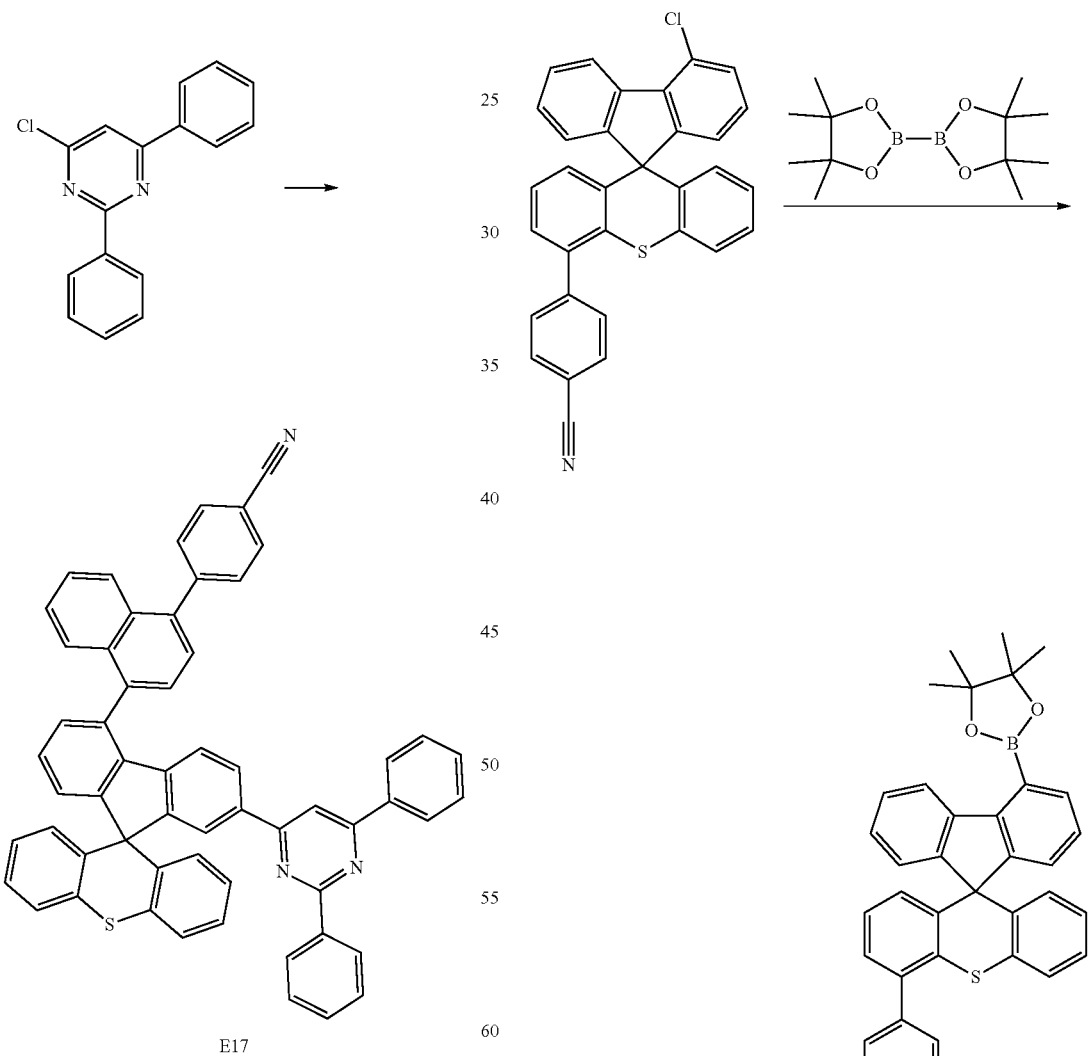
E17
A compound of Chemical Formula E11 was prepared in the same manner as in the preparation method of E1 of Example 1 except that each starting material was employed as in the reaction formula shown above.
MS [M+H]⁺=806
160
Example 18 (E18)
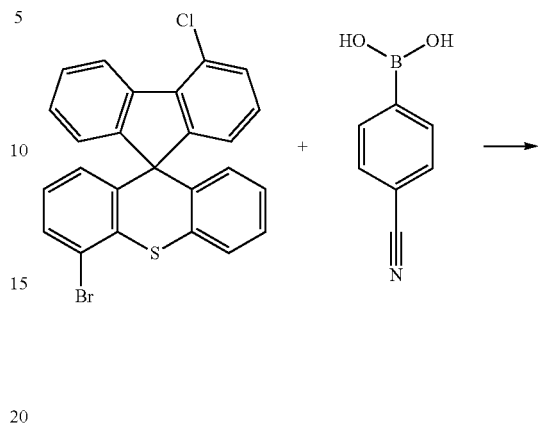

161
-continued
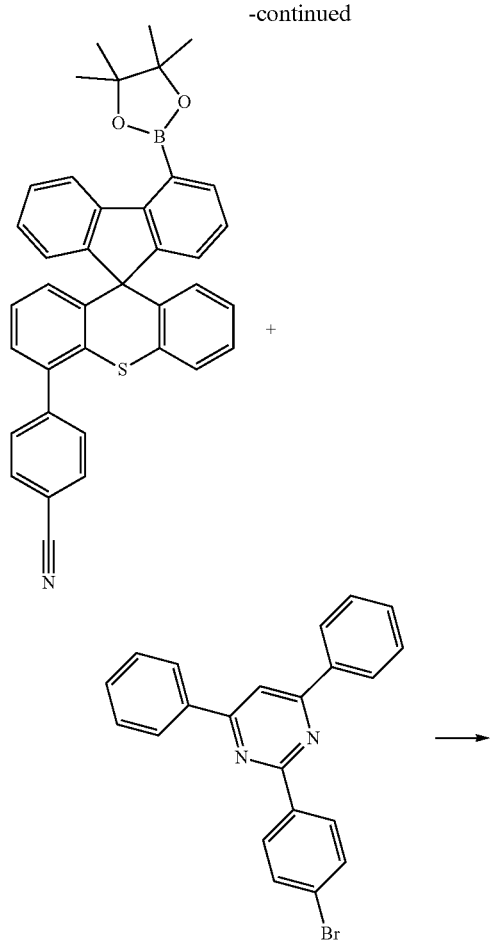
162
-continued
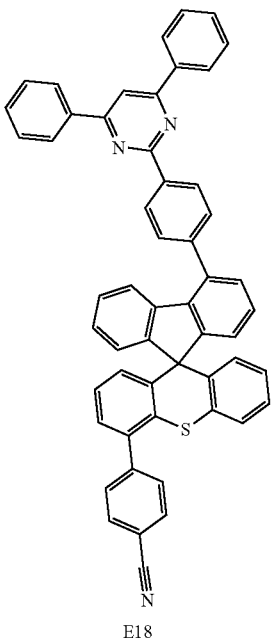
E18
A compound of Chemical Formula E18 was prepared in the same manner as in the preparation method of E1 of Example 1 except that each starting material was employed as in the reaction formula shown above.
MS [M+H]⁺=756
Example 19 (E19)
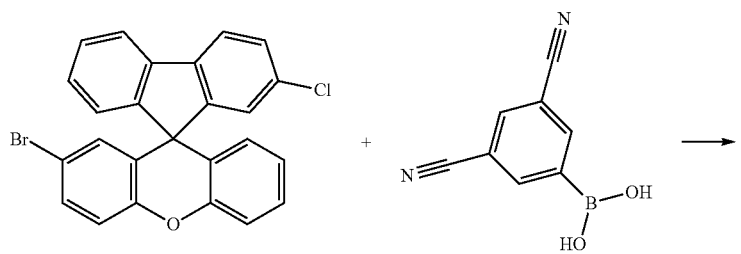
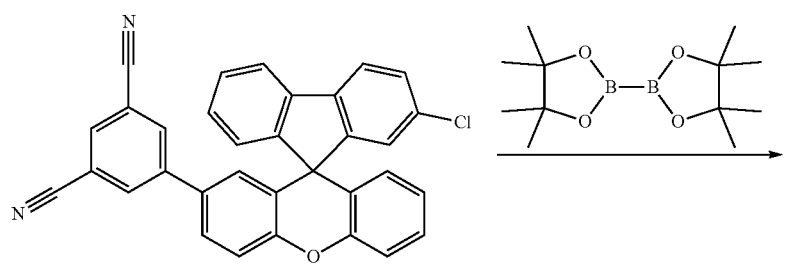

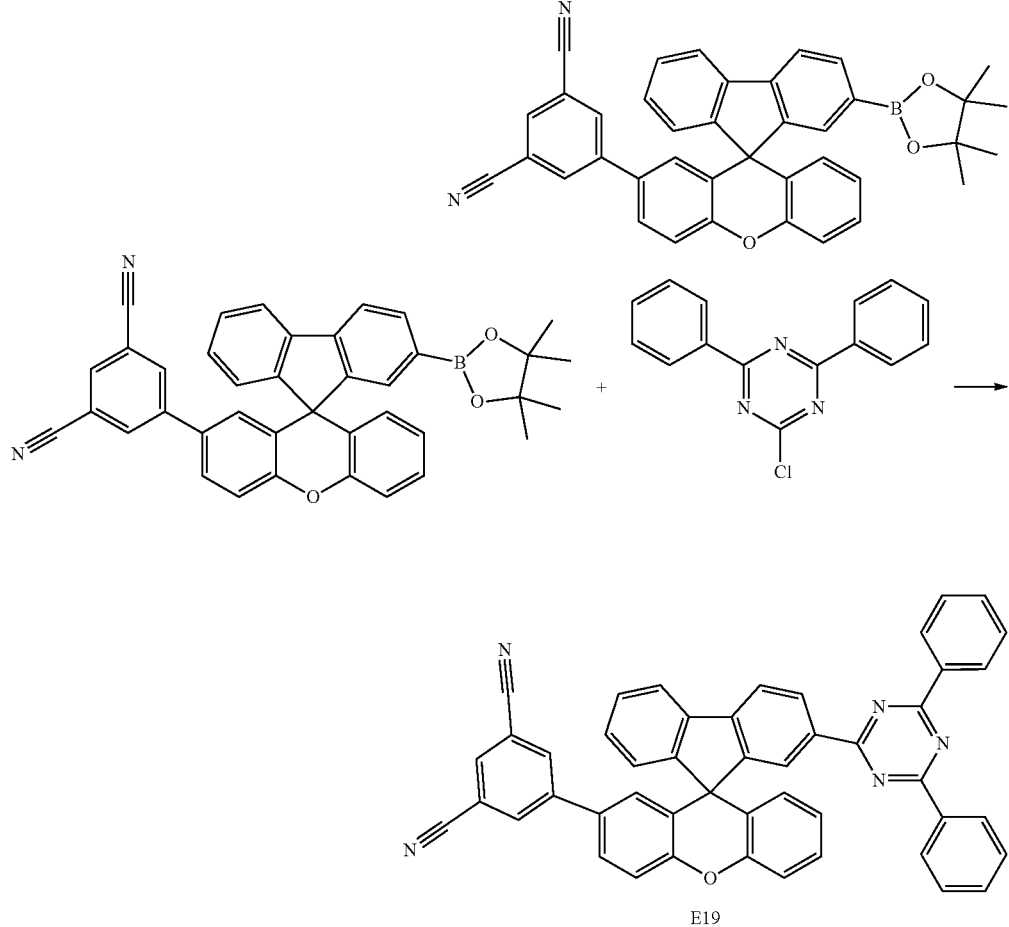
A compound of Chemical Formula E19 was prepared in the same manner as in the preparation method of E1 of Example 1 except that each starting material was employed as in the reaction formula shown above.
MS [M+H]$^+$=690
Example 20 (E20)
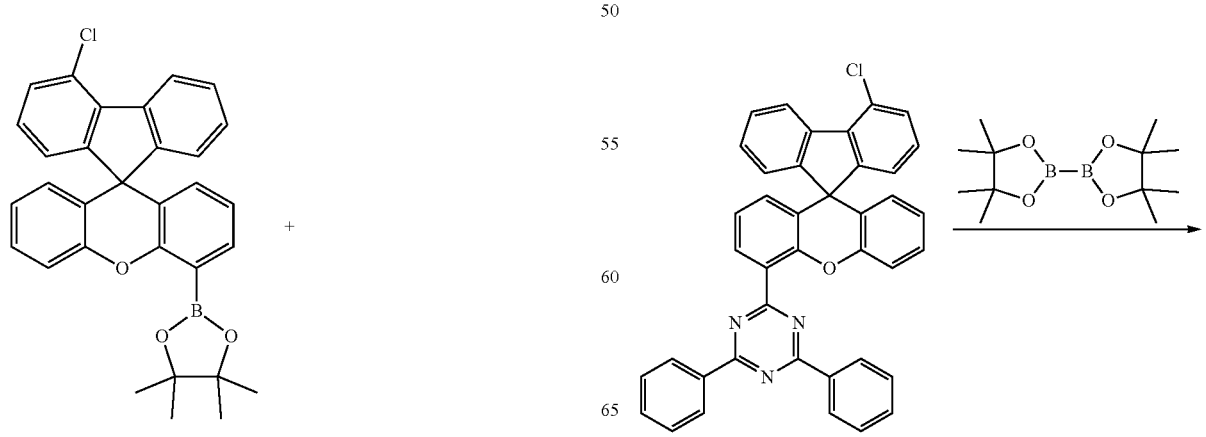

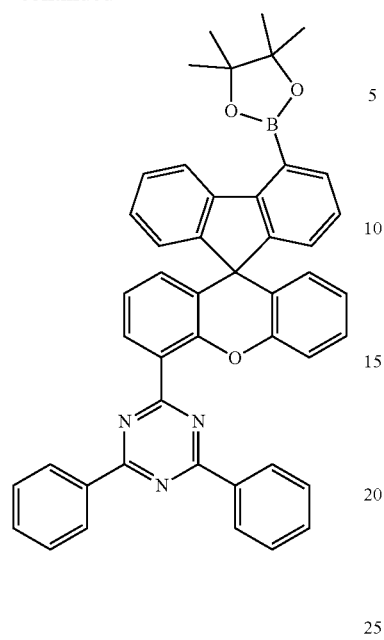
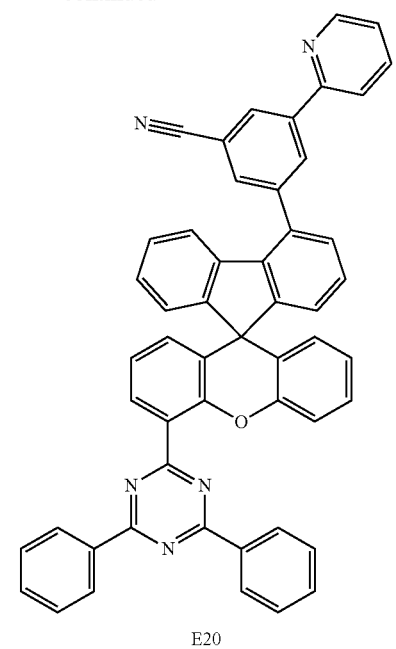
A compound of Chemical Formula E20 was prepared in the same manner as in the preparation method of E1 of Example 1 except that each starting material was employed as in the reaction formula shown above.
MS [M+H]$^+$=742
Example 21 (E21)
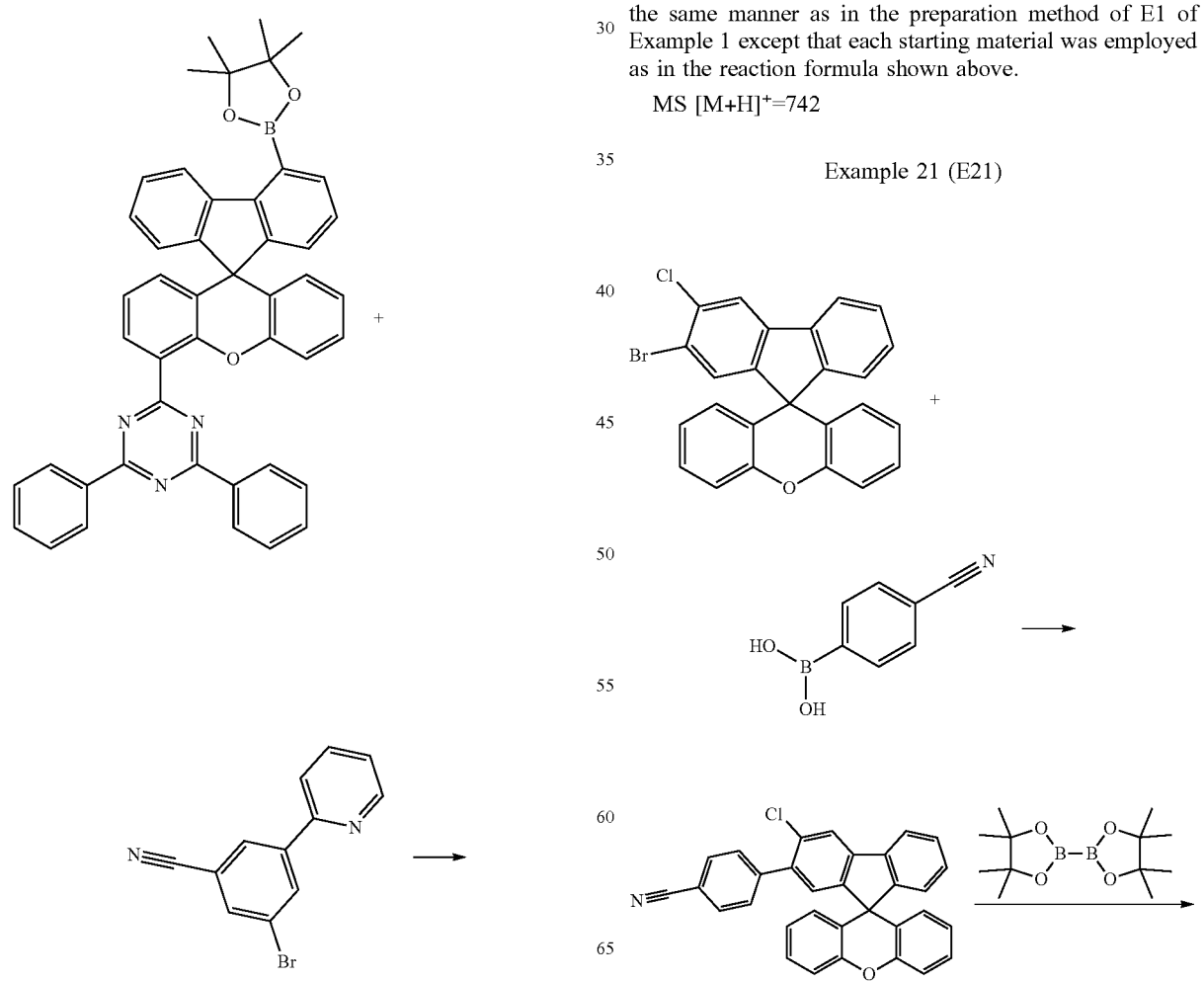

167
-continued
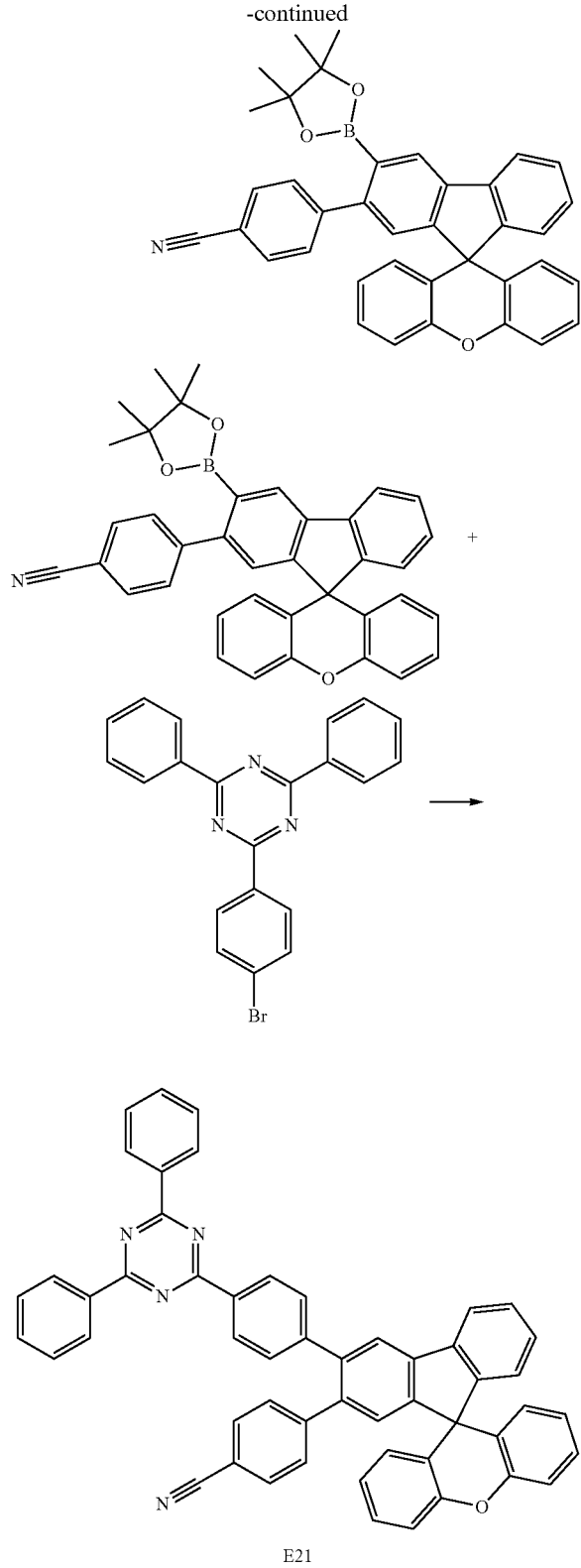
A compound of Chemical Formula E21 was prepared in the same manner as in the preparation method of E1 of Example 1 except that each starting material was employed as in the reaction formula shown above.
MS [M+H]⁺=741
168
Example 22 (E22)
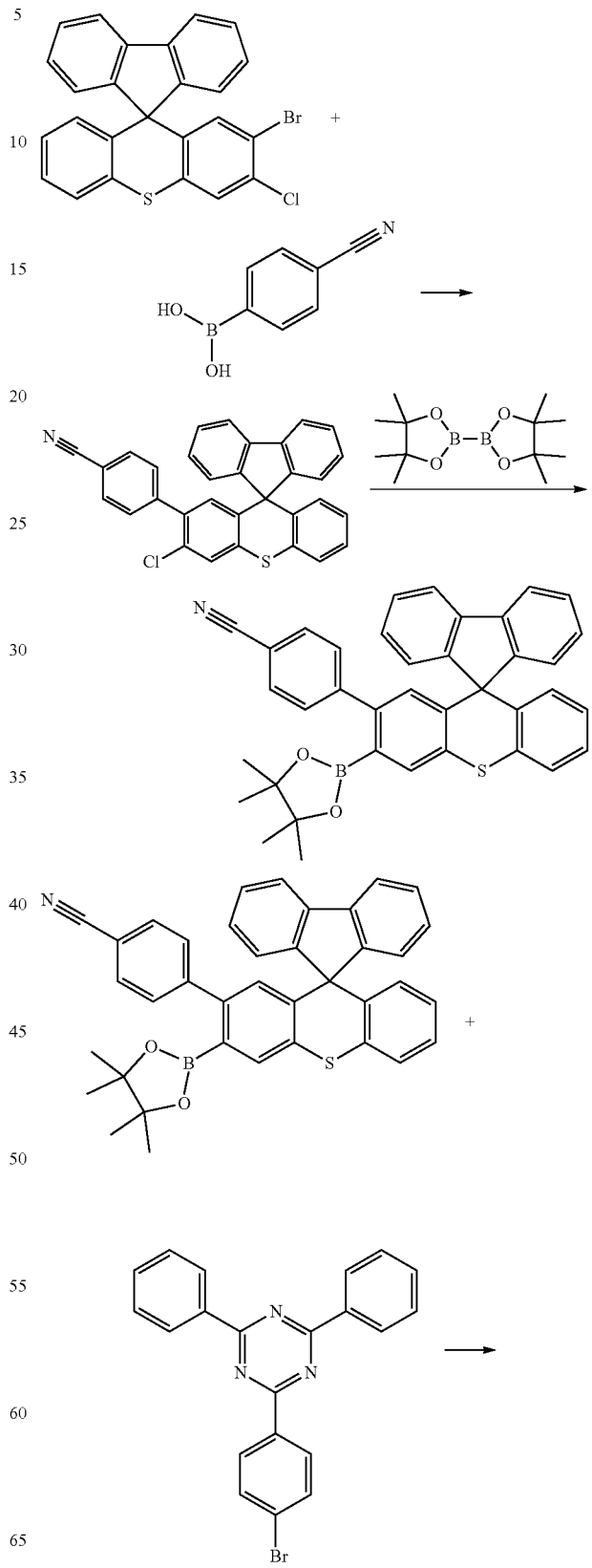

-continued

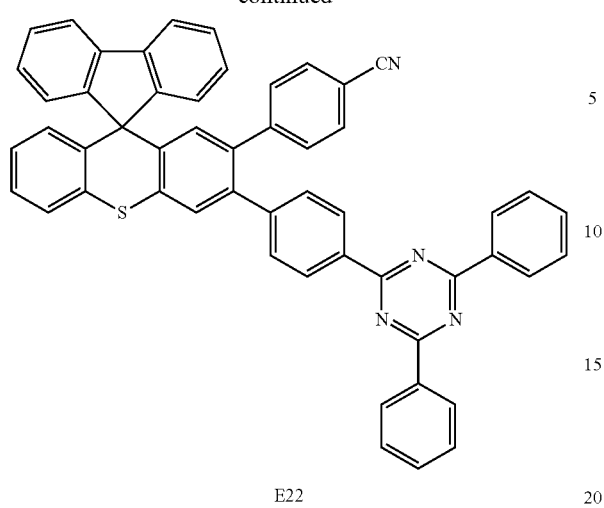

E22

A compound of Chemical Formula E22 was prepared in the same manner as in the preparation method of E1 of Example 1 except that each starting material was employed as in the reaction formula shown above.

MS [M+H]$^+$=757

Example 23 (E23)

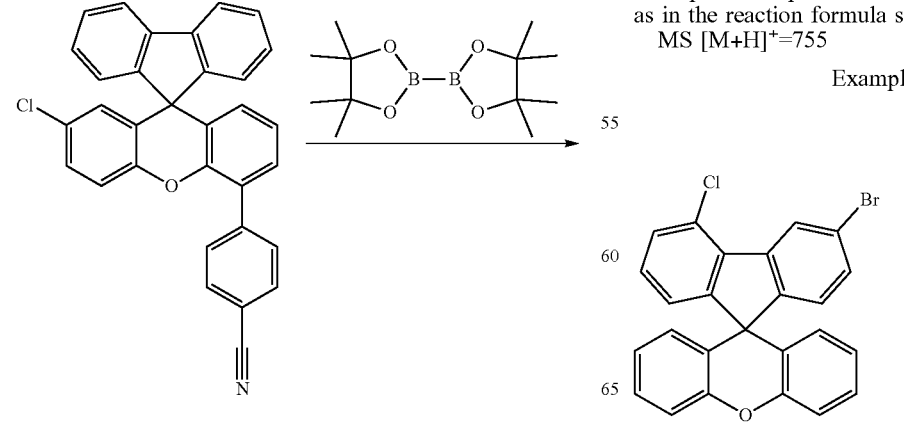

-continued

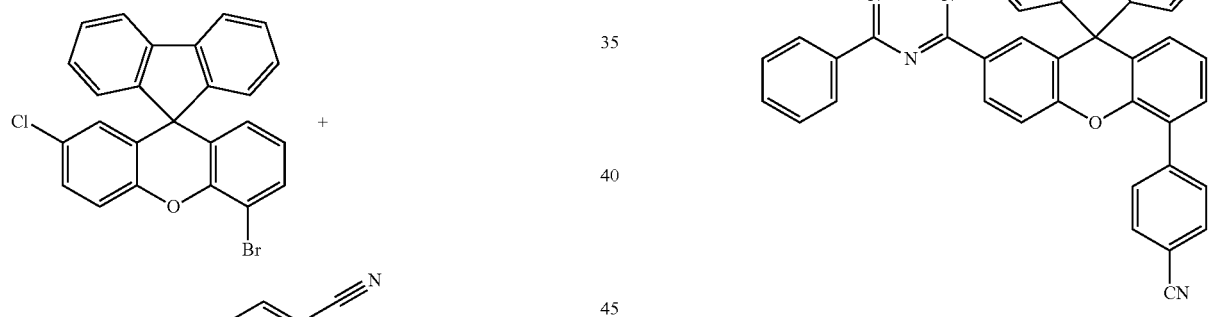

E23

A compound of Chemical Formula E23 was prepared in the same manner as in the preparation method of E1 of Example 1 except that each starting material was employed as in the reaction formula shown above.

MS [M+H]$^+$=755

Example 24 (E24)

-continued

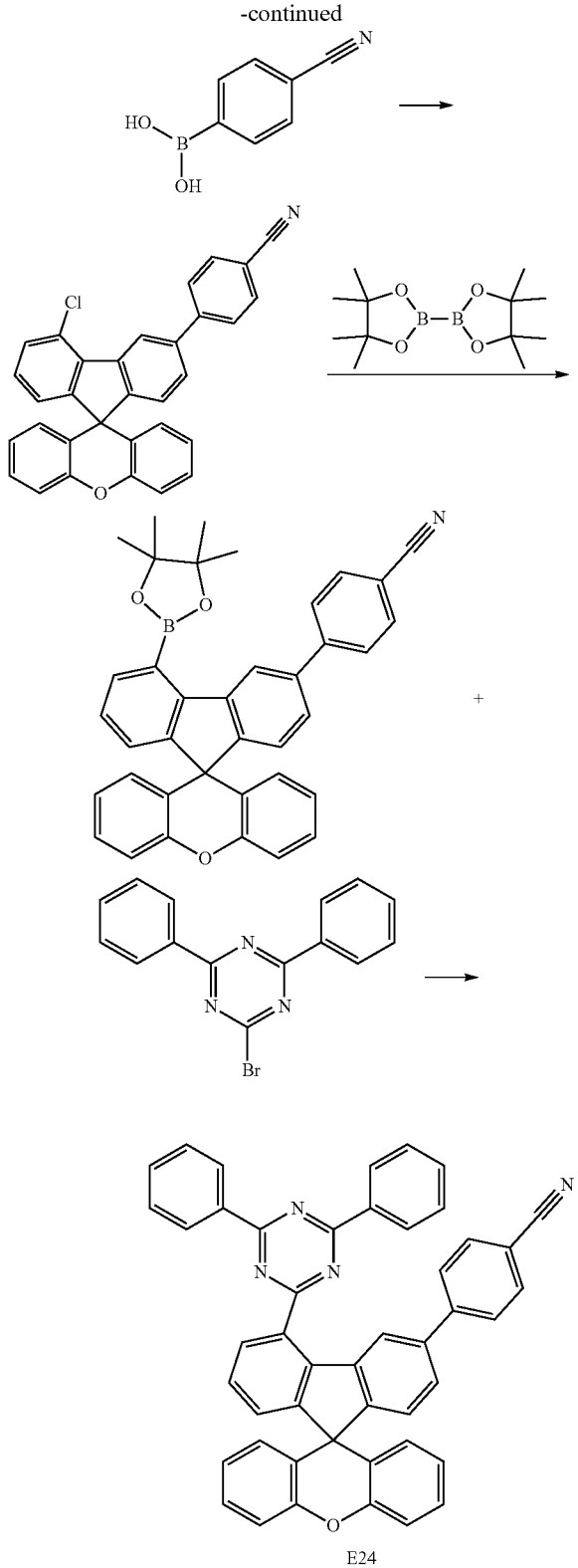

E24

A compound of Chemical Formula E24 was prepared in the same manner as in the preparation method of E1 of Example 1 except that each starting material was employed as in the reaction formula shown above.

MS $[M+H]^+=665$

Experimental Example 1-1

A glass substrate on which indium tin oxide (ITO) was coated as a thin film to a thickness of 1,000 Å was placed in distilled water containing dissolved detergent and ultrasonically cleaned. A product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol, then dried, and then transferred to a plasma cleaner. The substrate was cleaned for 5 minutes using oxygen plasma, and then transferred to a vacuum deposition apparatus.

On the transparent ITO electrode prepared as above, a hole injection layer was formed by thermal vacuum depositing the following HI-A compound to a thickness of 600 Å. On the hole injection layer, a first and second hole transfer layer was formed by consecutively vacuum depositing the following HAT compound (50 Å) and the following HT-A compound (60 Å).

Subsequently, a light emitting layer was formed on the hole transfer layer by vacuum depositing the following BH compound and BD compound in a weight ratio of 25:1 to a film thickness of 20 nm.

On the light emitting layer, an electron injection and transfer layer was formed to a thickness of 350 Å by vacuum depositing the compound (E1) of Example 1 and the following LiQ compound in a weight ratio of 1:1. On the electron injection and transfer layer, a cathode was formed by consecutively depositing lithium fluoride (LiF) to a thickness of 10 Å and aluminum to a thickness of 1,000 Å.

In the above-mentioned process, the deposition rates of the organic materials were maintained at 0.4 Å/sec to 0.9 Å/sec, the deposition rates of the lithium fluoride and the aluminum of the cathode were maintained at 0.3 Å/sec and 2 Å/sec, respectively, and the degree of vacuum during the deposition was maintained at $1\times10^{-7}$ torr to $5\times10^{-5}$ torr to manufacture an organic light emitting device.

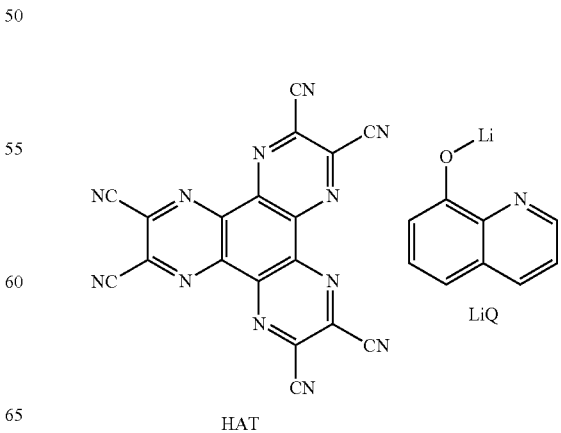

HAT          LiQ

-continued
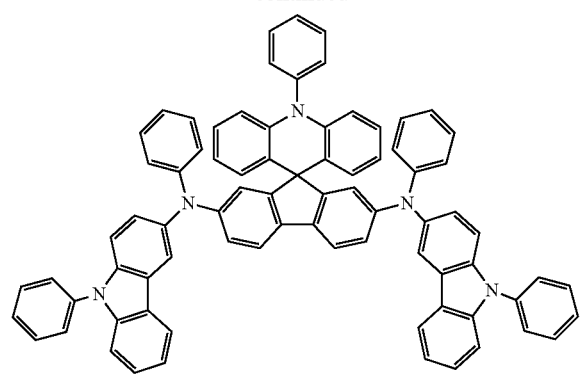
HI-A
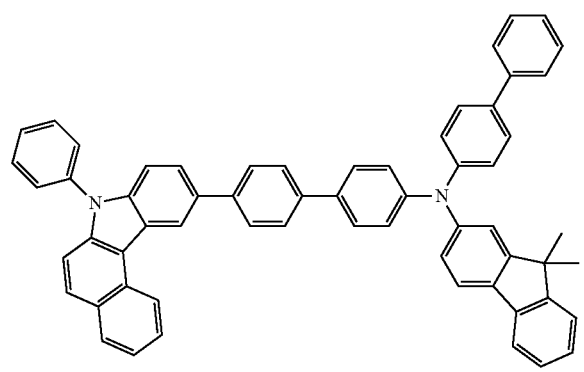
HT-A
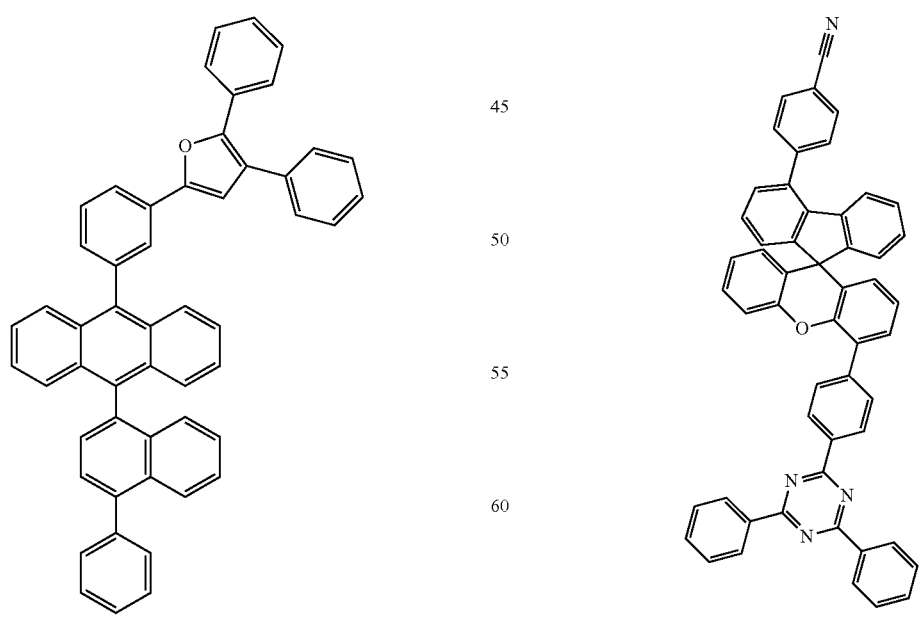
BH
-continued
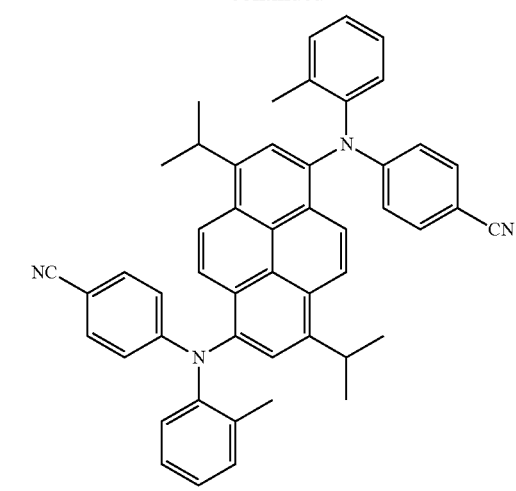
BD
Experimental Examples 1-2 to 1-24
Organic light emitting devices were manufactured in the same manner as in Experimental Example 1-1 except that compounds of Examples 2 to 24 (E2 to E24) were respectively used instead of the compound (E1) of Example 1.

175
-continued
E2
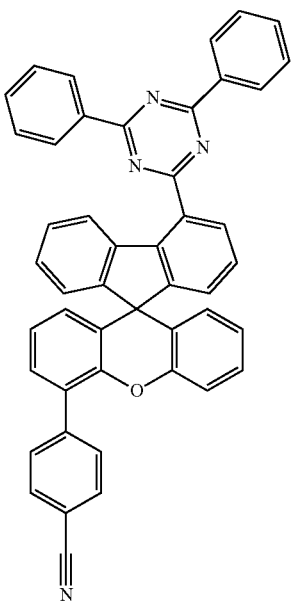
E3
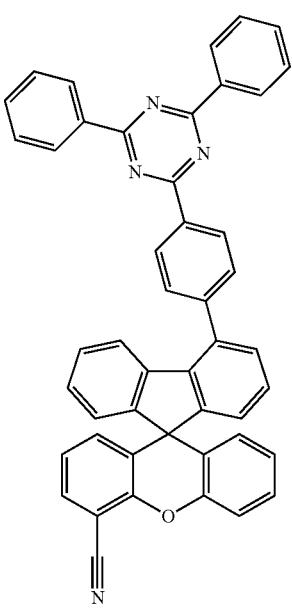
E4
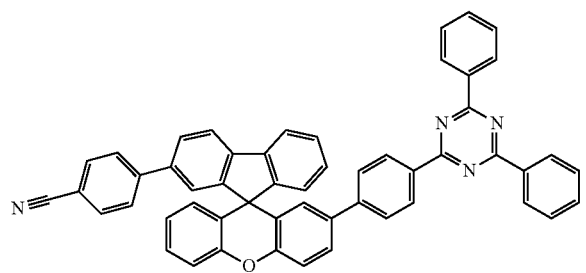
176
-continued
E5
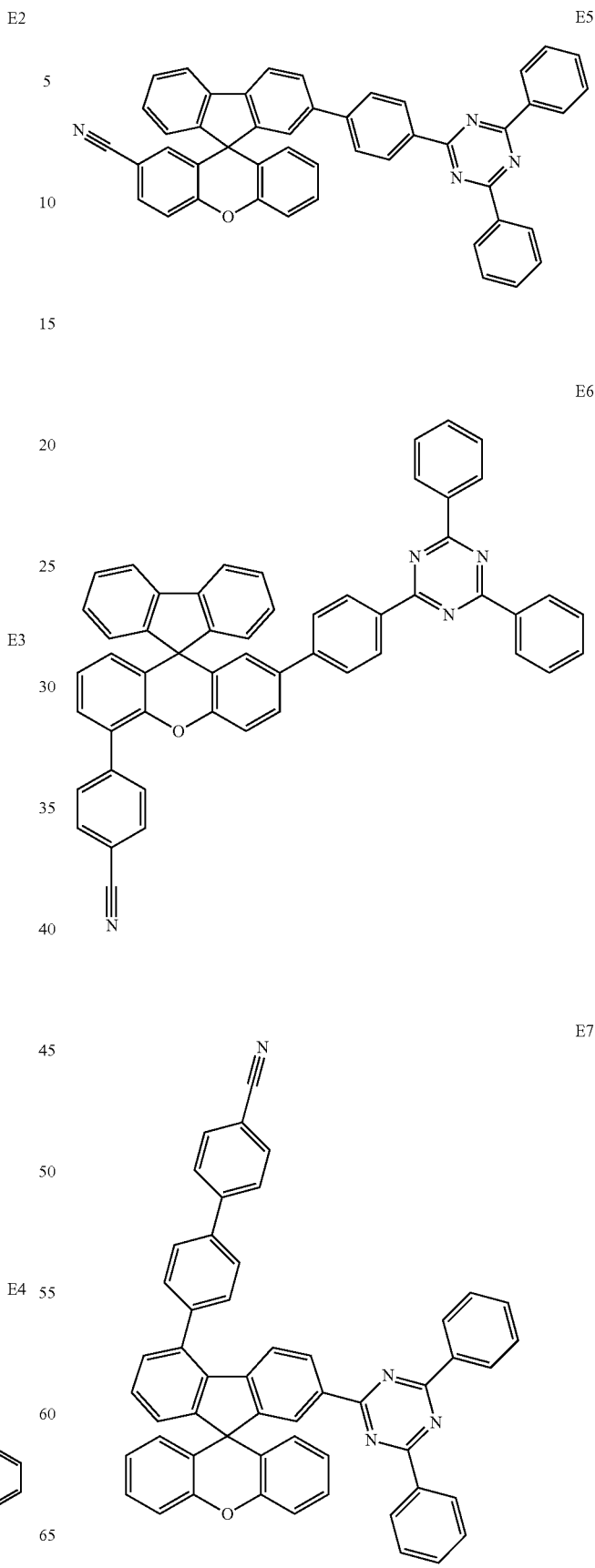
E6
E7

E8
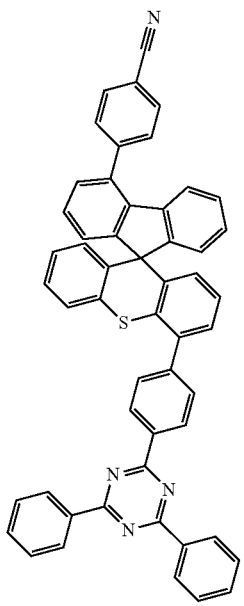
E9
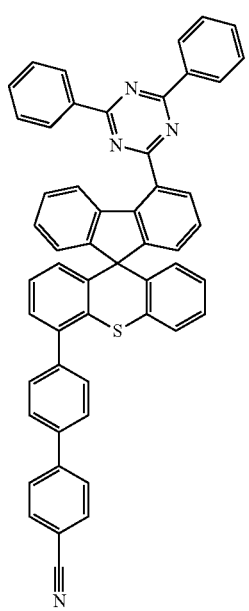
E10
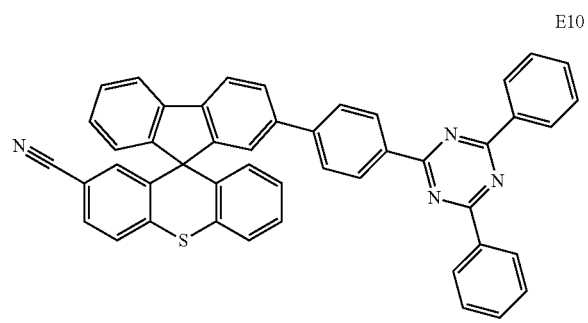
E11
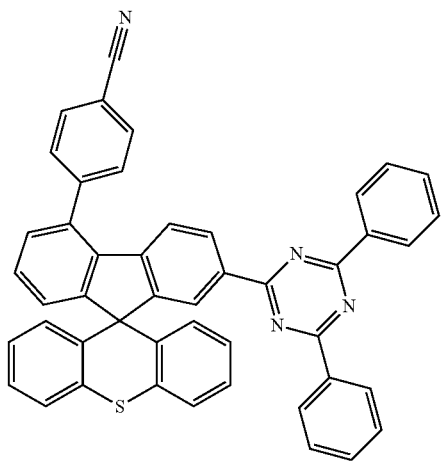
E12
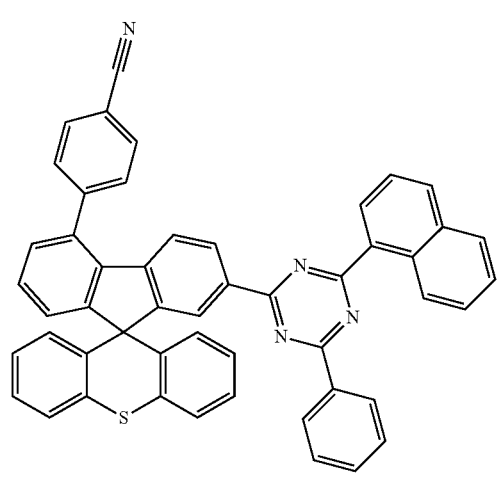
E13
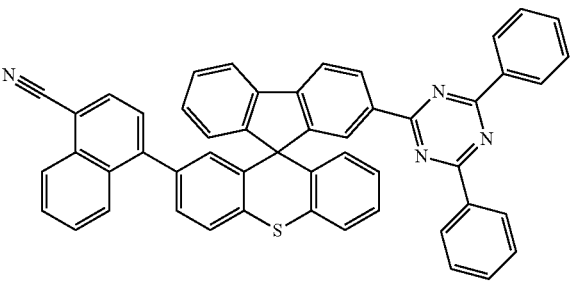

-continued
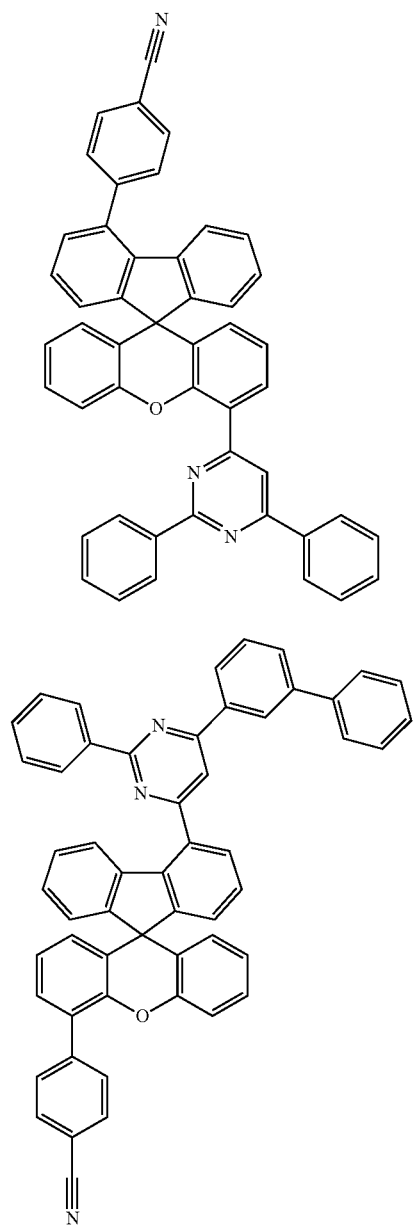
E14
E15
E16
-continued
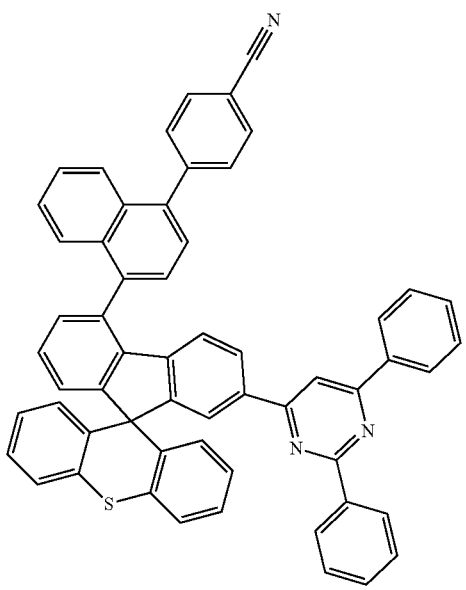
E17
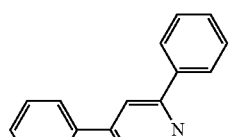
E18
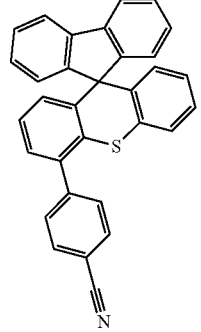
E19
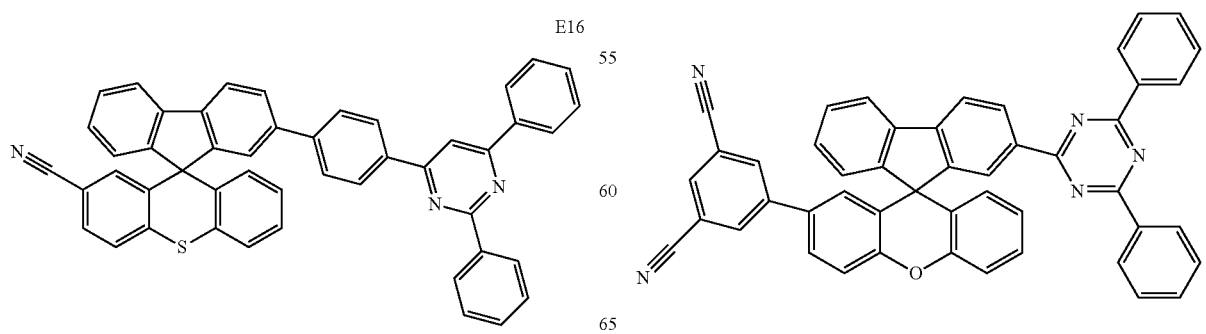

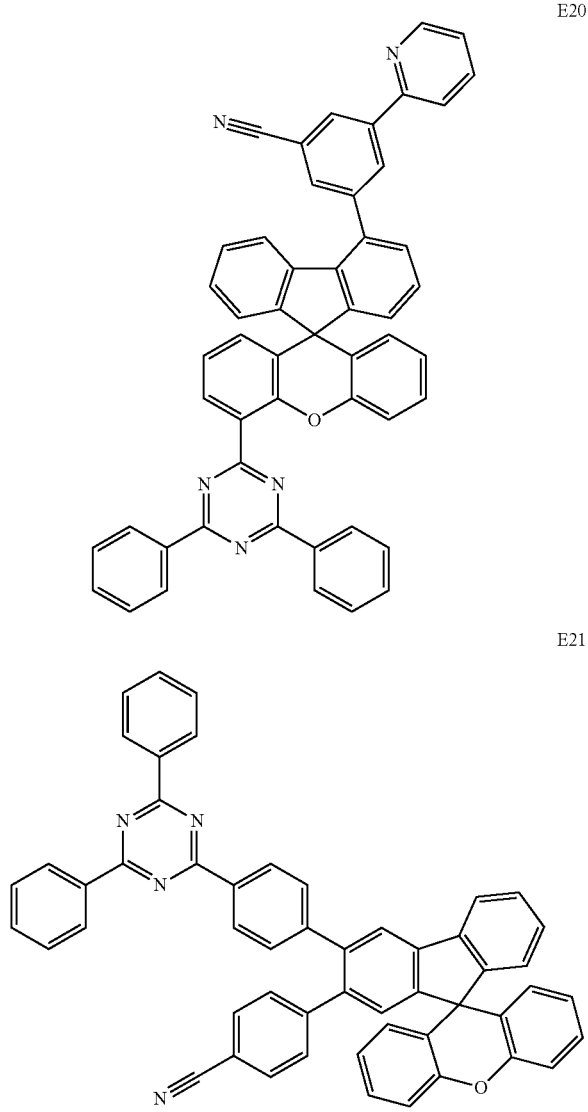
Comparative Examples 1-1 to 1-10
Organic light emitting devices were manufactured in the same manner as in Experimental Example 1-1 except that the following compounds (ET-1-A to ET-1-J) were respectively used instead of the compound (E1) of Example 1.
[ET-1-A]
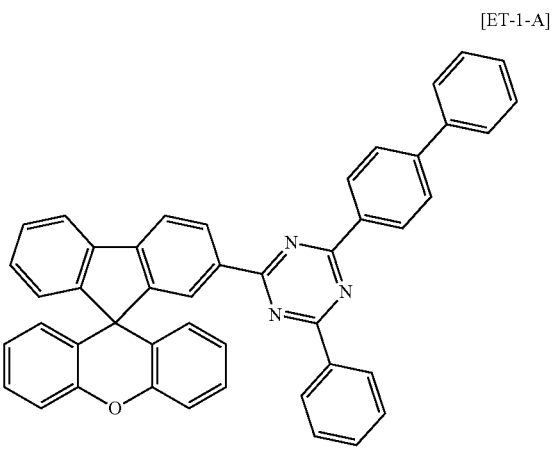

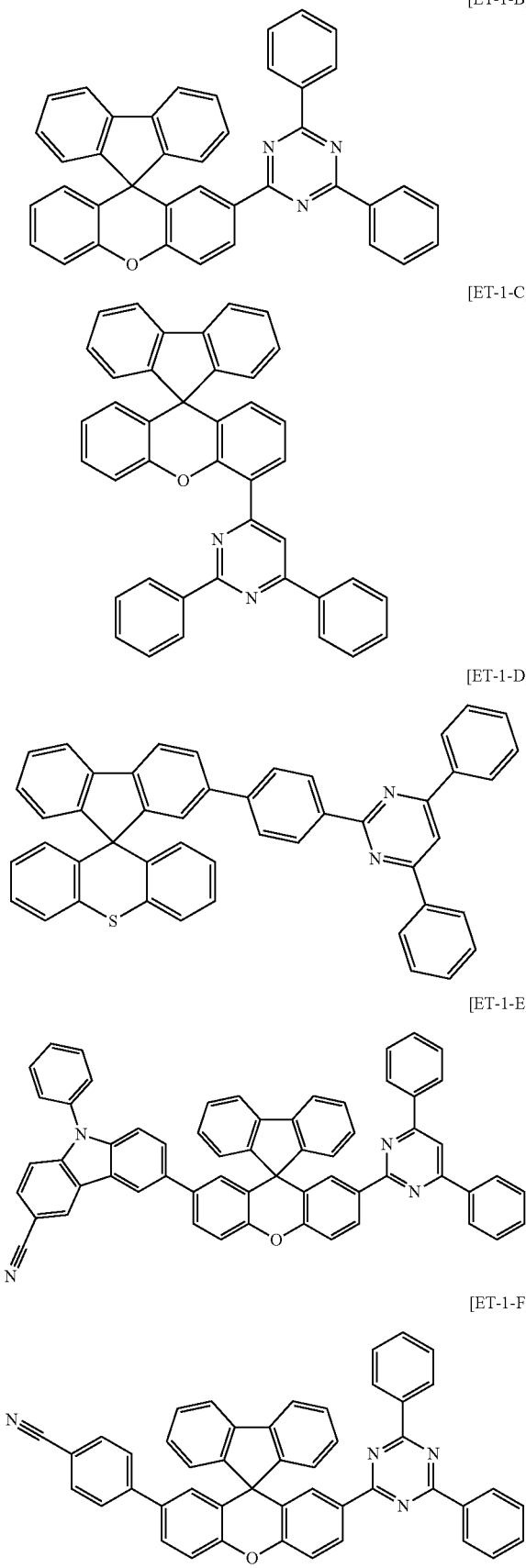
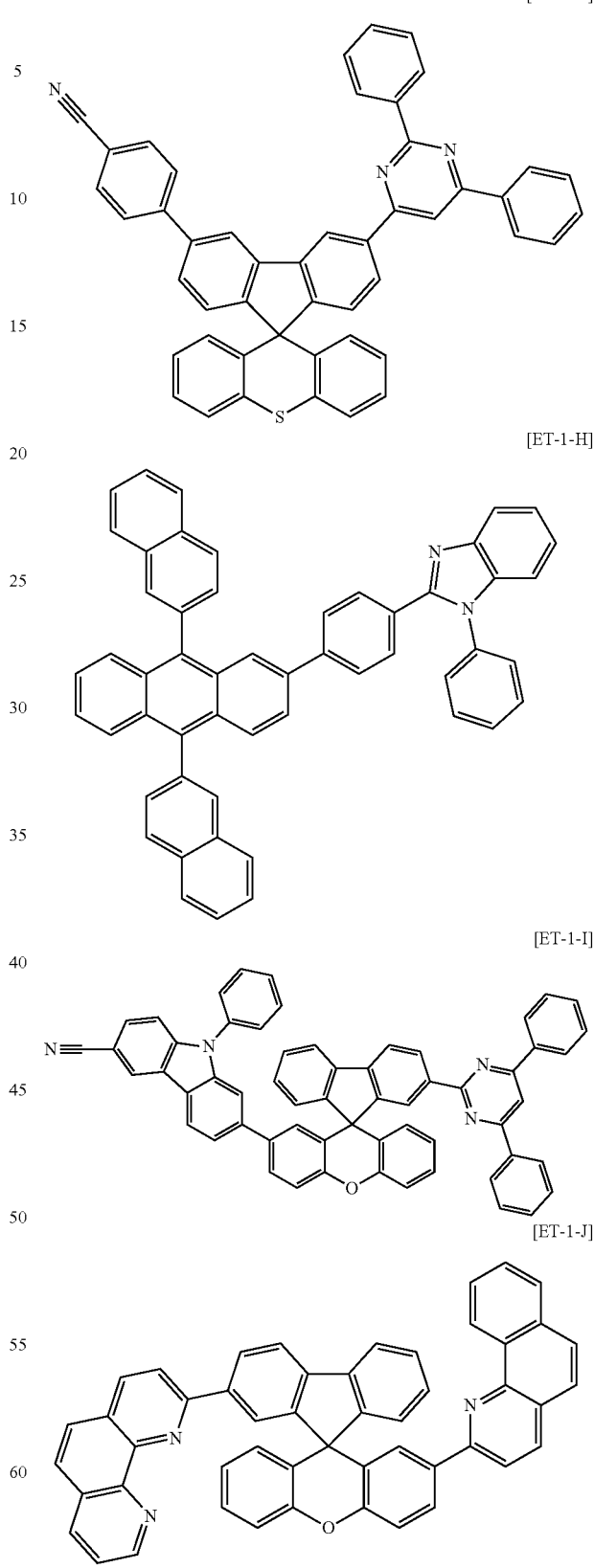
For the organic light emitting devices manufactured in the experimental examples and the comparative examples, driving voltage and light emission efficiency were measured at current density of 10 mA/cm², and time (T90) taken for the luminance decreasing to 90% with respect to the initial luminance was measured at current density of 20 mA/cm². The results are shown in the following Table 1.

TABLE 1

| Category (Compound) | Voltage (V @ 10 mA/cm²) | Efficiency (cd/A @ 10 mA/cm²) | Color Co-ordinate (x, y) | Lifetime (h) (T90 at 20 mA/cm²) |
|---|---|---|---|---|
| Experimental Example 1-1 (E1) | 4.37 | 5.10 | (0.142, 0.096) | 271 |
| Experimental Example 1-2 (E2) | 4.40 | 5.05 | (0.142, 0.096) | 302 |
| Experimental Example 1-3 (E3) | 4.42 | 5.06 | (0.142, 0.096) | 310 |
| Experimental Example 1-4 (E4) | 4.33 | 5.12 | (0.142, 0.096) | 268 |
| Experimental Example 1-5 (E5) | 4.40 | 5.07 | (0.142, 0.096) | 312 |
| Experimental Example 1-6 (E6) | 4.43 | 5.00 | (0.142, 0.097) | 333 |
| Experimental Example 1-7 (E7) | 4.42 | 4.98 | (0.142, 0.096) | 338 |
| Experimental Example 1-8 (E8) | 4.36 | 5.11 | (0.142, 0.099) | 269 |
| Experimental Example 1-9 (E9) | 4.38 | 5.09 | (0.142, 0.096) | 273 |
| Experimental Example 1-10 (E10) | 4.41 | 5.08 | (0.142, 0.099) | 310 |
| Experimental Example 1-11 (E11) | 4.45 | 4.95 | (0.142, 0.096) | 348 |
| Experimental Example 1-12 (E12) | 4.47 | 4.93 | (0.142, 0.097) | 350 |
| Experimental Example 1-13 (E13) | 4.38 | 5.15 | (0.142, 0.096) | 261 |
| Experimental Example 1-14 (E14) | 4.35 | 4.98 | (0.142, 0.096) | 240 |
| Experimental Example 1-15 (E15) | 4.37 | 4.96 | (0.142, 0.096) | 239 |
| Experimental Example 1-16 (E16) | 4.38 | 5.00 | (0.142, 0.097) | 241 |
| Experimental Example 1-17 (E17) | 4.40 | 4.89 | (0.142, 0.096) | 250 |
| Experimental Example 1-18 (E18) | 4.44 | 4.88 | (0.142, 0.096) | 244 |
| Experimental Example 1-19 (E19) | 4.48 | 4.99 | (0.142, 0.096) | 374 |
| Experimental Example 1-20 (E20) | 4.42 | 4.97 | (0.142, 0.095) | 265 |
| Experimental Example 1-21 (E21) | 4.30 | 5.18 | (0.142, 0.095) | 235 |
| Experimental Example 1-22 (E22) | 4.35 | 5.07 | (0.142, 0.095) | 248 |
| Experimental Example 1-23 (E23) | 4.39 | 4.97 | (0.142, 0.096) | 255 |
| Experimental Example 1-24 (E24) | 4.36 | 5.07 | (0.142, 0.095) | 310 |
| Comparative Example 1-1 (ET-1-A) | 4.42 | 4.22 | (0.142, 0.096) | 88 |
| Comparative Example 1-2 (ET-1-B) | 4.41 | 4.31 | (0.142, 0.096) | 74 |
| Comparative Example 1-3 (ET-1-C) | 4.46 | 3.94 | (0.142, 0.096) | 68 |
| Comparative Example 1-4 (ET-1-D) | 4.50 | 3.83 | (0.142, 0.096) | 79 |
| Comparative Example 1-5 (ET-1-E) | 5.01 | 2.91 | (0.142, 0.096) | 100 |
| Comparative Example 1-6 (ET-1-F) | 4.52 | 4.00 | (0.142, 0.096) | 186 |
| Comparative Example 1-7 (ET-1-G) | 4.55 | 3.87 | (0.142, 0.097) | 177 |
| Comparative Example 1-8 (ET-1-H) | 5.22 | 3.04 | (0.142, 0.097) | 70 |
| Comparative Example 1-9 (ET-1-I) | 4.80 | 3.95 | (0.142, 0.097) | 81 |
| Comparative Example 1-10 (ET-I-J) | 5.3 | 3.1 | (0.142, 0.096) | 105 |

A compound of Chemical Formula 1 can be used in an organic material layer capable of electron injection and electron transfer at the same time of an organic light emitting device.

When comparing Experimental Examples 1-1 and 1-5 with Experimental Examples 1-8 and 1-10 of Table 1, effects of both cores of the xanthene or the thioxanthene group were far superior with respect to driving voltage, efficiency and lifetime of the organic light emitting device without exception.

When comparing the experimental examples with Comparative Examples 1-1 to 1-4 of Table 1, the compounds having xanthene or thioxanthene substituted with triazine or pyrimidine and a cyano group as in Chemical Formula 1 according to the present disclosure were far superior with respect to efficiency and lifetime of the organic light emitting device compared to the compounds having xanthene or thioxanthene unsubstituted with a cyano group.

When comparing the experimental examples with Comparative Examples 1-5 to 1-7 of Table 1, the compounds having xanthene or thioxanthene asymmetrically substituted with triazine or pyrimidine and a cyano group as in Chemical Formula 1 according to the present disclosure were far superior with respect to efficiency and lifetime of the organic light emitting device compared to the compounds having xanthene or thioxanthene symmetrically substituted with triazine or pyrimidine and a cyano group.

Experimental Example 2

HOMO energy level and LUMO energy level values of Compound E2, Compound E5 and Compound ET-1-H of Comparative Example 1-8 are shown in the following Table 2.

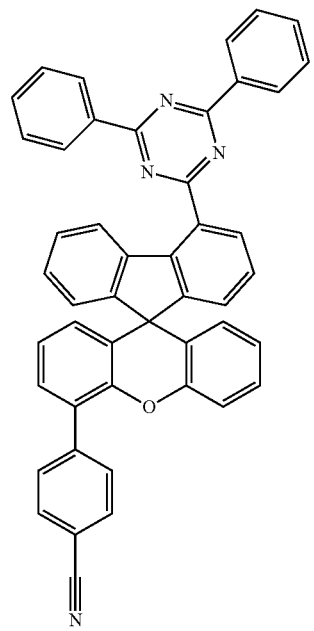

[E2]

-continued

[E5]

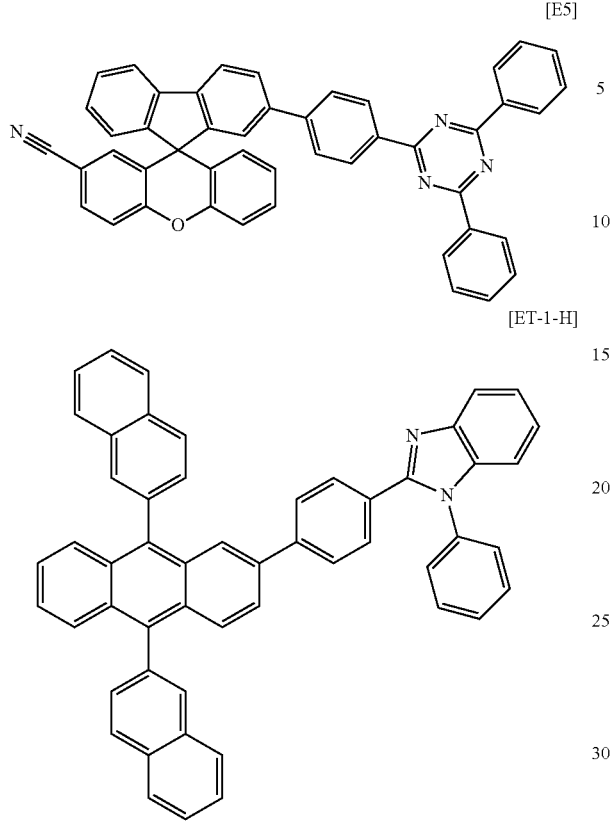

[ET-1-H]

The HOMO energy level was measured using a photoelectron spectrophotometer in air (AC3, manufactured by RIKEN KEIKI Co., Ltd.).

The LUMO energy level was calculated as a wavelength value measured through a light emission spectrum (photoluminescence, PL).

TABLE 2

| Chemical Formula | HOMO (eV) | LUMO (eV) |
|---|---|---|
| E2 | 6.38 | 3.26 |
| E5 | 6.32 | 3.21 |
| ET-1-H | 5.70 | 2.87 |

REFERENCE NUMERALS

1: Substrate
2: Anode
3: Hole Injection Layer
4: Hole Transfer Layer
5: Hole Control Layer
6: Light Emitting Layer
7: Electron Control Layer
8: Electron Transfer Layer
9: Electron Injection Layer
10: Cathode

The invention claimed is:

1. A compound of any one of the following Chemical Formulae 2 to 4 and 7:

[Chemical Formula 2]

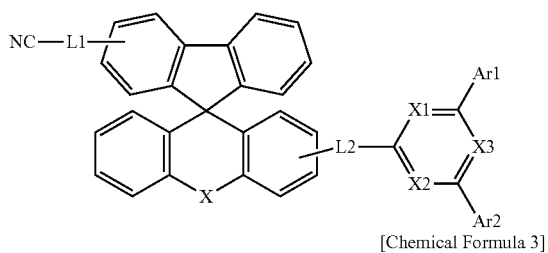

[Chemical Formula 3]

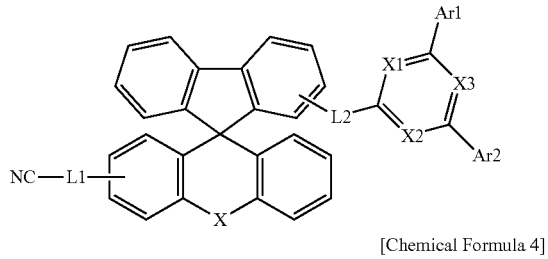

[Chemical Formula 4]

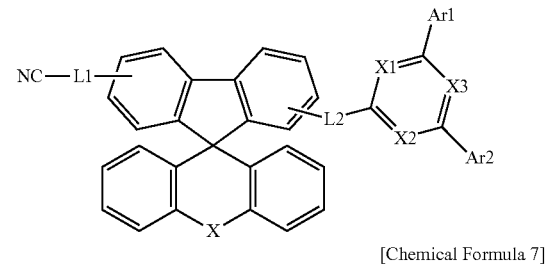

[Chemical Formula 7]

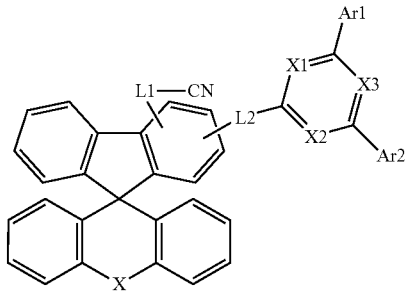

wherein, in Chemical Formulae 2 to 4 and 7:

X is O or S;

L1 is a direct bond or an arylene group that is unsubstituted or substituted with one or more selected from among deuterium, a cyano group, an aryl group, a heteroaryl group comprising an N-comprising hexagonal ring, and a heteroaryl group comprising one or more of O and S;

L2 is a direct bond or a substituted or unsubstituted arylene group;

X1 is N or CR1, X2 is N or CR2, X3 is N or CR3, and at least two of X1 to X3 are N;

R1 to R3 are the same as or different from each other, and each independently is hydrogen, deuterium, a substituted or unsubstituted alkyl group, a substituted or unsubstituted aryl group, or a substituted or unsubstituted heteroaryl group;

Ar1 and Ar2 are the same as or different from each other, and each independently is hydrogen, deuterium, a substituted or unsubstituted alkyl group, an aryl group having 6 to 24 carbon atoms that is unsubstituted or substituted with deuterium, a substituted or unsubstituted heteroaryl group having 2 to 20 carbon atoms and comprising one or more heteroatoms of O and S, or a substituted or unsubstituted heteroaryl group having 2 to 20 carbon atoms and comprising an N-comprising 6-membered ring; and positions at which

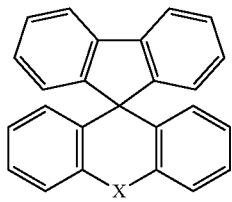

is substituted with

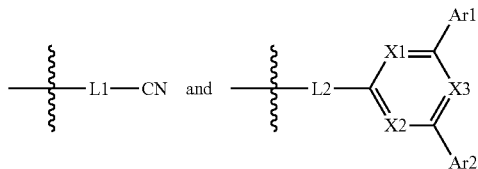

are asymmetric.

2. A compound of any one of the following Chemical Formulae 2 to 4 and 7:

[Chemical Formula 2]

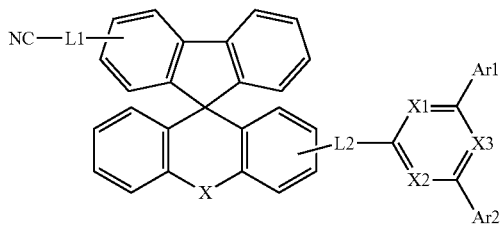

[Chemical Formula 3]

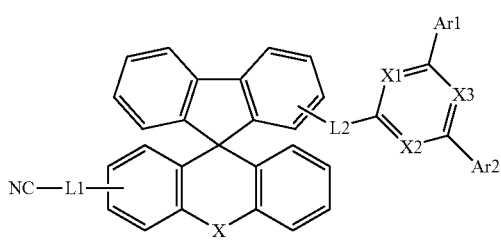

-continued

[Chemical Formula 4]

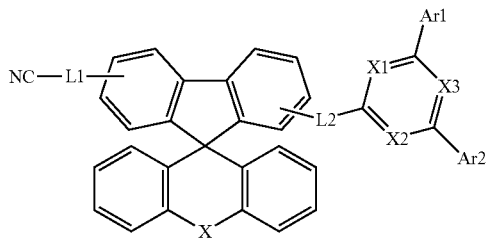

[Chemical Formula 7]

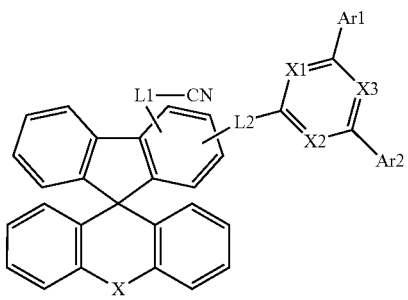

wherein, in Chemical Formulae 2 to 4 and 7:

X is O or S;

L1 is a direct bond; a phenylene group that is unsubstituted or substituted with a phenyl group, a cyano group, a pyridinyl group or a quinolinyl group; a biphenylene group that is unsubstituted or substituted with a cyano group or a phenyl group; an unsubstituted terphenylene group; an unsubstituted quaterphenylene group; a naphthylene group that is unsubstituted or substituted with a cyano group; an unsubstituted anthracenylene group; an unsubstituted phenanthrenylene group; an unsubstituted triphenylenylene group; an unsubstituted pyrenylene group; an unsubstituted 9,9-dimethylfluorenylene group; an unsubstituted 9,9-diphenylfluorenylene group; an unsubstituted 9,9-methylphenylfluorenylene group; or an unsubstituted spiro[cyclopentane-1,9'-fluorenylene] group;

L2 is a direct bond or a substituted or unsubstituted arylene group;

X1 is N or CR1, X2 is N or CR2, X3 is N or CR3, and at least two of X1 to X3 are N;

R1 to R3 are the same as or different from each other, and each independently is hydrogen, deuterium, a substituted or unsubstituted alkyl group, a substituted or unsubstituted aryl group, or a substituted or unsubstituted heteroaryl group;

Ar1 and Ar2 are the same as or different from each other, and each independently is hydrogen, deuterium, a substituted or unsubstituted alkyl group, an aryl group having 6 to 24 carbon atoms that is unsubstituted or substituted with deuterium, a substituted or unsubstituted heteroaryl group having 2 to 20 carbon atoms and comprising one or more heteroatoms of O and S, or a substituted or unsubstituted heteroaryl group having 2 to 20 carbon atoms and comprising an N-comprising 6-membered ring; and positions at which

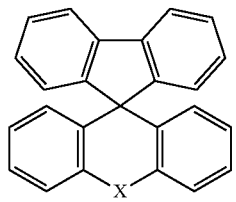

is substituted with

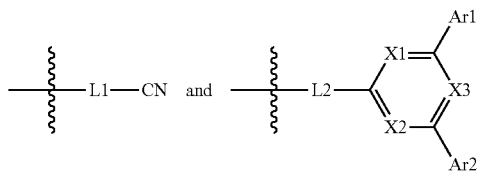

are asymmetric.

3. The compound of claim 1, wherein L2 is a direct bond, a substituted or unsubstituted phenylene group, a substituted or unsubstituted biphenylene group, a substituted or unsubstituted terphenylene group, a substituted or unsubstituted quaterphenylene group, a substituted or unsubstituted naphthylene group, a substituted or unsubstituted anthracenylene group, a substituted or unsubstituted phenanthrenylene group, a substituted or unsubstituted triphenylenylene group, a substituted or unsubstituted pyrenylene group, a substituted or unsubstituted 9,9-dimethylfluorenylene group, a substituted or unsubstituted 9,9-diphenylfluorenylene group, a substituted or unsubstituted 9,9-methylphenylfluorenylene group, or a substituted or unsubstituted spiro[cyclopentane-1,9'-fluorenylene] group.

4. The compound of claim 1, wherein Ar1 and Ar2 are the same as or different from each other, and each independently is hydrogen, deuterium, a phenyl group that is unsubstituted or substituted with deuterium, a biphenyl group that is unsubstituted or substituted with deuterium, a naphthyl group that is unsubstituted or substituted with deuterium, a dibenzofuranyl group that is unsubstituted or substituted with deuterium, or a dibenzothiophenyl group that is unsubstituted or substituted with deuterium.

5. The compound of claim 1, wherein the compound of Chemical Formula 2 is any one compound selected from among the following compounds:

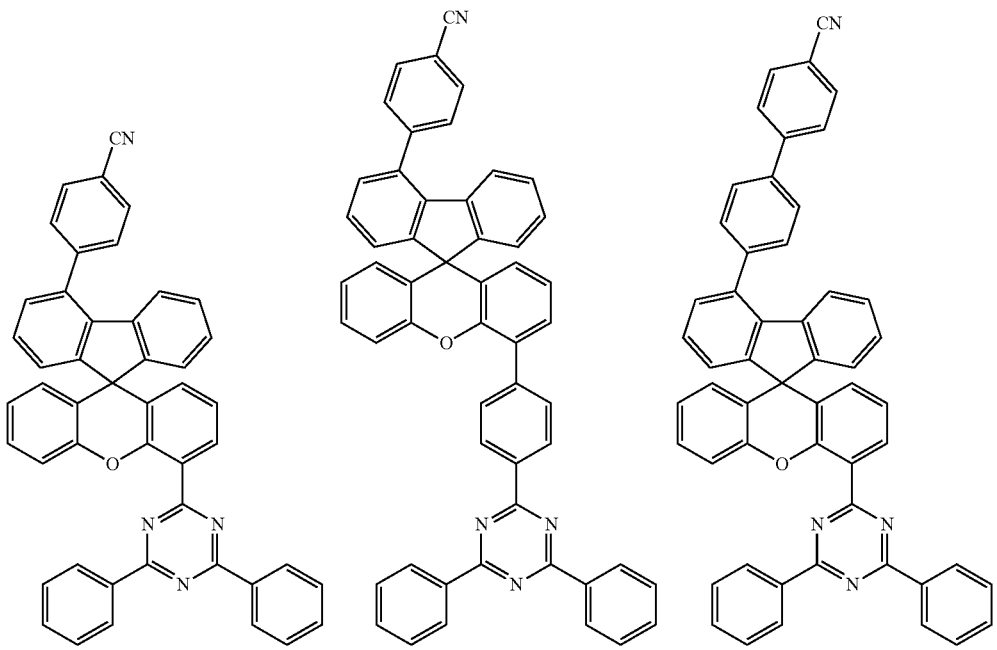

-continued
193
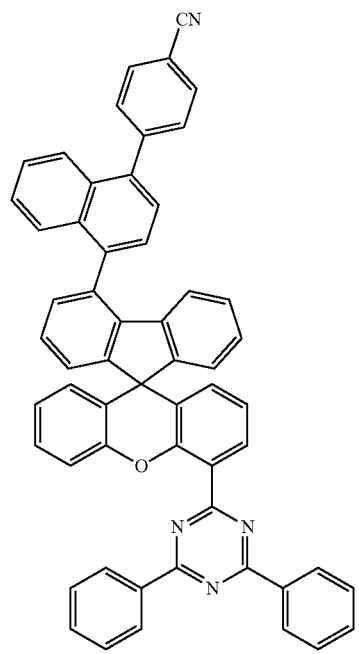 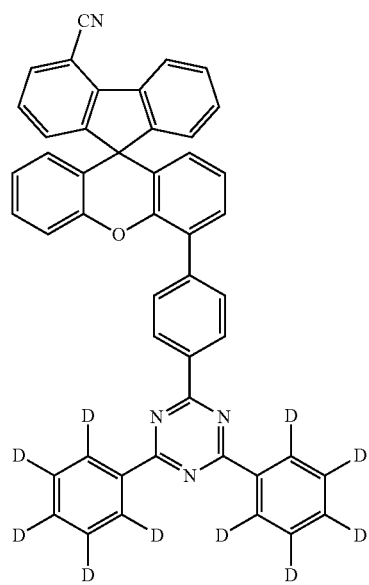
194
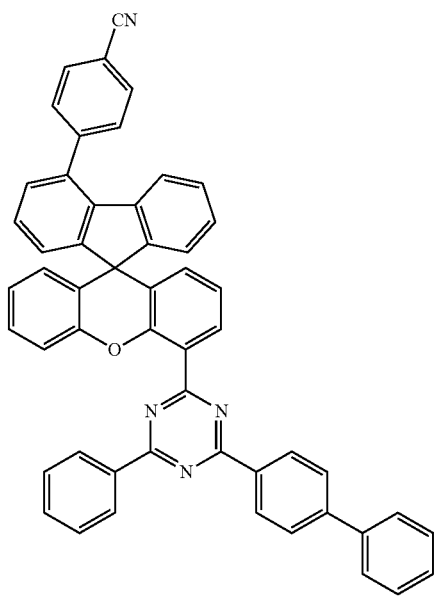
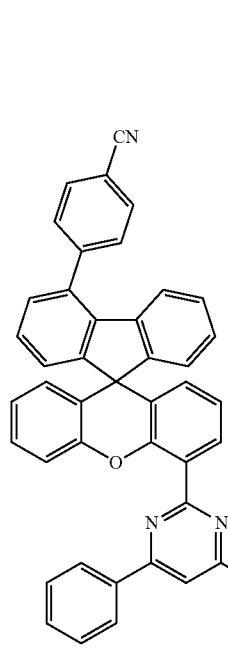 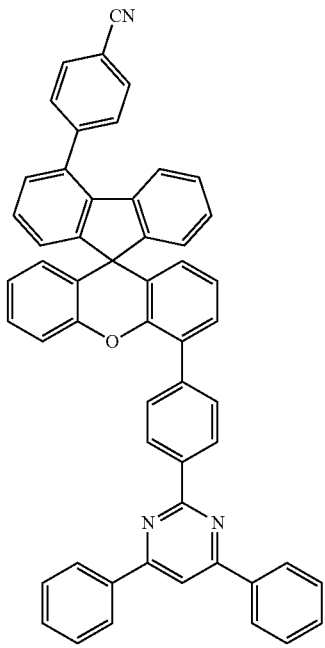 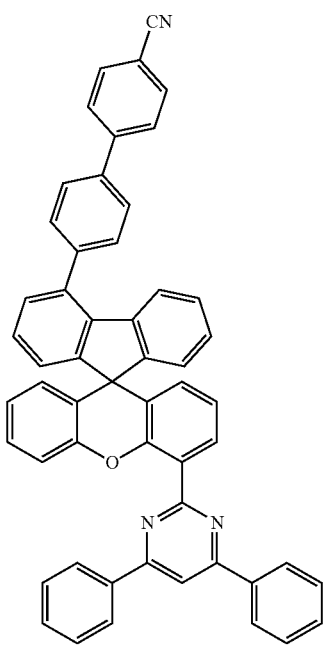

195
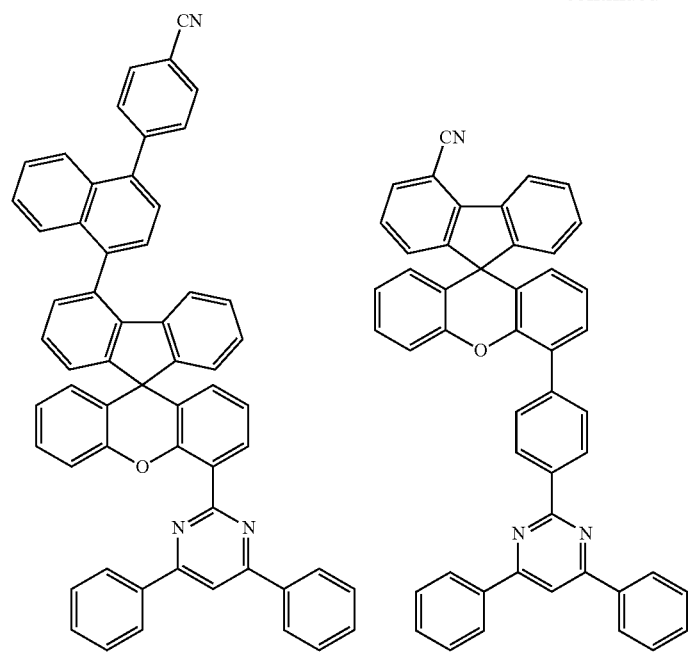
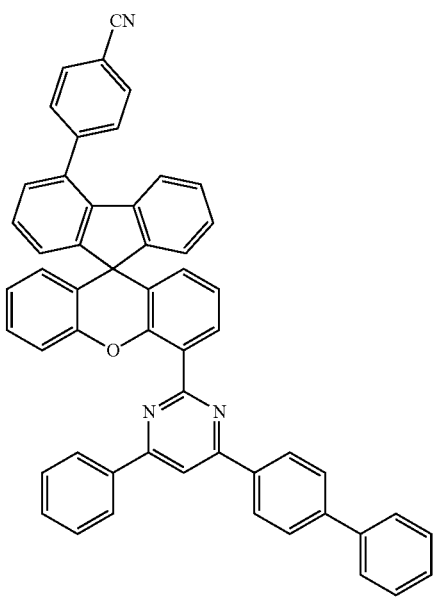
196
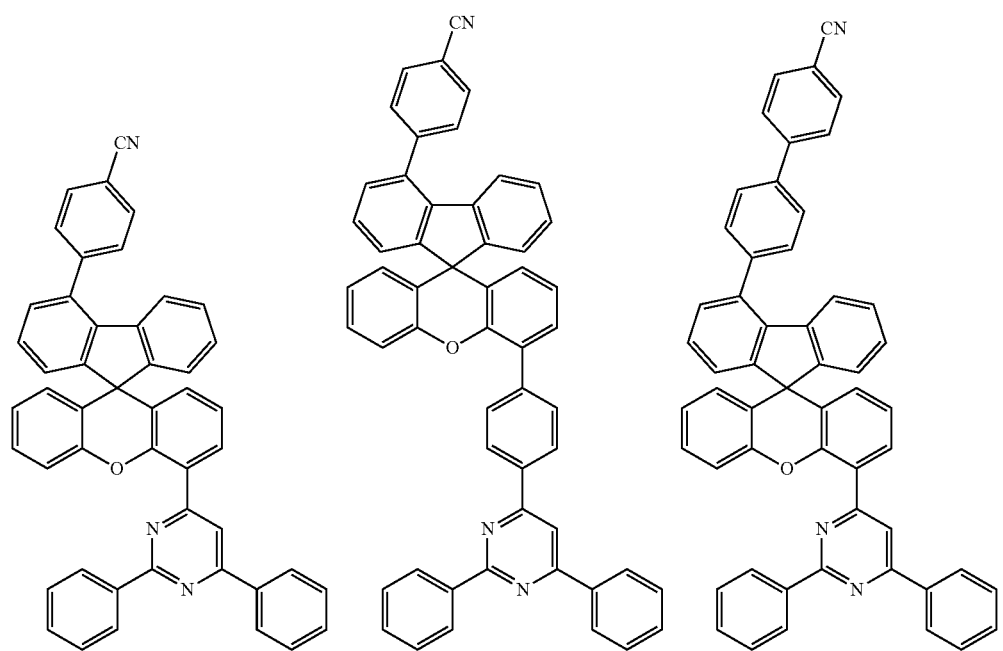

197 198
-continued
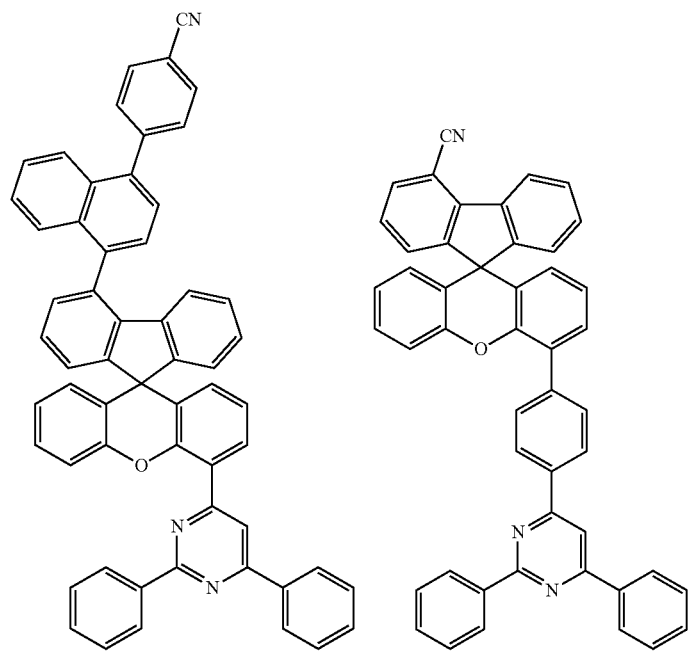
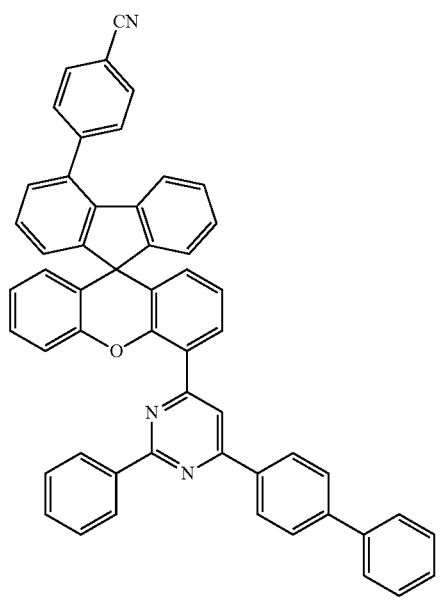
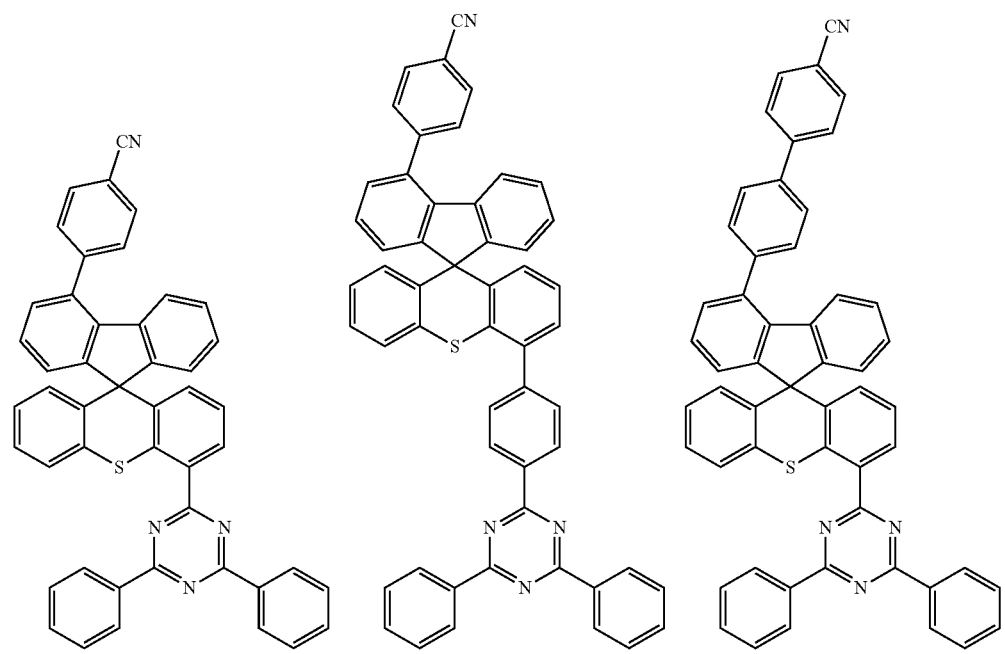

199
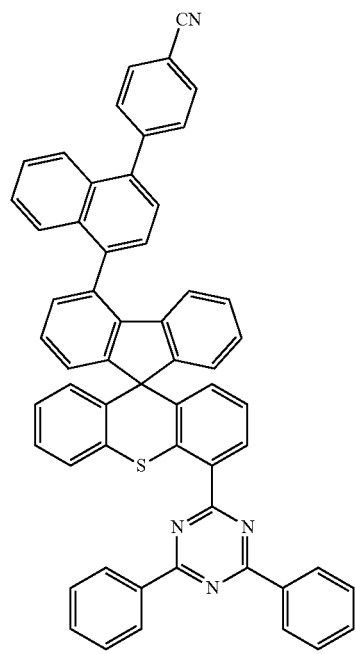
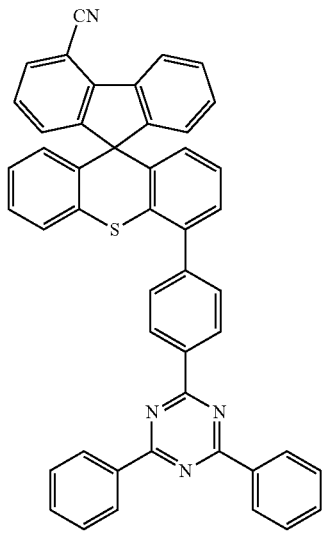
200
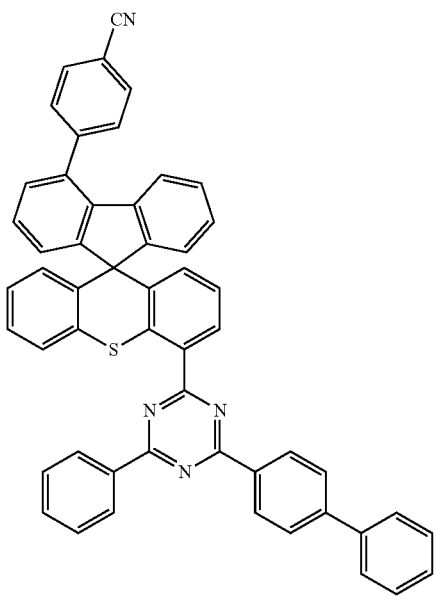
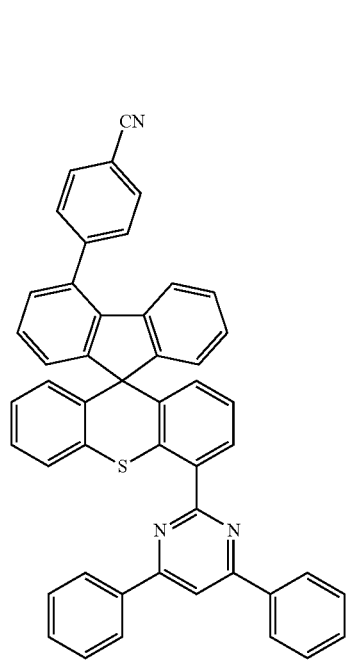
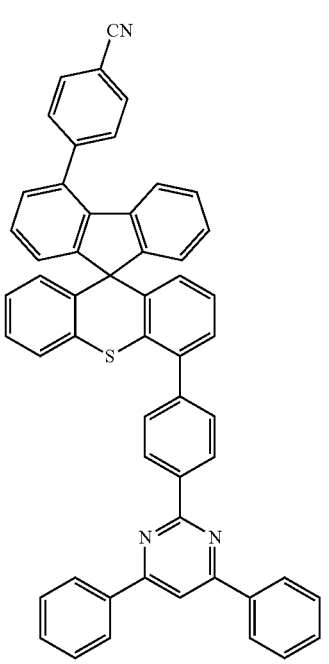
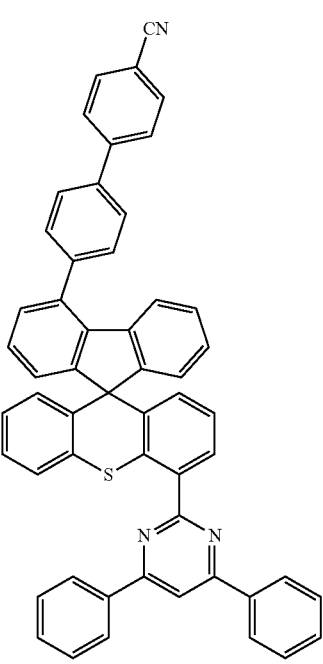

201
-continued
202
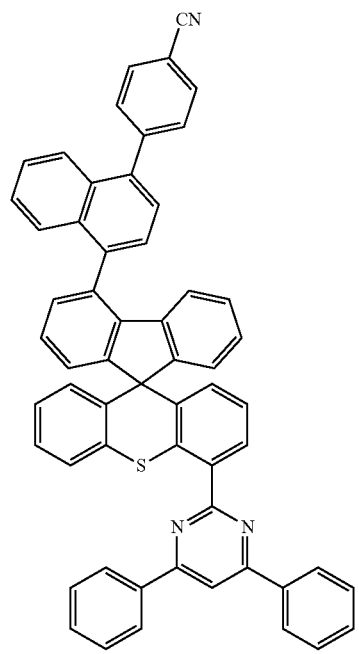 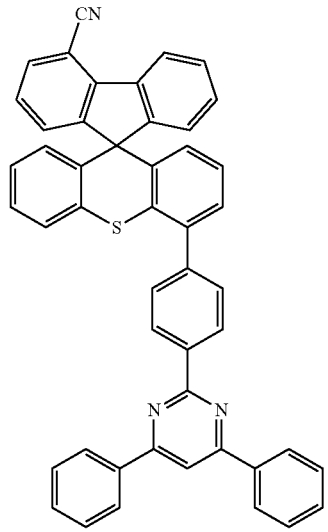 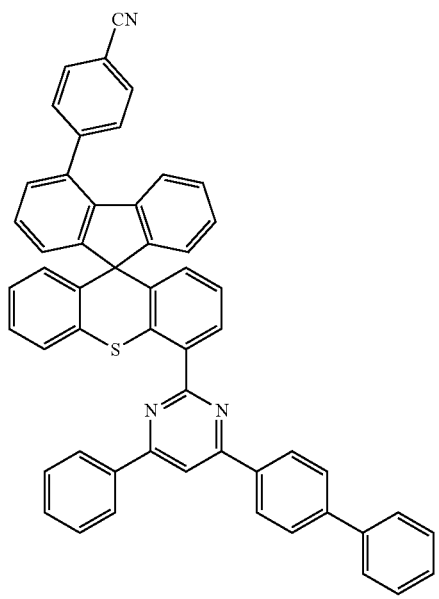
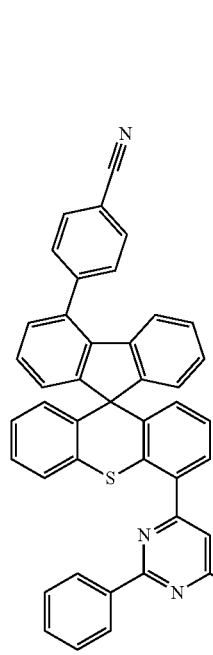 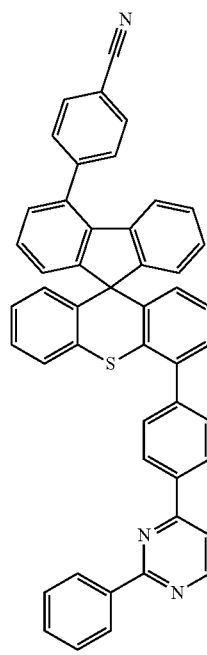 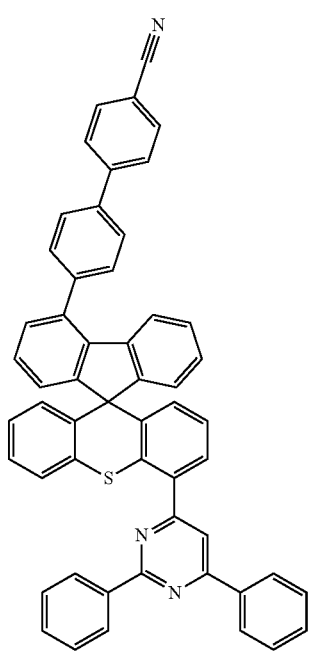

-continued
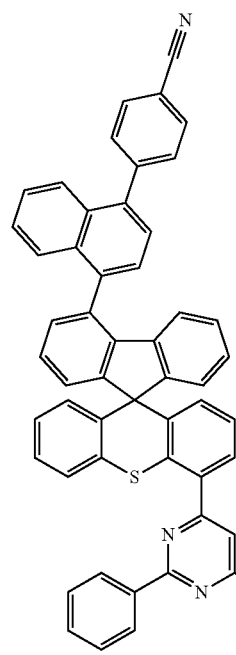
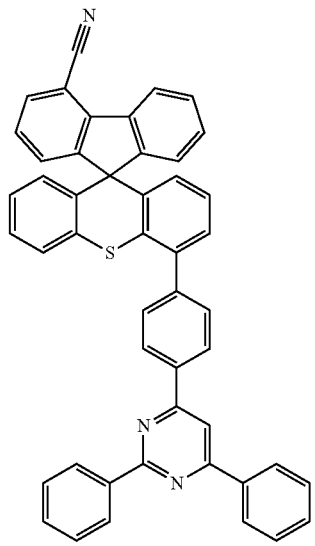
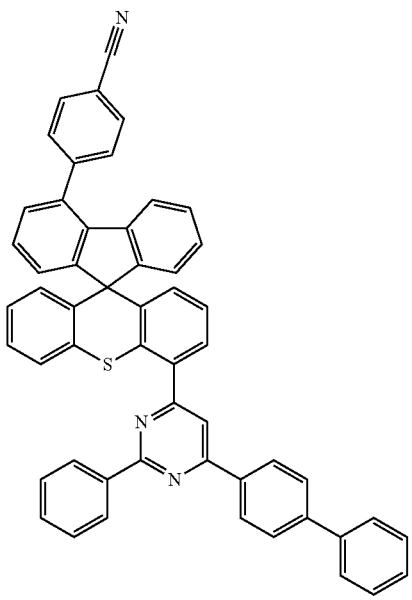
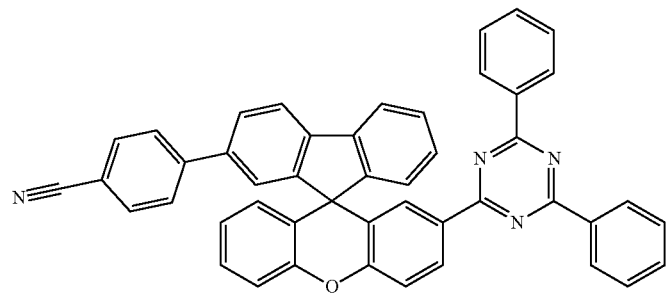
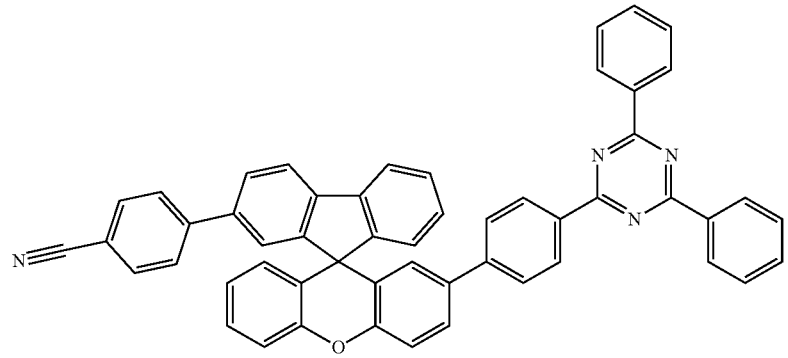
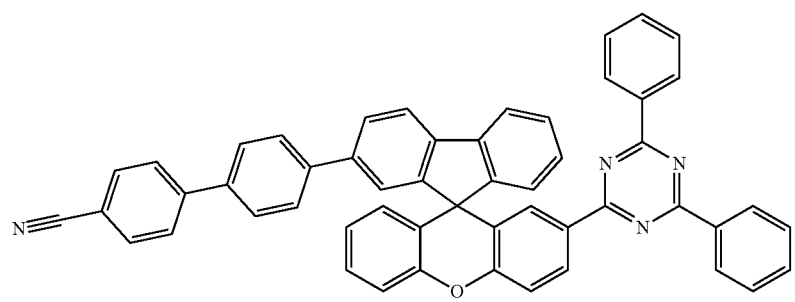

-continued
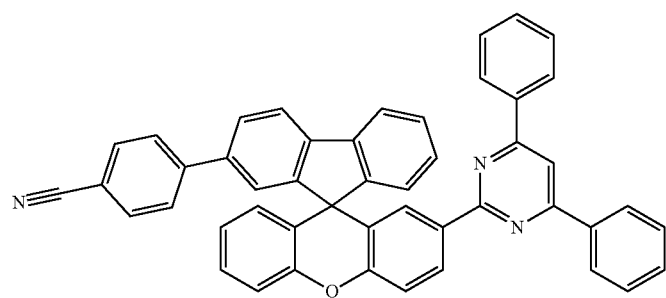
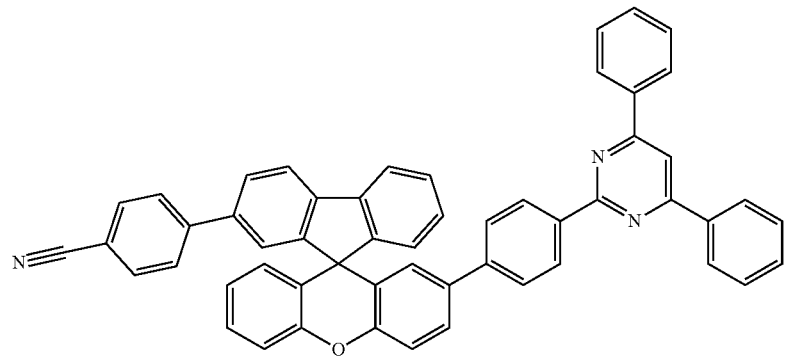
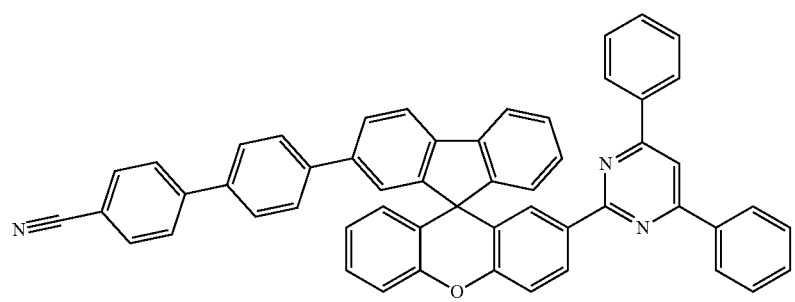
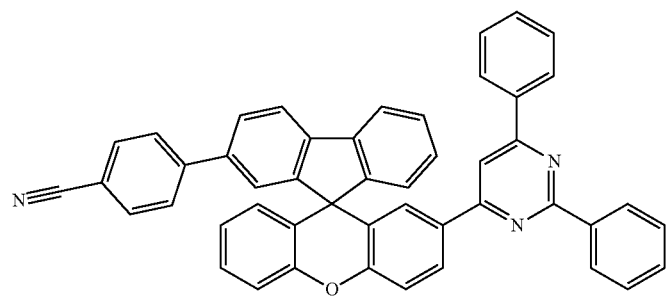
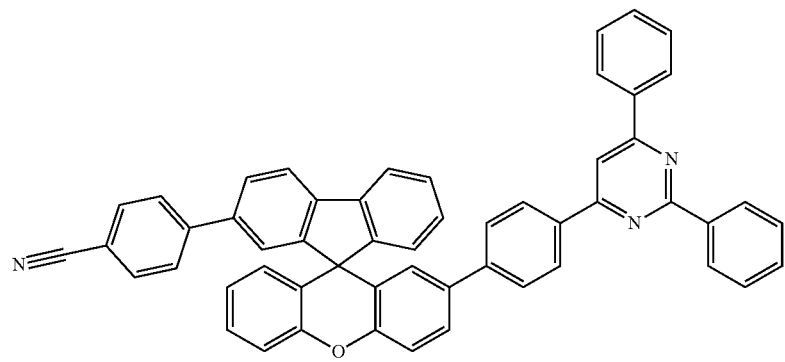

-continued
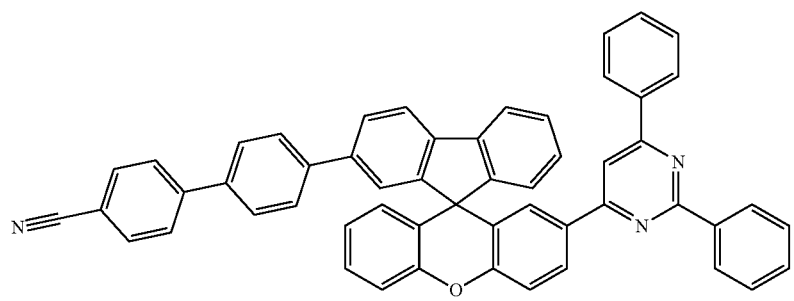
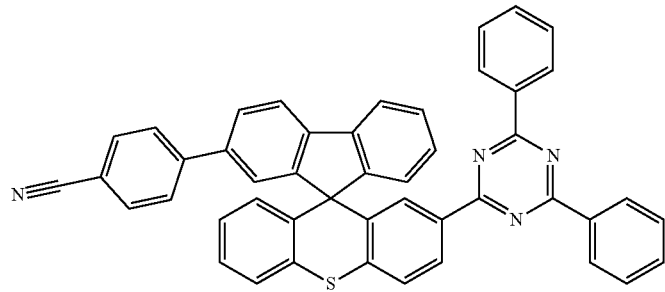
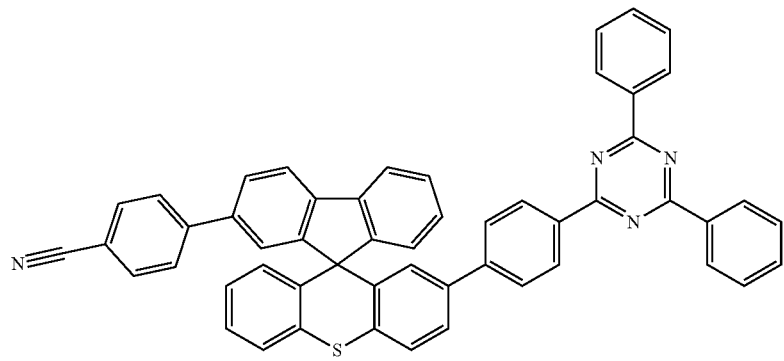
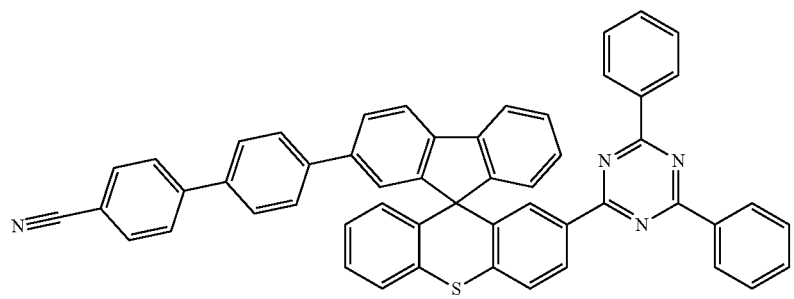
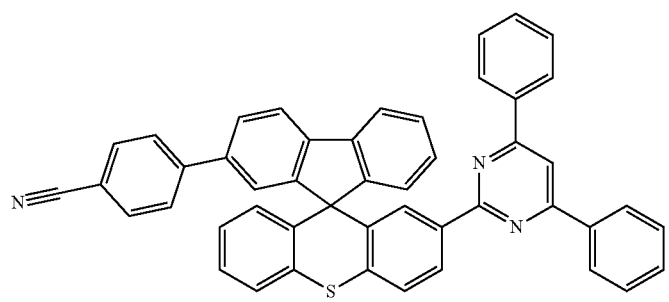

-continued
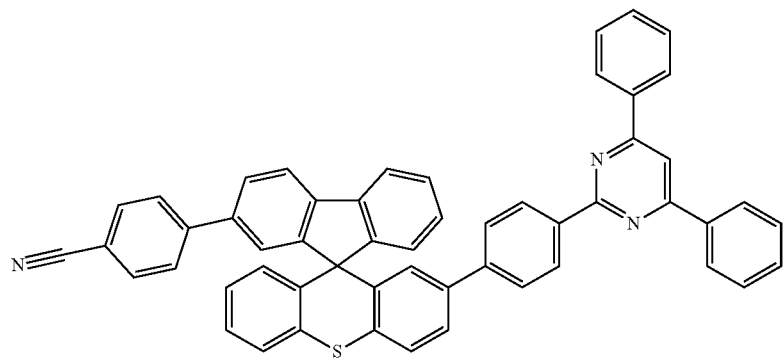
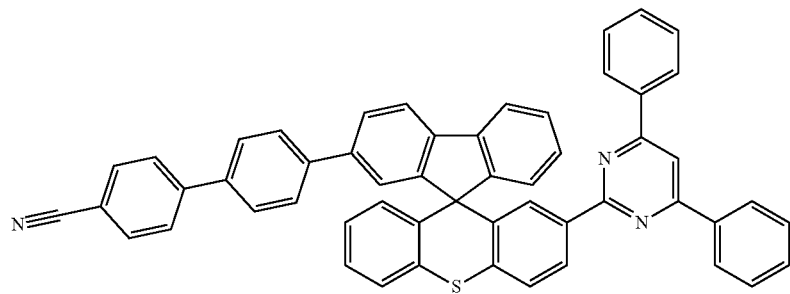
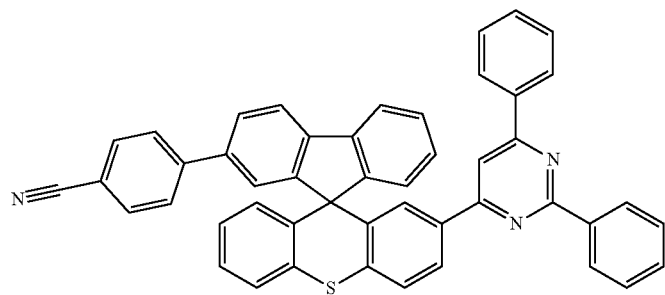
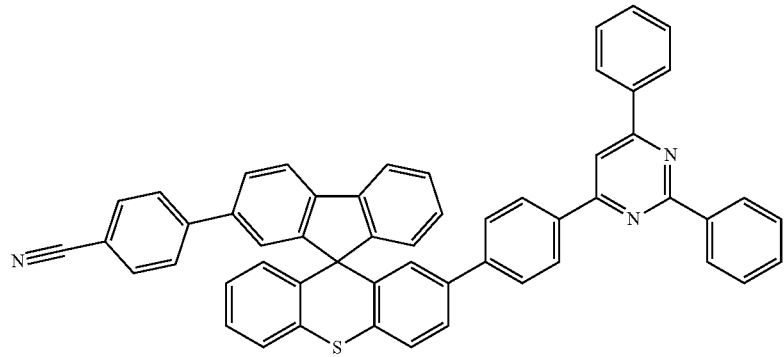
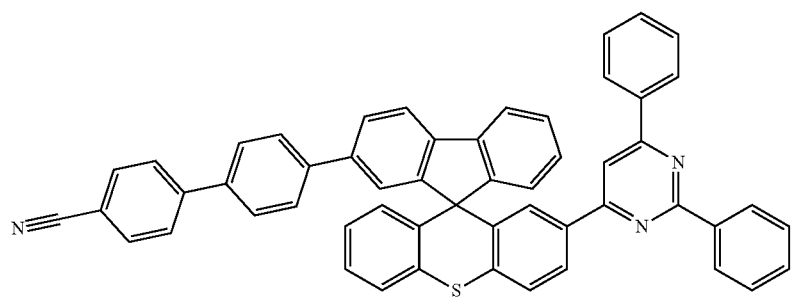

-continued
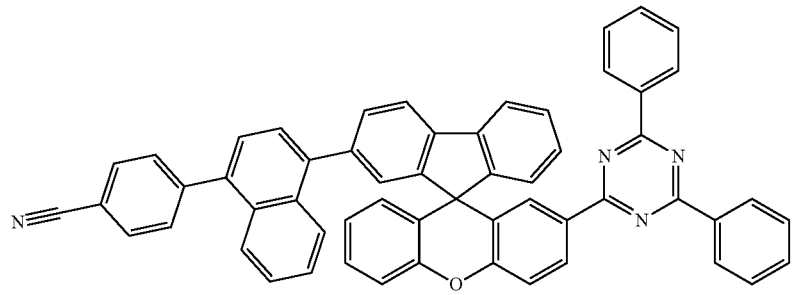
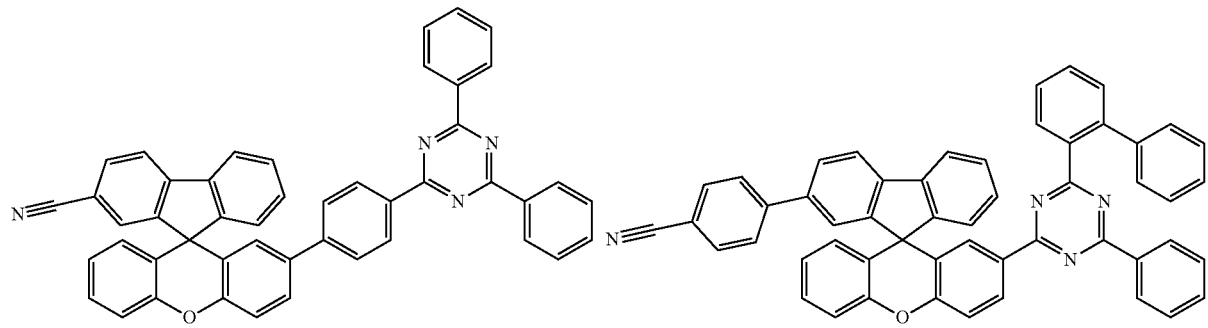
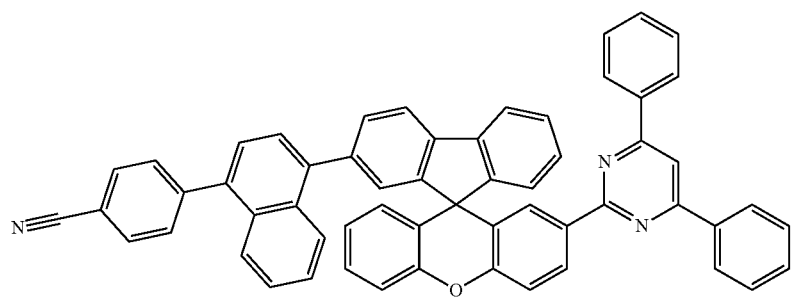
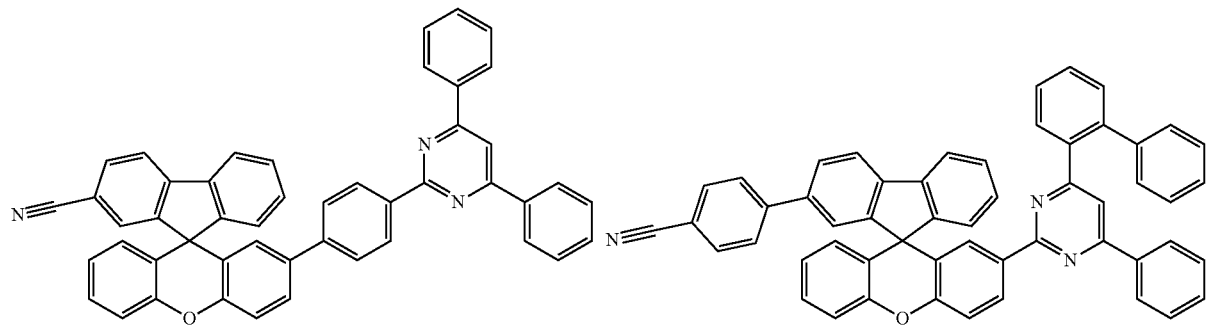
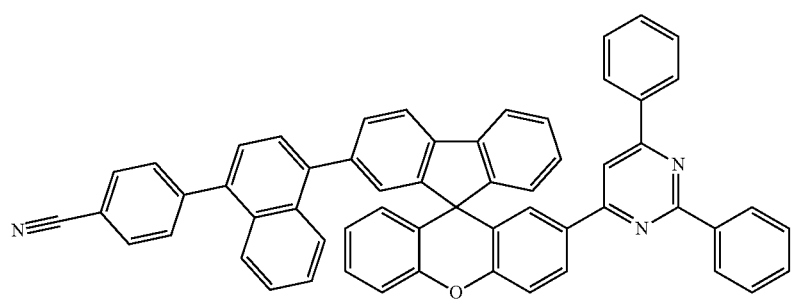

213 214
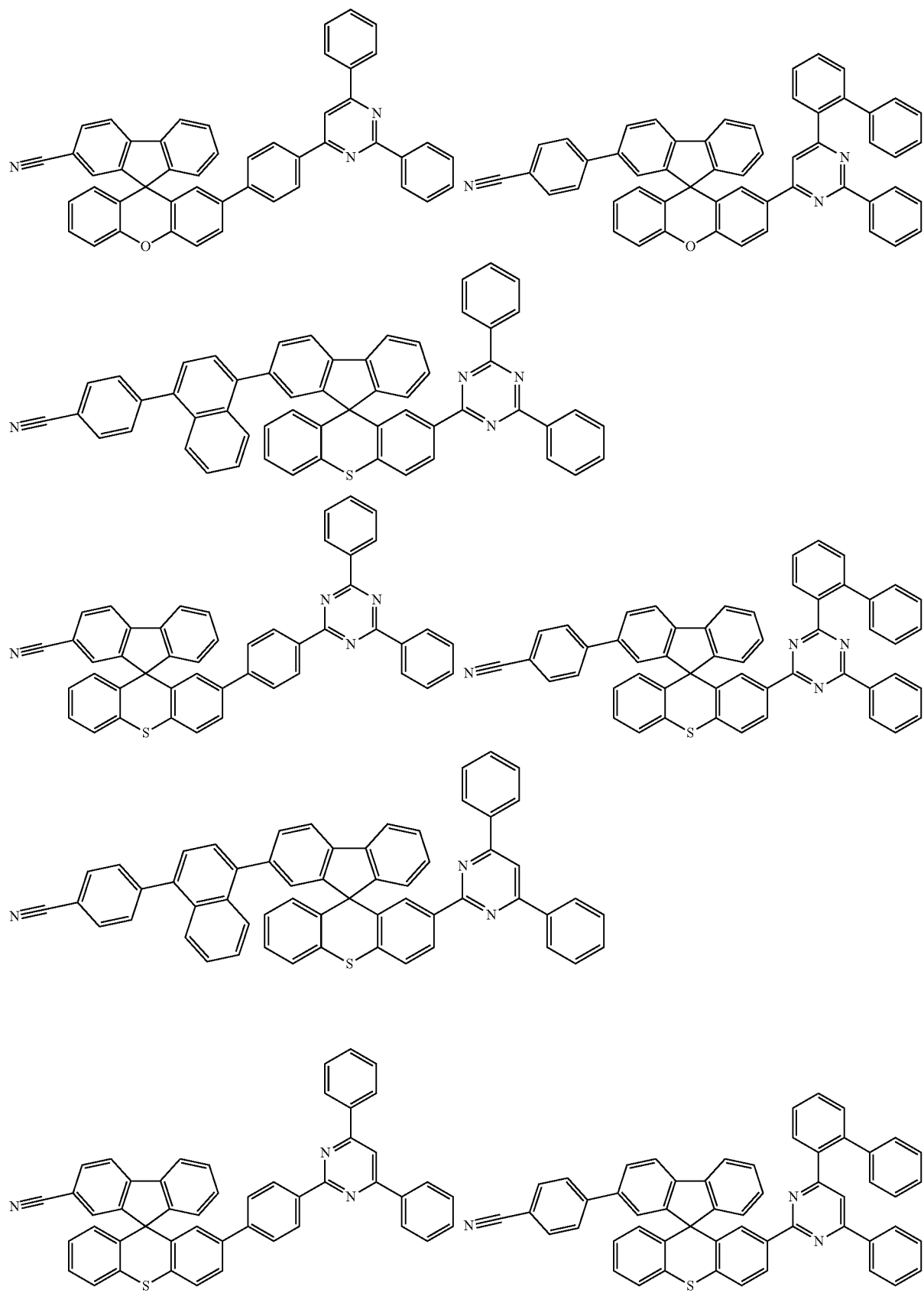
-continued

-continued
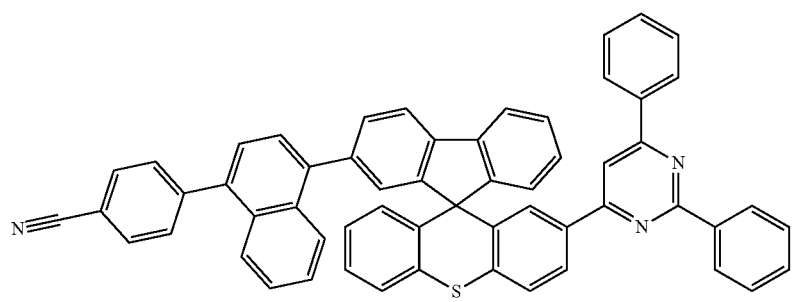
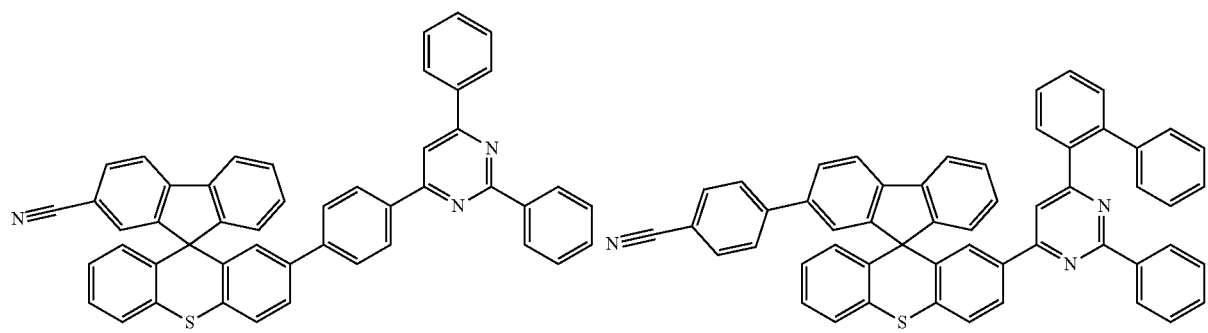
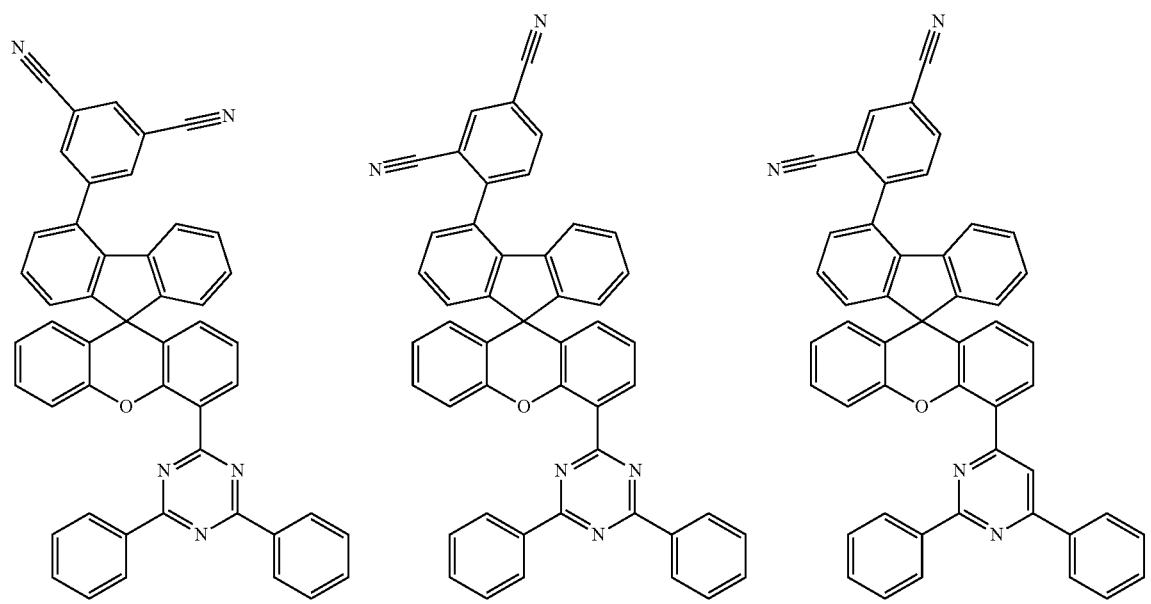

217 218
-continued
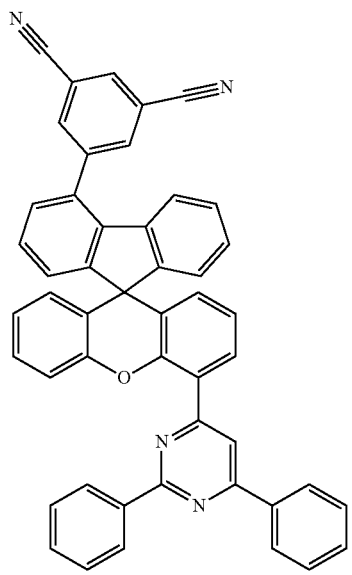
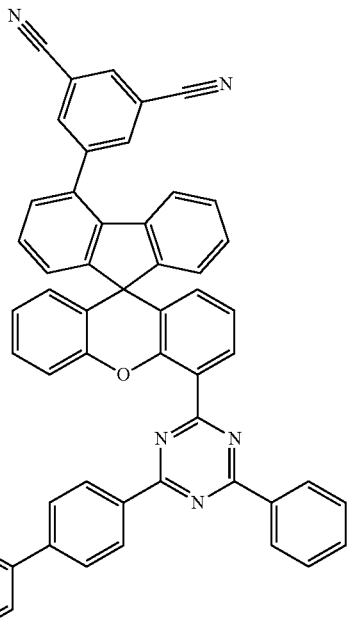
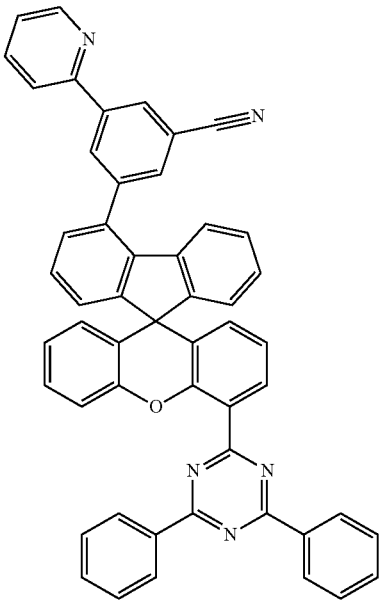
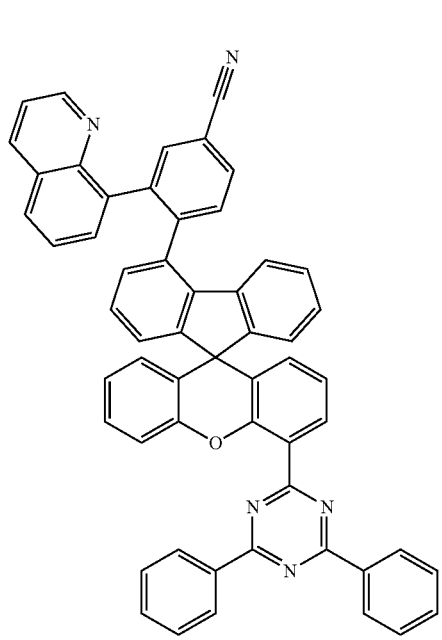
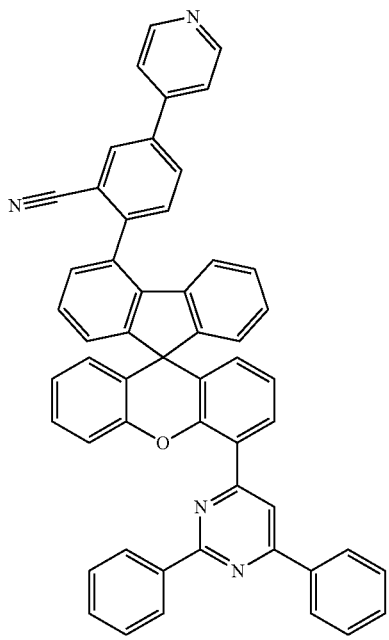

-continued
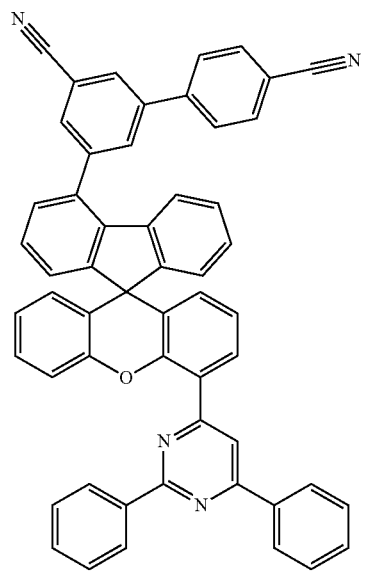
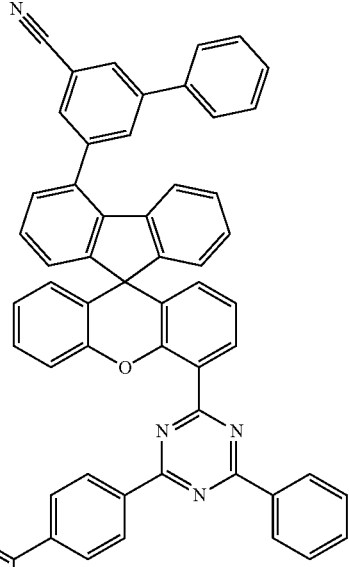
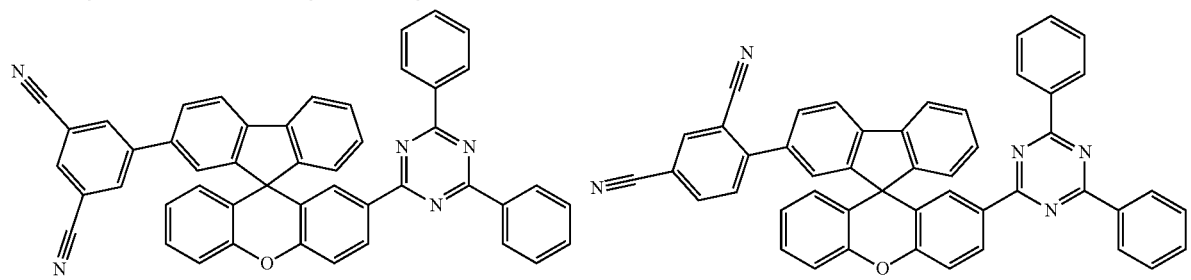
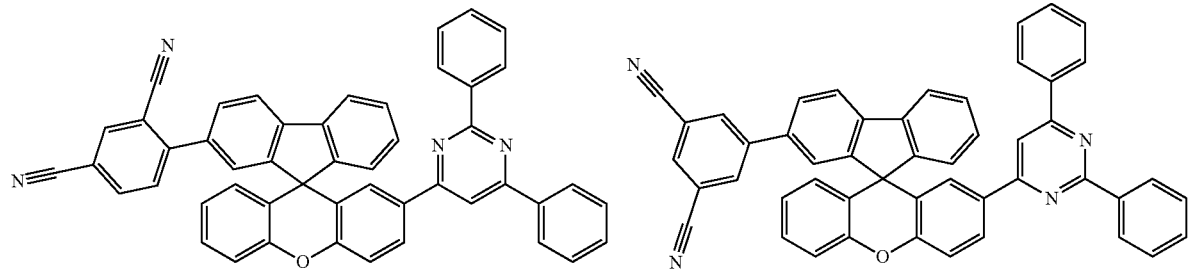
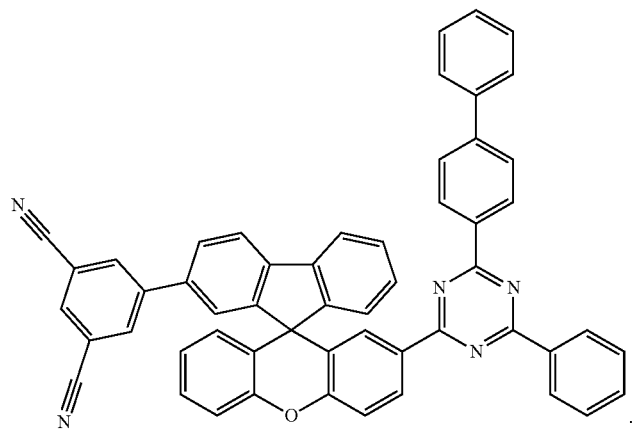

6. The compound of claim 1, wherein the compound of Chemical Formula 3 is any one compound selected from among the following compounds:
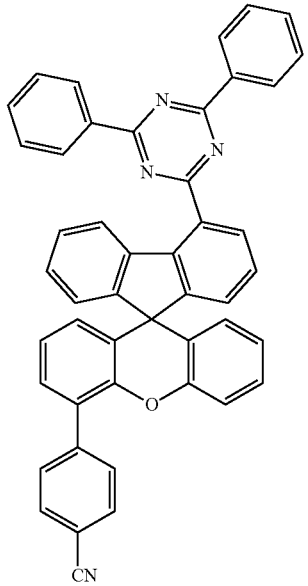
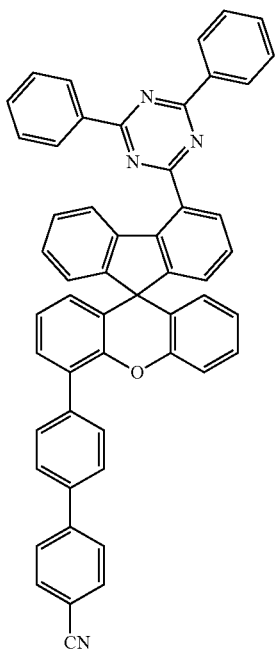
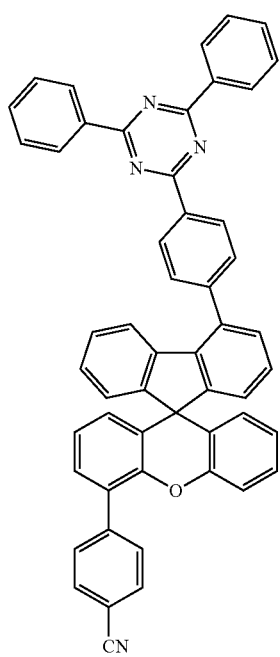
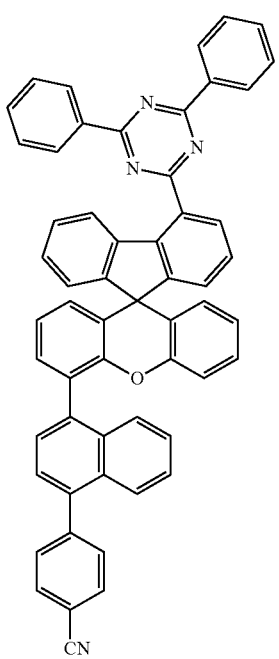

223
224
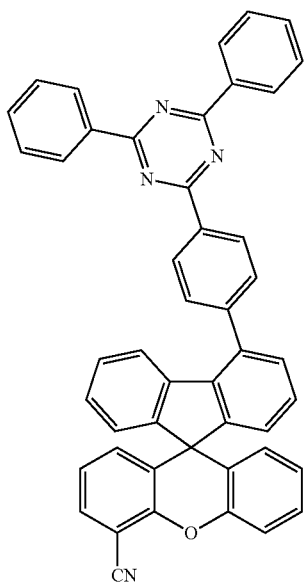
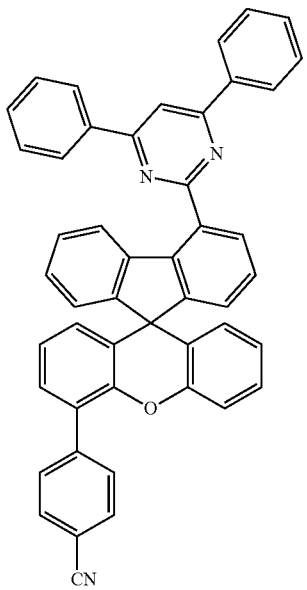

225
-continued
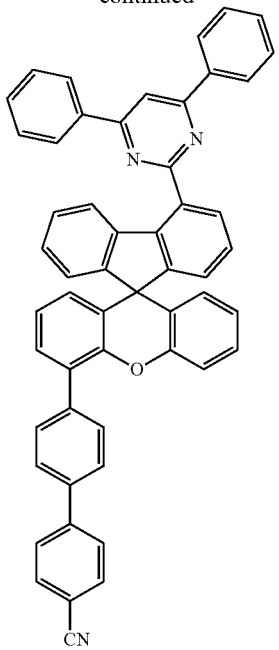
226
-continued
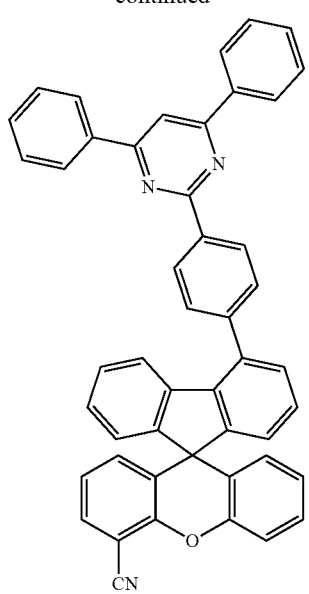
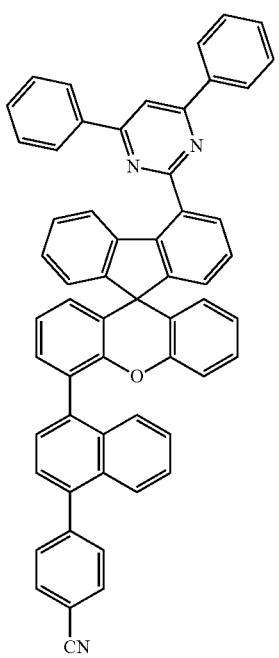
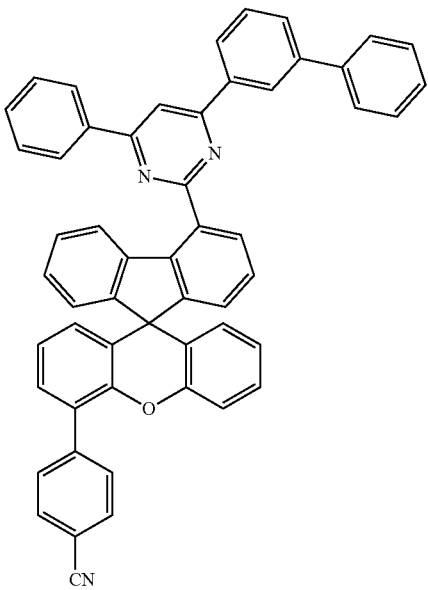

227
-continued
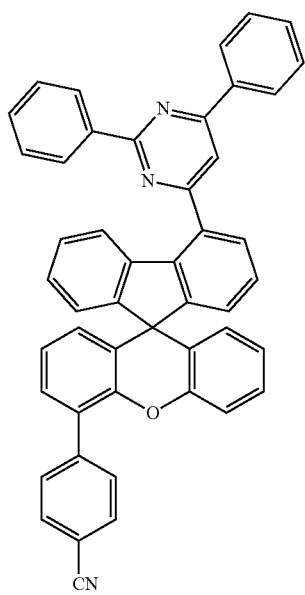
228
-continued
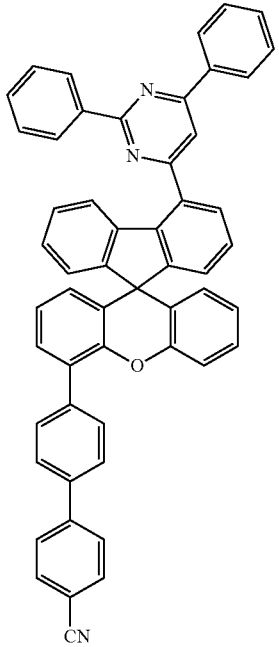
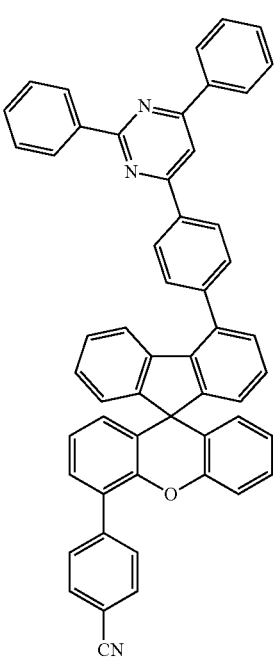
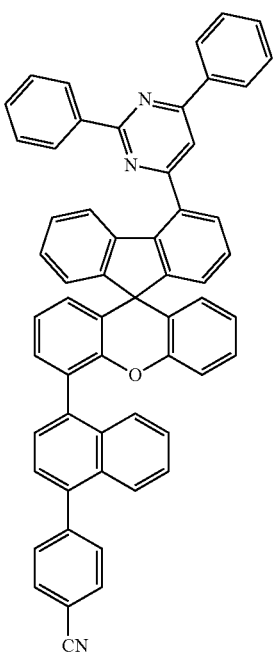

229
-continued
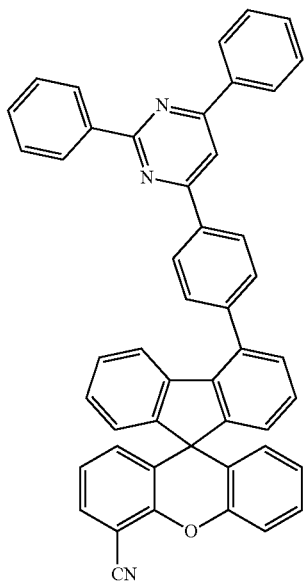
230
-continued
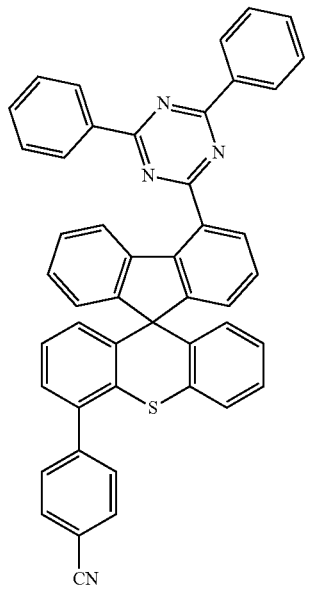
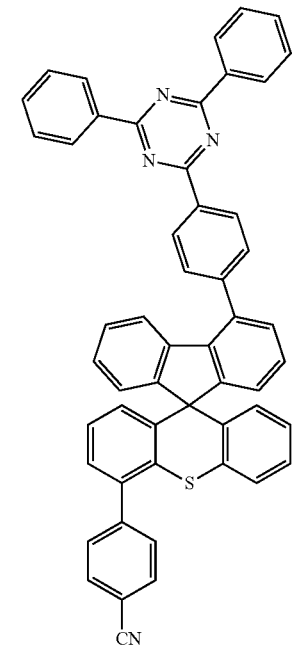

231
-continued
232
-continued
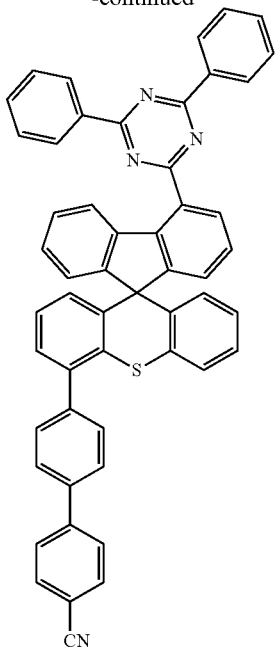
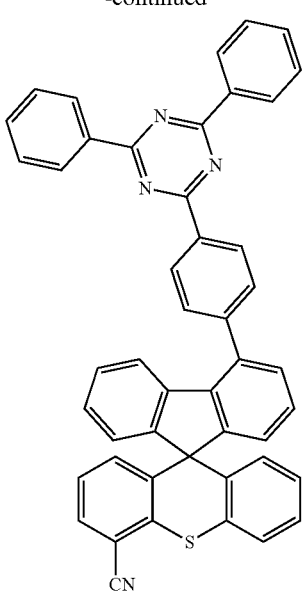

233
-continued
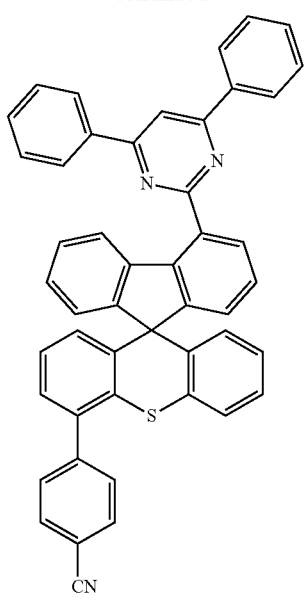
234
-continued
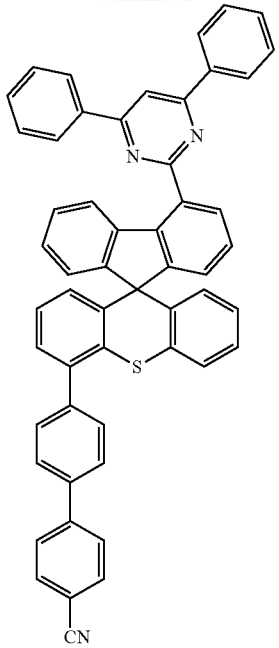

235
-continued
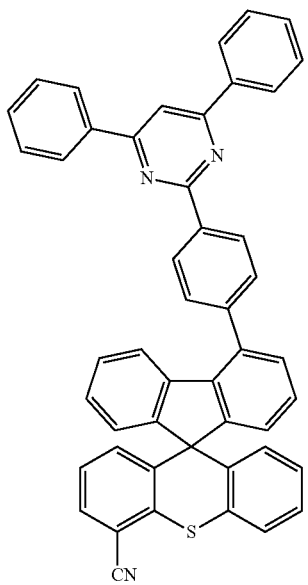
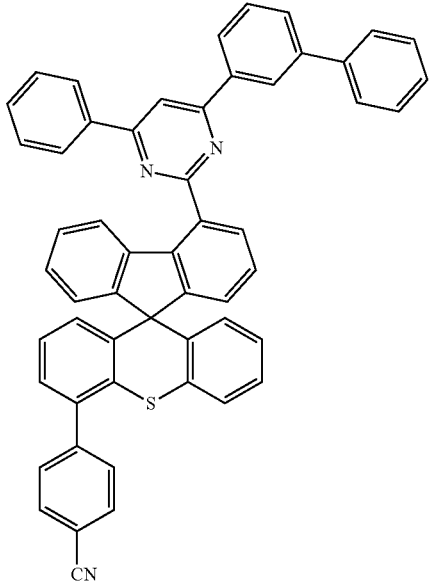
236
-continued
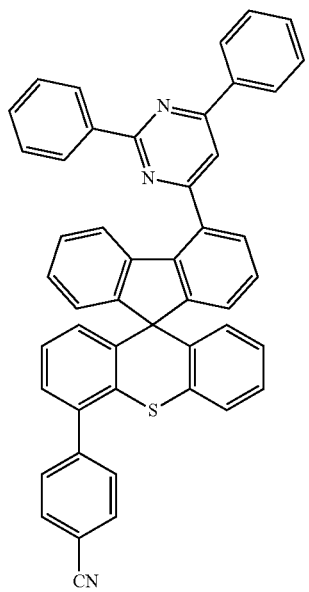
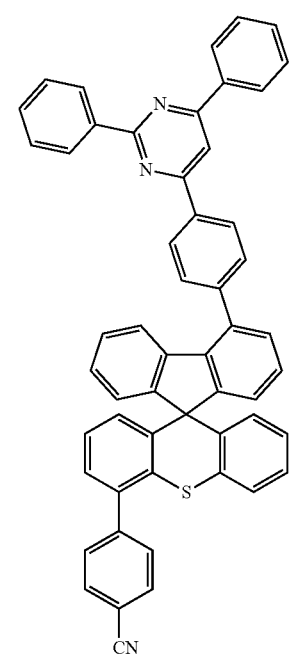

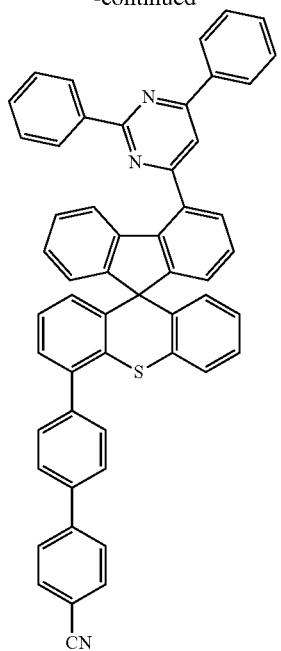
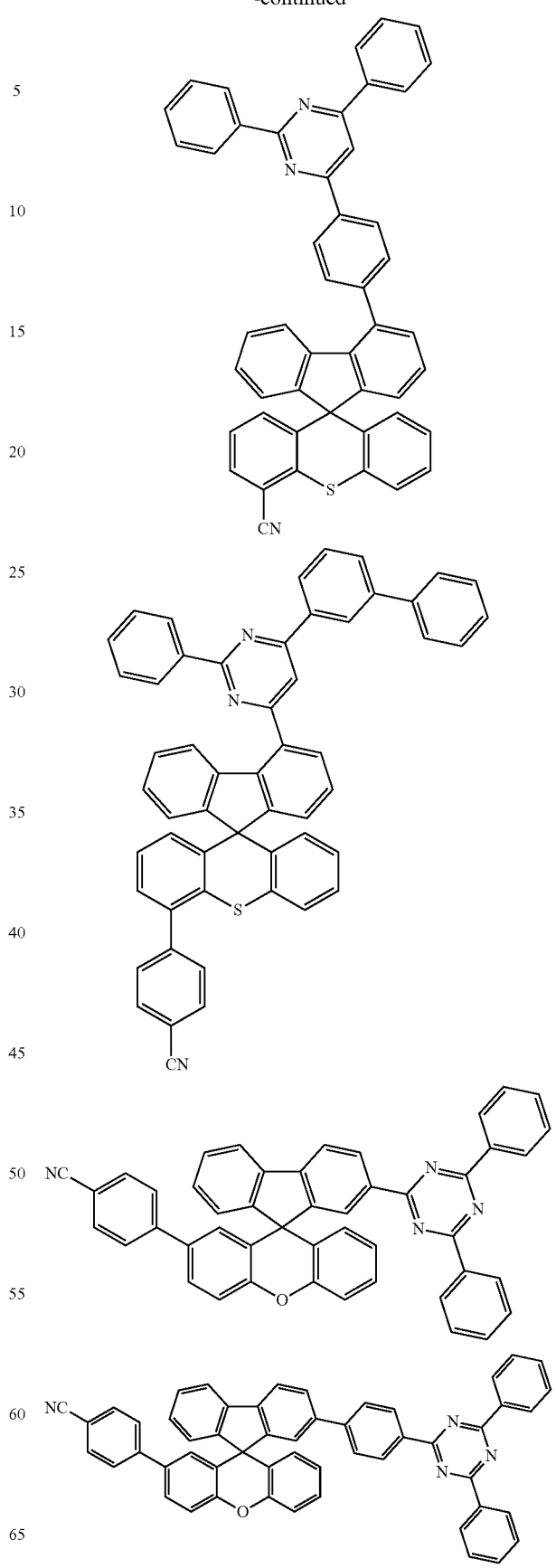

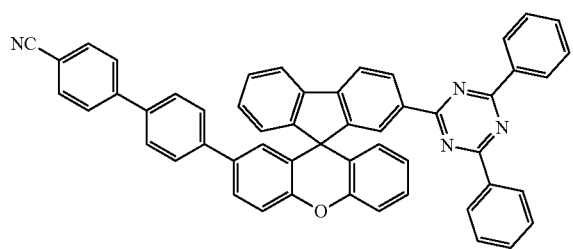
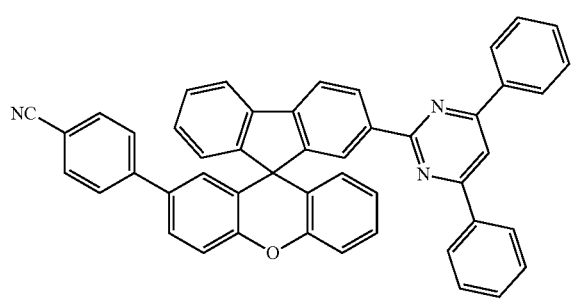
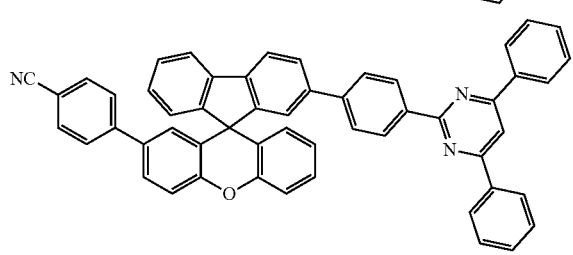
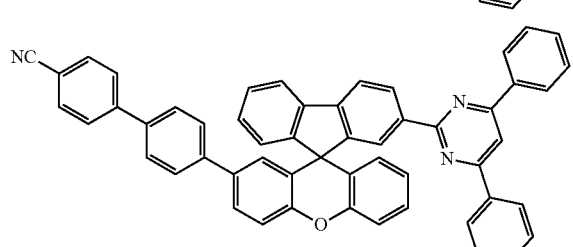
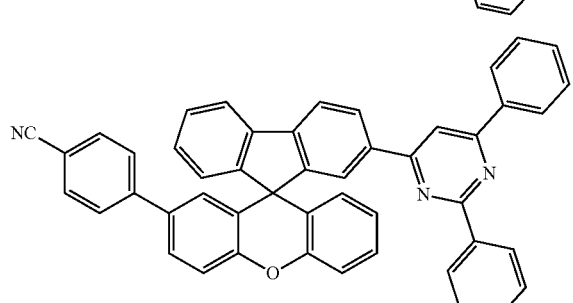
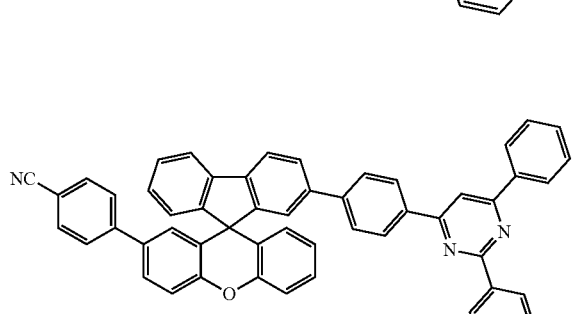
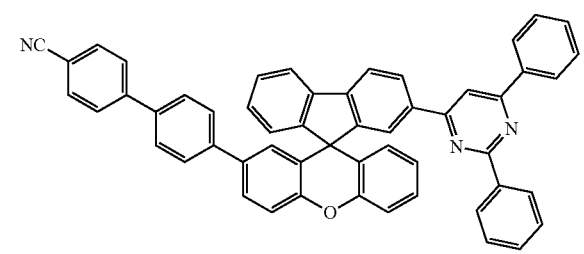
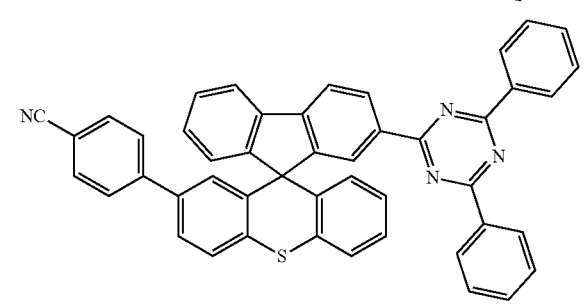
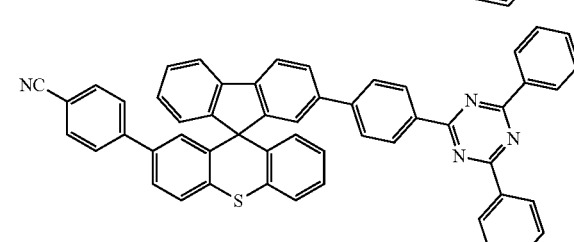
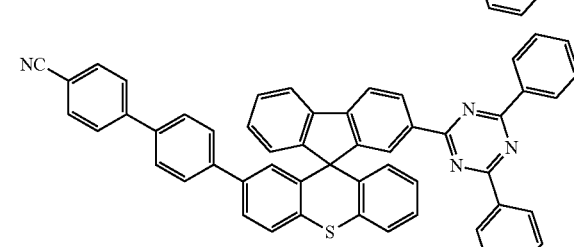
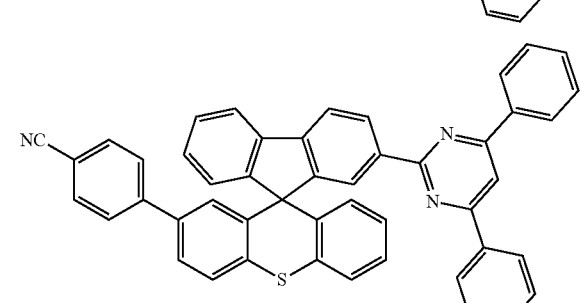
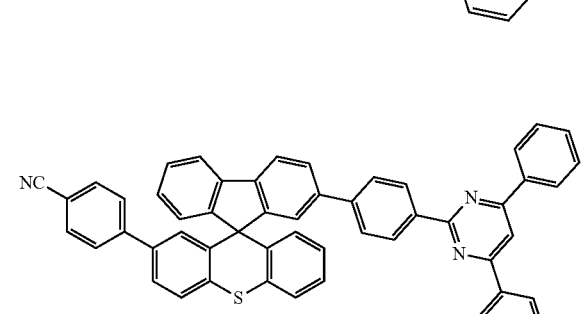

241
-continued
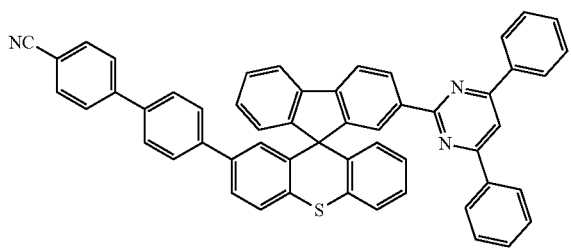
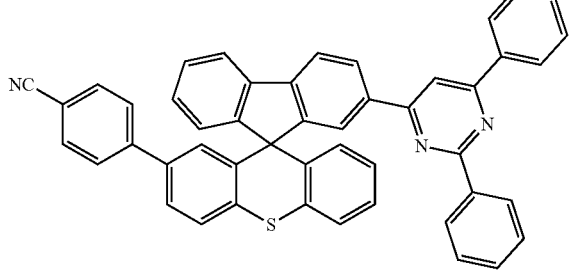
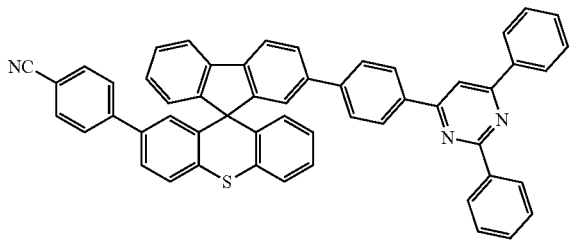
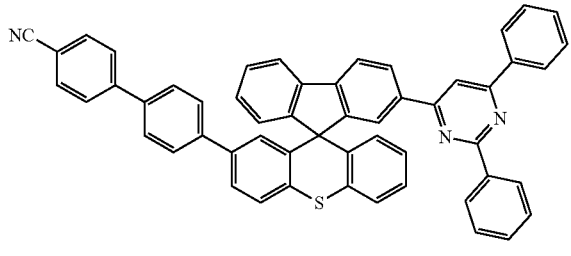
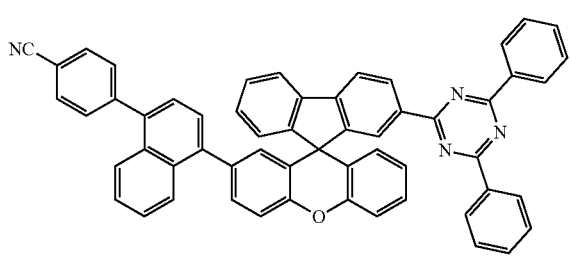
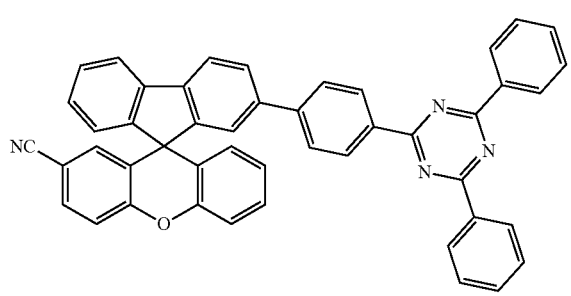
242
-continued
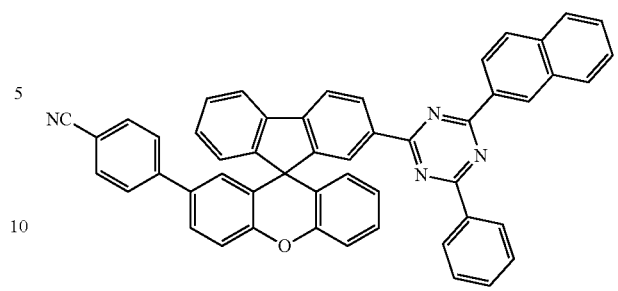
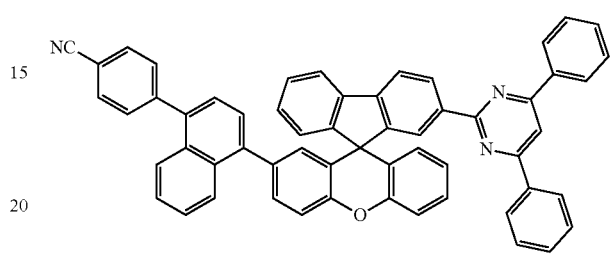
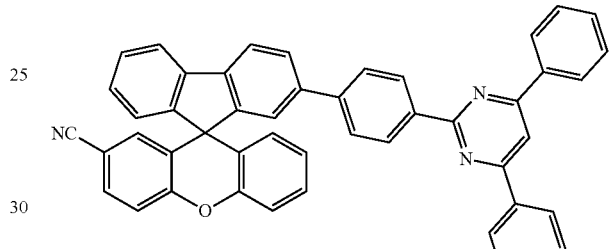
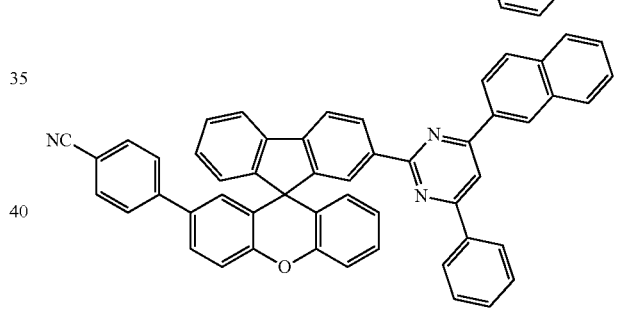
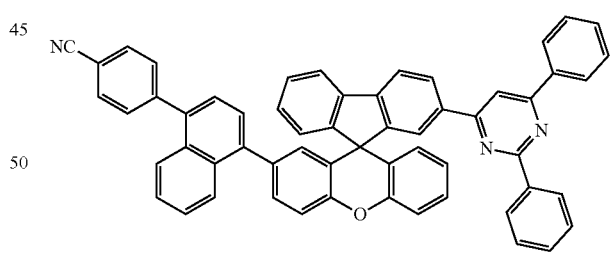
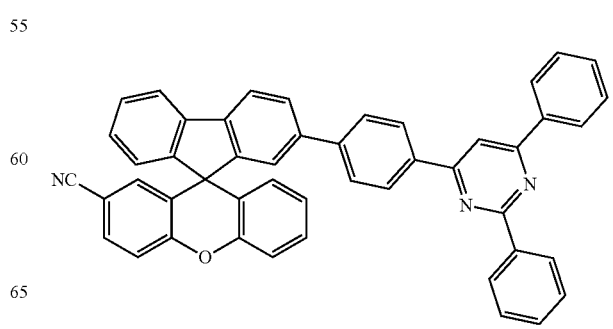

243
-continued
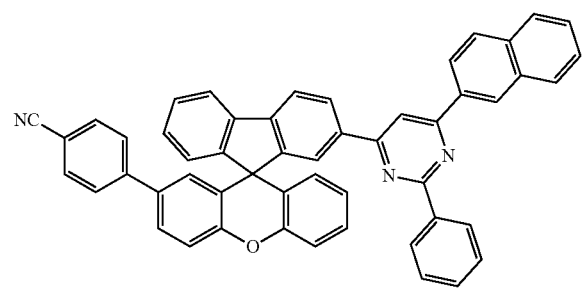
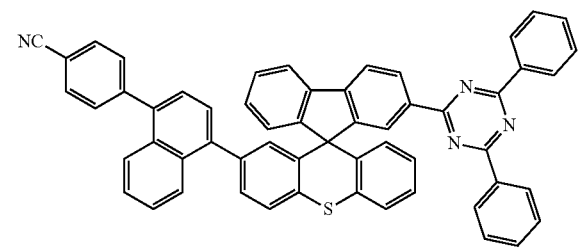
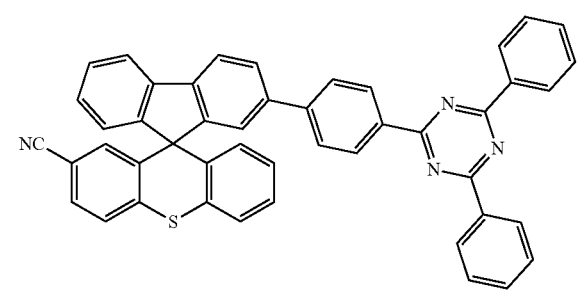
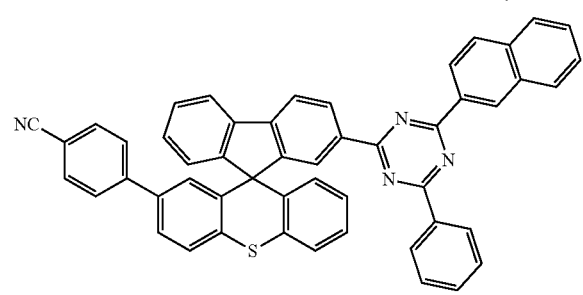
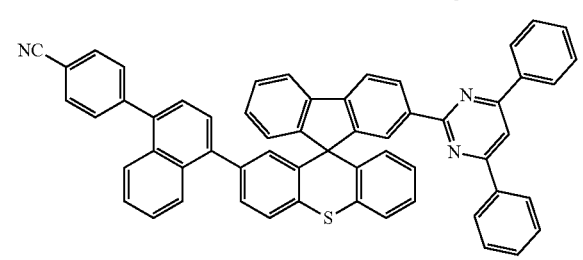
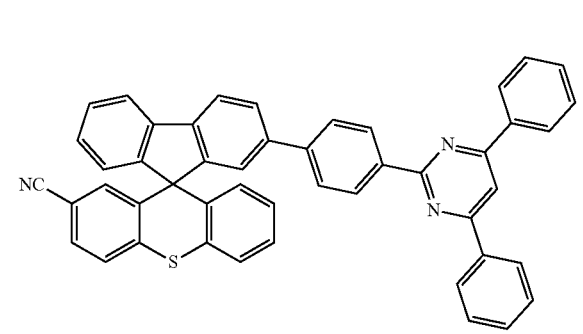
244
-continued
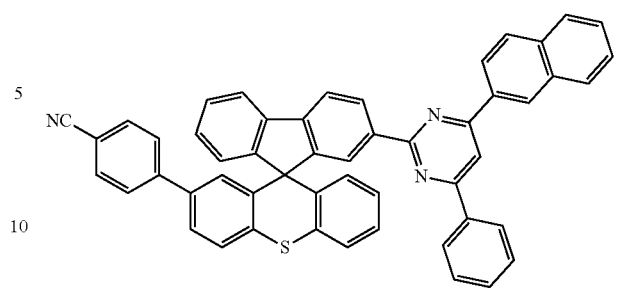
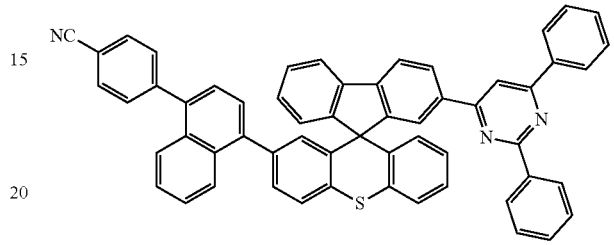
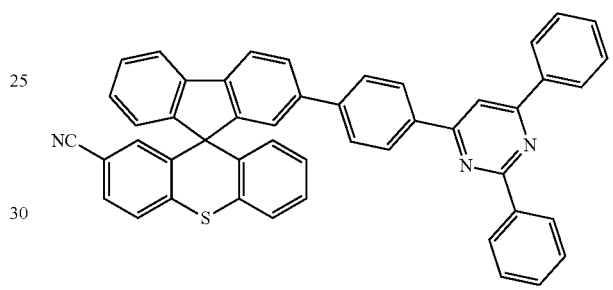
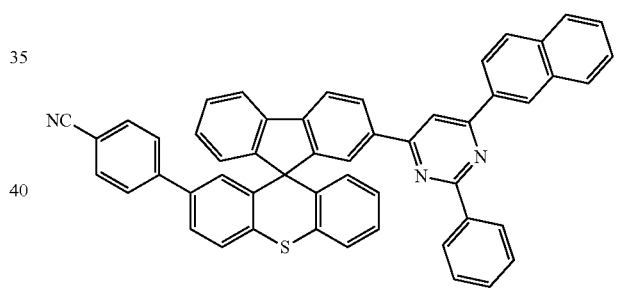
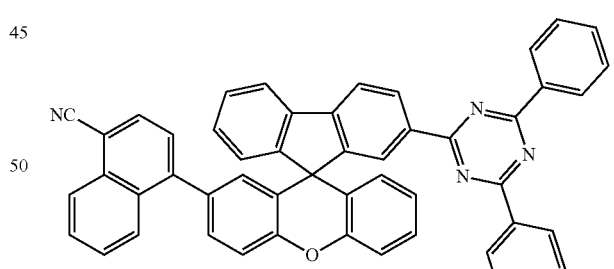
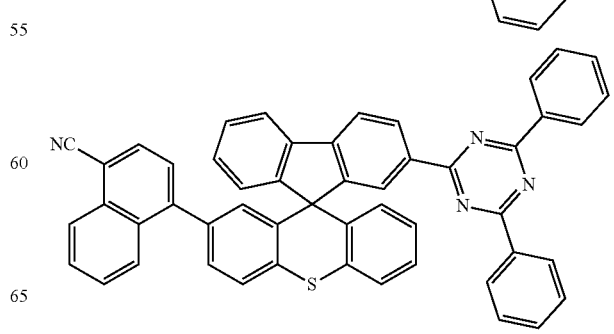

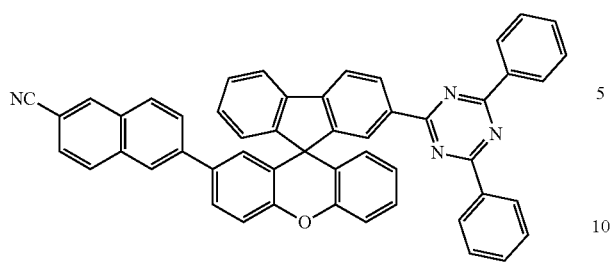
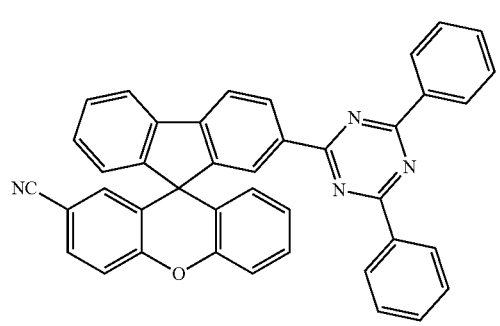
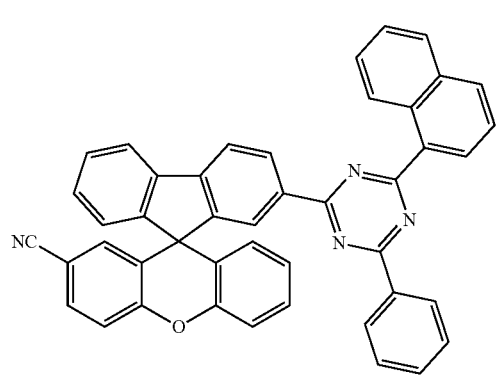
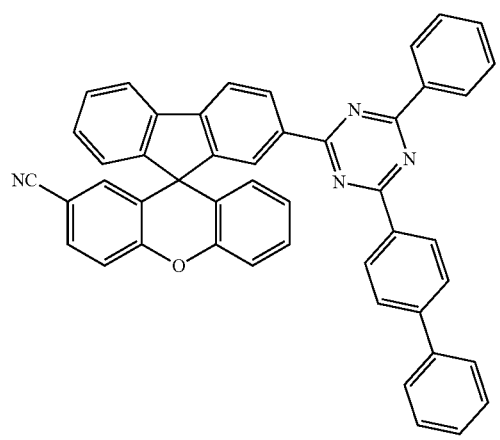
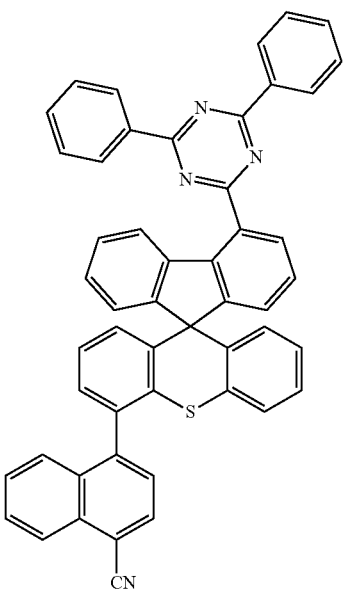
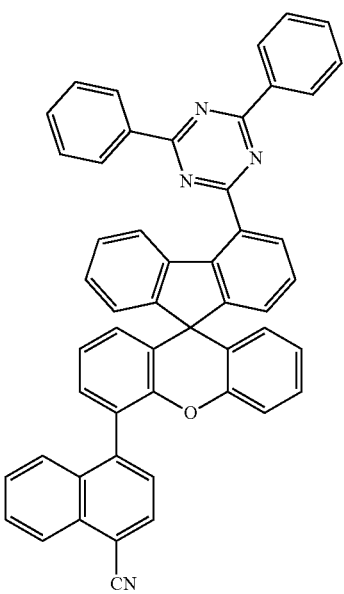
7. The compound of claim 1, wherein the compound of Chemical Formula 4 is any one compound selected from among the following compounds:

247
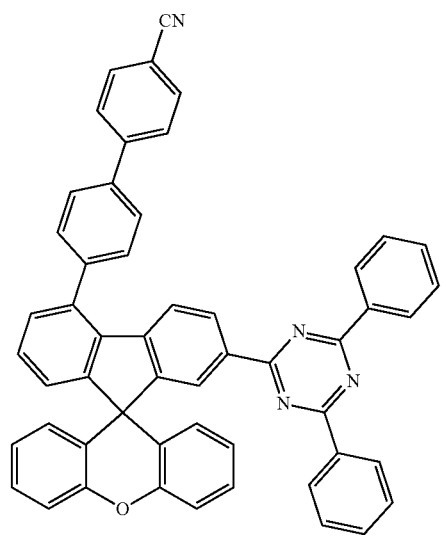
248
-continued
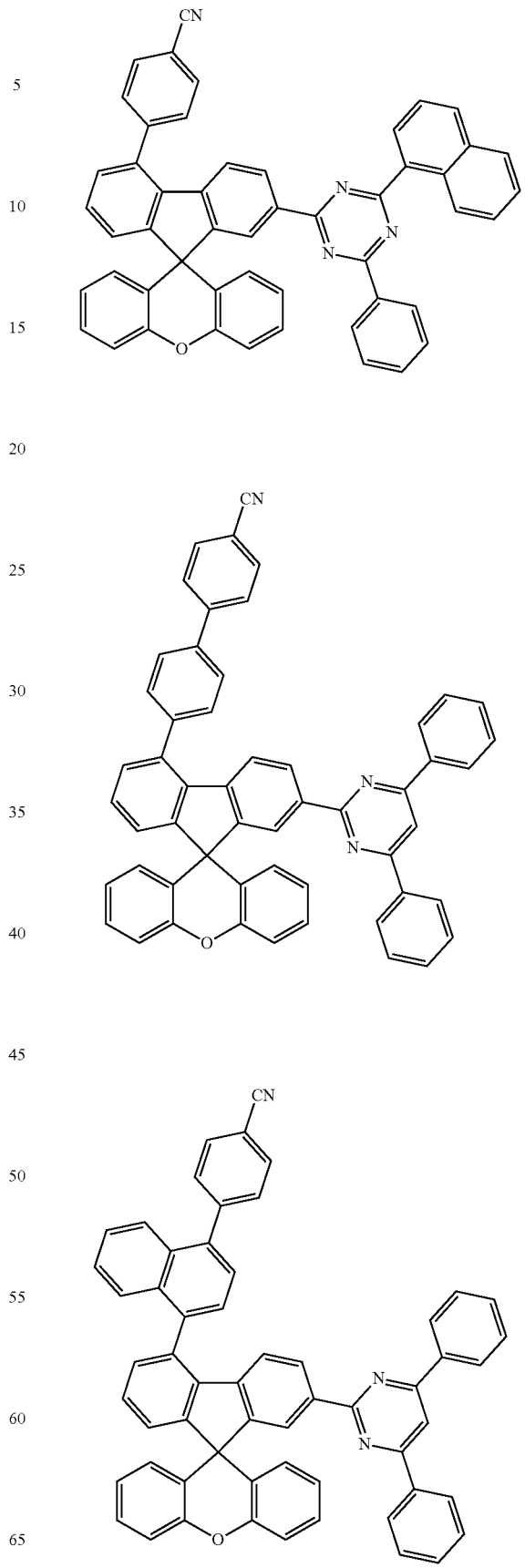

249
-continued
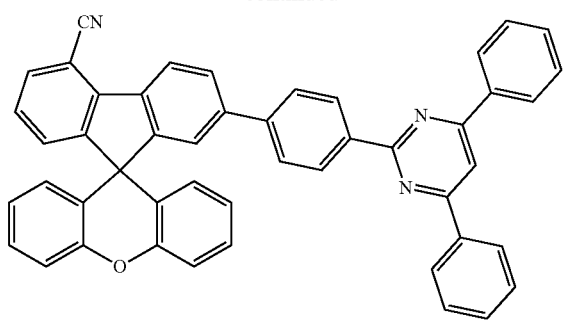
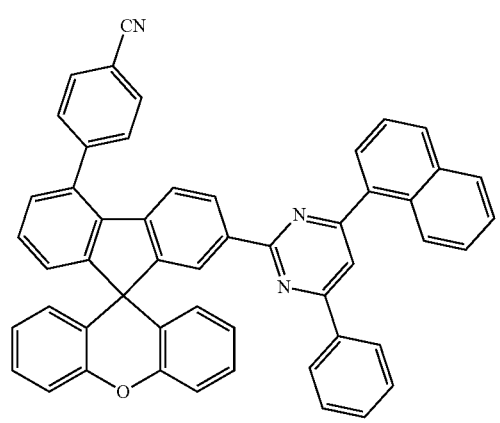
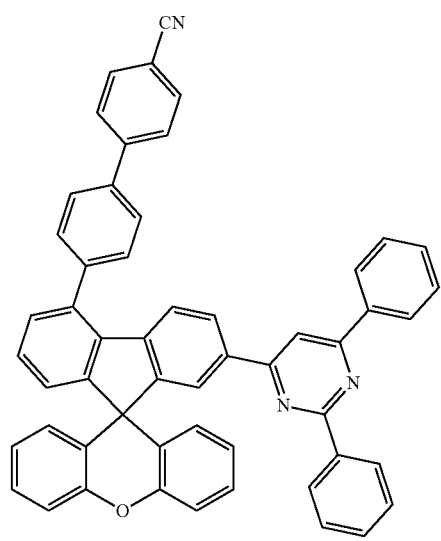
250
-continued
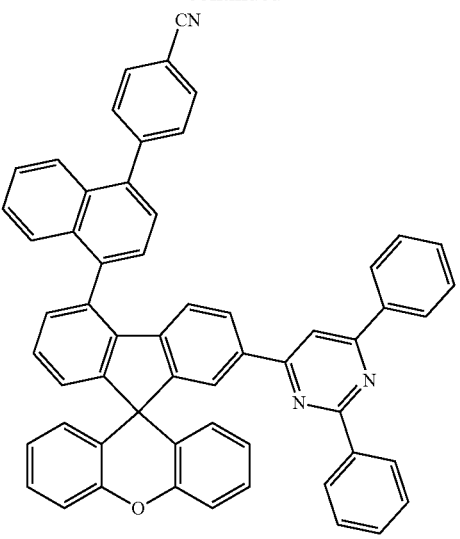
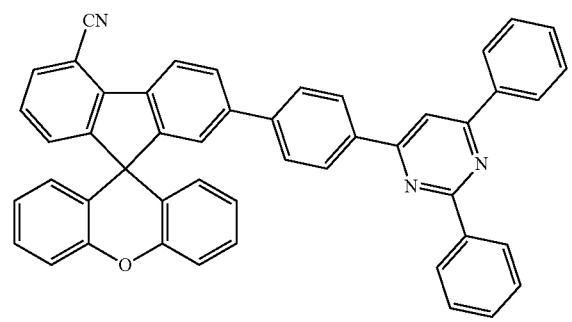
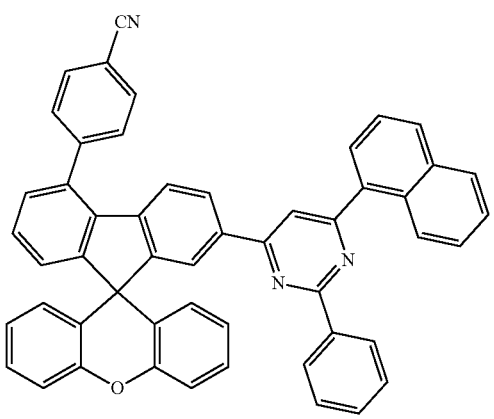

251
-continued
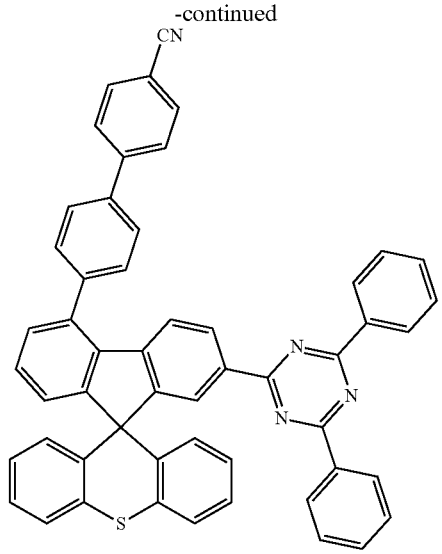
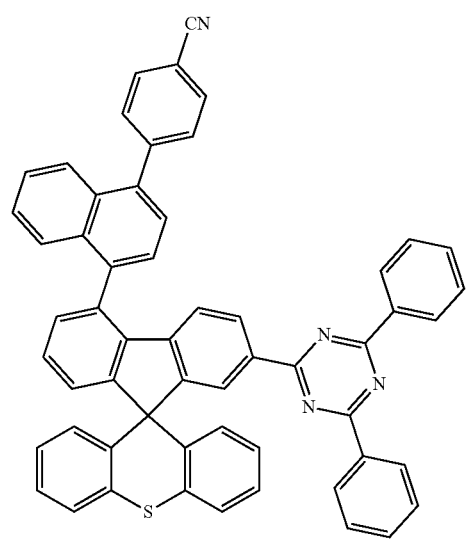
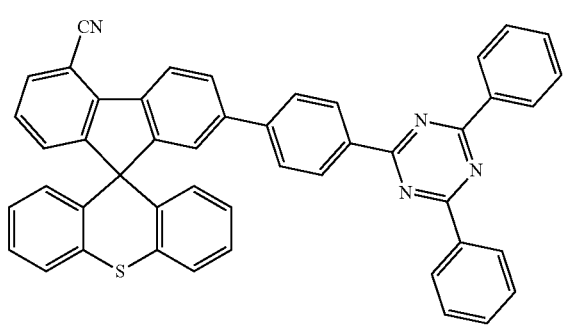
252
-continued
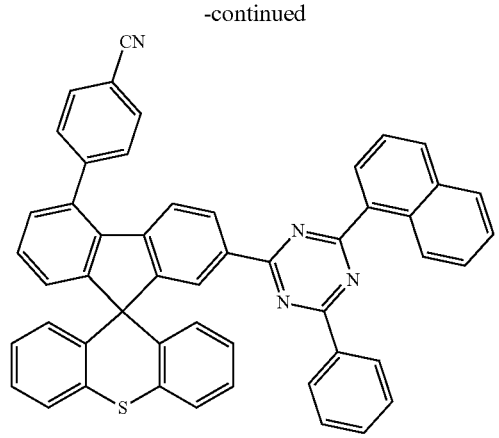
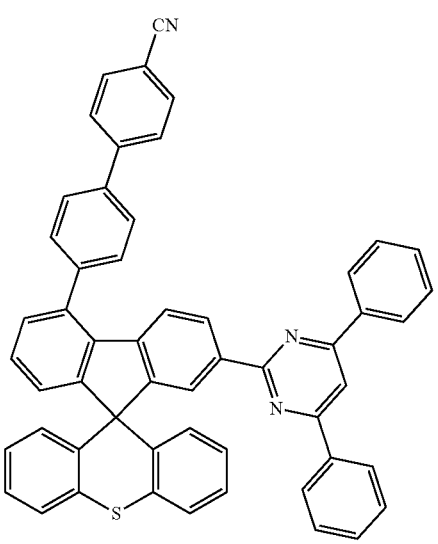
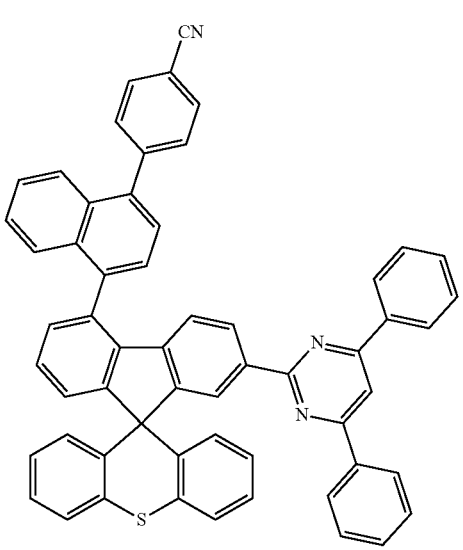

253
-continued
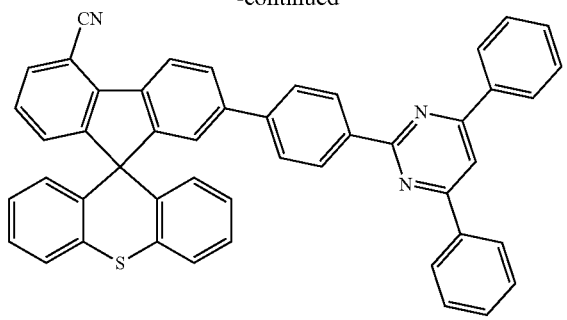
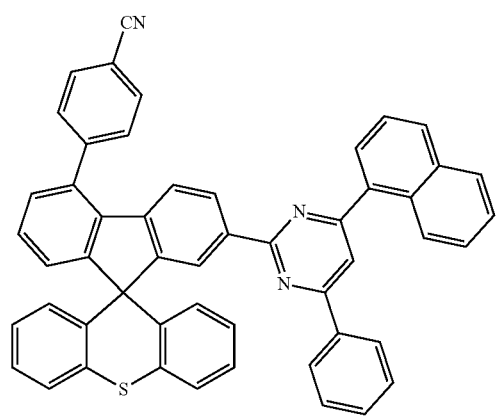
254
-continued
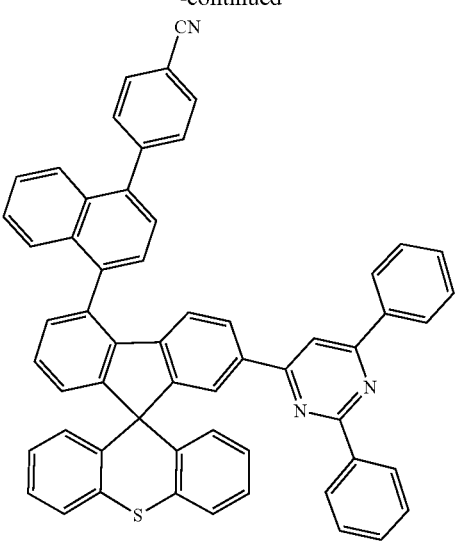
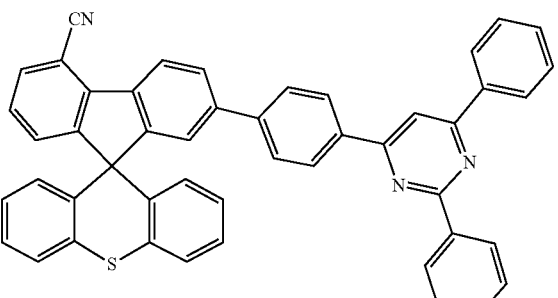
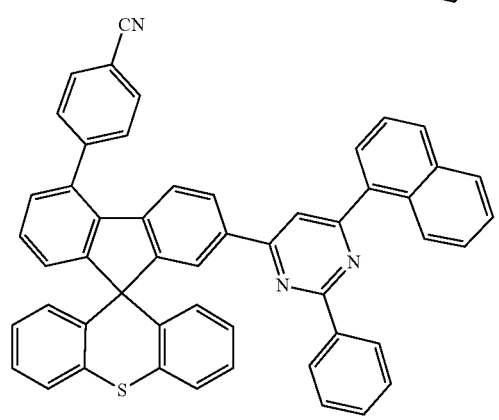
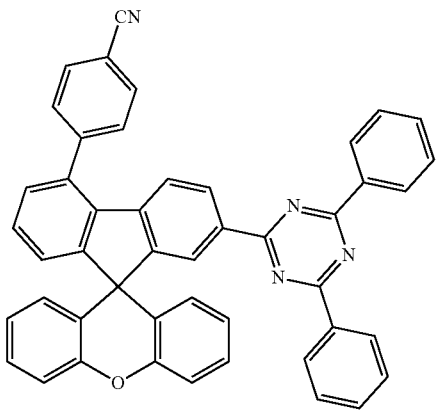

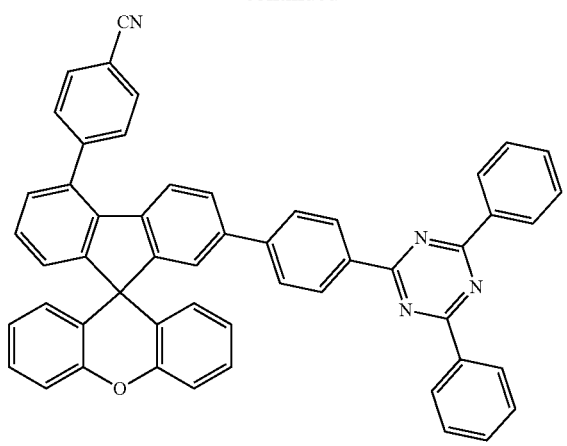
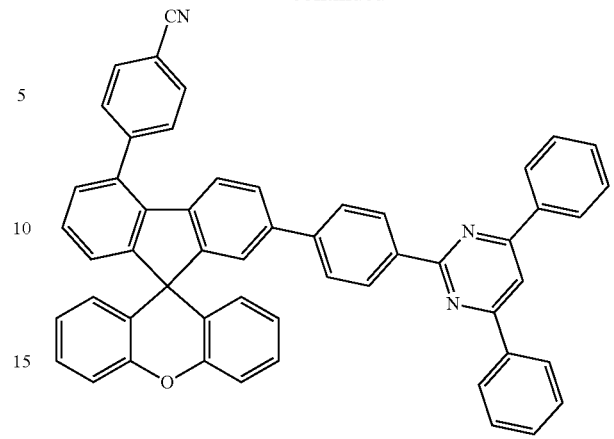
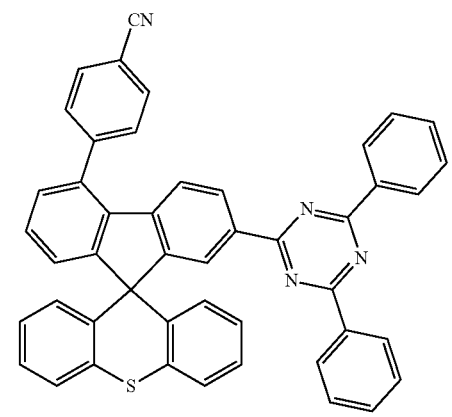
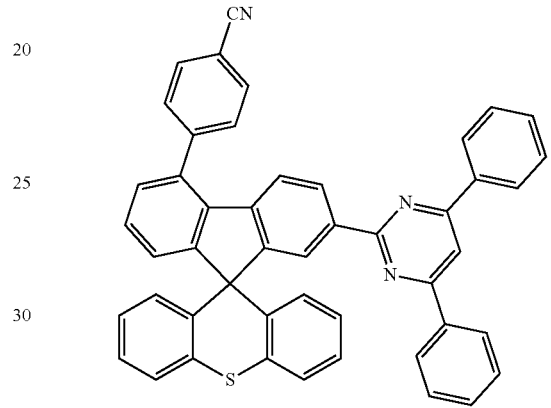
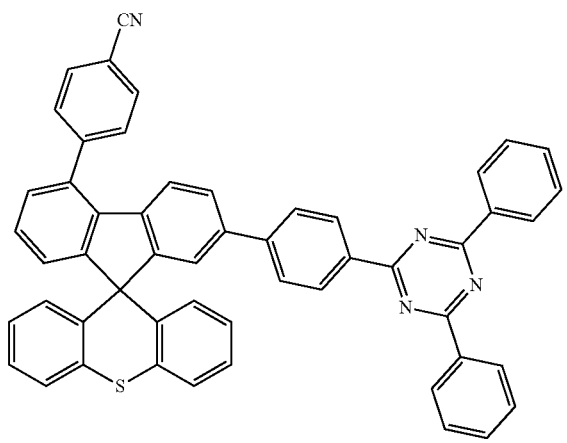
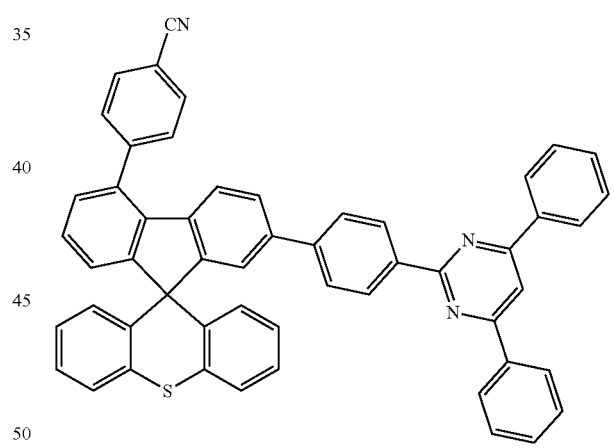
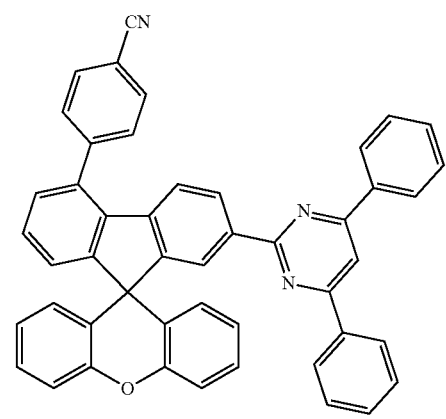
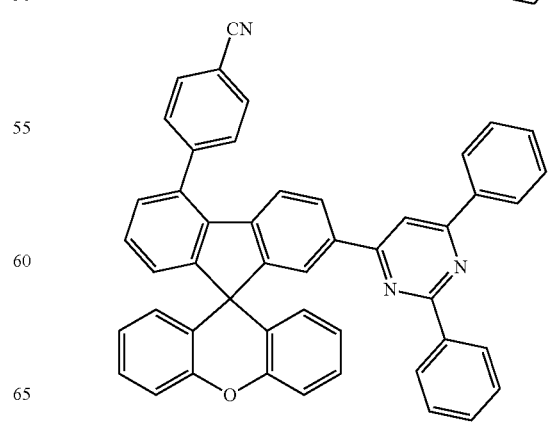

257
-continued
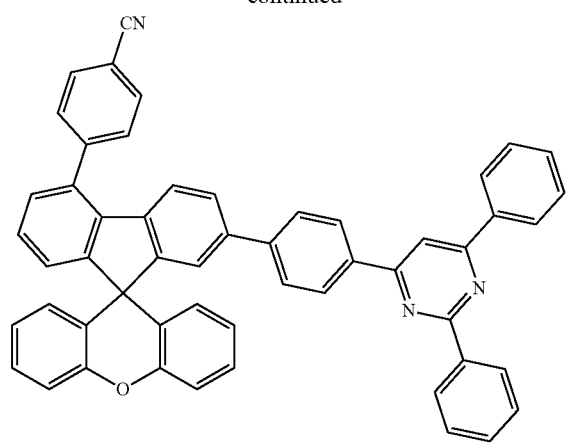
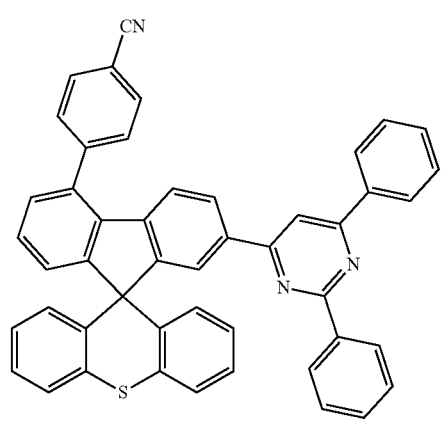
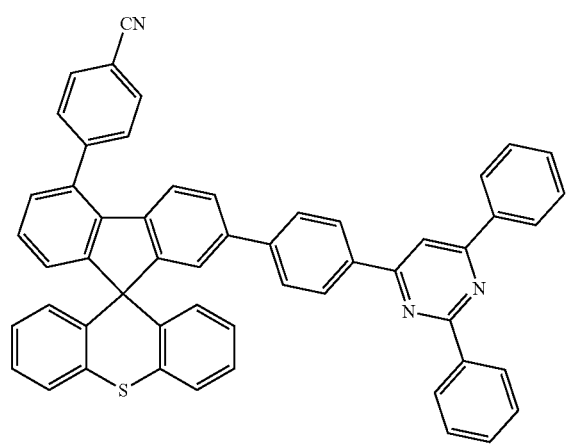
258
-continued
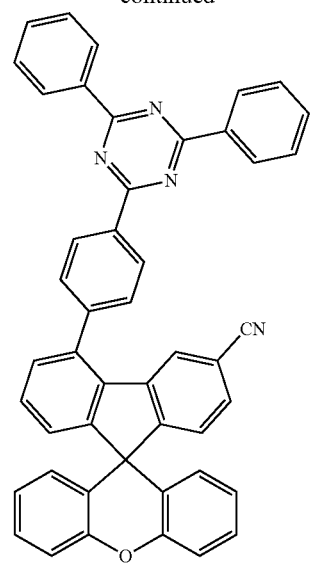
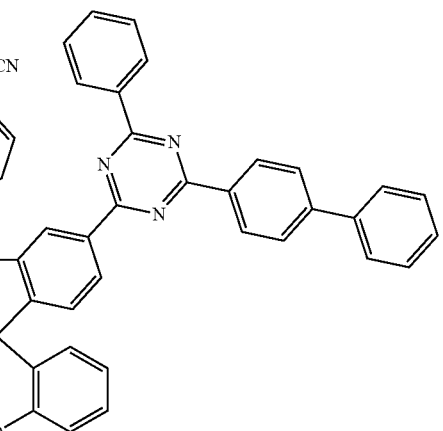
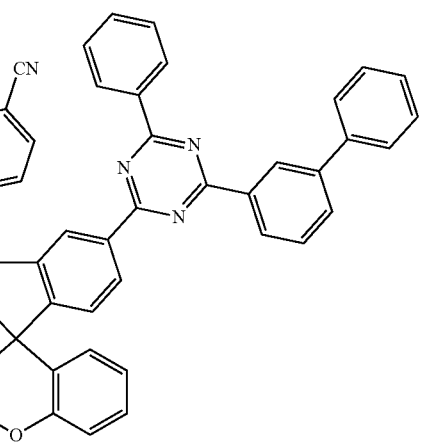

259
-continued
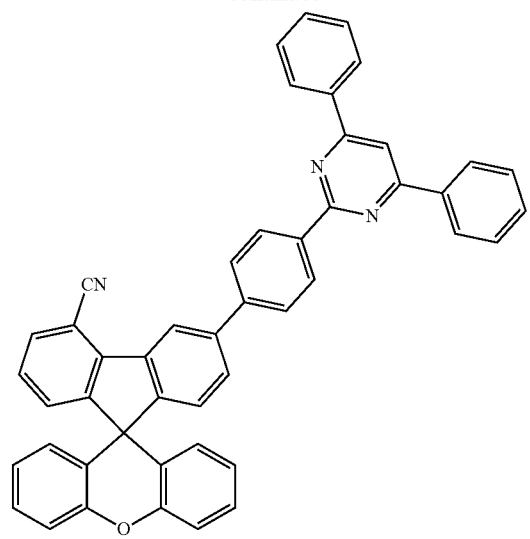
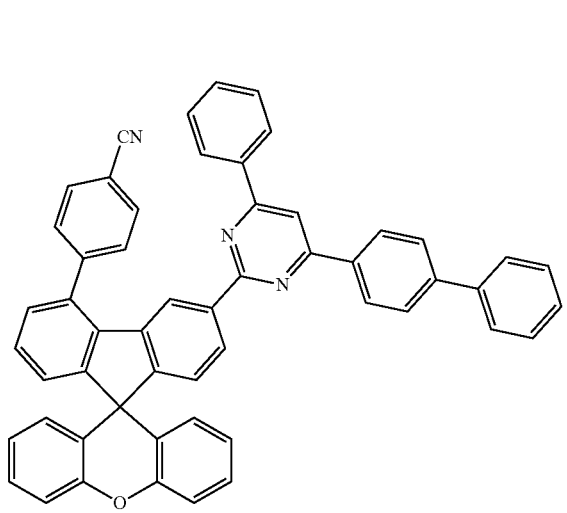
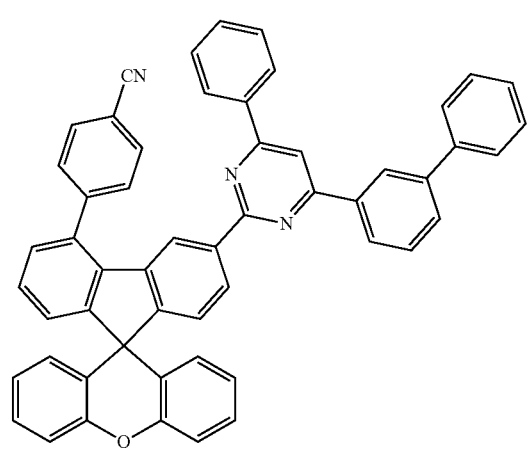
260
-continued
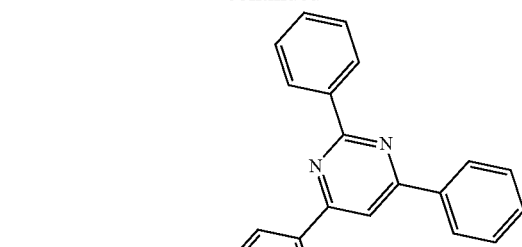
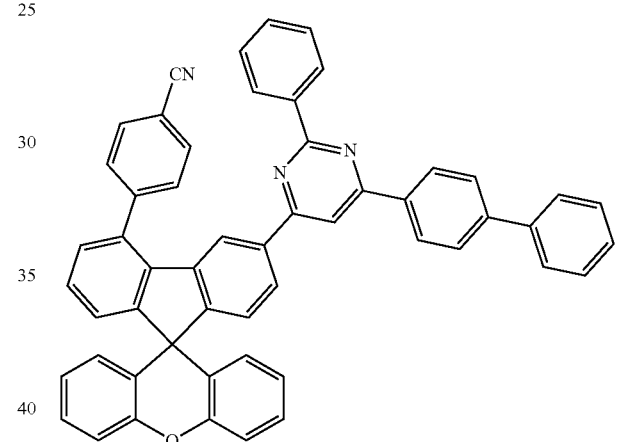
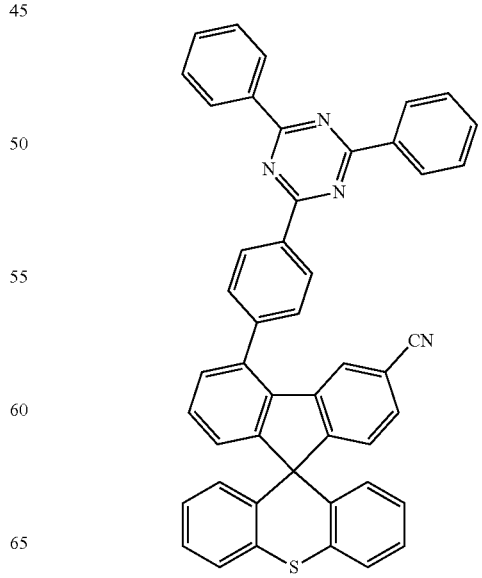

261
-continued
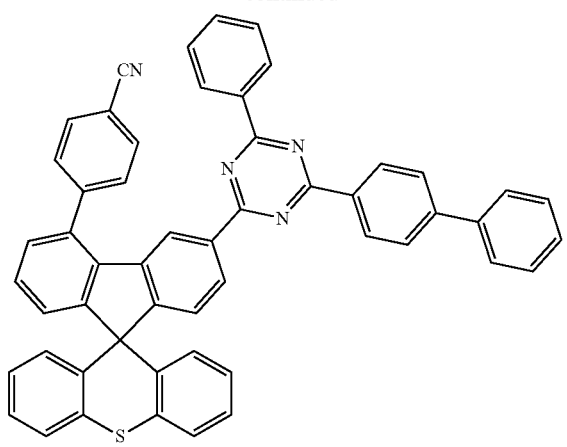
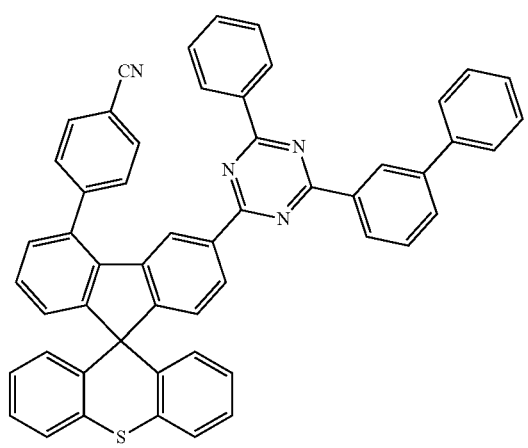
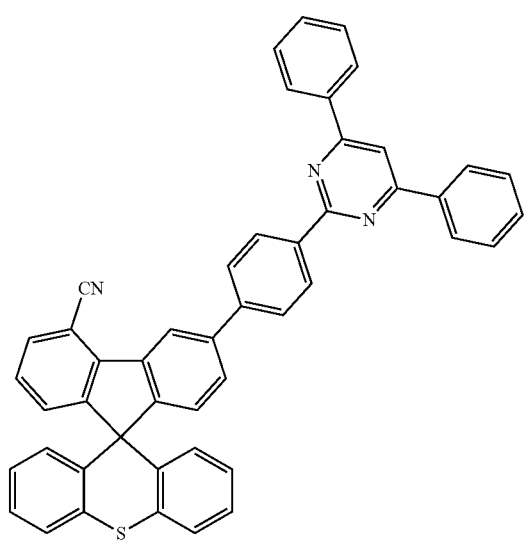
262
-continued
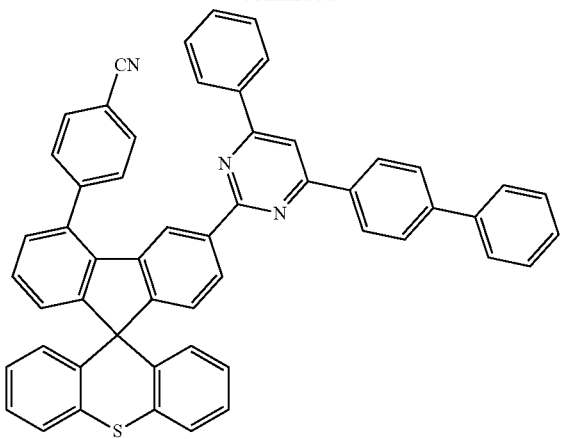
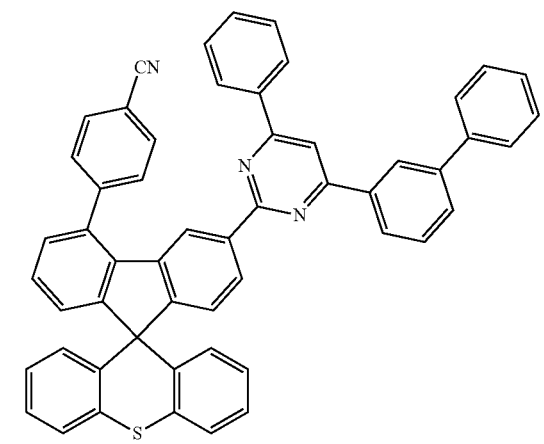
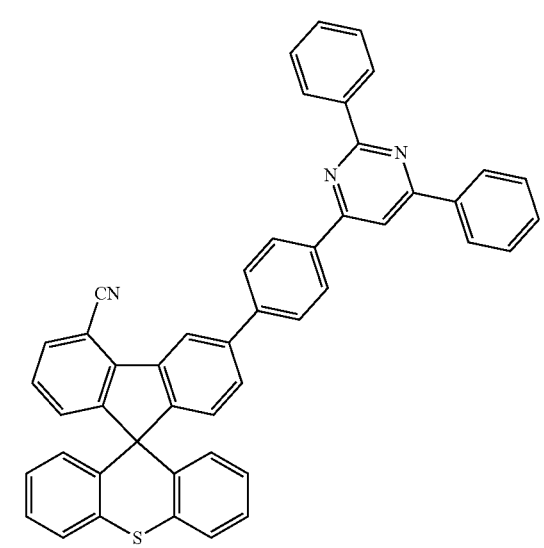

263
-continued
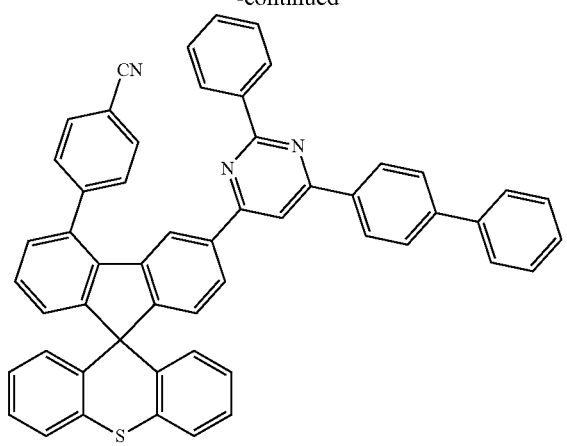
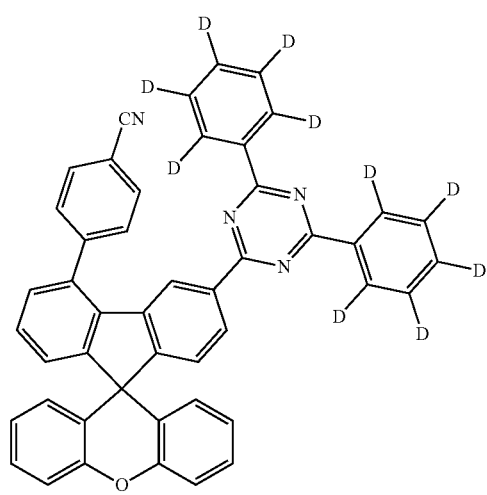
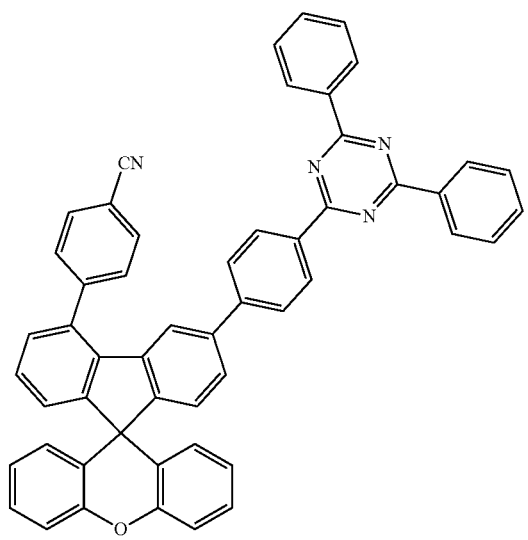
264
-continued
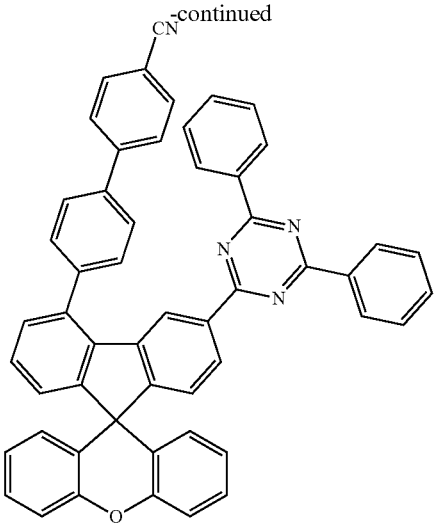
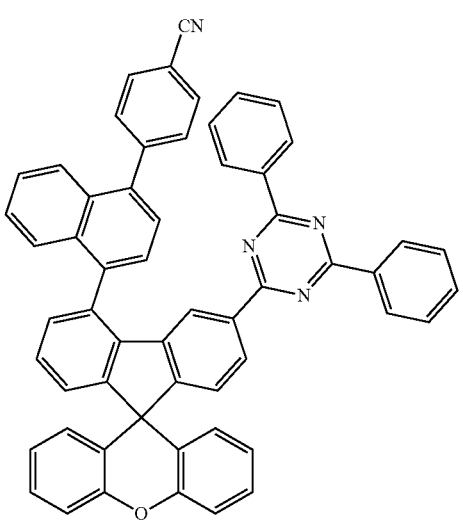
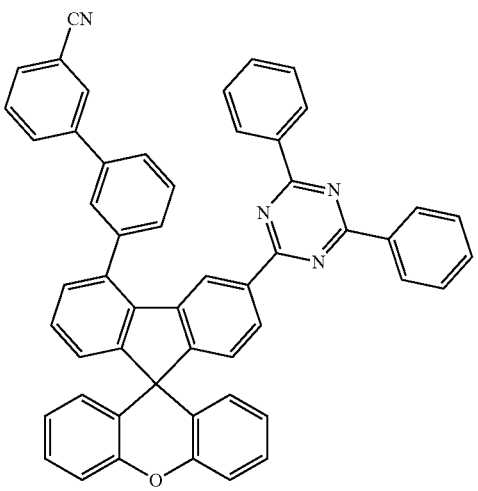

265
-continued
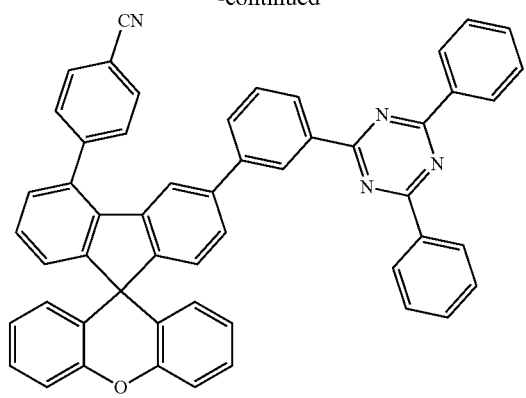
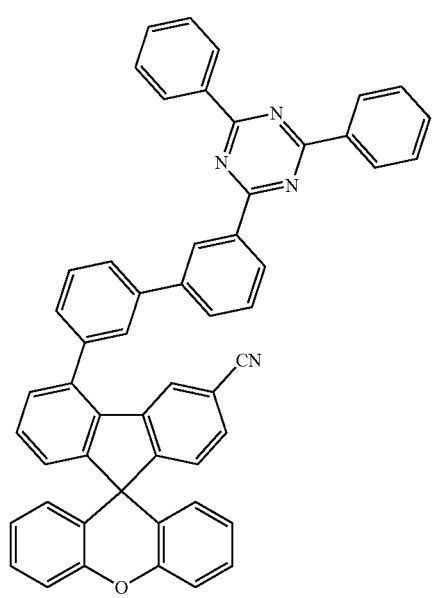
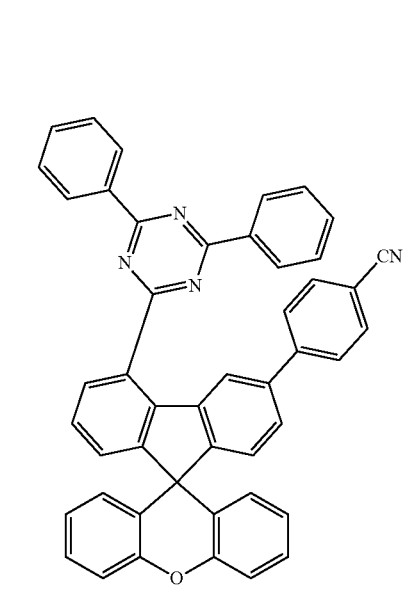
266
-continued
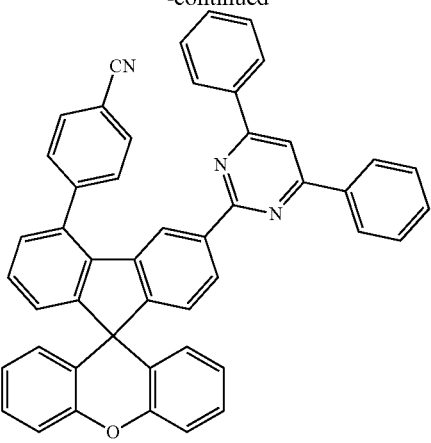
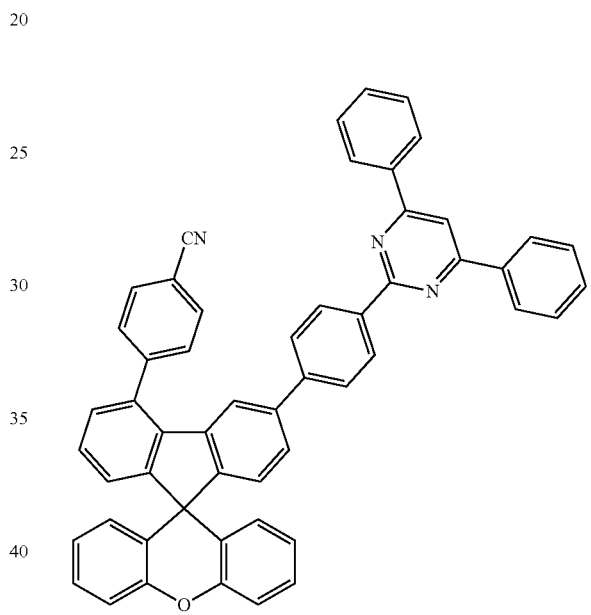
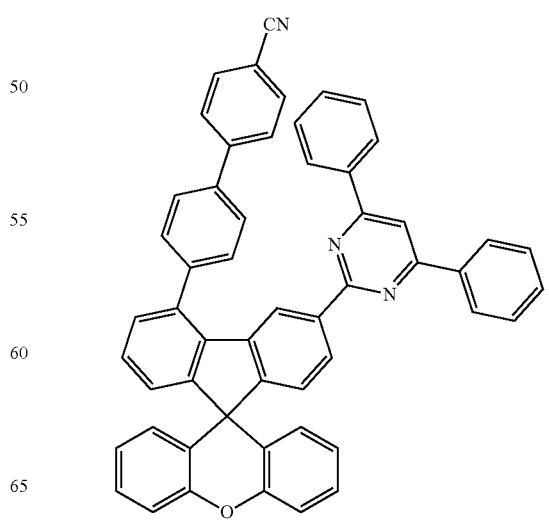

267
-continued
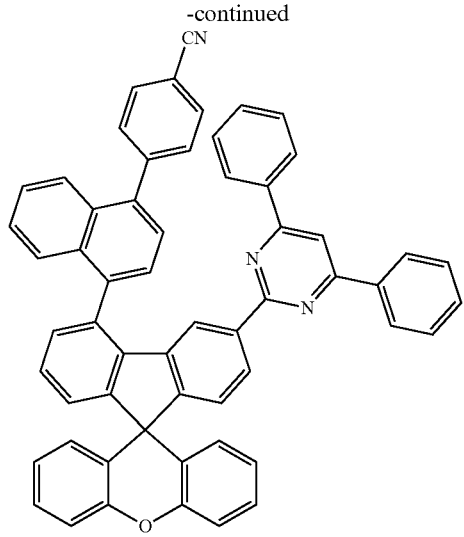
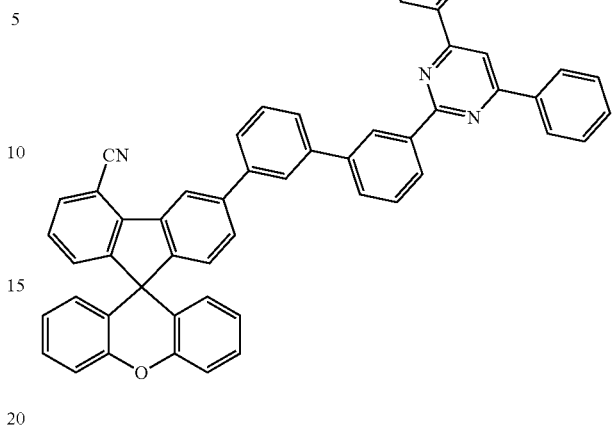
268
-continued
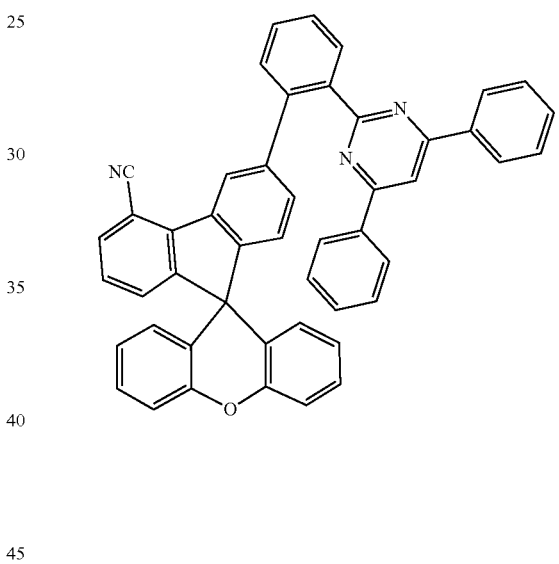
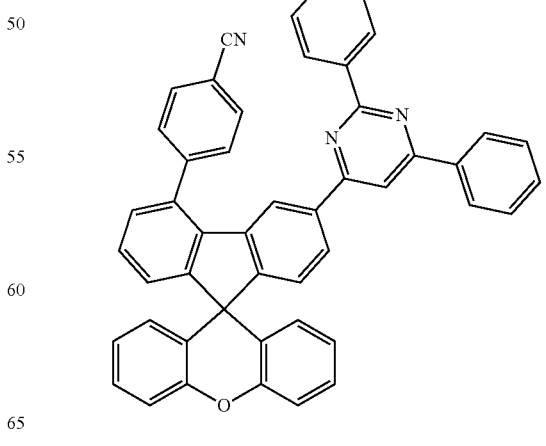

269
-continued
270
-continued
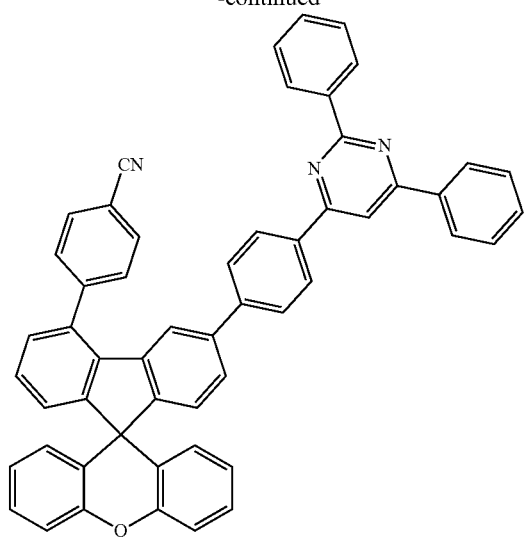
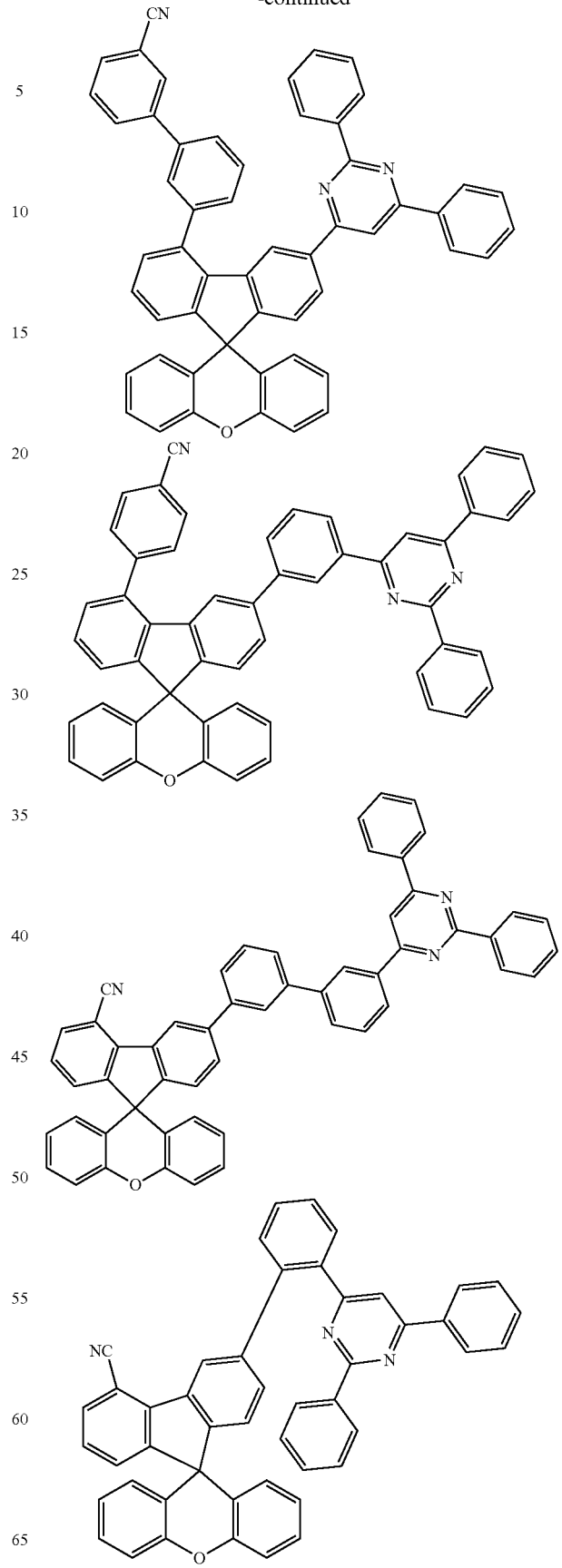

271
-continued
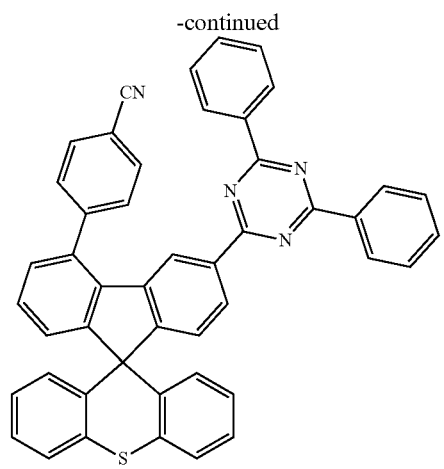
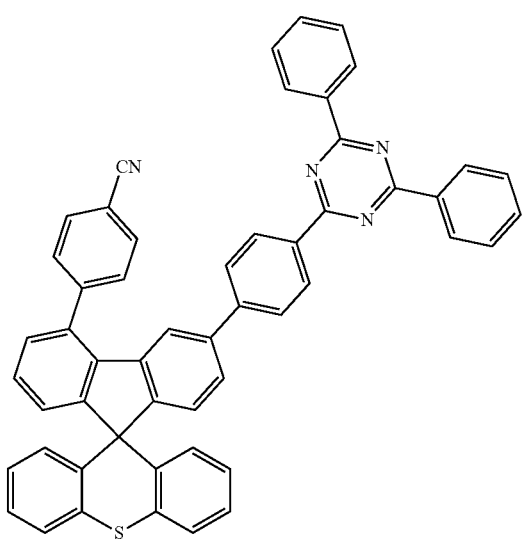
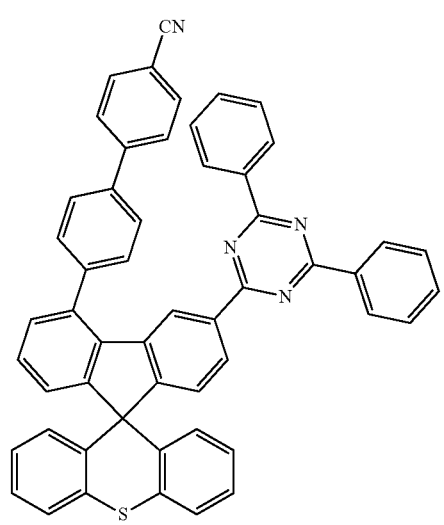
272
-continued
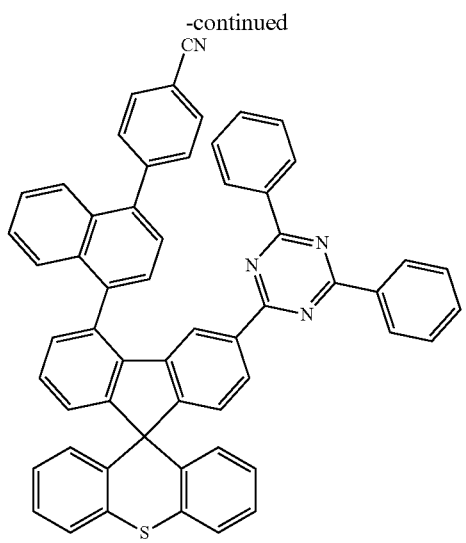
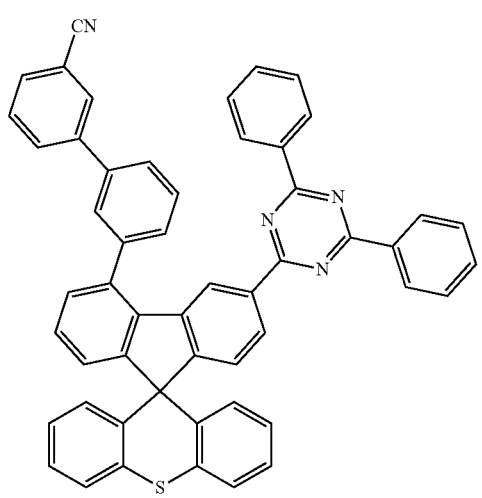
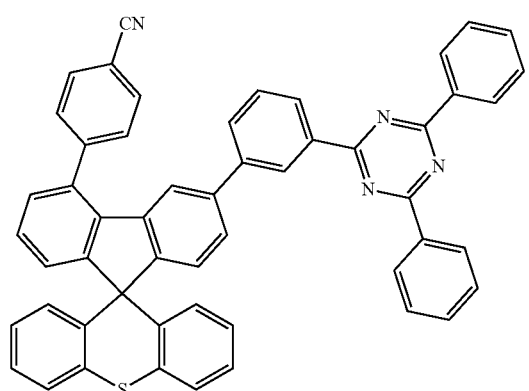

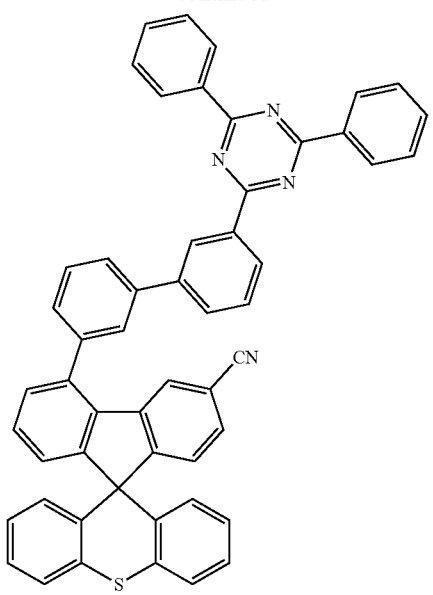
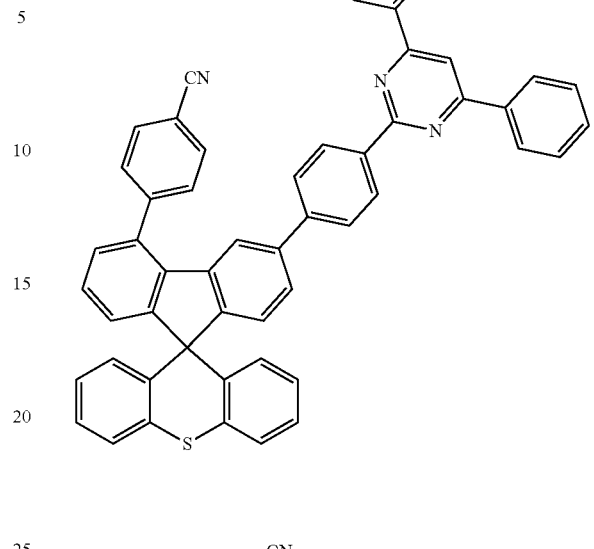
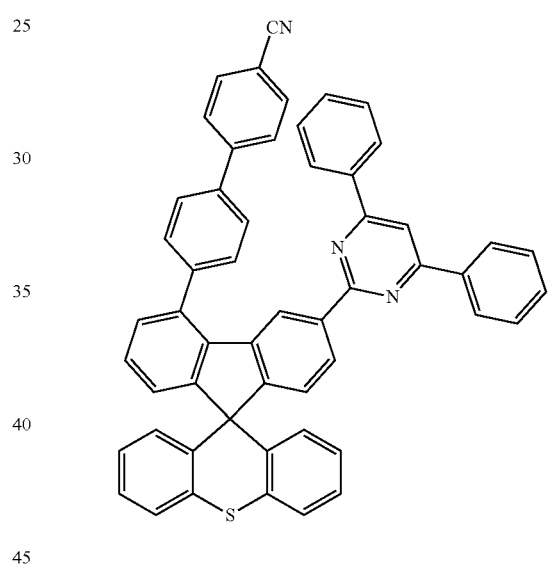
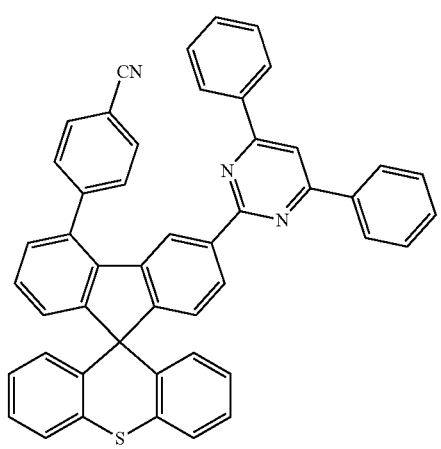
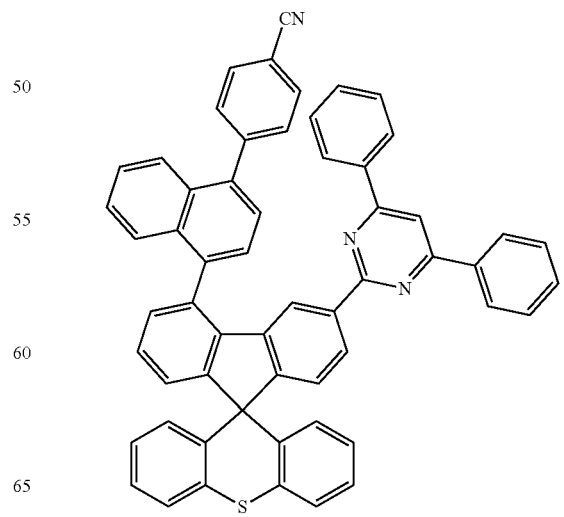

275
-continued
276
-continued
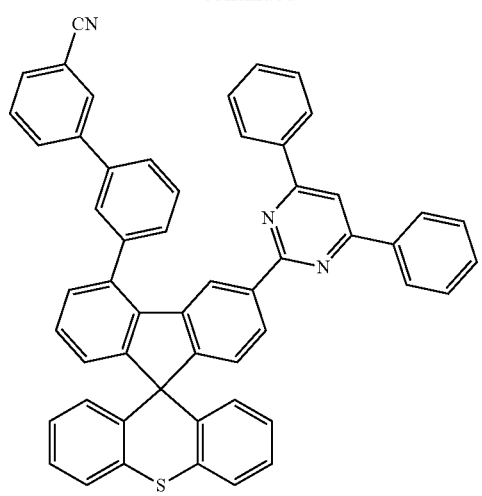
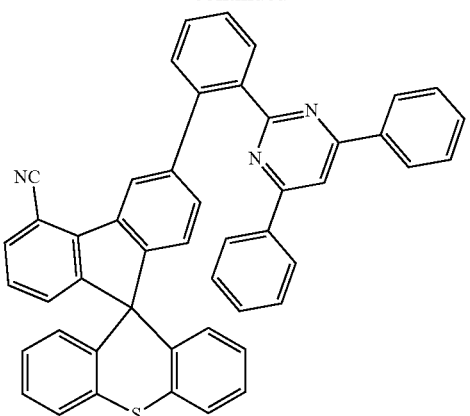
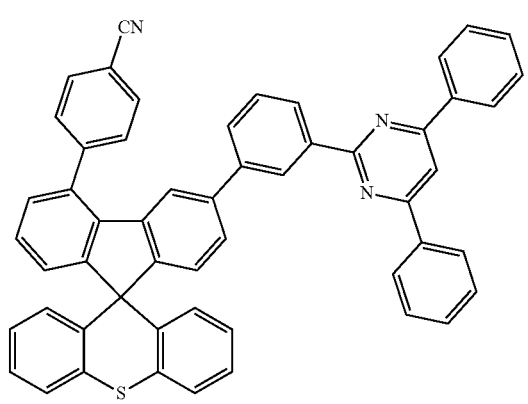
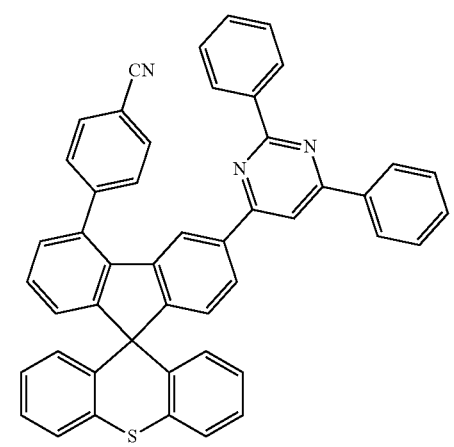
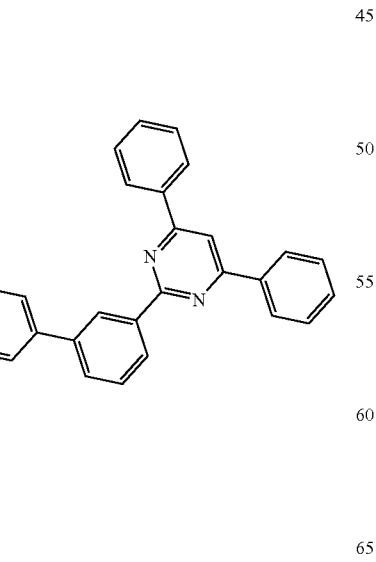
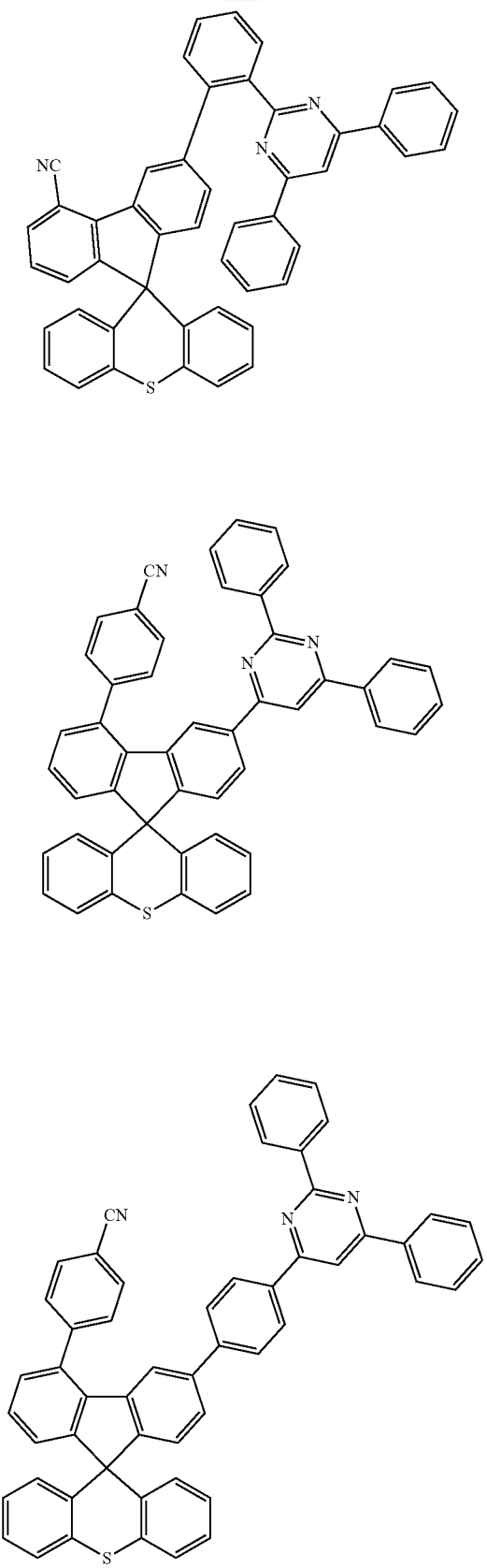

277
-continued
278
-continued
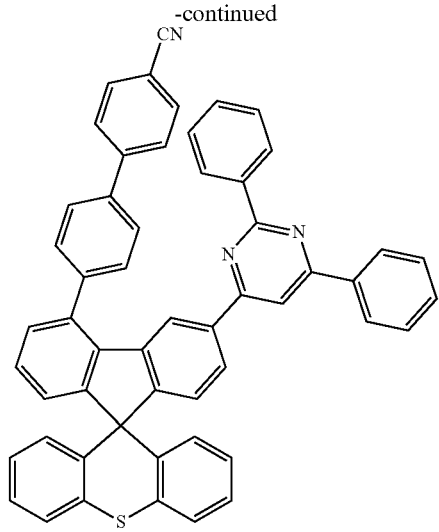
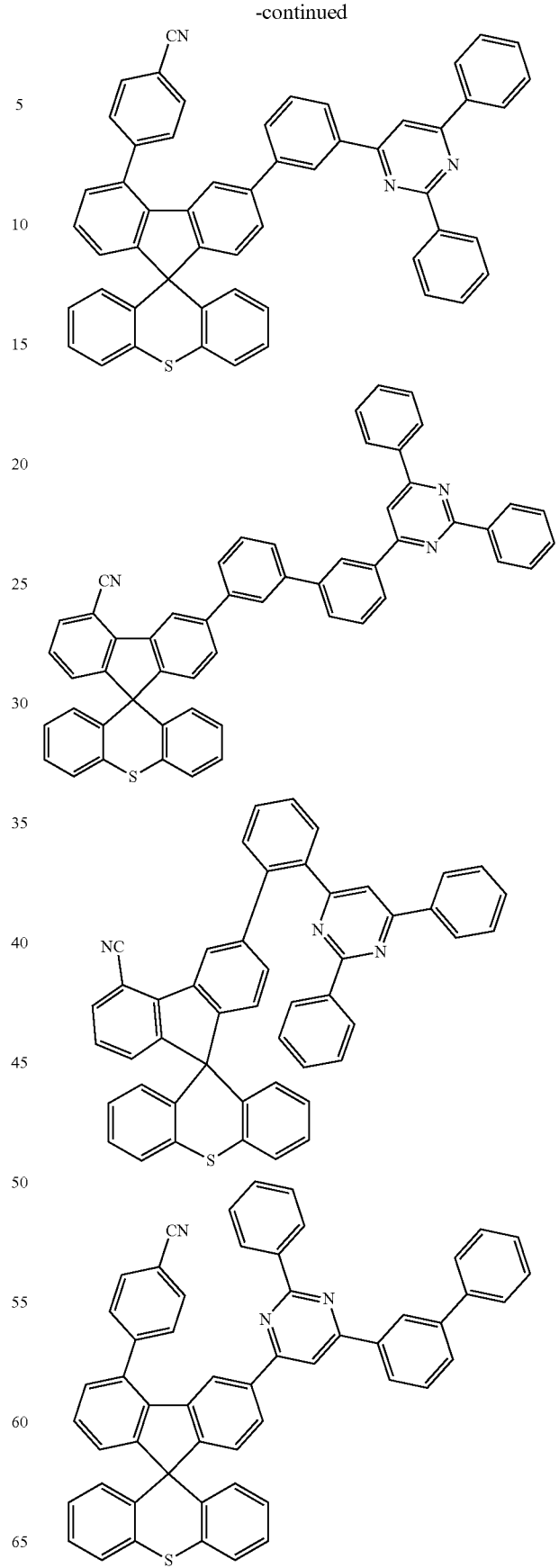

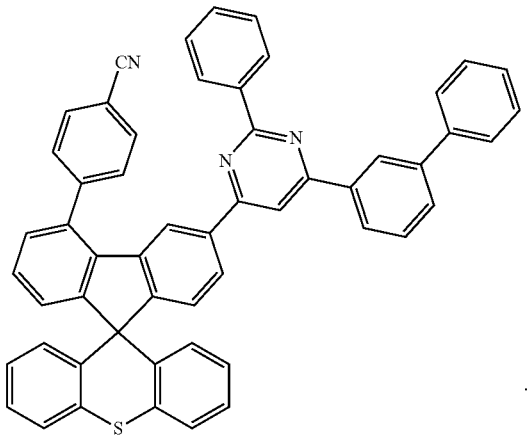
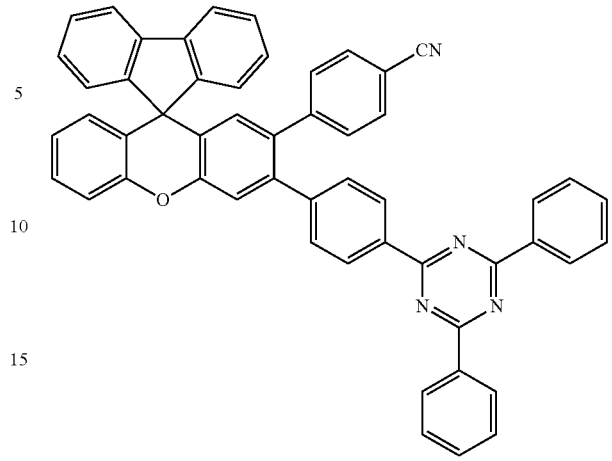
8. The compound of claim 1, wherein the compound of Chemical Formula 6 is any one compound selected from among the following compounds:
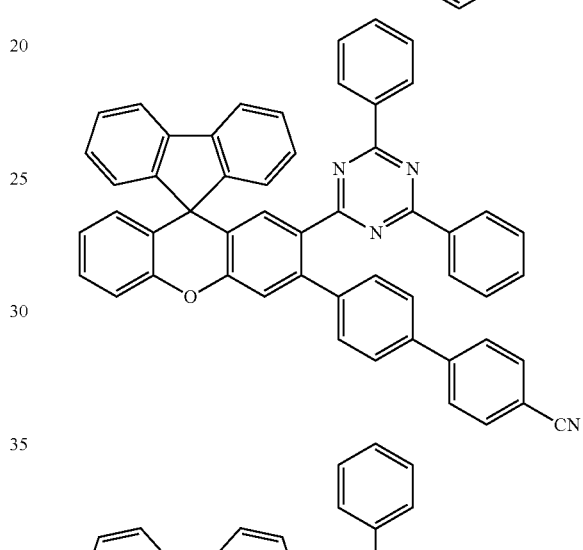
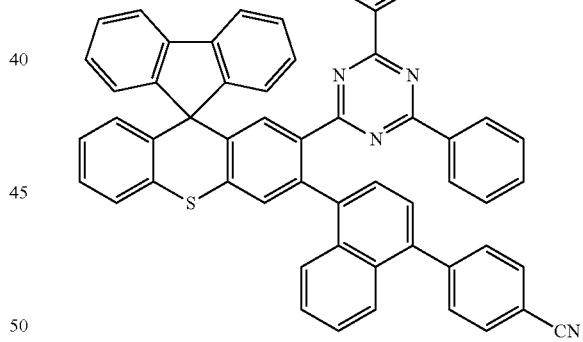
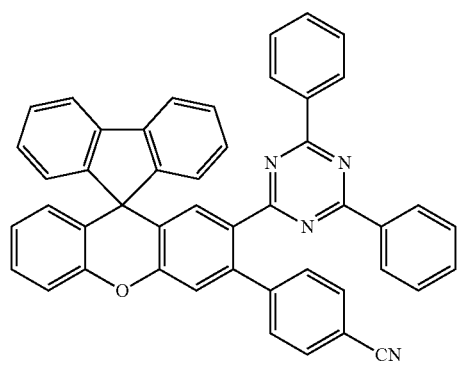
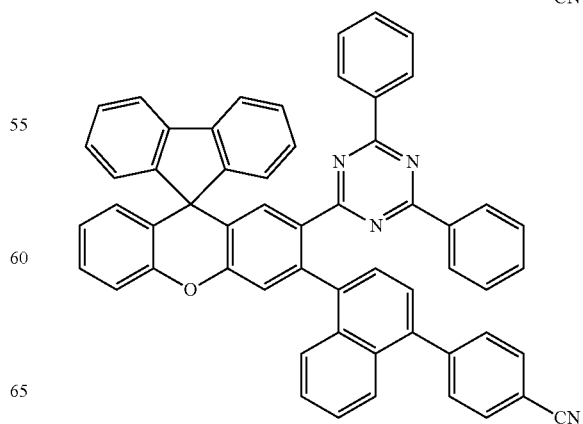

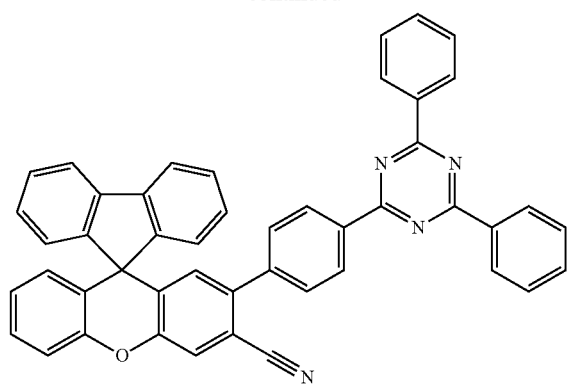
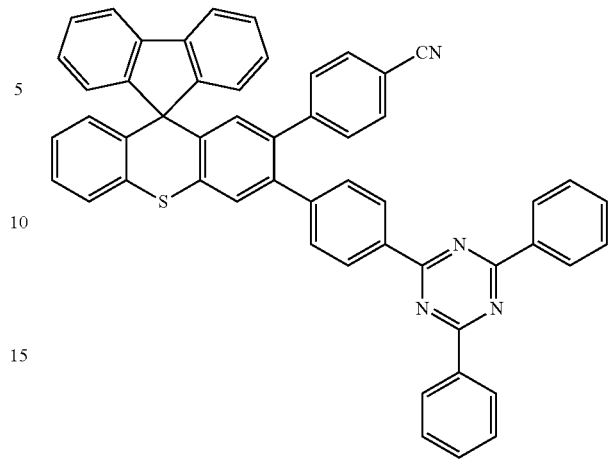
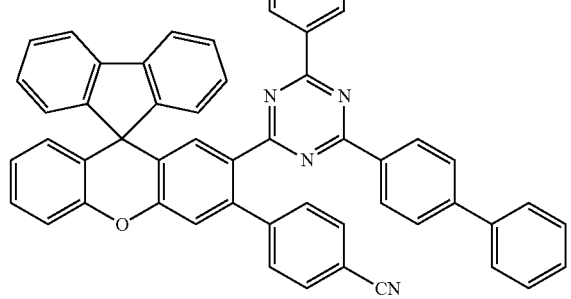
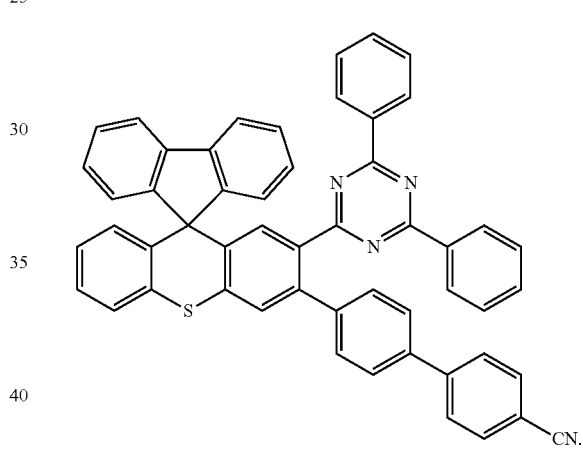
9. The compound of claim 1, wherein the compound of Chemical Formula 7 is any one compound selected from among the following compounds:
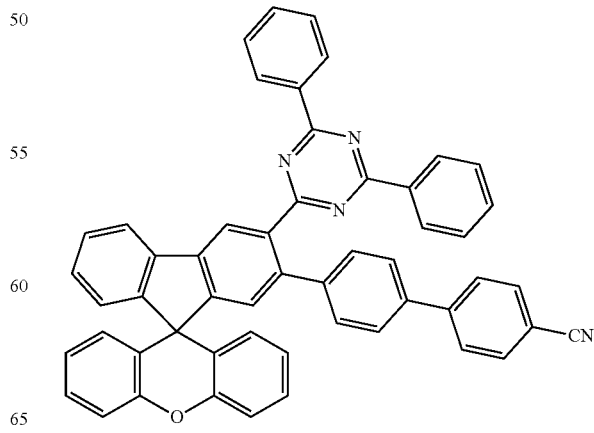

283
-continued
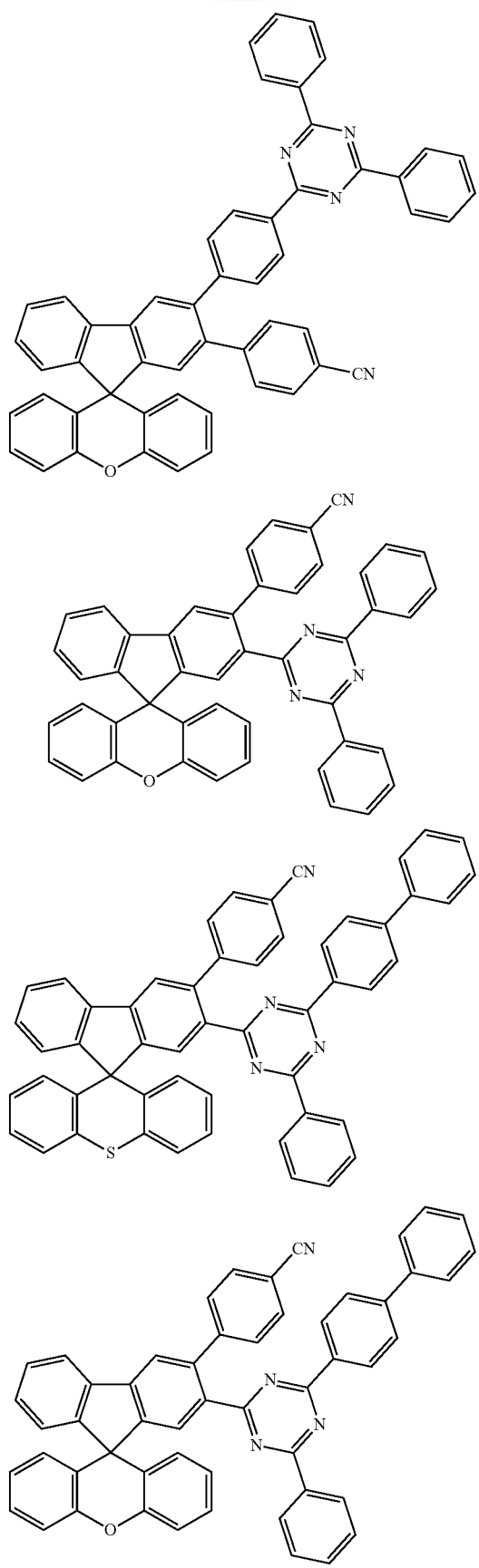
284
-continued
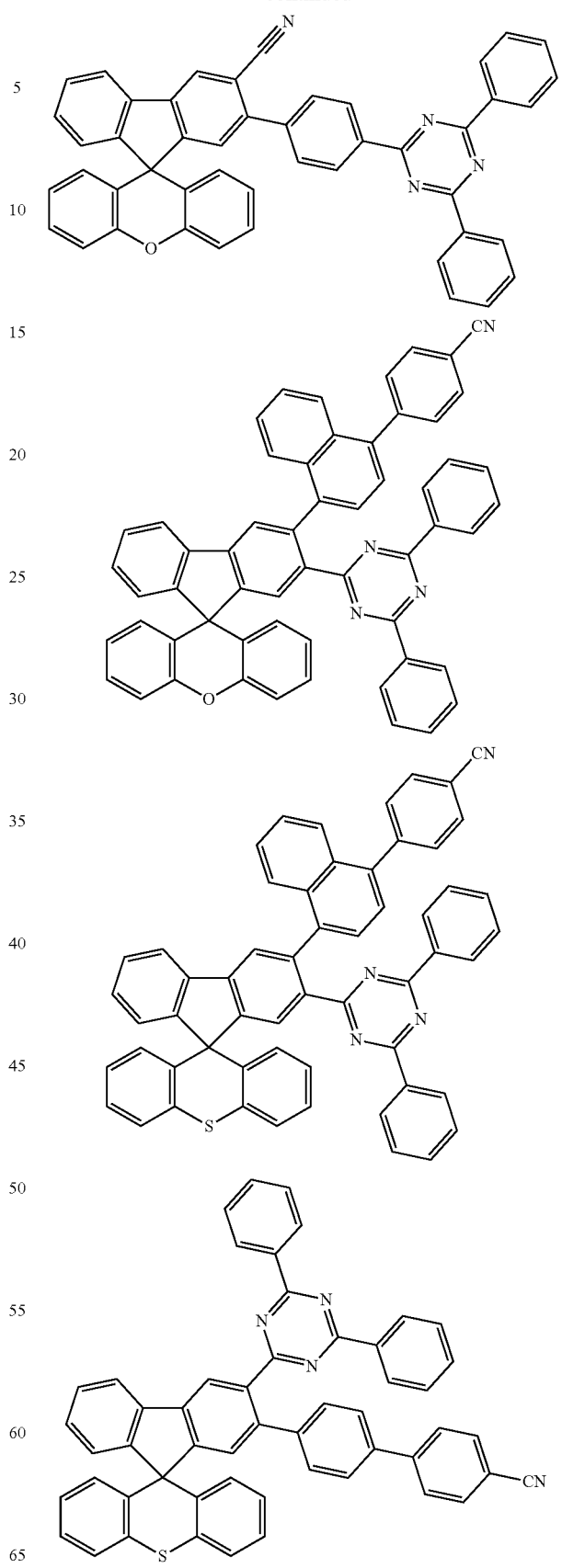

-continued

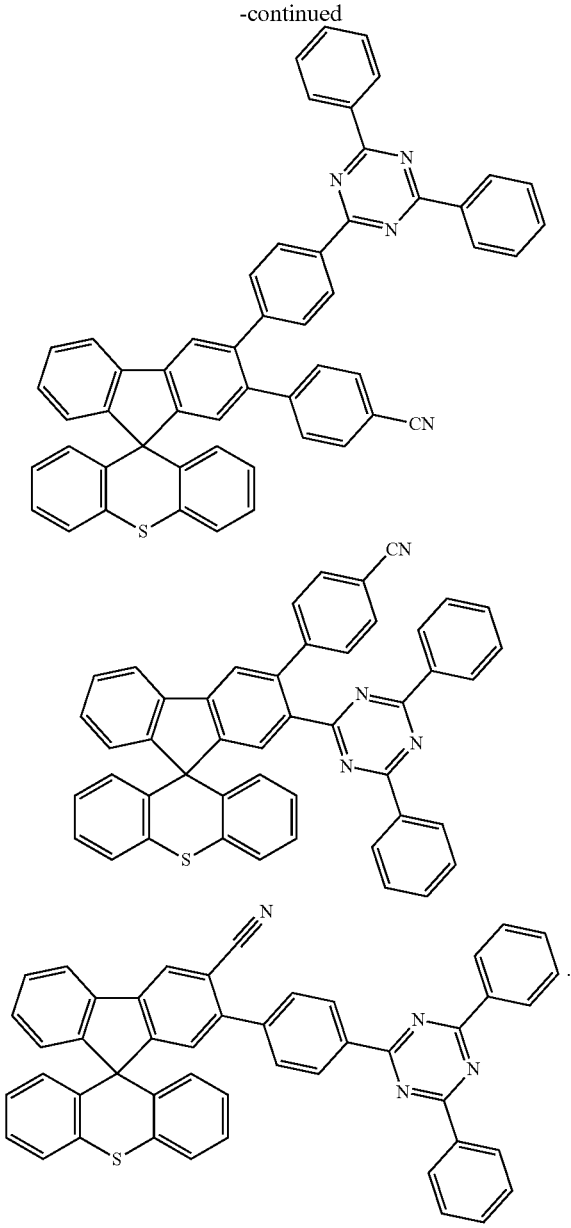

10. An organic light emitting device comprising:
a first electrode;
a second electrode; and
one or more organic material layers provided between the first electrode and the second electrode,
wherein the compound of claim 1 is included in the organic material layer provided between the first electrode and the second electrode.

11. The organic light emitting device of claim 10, wherein the organic material layer comprises at least one of an electron injection layer, an electron transfer layer, a layer carrying out electron injection and transfer at the same time, and an electron control layer, and the compound is included in at least one of the electron injection layer, the electron transfer layer, the layer carrying out electron injection and transfer at the same time, and the electron control layer.

12. The organic light emitting device of claim 10, wherein the organic material layer comprises a light emitting layer, and the compound is included in the light emitting layer.

13. The organic light emitting device of claim 10, wherein the organic material layer comprises at least one of a hole injection layer, a hole transfer layer, a hole control layer, and a layer carrying out hole transfer and injection at the same time, and the compound is included in at least one of the hole injection layer, the hole transfer layer, the hole control layer, and the layer carrying out hole transfer and injection at the same time.

14. An organic light emitting device comprising:
a first electrode;
a second electrode; and
one or more organic material layers provided between the first electrode and the second electrode,
wherein the compound of claim 2 is included in the organic material layer provided between the first electrode and the second electrode.

15. The organic light emitting device of claim 14, wherein the organic material layer comprises at least one of an electron injection layer, an electron transfer layer, a layer carrying out electron injection and transfer at the same time, and an electron control layer, and the compound is included in at least one of the electron injection layer, the electron transfer layer, the layer carrying out electron injection and transfer at the same time, and the electron control layer.

16. The organic light emitting device of claim 14, wherein the organic material layer comprises a light emitting layer, and the compound is included in the light emitting layer.

17. The organic light emitting device of claim 14, wherein the organic material layer comprises at least one of a hole injection layer, a hole transfer layer, a hole control layer, and a layer carrying out hole transfer and injection at the same time, and the compound is included in at least one of the hole injection layer, the hole transfer layer, the hole control layer, and the layer carrying out hole transfer and injection at the same time.

* * * * *